United States Patent
Burich et al.

(10) Patent No.: US 10,556,150 B2
(45) Date of Patent: Feb. 11, 2020

(54) GROUP PERFORMANCE MONITORING SYSTEM AND METHOD

(71) Applicant: adidas AG, Herzogenaurach (DE)

(72) Inventors: Meg Susan Burich, Chadds Ford, PA (US); Qaizar Hassonjee, Chadds Ford, PA (US); Roger Armitage, Cirencester (GB); Markus Strecker, Landenberg, PA (US)

(73) Assignee: adidas AG, Herzogenaurach (DE)

( * ) Notice: Subject to any disclaimer, the term of this patent is extended or adjusted under 35 U.S.C. 154(b) by 28 days.

(21) Appl. No.: 15/716,171

(22) Filed: Sep. 26, 2017

(65) Prior Publication Data

US 2018/0015329 A1 Jan. 18, 2018

Related U.S. Application Data

(63) Continuation of application No. 15/016,665, filed on Feb. 5, 2016, now Pat. No. 9,802,080, which is a (Continued)

(51) Int. Cl.
*A63B 24/00* (2006.01)
*G06F 19/00* (2018.01)
(Continued)

(52) U.S. Cl.
CPC ........ *A63B 24/0062* (2013.01); *A61B 5/0024* (2013.01); *A61B 5/1118* (2013.01); *G06F 11/3006* (2013.01); *G06F 11/3438* (2013.01); *G06F 19/3418* (2013.01); *G06F 19/3481* (2013.01); *G06Q 10/0639* (2013.01); *A61B 5/0002* (2013.01); *A61B 5/0015* (2013.01);
(Continued)

(58) Field of Classification Search
CPC ...... G06F 19/3481; G16H 20/30; A63B 43/00
See application file for complete search history.

(56) References Cited

U.S. PATENT DOCUMENTS 2,571,442 A 10/1951 Griffith
3,307,546 A 3/1967 Cherio et al.
(Continued)

FOREIGN PATENT DOCUMENTS

CN 101890215 A 11/2010
CN 102369046 A 3/2012
(Continued)

OTHER PUBLICATIONS

Garmin Corporation, "GPS II: Owner's Manual & Reference (Garmin)," 1996.
(Continued)

*Primary Examiner* — Reginald A Renwick
(74) *Attorney, Agent, or Firm* — Sterne, Kessler, Goldstein & Fox P.L.L.C.

(57) ABSTRACT

The present invention provides a group monitoring device for monitoring a plurality of individuals engaged in an athletic activity, the device including a display configured to display, during an athletic activity: a metric relating to each of a plurality of individuals engaged in the athletic activity, and a status of a system component used to monitor the athletic activity. The group monitoring device may also include an input configured to allow manipulation of the display.

25 Claims, 79 Drawing Sheets

Related U.S. Application Data continuation of application No. 13/543,428, filed on Jul. 6, 2012, now Pat. No. 9,317,660, which is a continuation-in-part of application No. 13/077,510, filed on Mar. 31, 2011, now Pat. No. 9,141,759.

(51) Int. Cl.

| | | |
|---|---|---|
| *G06F 11/30* | (2006.01) | |
| *G06F 11/34* | (2006.01) | |
| *A61B 5/00* | (2006.01) | |
| *A61B 5/11* | (2006.01) | |
| *G06Q 10/06* | (2012.01) | |
| *A61B 5/0205* | (2006.01) | |
| *A61B 5/024* | (2006.01) | |

(52) U.S. Cl.
CPC ............ *A61B 5/024* (2013.01); *A61B 5/0205* (2013.01); *A61B 5/1112* (2013.01); *A61B 5/1113* (2013.01); *A61B 5/1122* (2013.01); *A61B 5/1123* (2013.01); *A61B 2503/10* (2013.01); *A61B 2562/0204* (2013.01); *A61B 2562/0219* (2013.01); *A61B 2562/0223* (2013.01); *A61B 2562/0247* (2013.01)

(56) References Cited

U.S. PATENT DOCUMENTS

| | | |
|---|---|---|
| 3,534,727 A | 10/1970 | Roman |
| 3,874,368 A | 4/1975 | Asrican |
| 3,926,177 A | 12/1975 | Hardway, Jr. et al. |
| 4,016,868 A | 4/1977 | Allison |
| 4,033,332 A | 7/1977 | Hardway, Jr. et al. |
| 4,102,331 A | 7/1978 | Grayzel et al. |
| 4,202,350 A | 5/1980 | Walton |
| 4,289,142 A | 9/1981 | Kearns |
| 4,308,872 A | 1/1982 | Watson et al. |
| 4,312,358 A | 1/1982 | Barney |
| 4,373,534 A | 2/1983 | Watson |
| 4,387,722 A | 6/1983 | Kearns |
| 4,494,553 A | 1/1985 | Sciarra et al. |
| 4,572,197 A | 2/1986 | Moore et al. |
| 4,580,572 A | 4/1986 | Granek et al. |
| 4,753,088 A | 6/1988 | Harrison et al. |
| 4,777,962 A | 10/1988 | Watson et al. |
| 4,815,473 A | 3/1989 | Watson et al. |
| 4,817,625 A | 4/1989 | Miles |
| 4,889,131 A | 12/1989 | Salem et al. |
| 4,909,260 A | 3/1990 | Salem et al. |
| 4,962,469 A | 10/1990 | Ono et al. |
| 5,007,427 A | 4/1991 | Suzuki et al. |
| 5,074,129 A | 12/1991 | Matthew |
| 5,076,801 A | 12/1991 | Schroll |
| 5,099,855 A | 3/1992 | Yount |
| 5,111,818 A | 5/1992 | Suzuki et al. |
| 5,143,089 A | 9/1992 | Alt |
| 5,148,002 A | 9/1992 | Kuo et al. |
| 5,153,584 A | 10/1992 | Engira |
| 5,204,670 A | 4/1993 | Stinton |
| 5,210,540 A | 5/1993 | Masumoto |
| 5,241,300 A | 8/1993 | Buschmann |
| 5,295,490 A | 3/1994 | Dodakian |
| 5,329,932 A | 7/1994 | Yount |
| 5,348,008 A | 9/1994 | Bornn et al. |
| 5,353,793 A | 10/1994 | Bornn |
| 5,400,254 A | 3/1995 | Fujita |
| 5,416,961 A | 5/1995 | Vinay |
| 5,428,546 A | 6/1995 | Shah et al. |
| 5,454,376 A | 10/1995 | Stephens et al. |
| 5,583,776 A | 12/1996 | Levi et al. |
| 5,611,085 A | 3/1997 | Rasmussen |
| 5,724,025 A | 3/1998 | Tavori |
| 5,758,313 A | 5/1998 | Shah et al. |
| 5,769,755 A | 6/1998 | Henry et al. |
| 5,782,778 A | 7/1998 | De Briere et al. |
| 5,820,567 A | 10/1998 | Mackie |
| 5,862,511 A | 1/1999 | Croyle et al. |
| 5,937,854 A | 8/1999 | Stenzler |
| 5,991,922 A | 11/1999 | Banks |
| 6,002,982 A | 12/1999 | Fry |
| 6,047,203 A | 4/2000 | Sackner et al. |
| 6,066,093 A | 5/2000 | Kelly et al. |
| 6,145,551 A | 11/2000 | Jayaraman et al. |
| 6,148,262 A | 11/2000 | Fry |
| 6,179,786 B1 | 1/2001 | Young |
| 6,198,394 B1 | 3/2001 | Jacobsen et al. |
| 6,246,362 B1 | 6/2001 | Tsubata et al. |
| 6,254,551 B1 | 7/2001 | Varis |
| 6,266,623 B1 | 7/2001 | Vock et al. |
| 6,287,264 B1 | 9/2001 | Hoffman |
| 6,306,088 B1 | 10/2001 | Krausman et al. |
| 6,341,504 B1 | 1/2002 | Istook |
| 6,381,482 B1 | 4/2002 | Jayaraman et al. |
| 6,419,636 B1 | 7/2002 | Young et al. |
| 6,424,295 B1 | 7/2002 | Lange |
| 6,443,890 B1 | 9/2002 | Schulze et al. |
| 6,461,307 B1 | 10/2002 | Kristbjarnarson et al. |
| 6,463,385 B1 | 10/2002 | Fry |
| 6,478,736 B1 | 11/2002 | Mault |
| 6,513,532 B2 | 2/2003 | Mault et al. |
| 6,529,827 B1 | 3/2003 | Beason et al. |
| 6,551,252 B2 | 4/2003 | Sackner et al. |
| 6,579,231 B1 | 6/2003 | Phipps |
| 6,616,613 B1 | 9/2003 | Goodman |
| 6,687,523 B1 | 2/2004 | Jayaramen et al. |
| 6,790,178 B1 | 9/2004 | Mault et al. |
| 6,798,378 B1 | 9/2004 | Walters |
| 6,941,775 B2 | 9/2005 | Sharma |
| 6,970,731 B1 | 11/2005 | Jayaraman et al. |
| 7,254,516 B2 | 8/2007 | Case, Jr. et al. |
| 7,559,902 B2 | 7/2009 | Ting et al. |
| 7,604,603 B2 | 10/2009 | Sackner et al. |
| 7,670,263 B2 | 3/2010 | Ellis et al. |
| 7,670,295 B2 | 3/2010 | Sackner et al. |
| 7,715,982 B2 | 5/2010 | Grenfell et al. |
| 9,750,429 B1 | 9/2017 | Sackner et al. |
| 2002/0032386 A1 | 3/2002 | Sackner et al. |
| 2004/0010420 A1 | 1/2004 | Rooks |
| 2004/0176674 A1 | 9/2004 | Nazeri |
| 2004/0212545 A1 | 10/2004 | Li et al. |
| 2005/0054941 A1 | 3/2005 | Ting et al. |
| 2005/0073283 A1 | 4/2005 | Friedli et al. |
| 2006/0074338 A1 | 4/2006 | Greenwald et al. |
| 2006/0143645 A1 | 6/2006 | Vock et al. |
| 2007/0063850 A1 | 3/2007 | Devaul et al. |
| 2007/0191083 A1 | 8/2007 | Kuenzler et al. |
| 2007/0219059 A1 | 9/2007 | Schwartz et al. |
| 2008/0015454 A1 | 1/2008 | Gal |
| 2008/0219319 A1 | 9/2008 | Buckalew |
| 2010/0184563 A1* | 7/2010 | Molyneux ............ A43B 1/0054 482/1 |
| 2010/0184564 A1 | 7/2010 | Molyneux et al. |
| 2010/0274100 A1 | 10/2010 | Behar et al. |
| 2010/0292050 A1 | 11/2010 | DiBenedetto et al. |
| 2011/0054270 A1 | 3/2011 | Derchak |
| 2011/0054271 A1 | 3/2011 | Derchak et al. |
| 2011/0054272 A1 | 3/2011 | Derchak |
| 2011/0054289 A1 | 3/2011 | Derchak et al. |
| 2011/0054290 A1 | 3/2011 | Derchak |
| 2011/0087115 A1 | 4/2011 | Sackner et al. |
| 2011/0105861 A1 | 5/2011 | Derchak et al. |
| 2011/0130643 A1 | 6/2011 | Derchak et al. |
| 2011/0181419 A1 | 7/2011 | Mack et al. |
| 2011/0269517 A1* | 11/2011 | Englert ................ A63B 43/00 463/7 |
| 2011/0304497 A1 | 12/2011 | Molyneux et al. |
| 2012/0184367 A1* | 7/2012 | Parrott ................ G06F 1/163 463/31 |
| 2012/0210498 A1* | 8/2012 | Mack .................. A42B 3/0466 2/414 |
| 2012/0246795 A1 | 10/2012 | Scheffler et al. |
| 2012/0253484 A1 | 10/2012 | Burich et al. |

(56) References Cited

U.S. PATENT DOCUMENTS

2012/0254934 A1    10/2012   McBrearty et al.
2013/0245966 A1     9/2013   Burroughs et al.

FOREIGN PATENT DOCUMENTS

| EP | 1134555 A1 | 9/2001 |
|---|---|---|
| EP | 2108311 | 10/2009 |
| GB | 2259772 | 9/1992 |
| WO | WO-2002/067449 A2 | 8/2002 |
| WO | WO 2010/065886 A1 | 6/2010 |

OTHER PUBLICATIONS

U.S. Appl. No. 11/357,772, inventors Sackner et al., filed Feb. 17, 2006.

Revised Petition to Institute Derivation Proceeding referencing U.S. Appl. No. 13/543,428, filed in Case No. DER2014-00005 with the Patent Trial and Appeal Board on Nov. 21, 2013.

European Search Report for European Application No. 13 17 5499, European Patent Office, Munich, Germany, dated Jan. 5, 2015, 7 pages.

* cited by examiner

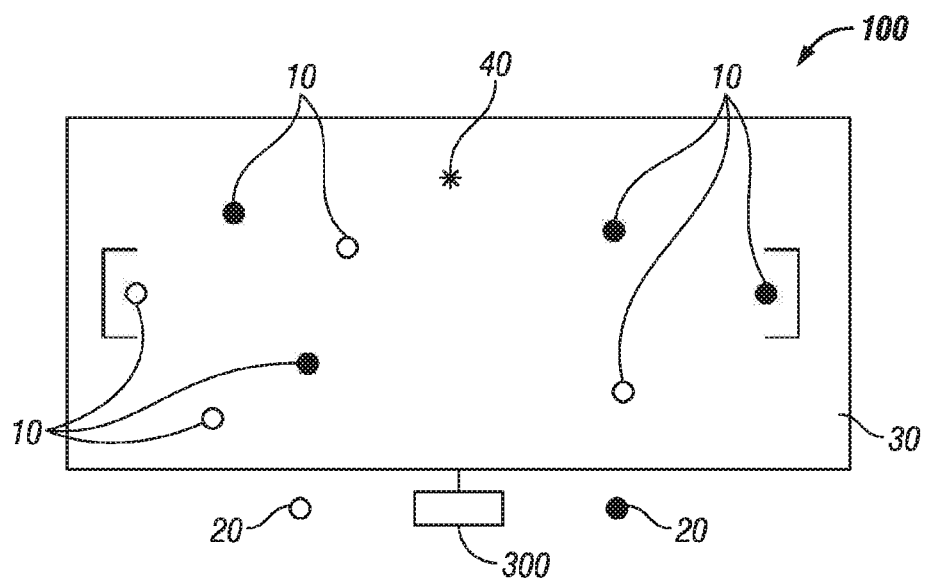
FIG. 1
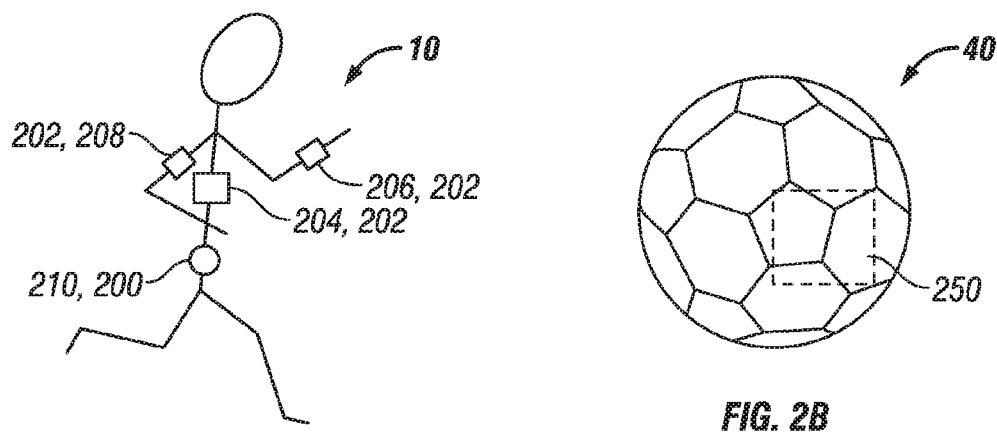
FIG. 2A
FIG. 2B
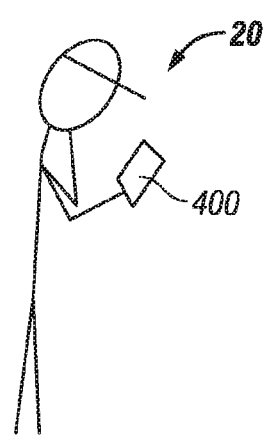
FIG. 3

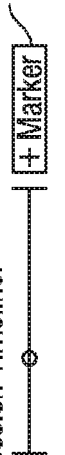

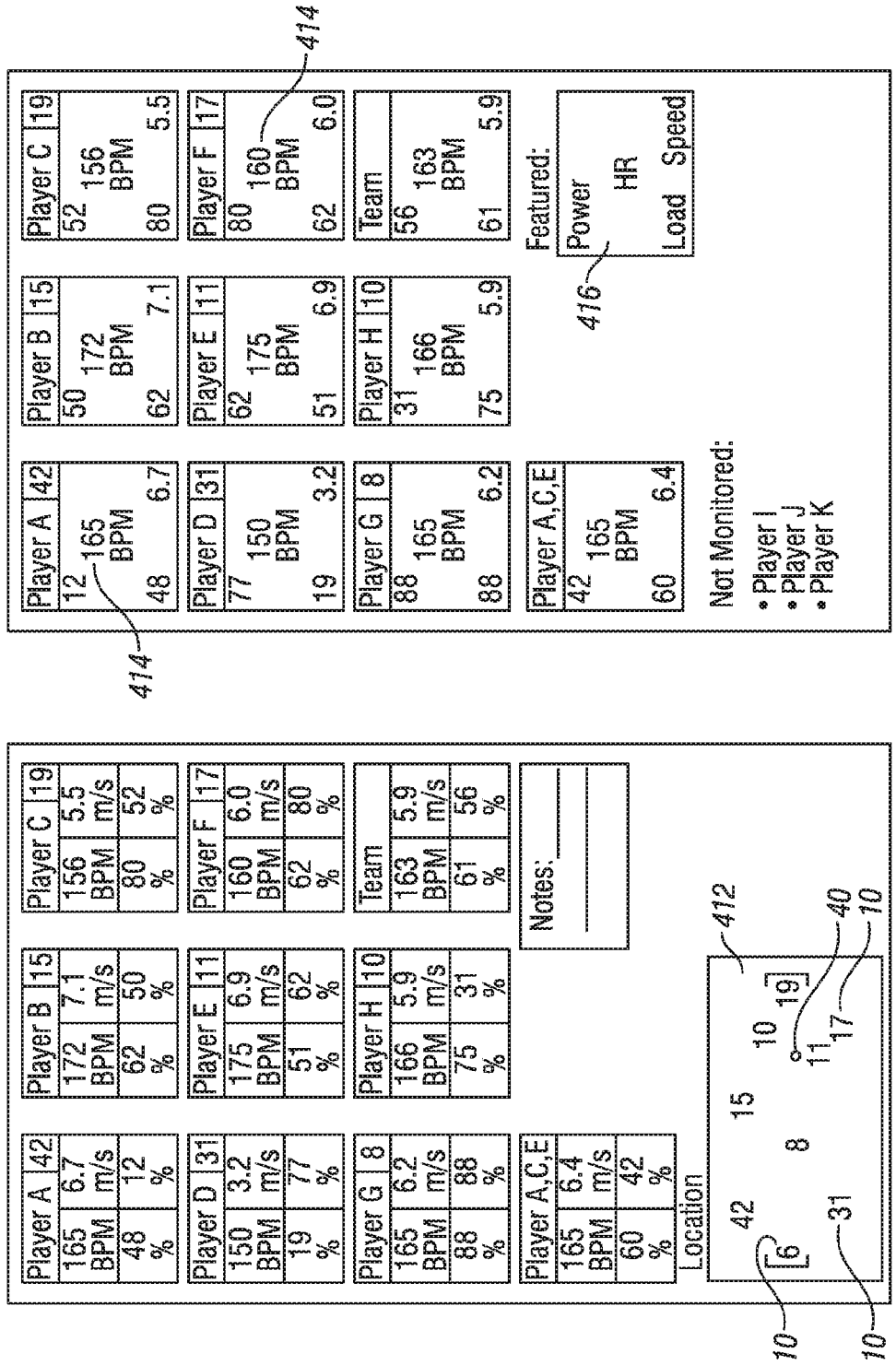

| | | Football Club | | | | 
|---|---|---|---|---|---|

Team Dashboard | Start/Stop Session | Assign Player Pods | Calibrate Field | Plan | Monitor | Analyze | Report

Team Chart

Status Session Name | Time | Edit

Today – 15 Mar 2011

- Free Session (no pre-planning has been done)
- Intensive Endurance Training – Game - 4 — 10:11 am - 12:00 pm
- Extensive Endurance Training – Game - 4, 7v7 — 1:00 pm - 3:00 pm Upcoming – 16 Mar 2011 - 23 Mar 2011

- Extensive Endurance Training – Game - 3 — 2:00 pm - 4:30 pm
- Extensive Endurance Training – Game - 2, 11v11 — 10:00 am - 12:00 pm
- Extensive Endurance Training – Game - 1 — 10:00 am - 12:00 pm
- Extensive Endurance Training – Game - 4, 5v5 — 2:00 pm - 4:00 pm
- Extensive Endurance Training – Game - 3 — 8:00 am - 11:00 am
- Extensive Endurance Training – Game - 2 — 10:00 am - 12:00 pm Labels: 402, 446, 464, 466, 468, 470, 492, 496

FIG. 76

GROUP PERFORMANCE MONITORING SYSTEM AND METHOD

CROSS-REFERENCE TO RELATED APPLICATIONS

This application is a continuation of U.S. application Ser. No. 15/016,665, filed Feb. 5, 2016, which is a continuation of U.S. application Ser. No. 13/543,428, filed Jul. 6, 2012, which is a continuation-in-part of U.S. application Ser. No. 13/077,510, filed Mar. 31, 2011, which are each incorporated herein in their entireties, by reference thereto.

BACKGROUND OF THE INVENTION

Field of the Invention

The present invention generally relates to an activity monitoring system, and in particular, to an athletic activity monitoring system that facilitates live monitoring of a plurality of individuals.

Background Art

Exercise is important to maintaining a healthy lifestyle and individual well-being. A common way for individuals to exercise is to participate in athletic activities, such as, for example, sports and training programs. A session of athletic activity may include, for example, a training session or a competitive session such as, for example, a soccer match or basketball game. When participating in athletic activities in a competitive or collaborative environment, one's performance may be dependent on the performance of other individuals. For example, in a team sport context, the performance of various athletic movements and endeavors may be influenced by the athletic movements and endeavors of teammates or adversaries. Often, a trainer (e.g., a coach) is monitoring such athletic activity.

To effectively monitor the athletic activity, the trainer, or other individual, typically gathers information about the participants in the athletic activity by viewing the athletic activity from, for example, the sidelines of a sports field. Thus, the information used to make decisions that influence the athletic activity is typically limited by what is observed by the trainer from the sidelines. A trainer may have assistants to help with this observation, or multiple trainers may work together, however there remains difficulty in monitoring a plurality of individuals so as to effectively track and manage performance of individuals during an athletic activity.

BRIEF SUMMARY OF THE INVENTION

Some embodiments provide a group monitoring device for monitoring a plurality of individuals engaged in an athletic activity, the device including a display configured to display, during an athletic activity: at least one metric relating to each of a plurality of individuals engaged in the athletic activity, and a status of a system component used to monitor the athletic activity. The group monitoring device may also include an input configured to allow manipulation of the display.

Some embodiments provide a method for monitoring a plurality of individuals engaged in an athletic activity, the method including displaying, during the athletic activity, a plurality of metrics relating to a plurality of individuals engaged in the athletic activity, and displaying, during the athletic activity, a status of a system component used to monitor the athletic activity.

Some embodiments provide a computer program product including computer-useable medium having computer program logic recorded thereon that, when executed by one or more processors, provides to a user performance information related to an athletic activity engaged in by a plurality of individuals, the computer program logic including first computer-readable program code that enables a processor to display, during the athletic activity, a plurality of metrics relating to a plurality of individuals engaged in the athletic activity, and second computer-readable program code that enables a processor to display, during the athletic activity, a status of a system component used to monitor the athletic activity.

Some embodiments provide a group monitoring device for monitoring a plurality of individuals engaged in an athletic activity, the device including a display configured to display, during the athletic activity, a plurality of metrics relating to a plurality of individuals engaged in the athletic activity, each metric relating to one of the plurality of individuals, and an input configured to allow manipulation of the display, wherein at least one metric of the plurality of metrics is a relative metric, and wherein the relative metric provides an indication of a level of performance of its associated individual, relative to personal ability of the associated individual.

Some embodiments provide a method for monitoring a plurality of individuals engaged in an athletic activity, the method including displaying, during the athletic activity, a plurality of metrics relating to a plurality of individuals engaged in the athletic activity, each metric relating to one of the plurality of individuals, wherein at least one metric of the plurality of metrics is a relative metric, and wherein the relative metric provides an indication of a level of performance of its associated individual, relative to personal ability of the associated individual.

Some embodiments provide a computer program product including computer-useable medium having computer program logic recorded thereon that, when executed by one or more processors, provides to a user performance information related to an athletic activity engaged in by a plurality of individuals, the computer program logic including computer-readable program code that enables a processor to display, during the athletic activity, a plurality of metrics relating to a plurality of individuals engaged in the athletic activity, each metric relating to one of the plurality of individuals, wherein at least one metric of the plurality of metrics is a relative metric, and wherein the relative metric provides an indication of a level of performance of its associated individual, relative to personal ability of the associated individual.

Some embodiments provide a group monitoring device for monitoring a plurality of individuals engaged in an athletic activity, the device including a display configured to display, during an athletic activity, a representation depicting locations on a playing field of a plurality of individuals engaged in the athletic activity, and a location of a movable sports object, wherein the representation is based on location information generated by individual monitors coupled to individuals of the plurality of individuals, and location information generated by an object monitor coupled to the sports object.

Some embodiments provide a method for monitoring a plurality of individuals engaged in an athletic activity, the method including displaying, during the athletic activity, a representation depicting locations on a playing field of a plurality of individuals engaged in the athletic activity, and a location of a movable sports object, wherein the representation is based on location information generated by individual monitors coupled to individuals of the plurality of individuals, and location information generated by an object monitor coupled to the sports object.

Some embodiments provide a computer program product including computer-useable medium having computer program logic recorded thereon that, when executed by one or more processors, provides to a user performance information related to an athletic activity engaged in by a plurality of individuals, the computer program logic including computer-readable program code that enables a processor to display, during the athletic activity, a representation depicting locations on a playing field of a plurality of individuals engaged in the athletic activity, and a location of a movable sports object, wherein the representation is based on location information generated by individual monitors coupled to individuals of the plurality of individuals, and location information generated by an object monitor coupled to the sports object.

Some embodiments provide a group monitoring system for monitoring a plurality of individuals engaged in an athletic activity, the system including a plurality of individual monitors, each individual monitor configured to monitor the performance of an individual engaged in the athletic activity, a first base station, configured to receive a first set of metrics from the plurality of individual monitors, wherein metrics of the first set of metrics are indicative of the performance of the individuals, and a second base station, configured to receive a second set of metrics from the plurality of individual monitors, wherein metrics of the second set of metrics are indicative of the performance of the individuals, wherein the first set of metrics is different from the second set of metrics.

Some embodiments provide a group monitoring system for monitoring a plurality of individuals engaged in an athletic activity, the system including a plurality of individual monitors, each individual monitor configured to monitor the performance an individual engaged in the athletic activity, and a base station, configured to receive metrics from the plurality of individual monitors, wherein the metrics are indicative of the performance of the individuals, and wherein the base station is configured to send the metrics to a web server system configured to provide the metrics to remote devices.

Some embodiments provide a method for monitoring a plurality of individuals engaged in an athletic activity, the method including monitoring the performance of a plurality of individuals engaged in the athletic activity, using a plurality of individual monitors, receiving metrics from the plurality of individual monitors, at a base station, and sending the metrics, from the base station, to a web server system configured to provide the metrics to remote devices, wherein the metrics are indicative of the performance of the individuals.

Some embodiments provide a computer program product including computer-useable medium having computer program logic recorded thereon that, when executed by one or more processors, provides to a user performance information related to an athletic activity engaged in by a plurality of individuals, the computer program logic including first computer-readable program code that enables a processor to monitor the performance of a plurality of individuals engaged in the athletic activity, using information received from a plurality of individual monitors, second computer-readable program code that enables a processor to receive metrics from the plurality of individual monitors, at a base station, and second computer-readable program code that enables a processor to send the metrics to a web server system configured to provide the metrics to remote devices, wherein the metrics are indicative of the performance of the individuals.

Some embodiments provide a method for defining a playing field, the method including displaying, using an administrative device, an instruction to locate a position sensor at a first location, receiving first position data from the position sensor, defining the first position data as the position of the first location, displaying, using the administrative device, an instruction to locate the position sensor at a second location, receiving second position data from the position sensor, and defining the second position data as the position of the second location, wherein the position of the first location and the position of the second location together define the playing field.

Some embodiments provide a method for automatically adjusting a training plan based on performance data, the method including receiving, using a group monitoring system, data relating to an athletic performance of an individual, analyzing the data to identify an area for improvement in the athletic performance, determine a training recommendation based on the identified area for improvement, identify an established training plan, compare the established training plan to the training recommendation, in response to a determination that the training plan does not include training of the training recommendation, adjusting the training plan to include the training of the training recommendation.

Some embodiments provide a system for monitoring an activity, the system including a base station, an object monitor configured to communicate wirelessly with the base station, a plurality of object sensors, each object sensor in communication with the object monitor and configured to sense a characteristic of a mobile sports object being used in the activity and to transmit, during the activity, data indicative of the characteristic of the object to the object monitor, and a group monitoring device configured to communicate wirelessly with the base station, wherein the object monitor is configured to transmit, during the activity, the data indicative of the characteristic of the object to the base station, wherein the base station is configured to receive the data and to transmit, during the activity, a metric based on the data to the group monitoring device, and wherein the group monitoring device is configured to display a representation of the metric.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention. In the drawings, like reference numbers, letters, or renderings indicate identical or functionally similar elements.

FIG. 1 depicts a monitoring system according to an exemplary embodiment of the present invention.

FIG. 2A depicts an individual monitor and associated components according to an exemplary embodiment of the present invention.

FIG. 2B depicts an object monitor according to an exemplary embodiment of the present invention.

FIG. 3 depicts an exemplary group monitoring device according to an exemplary embodiment of the present invention.

FIG. 13 depicts a display of a group monitoring device according to an exemplary embodiment of the present invention.

FIG. 14 depicts a display of a group monitoring device according to an exemplary embodiment of the present invention.

FIG. 17 depicts a display of a group monitoring device according to an exemplary embodiment of the present invention.

FIG. 18 depicts a display of a group monitoring device according to an exemplary embodiment of the present invention.

FIG. 27 depicts a display of a group monitoring device according to an exemplary embodiment of the present invention.

FIG. 33A depicts a display of a group monitoring device according to an exemplary embodiment of the present invention.

FIG. 48 depicts a display of a group monitoring device according to an exemplary embodiment of the present invention.

Figure 49:
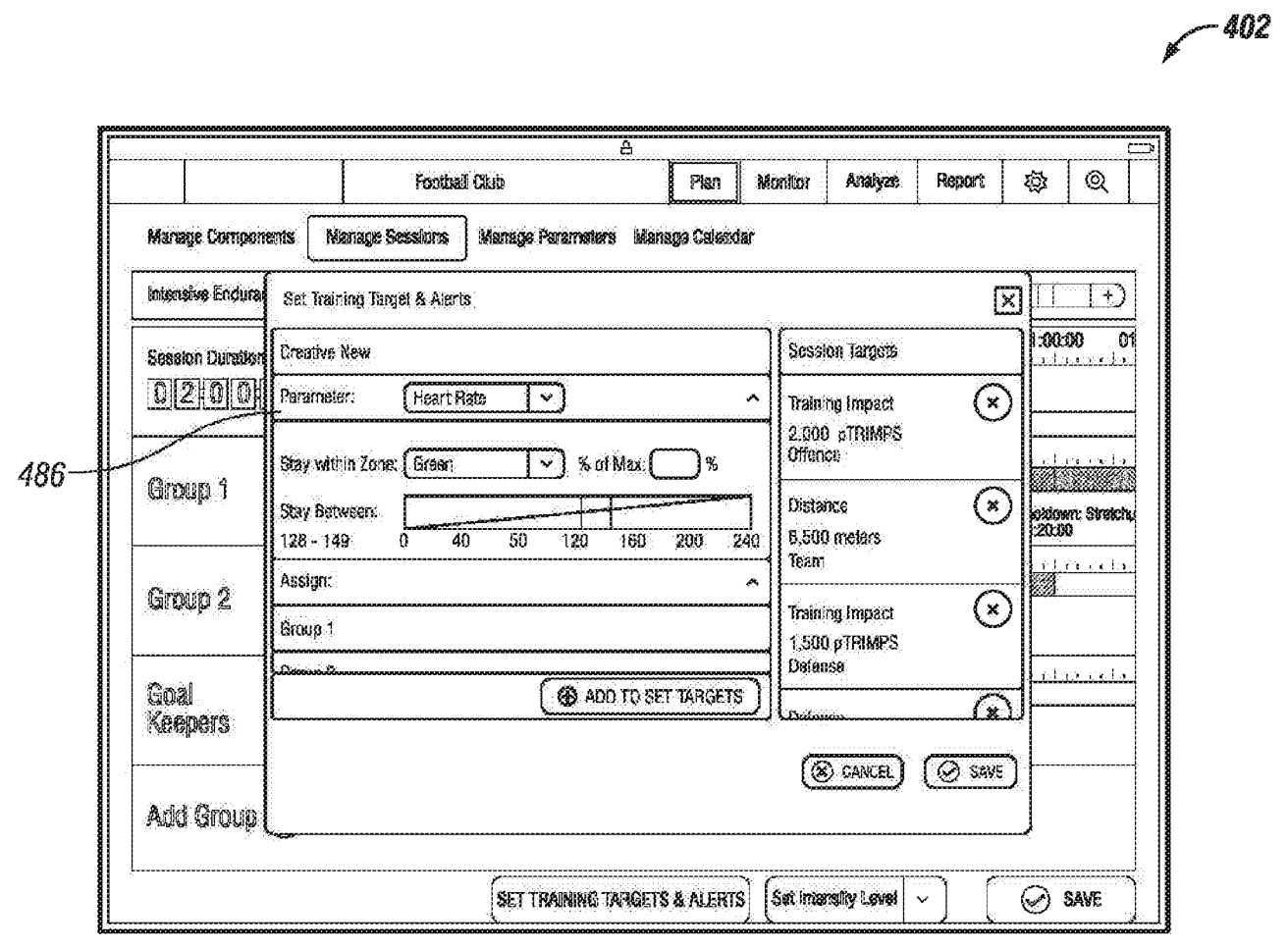

FIG. 49 depicts a display of a group monitoring device according to an exemplary embodiment of the present invention.

FIG. 50 depicts a display of a group monitoring device according to an exemplary embodiment of the present invention.

FIG. 51 depicts a display of a group monitoring device according to an exemplary embodiment of the present invention.

FIG. 52 depicts a display of a group monitoring device according to an exemplary embodiment of the present invention.

FIG. 53 depicts a display of a group monitoring device according to an exemplary embodiment of the present invention.

FIG. 59 depicts a display of a group monitoring device according to an exemplary embodiment of the present invention.

FIG. 61 depicts a display of a group monitoring device according to an exemplary embodiment of the present invention.

FIG. 64 depicts a display of a group monitoring device according to an exemplary embodiment of the present invention.

FIG. 65 depicts a display of a group monitoring device according to an exemplary embodiment of the present invention.

FIG. 76 depicts a display of a group monitoring device according to an exemplary embodiment of the present invention.

DETAILED DESCRIPTION OF THE INVENTION

Figure 4:
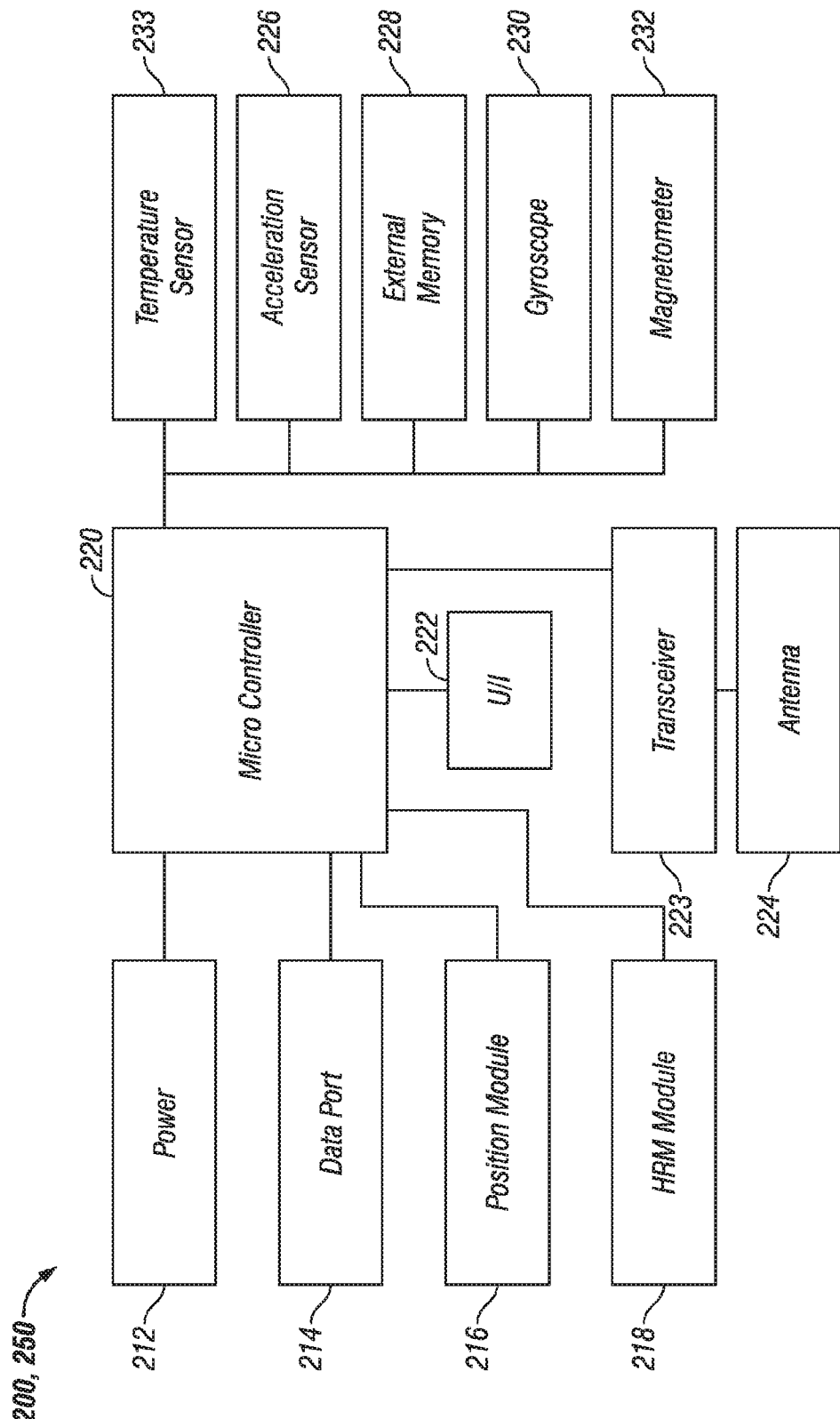
FIG. 4 depicts a diagram of an individual monitor according to an exemplary embodiment of the present invention.

The present invention will now be described in detail with reference to embodiments thereof as illustrated in the accompanying drawings. References to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, tangible computer readable or computer usable storage media having instructions stored thereon, or a combination thereof, and may be implemented in one or more computer systems or other processing systems.

Individuals participating in an athletic activity and trainers (e.g., a coach, physician, or other authorized individual) may work together during a session of athletic activity for a variety of reasons. For example, it may be desired that the trainer monitors the performance of the individuals and makes recommendations or otherwise influences their performance in order to maximize the individuals' fitness level. Alternatively or additionally, it may be desired that the trainer monitors and influences the individuals to help maximize the effectiveness of the individuals in the athletic activity. Further, it may be desired that the trainer monitors and influences the individuals to help maximize the probability of success in the athletic activity (where success may be, for example, defeating an opposing team in a game, such as, for example, soccer, or achieving/maintaining a desired level of fitness for one or more individuals participating in the athletic activity). A session of athletic activity may include, for example, a training session (e.g., a field session, a gym session, a track session) or a competitive session (e.g., a soccer match or a basketball game)

In some exemplary embodiments, the trainer may monitor and influence the individuals in order to track and maintain the individuals' health and safety. In such an embodiment, it may be beneficial for the trainer to be provided with information relating to health and safety, for example, injuries, illnesses, and dangerous conditions.

The trainer must consider these and other goals, monitor the individuals, and make decisions to influence the performance of the individuals both individually and as a group. In doing so, the trainer depends on information about the individuals and their performance while participating in a session of athletic activity. The trainer may benefit from receipt of information in addition to that which is directly observable by the trainer. A group monitoring system according to an exemplary embodiment of the present invention can provide the trainer with easy-to-understand information about individuals participating in the athletic activity, beyond that which can be directly observed, thereby facilitating quick and effective decision-making by the trainer to maximize the probability of achieving success in the athletic activity. Detailed player profiles with performance metrics over time can be generated and maintained. By using information provided by the group monitoring system, trainers can view trends over time, which can help identify, for example, unfit athletes, athletes who are over-training, and athletes having relatively high risk for injury. Special training programs can be planned to address these conditions enabling peak performance (e.g., at game time).

Conventionally, a trainer would plan a session of athletic activity hoping to deliver a certain workload (e.g., represented by target values for one or more metrics) to a team or to particular individuals or subsets thereof, but would not have a reliable way to measure if the intended workload was actually delivered. With a group monitoring system according to embodiments of the present invention, a trainer now can determine whether the intended workload was actually delivered (e.g., by direct measurement of one or more metrics indicating or providing the basis for a determination of total workload). This enables the trainer to more precisely plan and adapt sessions of athletic activity by basing such planning and adapting on measured values representing individual or team performance. Such a group monitoring system may provide feedback that the trainer can act on to revise training as needed. In an exemplary embodiment, the group monitoring system can provide alerts to the trainer to flag critical or important conditions that the trainer would not otherwise be able to observe directly, such as, for example, fatigue of an individual or heart rate of an individual being above a threshold value.

Figure 11:
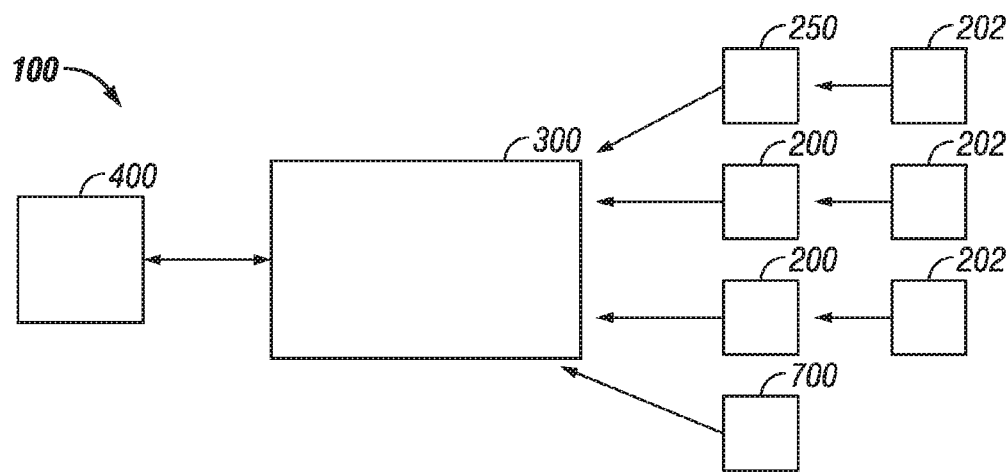
FIG. 11 depicts a diagram of a portion of a monitoring system according to an exemplary embodiment of the present invention.

In an exemplary embodiment, group monitoring system 100, depicted in, for example, FIGS. 1 and 11, includes individual monitors 200 (see FIG. 2A), an object monitor 250, a base station 300, and at least one group monitoring device 400 (see FIG. 3). Individual monitor 200 may be coupled to an individual 10, as shown in FIG. 2A. Object monitor 250 may be coupled to a sports object 40, as shown in FIG. 2B. Individual 10 may be, for example, a participant in an athletic activity (e.g., a player; a referee; or a support person such as a ball boy, golf caddy, or line man). Sports object 40 may be, for example a sports object, for example, any type of sport ball, any type of sport "stick" (e.g., a baseball bat, hockey stick, golf club, table tennis paddle, or tennis racquet), a sport glove (e.g., a boxing glove), a bicycle, an oar, a shoe, a boot, a ski, a hat, a helmet, a band, a skateboard, a surfboard, or a pair of glasses or goggles) used by an individual (e.g., individual 10) during an athletic activity. Individual monitor 200 and/or object monitor 250 may include or be in communication with a variety of sensors 202, including, but not limited to, an accelerometer, a pedometer, a heart rate monitor, a position sensor, an impact sensor, a camera, a magnetometer, a gyroscope, a microphone, a temperature sensor, a pressure sensor, a respiration sensor, a posture sensor, a lactate sensor, and a wind sensor. Group monitoring system 100 can include any or all of these or other sensors, eliminating the need for separate systems to monitor different characteristics. Further, by integrating and processing data streams from multiple different sensors, group monitoring system 100 can determine and provide metrics based on data representing different monitored characteristics. This eliminates the need to manually combine data streams to determine metrics based on multiple data streams (e.g., to determine high level training insights).

In an exemplary embodiment, individual monitor 200 may include a sensor garment 204, a heart rate monitor 206, and a position sensor 208. In an exemplary embodiment, object monitor 250 may include a position sensor 208, an acceleration sensor 210 and a magnetometer 232. Position sensor 208 may include, for example, a position sensor for use with a satellite-based positioning system (e.g., GPS (global positioning system)), a position sensor for use with a beacon system (e.g., position determination using triangulation and/or time differences of signals received by antennas at known positions about a field or activity area), or a position sensor for use with any other suitable position-determining system.

In some exemplary embodiments, group monitoring device 400 may be used by a trainer 20, as shown in FIG. 3. In an exemplary embodiment, group monitoring system 100 and/or components thereof (e.g., individual monitor 200, object monitor 250) may include or be used with elements of another monitoring system, such as, for example, those disclosed in U.S. patent application Ser. No. 12/467,944, filed May 18, 2009; U.S. patent application Ser. No. 12/467,948, filed May 18, 2009; U.S. patent application Ser. No. 13/077,494, filed Mar. 31, 2011; U.S. patent application Ser. No. 13/077,520, filed Mar. 31, 2011; U.S. patent application Ser. No. 13/077,510, filed Mar. 31, 2011; U.S. patent application Ser. No. 13/446,937, filed Apr. 13, 2012; U.S. patent application Ser. No. 13/446,982, filed Apr. 13, 2012; and U.S. patent application Ser. No. 13/446,986, filed Apr. 13, 2012, each of which is incorporated herein in its entirety by reference thereto.

Generally, sensors 202 are mounted to individuals 10 in preparation for participation by individuals 10 in a session of athletic activity. Sensors 202 mounted to a particular individual 10 are coupled, either via wires or wirelessly, to individual monitor 200, also mounted on the particular individual 10. Sensors 202 in communication with an individual 10's individual monitor 200 may sense characteristics about individual 10 during participation by individual 10 in the session of athletic activity, and may transmit data indicative of the characteristics to individual monitor 200. Individual monitor 200 in turn may transmit the data to base station 300 during or after the session of athletic activity.

Sensors 202 in communication with an object 40's object monitor 250 may sense characteristics about object 40, for example while object 40 is used (e.g., by individual 10) during the session of athletic activity, and may transmit data indicative of the characteristics to object monitor 250. Object monitor 250 in turn may transmit the data to base station 300 during or after the session of athletic activity.

In some embodiments, a first individual monitor 200 may transmit data indicative of characteristics about its monitored individual 10 to a second monitor (e.g., an individual monitor 200 monitoring a different individual 10, or an object monitor 250 monitoring a sports object 40). In some embodiments, a first object monitor 250 may transmit data indicative of characteristics about its monitored object 40 to a second monitor (e.g., an individual monitor 200 monitoring an individual 10, or a second object monitor 250 monitoring a different sports object 40). Such communication among monitors 200, 250 may be wireless according to any suitable protocol. For example, such communication may be based on RFID (radio frequency identification) signals, magnetic signals, WLAN (wireless local area network) signals, ISM (industrial, scientific, and medical) band signals, Bluetooth® (or Bluetooth® Low Energy (BTLE)) signals, or cellular signals.

Such communication among monitors 200, 250 may facilitate determinations and calculations based on data from more than one source. For example, if two monitored individuals 10 kick a sports object 40 (e.g., a ball), object monitor 250 of sports object 40 can receive data from each of the individual monitors 200 of the individuals 10. Such data can be compared with data from the object monitor 250 of sports object 40 and can be used to determine (e.g., at sports object 40, base station 300, or an accessing device) which of the two individuals kicked sports object 40 first. Also for example, if a monitored individual 10 kicks a sports object 40 (e.g., a ball), individual monitor 200 of individual 10 can receive data from object monitor 250 of sports object 40 indicating the force with or speed at which the sports object 40 was kicked, or the resulting speed, direction of motion, or predicted landing location of the sports object 40 due to the kick. Such data may be sensed by a pressure sensor of the sports object 40, and transmitted wirelessly to the individual monitor 200 of the monitored individual 10. Such data can be compared with data from the individual monitor 200 and can be used to determine characteristics of the kick of individual 10. In some embodiments, based on such data, group monitoring system 100 may provide a recommendation as to how individual 10 may improve his or her kick (e.g., to achieve greater distance, speed, height).

In some exemplary embodiments, some or all of transmissions of data among system components of group monitoring system 100 may occur in real time. "Real time" as used herein may include delays inherent to transmission technology, delays designed to optimize resources, and other inherent or desirable delays that would be apparent to one of skill in the art. In some exemplary embodiments, some or all of these transmissions may be delayed from real time, or may occur after completion of the activity. Base station 300 receives the data and determines metrics from the data, where the metrics may be representations of the characteristics measured by sensors 202, or may be representations of further characteristics derived from the data through the use of algorithms and other data manipulation techniques. Metrics may be based on data from individual monitors 200 only, from object monitors 250 only, or from both individual monitors 200 and object monitors 250. Base station 300 in turn transmits the metrics during the session of athletic activity to group monitoring device 400, which receives the metrics and displays a representation of the metrics.

Group monitoring device 400 may receive metrics associated with a plurality of individuals 10 and/or one or more objects 40, and may display the received metrics in association with the individual 10 and/or object 40 with which they are associated. In this way, trainer 20 viewing group monitoring device 400 during the session of athletic activity receives detailed information about multiple individuals 10 and/or object(s) 40, and can act on that information as it is determined necessary or expedient, thereby efficiently monitoring and managing individuals 10 during the session of athletic activity.

Display of the metrics can represent real-time summaries of individuals 10 or groups thereof, and can facilitate comparison of one or more individuals 10 or groups thereof with one or more other individuals 10 or groups thereof, or comparison of one or more individuals 10 or groups thereof from a first time with one or more individuals 10 or groups thereof from a second time.

In some exemplary embodiments, individual monitors 200 and/or object monitors 250 calculate metrics based on the data (e.g., data generated by sensors 202), and transfer these metrics to base station 300 along with or instead of the data. In some exemplary embodiments, base station 300 transmits the data to group monitoring device 400, along with or instead of the metrics. In some exemplary embodiments, group monitoring device 400 calculates metrics based on the data.

In an exemplary embodiment, as shown in FIG. 4, individual monitor 200 and/or object monitor 250 may include a battery 212, a data port 214, a position module 216, a heart rate monitor module 218, a controller 220, a user interface 222, a transceiver 223, an antenna 224, an acceleration sensor module 226, a memory 228, a gyroscope module 230, a magnetometer module 232, and a temperature sensor module 233. The sensors and corresponding modules discussed herein are exemplary only; other sensors and modules can be used in conjunction with embodiments of the present invention. Battery 212 (or any other suitable power source) can provide power to individual monitor 200 and/or object monitor 250 and may be, for example, built into or removable from individual monitor 200 and/or object monitor 250, and may be rechargeable or non-rechargeable. Data port 214 can facilitate information transfer to and from individual monitor 200 and/or object monitor 250 and may be, for example, a universal serial bus (USB) port. In some exemplary embodiments, data port 214 can additionally or alternatively facilitate power transfer to battery 212, in order to charge battery 212. As will be appreciated, transceiver 223 may include data transmitting and receiving capability and may include a single component or separate components.

Elements of individual monitor 200 (or object monitor 250) may interconnect with one another using a variety of techniques, such as, for example, wires, printed circuit boards, conductive yarn, conductive fabric, printed conductive layers on fabric, a printed (wire) harness, wireless communications technology, serial ports, serial peripheral interfaces, other connection techniques, or a combination thereof. Each monitor 200, 250 is portable with respect to base station 300. In some embodiments, each individual monitor 200 can be carried by an individual 10 participating in an athletic activity. Each monitor 200, 250 may itself include sensors 202, and/or may be in communication with sensors 202 carried by individual 10 and/or sports object 40 and located remotely from monitor 200, 250. Each monitor 200, 250 can be paired with base station 300 and associated with an individual 10 and/or sports object 40. Each monitor 200, 250 may include a unique identifier. The unique identifier may be represented by, for example, a number imprinted on a viewable surface of individual monitor 200 and/or object monitor 250 (or an article associated therewith, such as, for example, a garment or sports object), or data communicated or displayed when a button associated with individual monitor 200 and/or object monitor 250 is pressed or when a request signal is received from base station 300.

Figure 23:
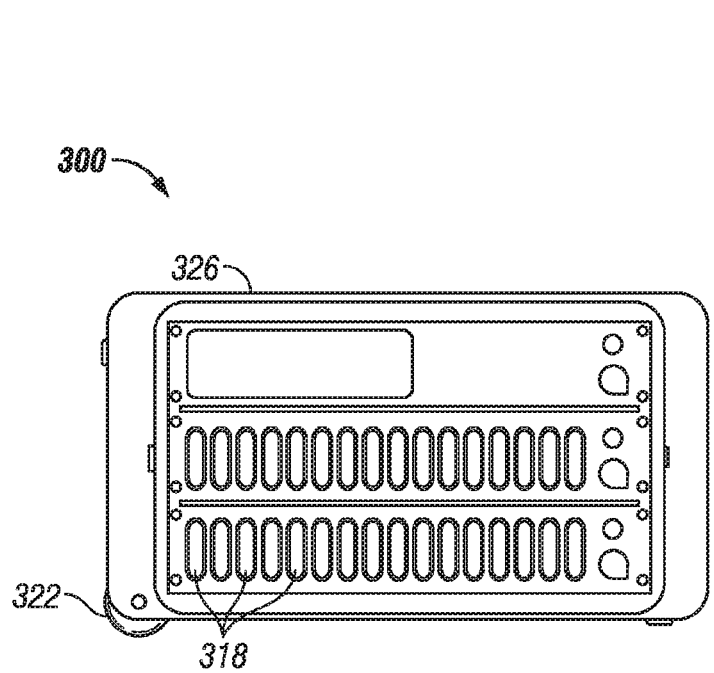
FIG. 23 depicts a base station according to an exemplary embodiment of the present invention.
Figure 24:
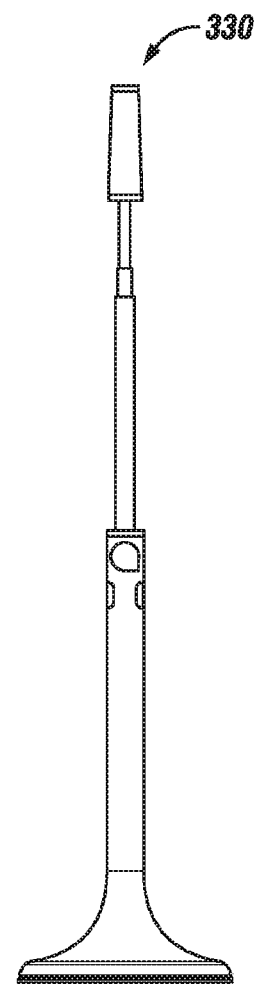
FIG. 24 depicts an antenna of a base station according to an exemplary embodiment of the present invention.
Figures 25, 26:
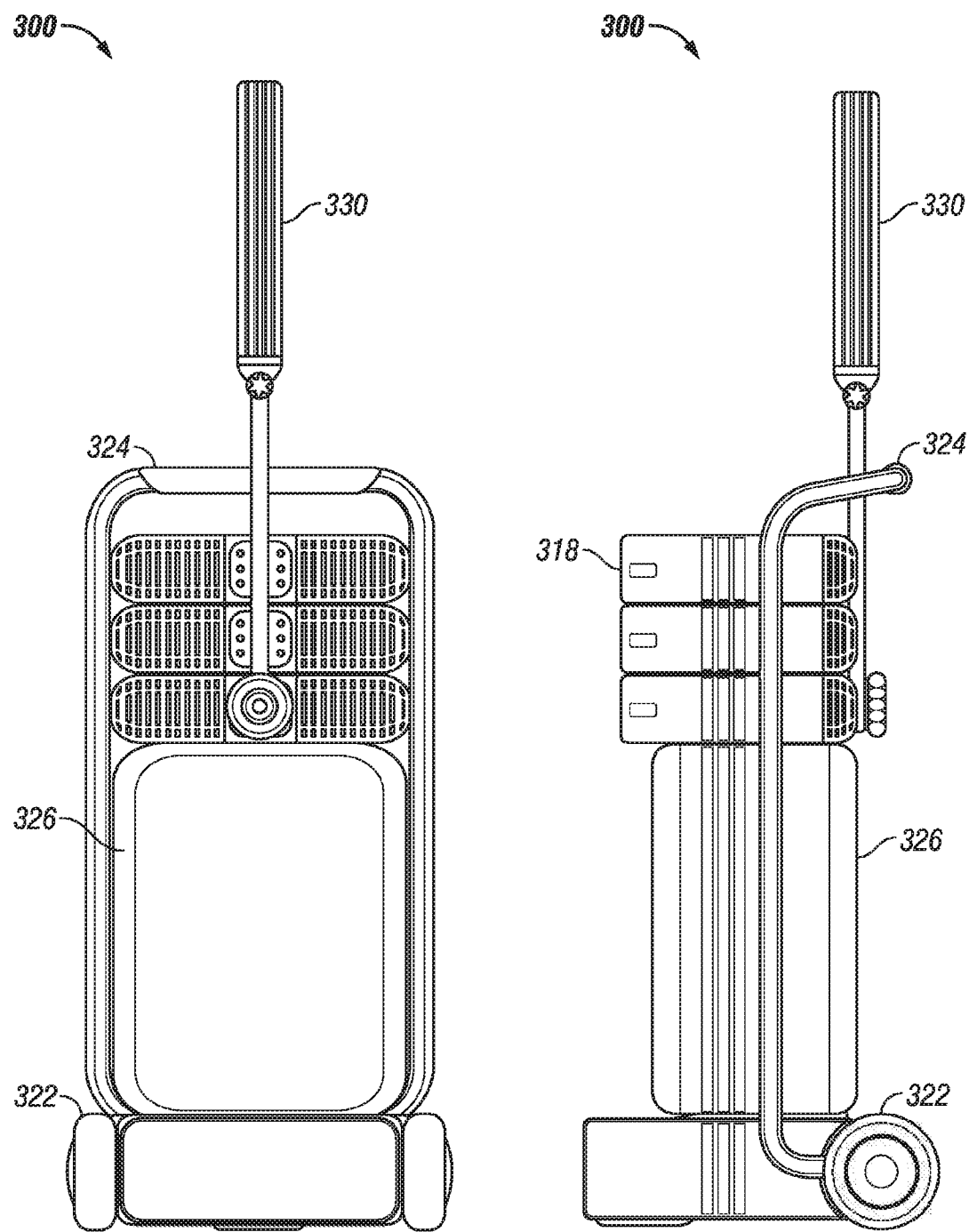
FIG. 25 depicts a base station according to an exemplary embodiment of the present invention.
FIG. 26 depicts a base station according to an exemplary embodiment of the present invention.
Figure 28:
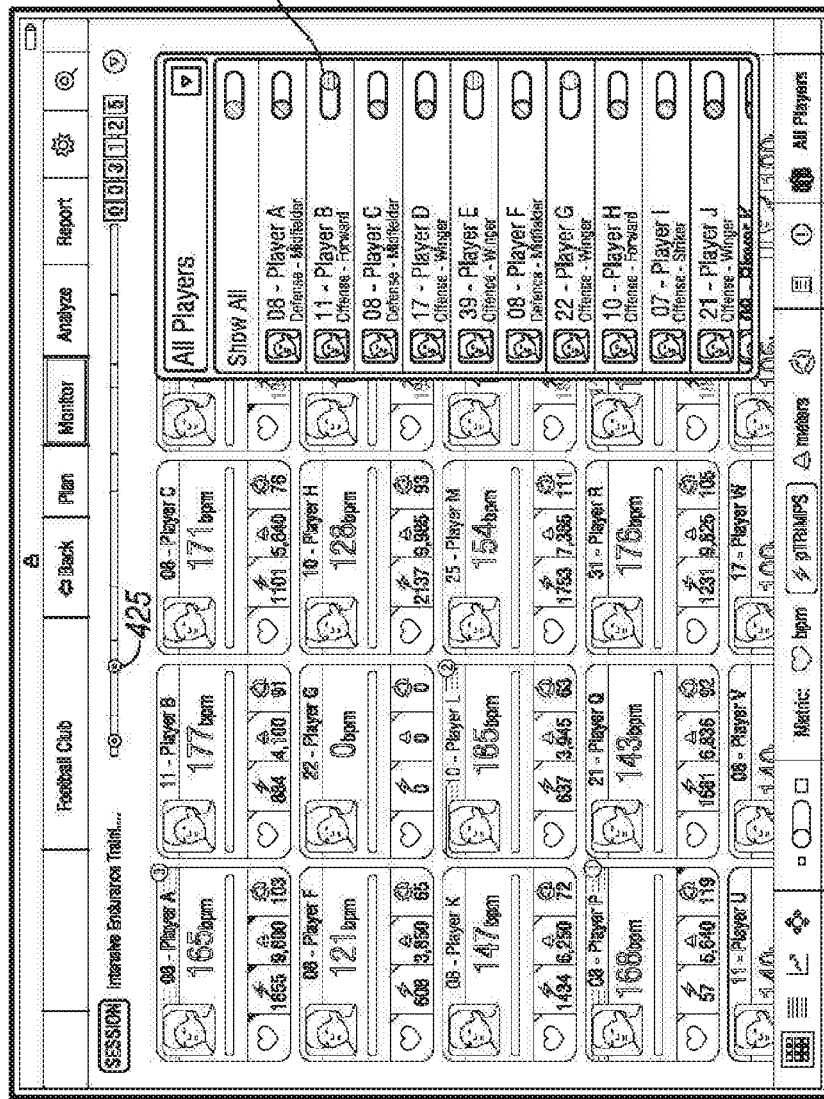
FIG. 28 depicts a display of a group monitoring device according to an exemplary embodiment of the present invention.
Figure 29:
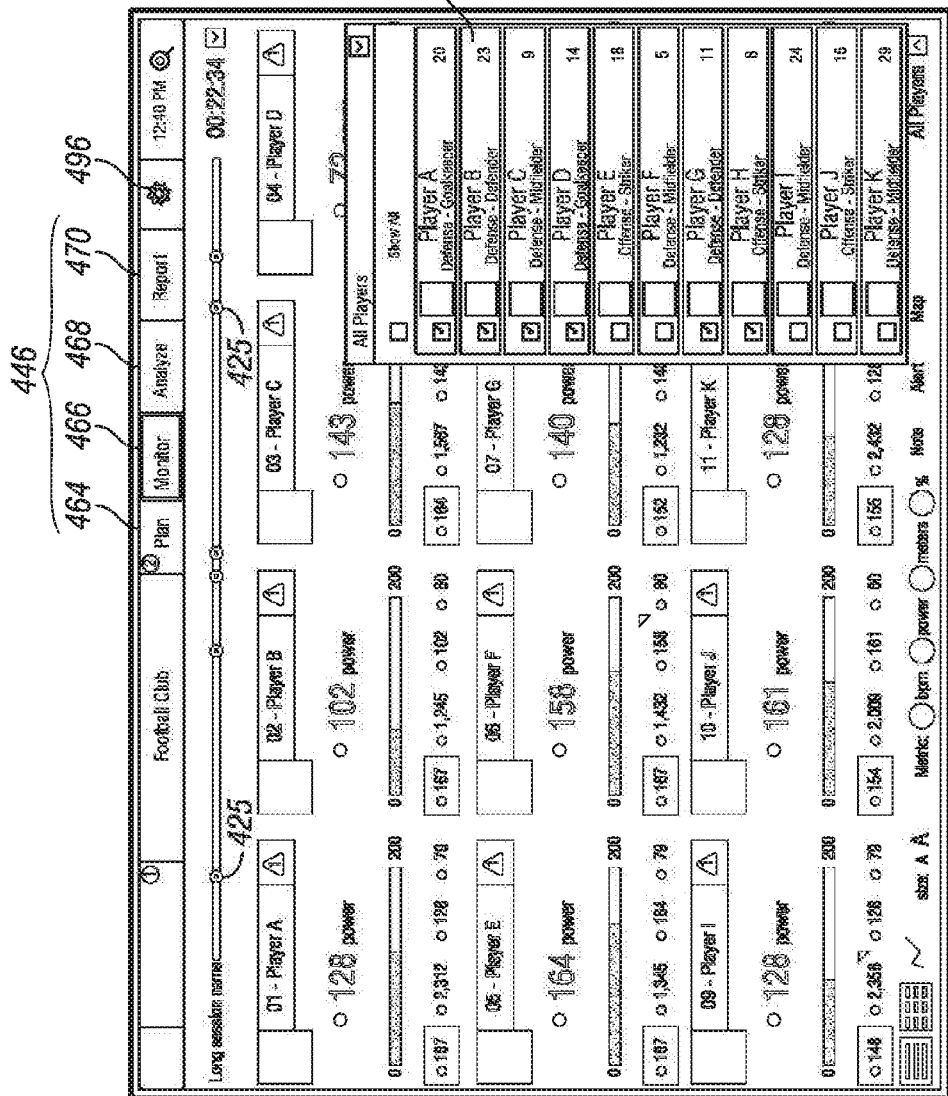
FIG. 29 depicts a display of a group monitoring device according to an exemplary embodiment of the present invention.
Figure 30:
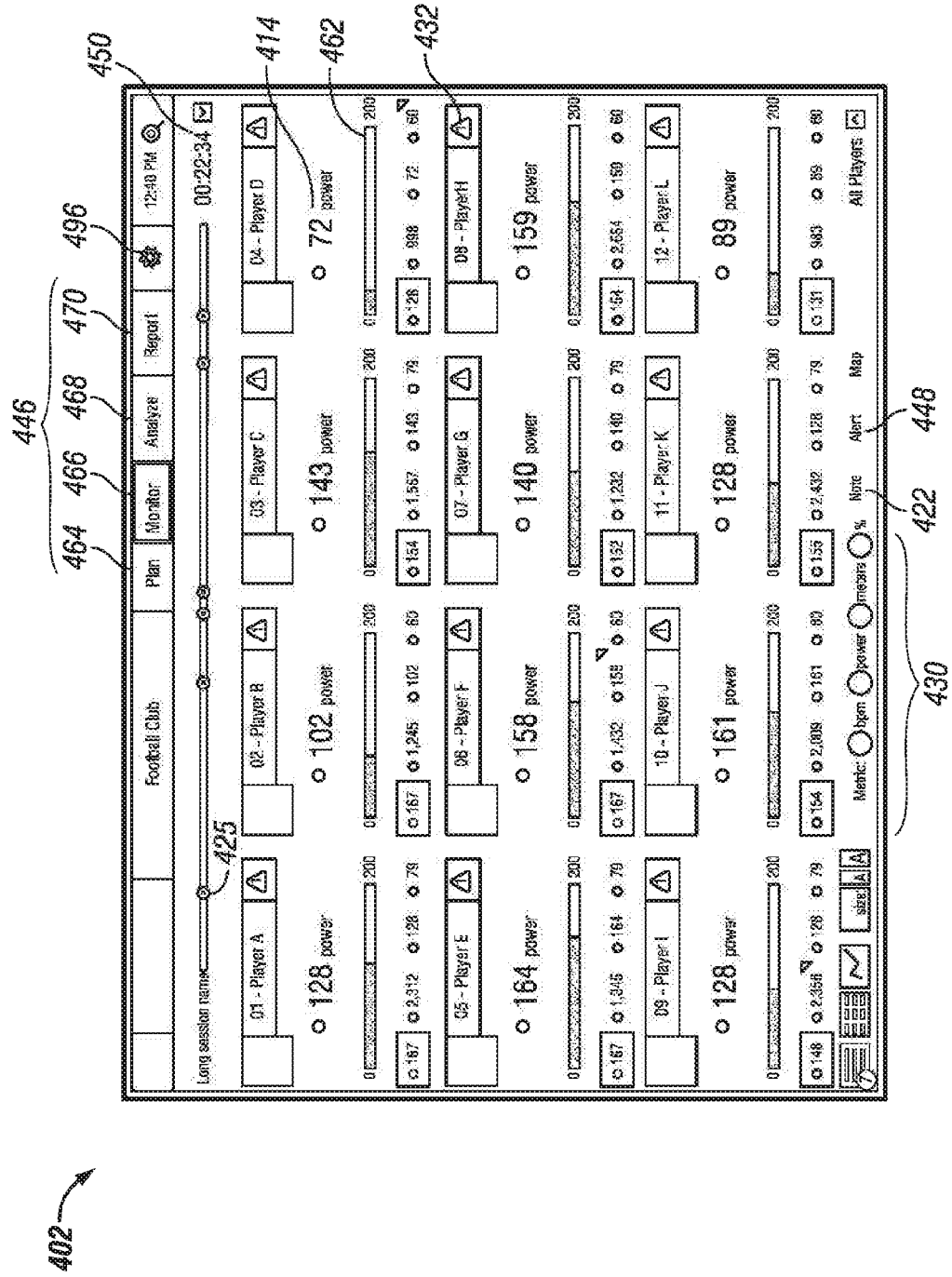
FIG. 30 depicts a display of a group monitoring device according to an exemplary embodiment of the present invention.
Figure 31:
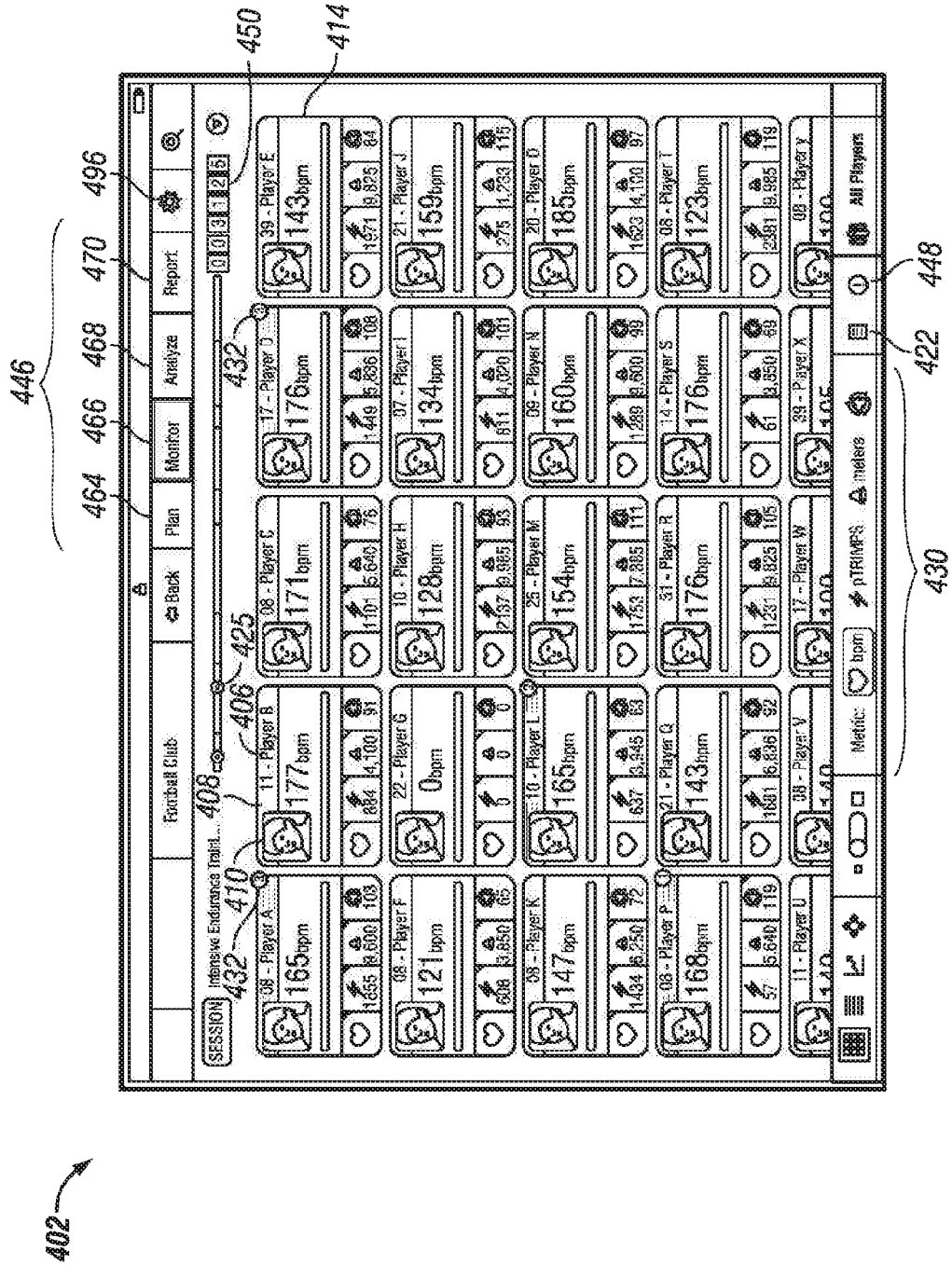
FIG. 31 depicts a display of a group monitoring device according to an exemplary embodiment of the present invention.
Figure 32:
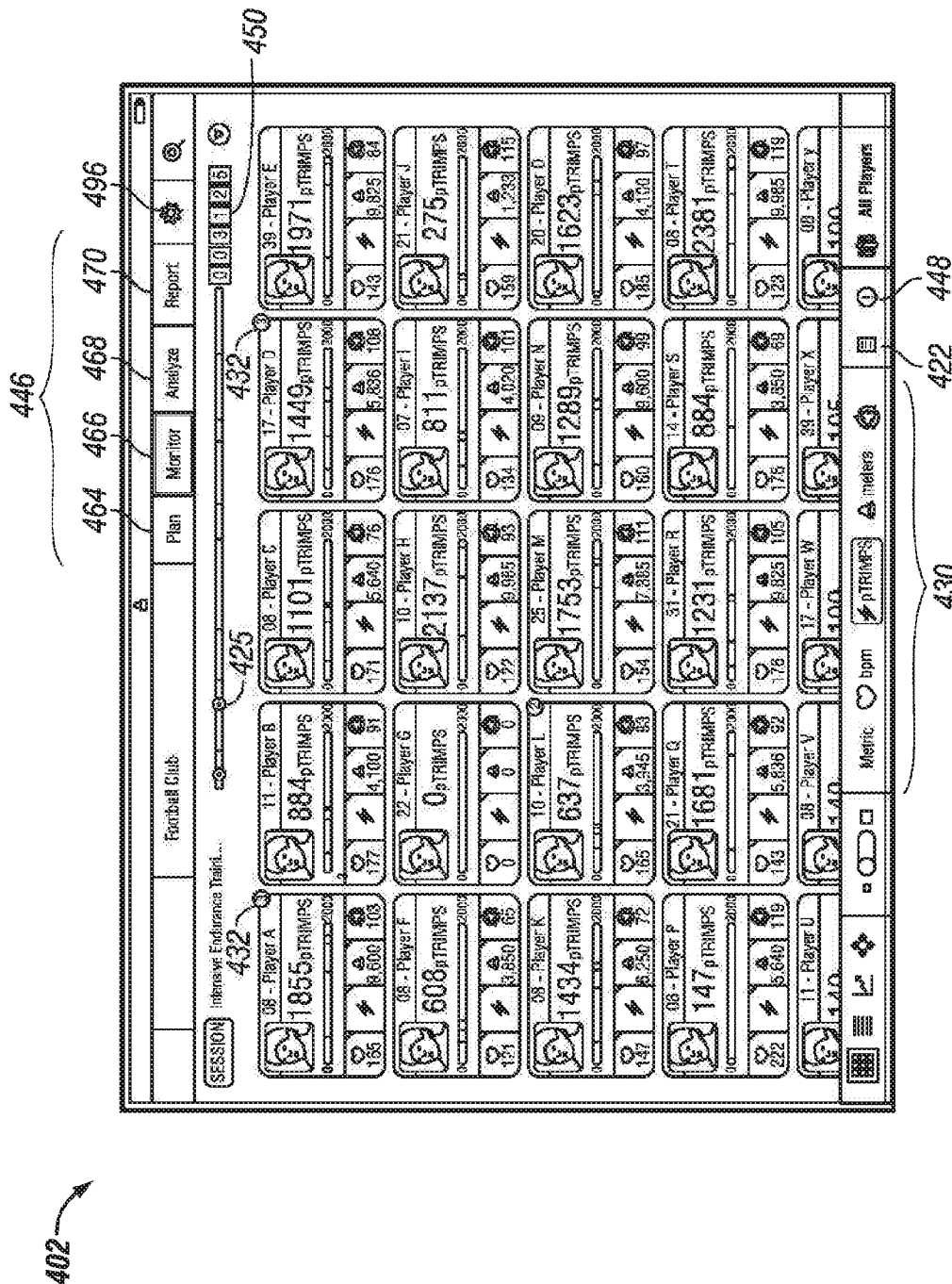
FIG. 32 depicts a display of a group monitoring device according to an exemplary embodiment of the present invention.

To be paired with base station 300, individual monitor 200 and/or object monitor 250 can be received by or otherwise communicatively connected to base station 300 (e.g., via a docking port 318 of base station 300—see, e.g., FIG. 23). Base station 300 can then record the unique identifier of the individual monitor 200 and/or object monitor 250, and can assign a unique encryption key to the individual monitor 200 and/or object monitor 250. This encryption key can be used to support secure transmission of data during the session of athletic activity. Such secure transmission of data may be, for example, from individual monitors 200 and/or object monitors 250 to base station 300, from base station 300 to individual monitors 200 and/or object monitors 250, and from one individual monitor 200 and/or object monitor 250 to one or more other individual monitors 200 and/or object monitors 250. The encryption key can be renewed when required or desired (e.g., at the beginning of each new session of athletic activity).

Figure 53:
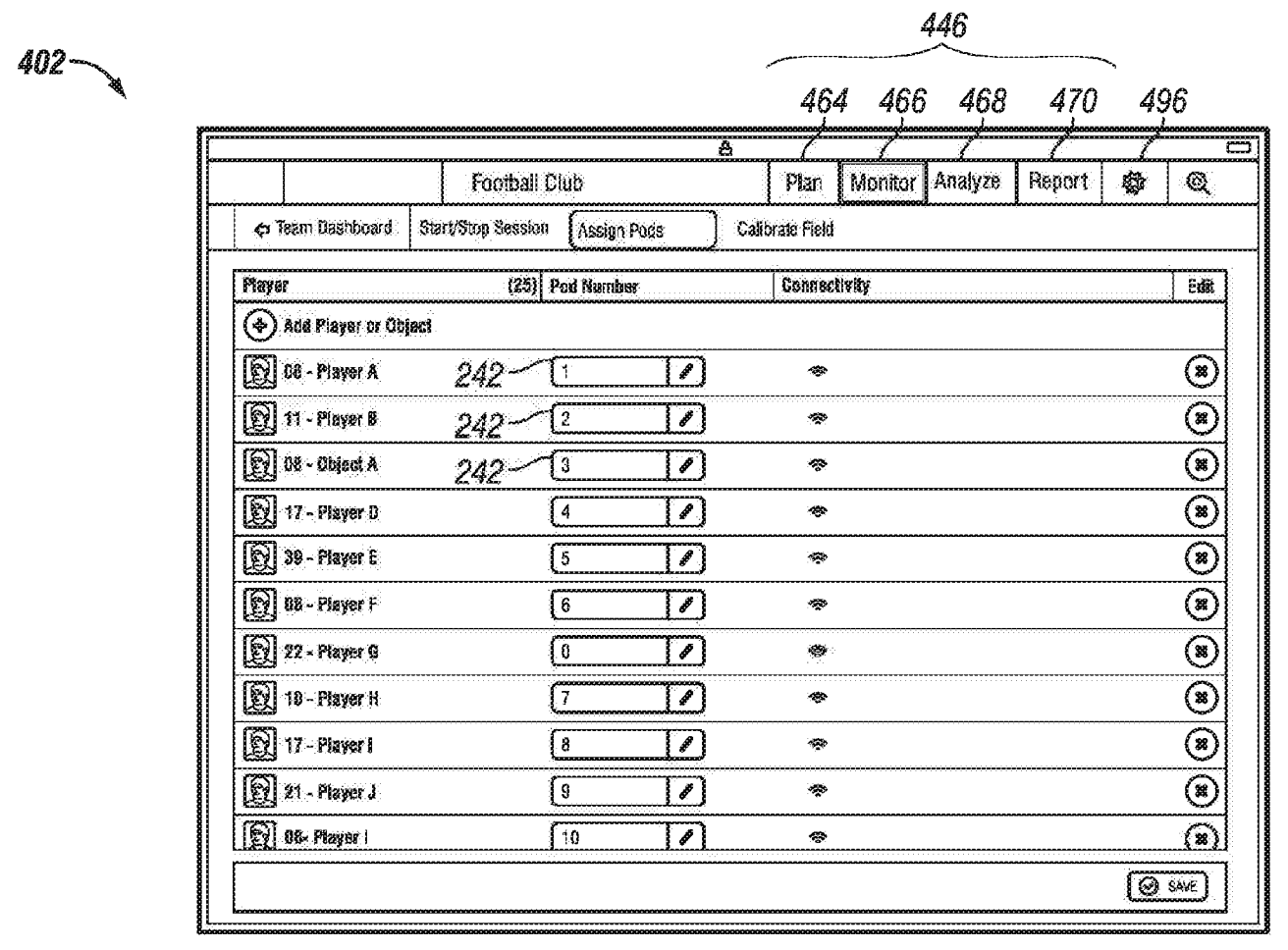

In some exemplary embodiments, assigning of individual monitors 200 and/or object monitor 250 to individuals 10 and/or sports objects 40 can be facilitated by use of group monitoring device 400, as depicted in, for example, FIG. 53. For example, display 402 of group monitoring device 400 may display a representation of a team or other group of individuals 10, and/or one or more sports objects 40, along with monitor identifying information 242 (indicative of the unique identifier of an individual monitor 200 and/or object monitor 250) of individual monitors 200 and/or object monitor 250 associated with individuals 10 and/or sports object(s) 40. A user of group monitoring device 400 may change this association by selecting the identifying information 242 of a particular individual monitor 200 and/or object monitor 250 associated with an individual 10 and/or sports object 40, and inputting identifying information 242 of a different individual monitor 200 and/or object monitor 250 to be associated with the individual 10 and/or sports object 40. Display 402 may also display an indication of the connectivity or signal strength between monitors 200, 250 and base station 300 (see, e.g., FIG. 61).

Via an administrative interface of base station 300, (which may be, e.g., an input and display located on base station 300, or which may be incorporated into a remote device such as, e.g., group monitoring device 400 or analysis device 600) identification information of individual 10 (e.g., individual 10's name and/or jersey number) and/or sports object 40 (e.g., sports object 40's type and/or size) can be associated with the unique identifier of the individual monitor 200 and/or object monitor 250 to be carried by individual 10 and/or sports object 40. Once properly paired with base station 300 and associated with individual 10, individual monitor 200 can be disconnected from base station 300 (e.g., by being removed from docking port 318). If not mounted to individual 10 and/or sports object 40, individual monitor 200 and/or object monitor 250 may be mounted on individual 10 and/or sports object 40, and any external sensors 202 can be appropriately mounted on individual 10 and/or sports object 40 and connected to individual monitor 200 and/or object monitor 250.

In an exemplary embodiment, such as that depicted in FIGS. 4-7, individual monitor 200 is a pod-like device and includes a position module 216 for determining data indicative of the location of individual monitor 200 (and thus the location of individual 10 carrying individual monitor 200), a heart rate monitor module 218 for determining data indicative of the heart rate of individual 10, a three-axis acceleration sensor module 226 for determining data indicative of the acceleration of individual 10, a gyroscope module 230 for determining data indicative of the orientation of individual 10 with respect to, for example, a playing field and/or base station 300, and a magnetometer module 232 for calibrating body motion data determined by gyroscope module 230 and acceleration sensor module 226. Such a pod-like device can be carried by individual 10, for example, in a shirt, shoe, or other apparel or equipment worn by individual 10. In some embodiments, individual monitor 200 may be a near-field communication (NFC) device (e.g., a radio-frequency identification (RFID) tag) or any active or passive communication device.

Similarly, in an exemplary embodiment object monitor 250 is a device that includes a position module 216 for determining data indicative of the location of object monitor 250 (and thus the location of sports object 40 carrying object monitor 250), a heart rate monitor module 218 for determining data indicative of the heart rate of an individual (e.g., individual 10) interacting with sports object 40 (e.g., gripping or otherwise holding sports object 40 such that a heart rate sensor of object monitor 250 can sense a pulse of the individual), a three-axis acceleration sensor module 226 for determining data indicative of the acceleration of sports object 40, a gyroscope module 230 for determining data indicative of the orientation of sports object 40 with respect to, for example, a playing field and/or base station 300, and a magnetometer module 232 for calibrating motion data determined by gyroscope module 230 and acceleration sensor module 226. In some embodiments, object monitor 250 is a pod-like device, which may be configured for attachment to a sports object 40 (e.g., coupled to a racquet or bat upon an external surface thereof). In some embodiments, object monitor 250 is a chip integrated within a sports object 40 (e.g., coupled to a ball beneath the exterior surface thereof). In some embodiments, object monitor 250 may be a near-field communication (NFC) device (e.g., a radio-frequency identification (RFID) tag) or any active or passive communication device.

Each of position module 216, heart rate monitor module 218, acceleration sensor module 226, gyroscope module 230, and magnetometer module 232 may themselves include associated sensors (e.g., a GPS sensor, a heart rate sensor, an acceleration sensor, a gyroscope, and a magnetometer, respectively), or may be in communication with such an associated sensor. Such communication may be wired or wireless. In the case of wireless communication, each module may be communicatively paired with an associated sensor, to avoid miscommunication and interference due to communication of other components. In some exemplary embodiments, some or all of these and other modules may be included in a single module.

In an exemplary embodiment, some or all of sensors 202 are incorporated into sensor garment 204. In such an embodiment, sensors 202 incorporated into sensor garment 204 may connect to individual monitor 200 via wires also incorporated into sensor garment 204.

During participation by individual 10 in the session of athletic activity, sensors 202 of individual monitor 200 sense various characteristics of individual 10, generate data indicative of those characteristics, and transmit that data to memory 228 of individual monitor 200, where it is stored. During use of sports object 40 in the session of athletic activity, sensors 202 of object monitor 250 sense various characteristics of sports object 40, generate data indicative of those characteristics, and transmit that data to memory 228 of object monitor 250, where it is stored. In turn, individual monitor 200 and/or object monitor 250 wirelessly transmit the generated data to base station 300. The resolution at which the data is stored in memory 228 (of individual monitor 200 and/or of object monitor 250) and at which the data is transmitted to base station 300 may be different, in order to optimize bandwidth, to optimize battery life, or for any other reason. For example, the heart rate of individual 10 may be sampled by heart rate monitor module 218 at 200 Hz, and data indicative of the heart rate may be generated at 200 Hz and stored in memory 228 at 200 Hz, but may be transmitted wirelessly to base station 300 at 2 Hz during the athletic activity. In some embodiments memory 228 is sufficient to store data from a single session of athletic activity (e.g., 3 hours of data collection), and in some embodiments memory 228 is sufficient to store data from up to 5 sessions of athletic activity (e.g., up to 15 hours of data collection).

Acceleration sensor module 226 can determine data indicative of acceleration, which can be used in calculating, for example, speed, distance, and metrics that will be discussed below. In some exemplary embodiments, the data indicative of acceleration can be used to increase accuracy of position data by, for example, using an accelerometer as a step counter or to determine a filter for a GPS signal calculation. In some exemplary embodiments, the data indicative of acceleration can be used, in conjunction with pattern recognition software, to determine the activity (e.g., the sport, movement, and/or drill) that an individual 10 is performing, and/or that sports object 40 is being used in.

Additionally, acceleration sensor module 226 can be used in conjunction with magnetometer module 232 and gyroscope module 230 in order to calibrate motion determinations. For example, information indicative of impact, change in motion, gravity, and step or other impact counting can be obtained using acceleration sensor module 226. Angular movement can be obtained using gyroscope module 230, and the absolute "North" orientation can be obtained using magnetometer module 232. These sensor readings can be used to determine, for example, the posture of an individual 10, gravity, orientation of individual 10 and/or object 40 in space, and heading of individual 10 and/or object 40.

Position module 216 may determine data indicative of absolute position at, for example, 10 Hz. Acceleration sensor module 226 may determine data indicative of acceleration at, for example, 200 Hz. Gyroscope module 230 may determine data indicative of change of position and orientation at, for example, 200 Hz. Magnetometer module 232 may determine data indicative of orientation at, for example, 200 Hz. Data may be transmitted from individual monitor 200 and/or object monitor 250 (via antenna 224) to base station 300 using a radio frequency (RF) link. The RF link between individual monitor 200 and base station 300 and/or between object monitor 250 and base station 300 should be sufficiently robust to cover the expected area of the athletic activity (e.g., playing field 30). In some exemplary embodiments, the RF link is sufficient to cover a distance of 50-300 meters under all operating conditions. In some exemplary embodiments, the RF link uses a globally available, license-free band (e.g., the 2.4 GHz frequency). In some exemplary embodiments, the RF link is configurable to cover multiple license-free bands used throughout the world. As will be described in greater detail below, in some exemplary embodiments base station 300 is capable of using the RF link to link to a plurality of individual monitors 200 and/or object monitors 250 simultaneously, for example, up to 25 individual monitors 200 and/or object monitors 250, or up to 30 individual monitors 200 and/or object monitors 250.

Figures 5, 6:
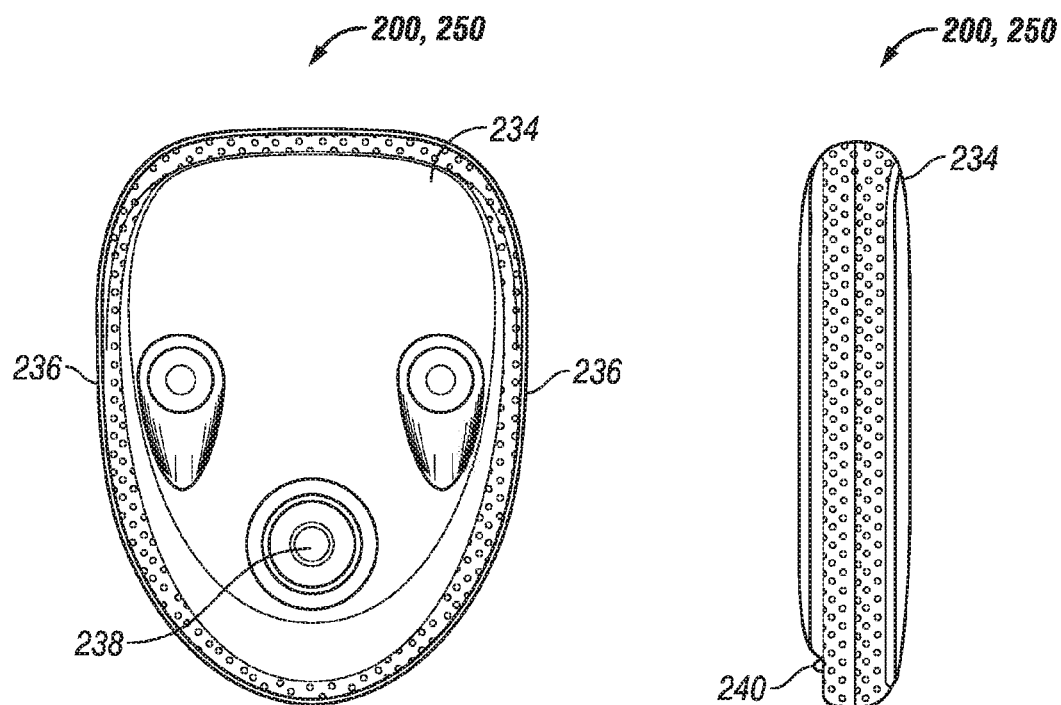
FIG. 5 depicts an individual monitor according to an exemplary embodiment of the present invention.
FIG. 6 depicts an individual monitor according to an exemplary embodiment of the present invention.
Figure 7:
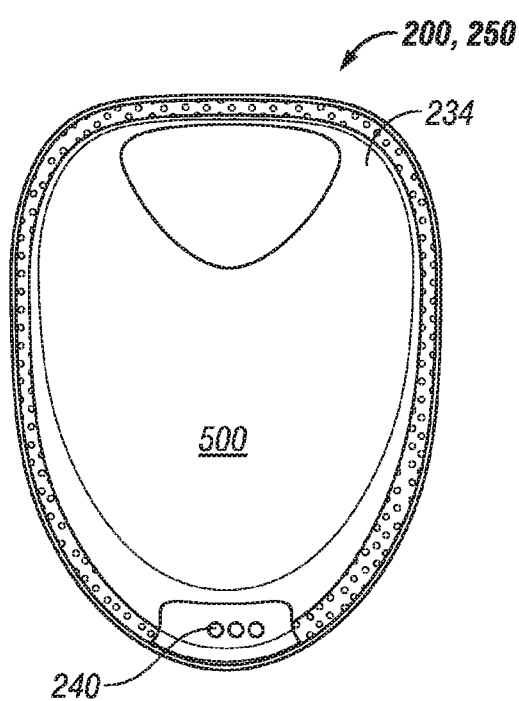
FIG. 7 depicts an individual monitor according to an exemplary embodiment of the present invention.

Individual monitor 200 may be, for example, a pod-like device, as shown in FIGS. 5-7, including a plastic housing 234 that contains components of individual monitor 200, such as the modules discussed above, for example. Object monitor 250 may also be, for example, a pod-like device, including a plastic housing 234 that contains components of object monitor 250, such as the modules discussed above, for example. Object monitor 250 may be configured for attachment to a sports object 40 (e.g., coupled to a racquet or bat upon an external surface thereof) or may be a chip integrated within a sports object 40 (e.g., coupled to a ball beneath the exterior surface thereof).

Individual monitor 200 and/or object monitor 250 may include connectors 236 that can provide connection to conductors to removably connect individual monitor 200 and/or object monitor 250 to, for example, sensors 202. Connectors 236 may removably connect to sensors 202 via, for example, snaps, clips, latches, or any other suitable technique. Individual monitor 200 and/or object monitor 250 may further include or be coupled to an input 238, which may be a button and which may function to turn individual monitor 200 and/or object monitor 250 on or off, when appropriately manipulated. Input 238 may include a background light indicator, which may be, for example, one or more light emitting diodes (LEDs) that indicate qualities of individual monitor 200 and/or object monitor 250. Such qualities may include, for example, state of operation (e.g., on, off, active, inactive, charging, low battery), memory status, and battery status. In some exemplary embodiments, individual monitor 200 and/or object monitor 250 includes or is coupled to a visual display, such as, for example, a liquid crystal display (LCD) screen, that can display this and other information.

Individual monitor 200 and/or object monitor 250 may further include or be coupled to a docking port 240, which facilitates wired communication with base station 300, and which can facilitate charging of battery 212 of individual monitor 200 and/or object monitor 250, when individual monitor 200 and/or object monitor 250 is docked with base station 300. Housing 234 of individual monitor 200 and/or object monitor 250 may be sized so as to accommodate components of individual monitor 200 and/or object monitor 250 while minimally interfering with individual 10's performance of the athletic activity, and/or with use of sports object 40 during the athletic activity. Housing 234 may be sized, for example, to fit into a pocket or cavity of a garment (e.g., sensor garment 204) or sports object 40. In some exemplary embodiments, dimensions of housing 234 do not exceed 70 mm by 55 mm by 11 mm.

In some exemplary embodiments, housing 234 is water resistant, and all openings (e.g., docking port 240, connectors 236) are sealed while in use during athletic activity. Such water resistance can be achieved by a close fit between exposed parts of individual monitor 200 (particularly housing 234), by use of plugs (e.g., plastic or rubber) that fit into openings, by use of a water resistant sealing compound, by other techniques, or by any combination thereof.

Individual monitor 200 and/or object monitor 250 may include data processing capabilities, such as raw data reduction and filtering. For example, a processor of individual monitor 200 (e.g., controller 220) may be configured to receive raw data from sensors 202 and to process such data at the individual monitor 200 and/or object monitor 250, prior to transmission to base station 300. For example, rather than transmitting raw data representing electrical activity sensed by heart rate monitor sensor 206 or acceleration sensor 210, controller 220 of individual monitor 200 and/or object monitor 250 may process the raw data to calculate heart rate, number of heart beats in a given period, magnitude of acceleration, rate of change of acceleration, or other metrics of interest, which can be transmitted to base station 300. In some exemplary embodiments, controller 220 of individual monitor 200 and/or object monitor 250 may use a unique encryption key (assigned by data processing module 304 of base station 300) to encrypt data in order to securely transmit such data to base station 300. Such processing of data at individual monitor 200 and/or object monitor 250 is not necessary, however, and raw data can be transmitted directly to base station 300 without such processing.

Operation of individual monitor 200 and/or object monitor 250 may be controlled by software stored in individual monitor 200 and/or object monitor 250 (e.g., stored in memory 228). This software can be updated when necessary or appropriate. Software can be updated via communication with base station 300, which may send software updates to individual monitor 200 and/or object monitor 250 wirelessly. Alternatively or additionally, software of individual monitor 200 and/or object monitor 250 may be updated through direct connection with base station 300 via docking ports 318 (as will be described below), such that firmware of individual monitor 200 and/or object monitor 250 may be flashed appropriately.

Sensors 202 are selected and configured to provide a basis for determination of metrics of the individual 10 and/or sports object 40 with which they are associated. As used herein, "metrics" may refer to representations of characteristics relevant to individual 10 and/or sports object 40 or one or more groups of individuals 10 and/or sports objects 40, and may be, for example, physiological-, performance-, or location-based. A "metric" may simply be a representation of a characteristic sensed by one of sensors 202, or may be a representation of a quality derived from data indicative of characteristics measured by one of sensors 202. For example, an acceleration sensor 210 senses acceleration, and provides data indicative of this characteristic. This data can be represented as a metric. Additionally, this data can be further processed to determine further metrics such as velocity, direction of acceleration, and distance. Processing involving formulas and algorithms that work on the data received from sensors 202 (including data from different sensors 202) and other sources can be used to determine a wide variety of results (including, for example, metrics, alerts, markers, targets, goals) determined to be useful to trainer 20, including custom-designed results.

In some embodiments, such other sources that can provide data to group monitoring system 100 may include, for example, other sensors in communication with system components (e.g., a temperature or wind sensor coupled to base station 300) or sensors of personal equipment of individuals 10 (e.g., a pedometer, heart rate monitor, weight scale, sleep monitor, or respiration monitor).

The data from such other sources may be gathered separate from or during the monitored athletic activity. For example, such data may be gathered during a private training session for an individual 10 (and may be used, for example, during a group training session monitored by group monitoring system 100) or during training in a different sport, group, or season than the sport, group, or season being monitored.

Such other sources may communicate with group monitoring system 100 in any suitable way, such as, for example, via wired or wireless communication with a system component or by manual input of data output from such other sources (e.g., individual 10 reading the output of his or her personal pedometer, and inputting it into group monitoring system 100 via an input of a system component). In some embodiments, such other sources may transmit data to a database, which may in turn transmit such data to group monitoring system 100 (e.g., via web server system 500 or base station 300).

Metrics can provide useful information individually about multiple individuals 10 and/or sports objects 40, and can provide useful information about groups of individuals 10 and/or sports objects 40. Metrics can also take into account attributes of a particular individual 10 or group of individuals 10, such as, for example, height, weight, endurance, and top speed. Metrics can also take into account attributes of a particular sports object 40 or group of sports objects 40, such as, for example, speed, trajectory, flight time, reaction time, acceleration, flight distance, launch angle, orientation, and rotation rate.

Metrics can also relate to an athletic activity itself, or to game events. For example, the character of a force sensed at sports object 40 may indicate that sports object has been passed from one individual 10. Also for example, the character of a decrease in speed and/or rotation may be caused by sports object 40 contacting a net, such as a goal net, and may indicate that a goal has been scored. Also for example, a coincident decrease in movement or speed of a number of individuals 10 may indicate the end of a period of play.

Base station 300 may be a self-contained portable system, such as the exemplary embodiments depicted in FIGS. 21-26, containing all hardware required or desired to perform the functions of base station 300 described herein. In some exemplary embodiments, base station 300 weighs no more than 25 kilograms. In some exemplary embodiments, base station 300 is sized so as to fit easily into the trunk of a car or the overhead storage area of a passenger aircraft. In some exemplary embodiments, base station 300 includes a pair of wheels 322 at one end, and a handle 324 at the other end, to facilitate mobility of base station 300. In some exemplary embodiments, base station 300 is waterproof, and can withstand impacts associated with regular use and transport. In some exemplary embodiments, base station 300 is contained within a hard shell-style case 326. In some exemplary embodiments, base station 300 is contained within a soft duffel bag-style case 328.

In some exemplary embodiments base station 300 is configured to be portable. In some exemplary embodiments, base station 300 is configured to be positioned at an activity site. In some exemplary embodiments base station 300 is configured to be movable between activity sites such that it can be positioned at various activity sites. In some exemplary embodiments base station 300 is configured to be portable with respect to at least one of individual monitors 200, object monitors 250, and group monitoring device 400. In some exemplary embodiments base station 300 is configured to be portable with respect to each of individual monitors 200, object monitors 250, and group monitoring device 400.

In some exemplary embodiments, base station 300 itself includes sensors, such as, for example, a GPS sensor (or other position sensor), a gyroscope, a magnetometer, a temperature sensor, a humidity sensor, and/or a wind sensor. Such sensors can provide valuable data that can be used in algorithms to determine metrics associated with individuals 10 and/or sports objects 40, as will be described below.

In some exemplary embodiments, base station 300 includes a reference sensor 334 (e.g., a GPS reference sensor), which may be physically included within base station 300 or independent of and located remote from base station 300 at a known position with respect thereto. Reference sensor 334 can be connected to base station 300 via wires or wirelessly. Reference sensor 334 can be used to detect a deviation signal and use it to calculate a correction signal for received position signals (e.g., GPS data). This correction signal can be sent to monitors 200, 250 (e.g., via base station 300). This correction signal can be used to correct position determinations of monitors 200, 250, thereby increasing their accuracy. Determining such a correction signal and then sending it to monitors 200, 250 achieves efficient use of processing capacity, because monitors 200, 250 are not burdened with determining a correction signal themselves, but simply receive and use a correction signal determined at base station 300 or reference sensor 334.

Figure 8:
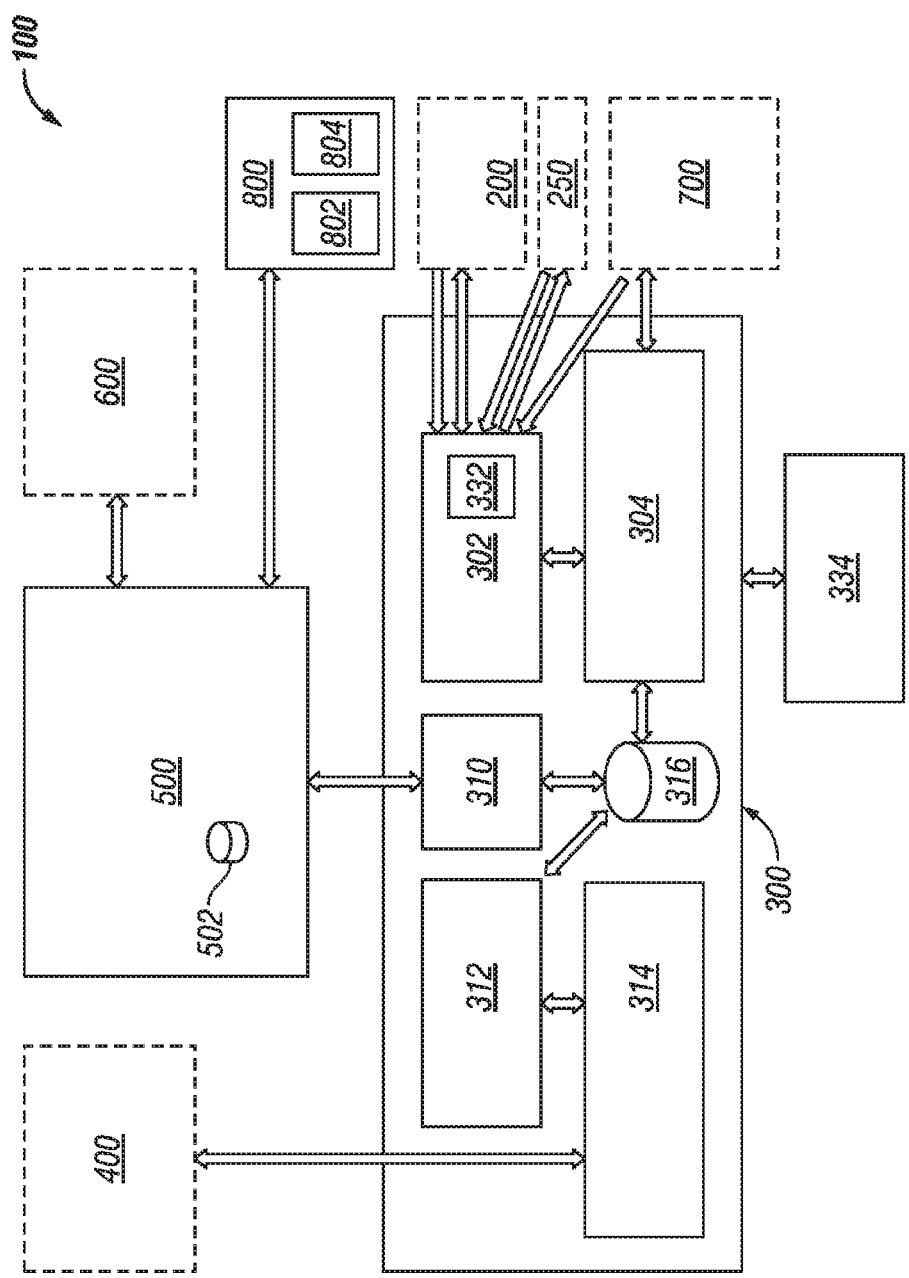
FIG. 8 depicts a diagram of a monitoring system according to an exemplary embodiment of the present invention.

Base station 300 may transmit and receive data from monitors 200, 250 via an antenna 330 configured for one or more of RF communication, WLAN communication, ISM communication, cellular (e.g., GSM broad band 2.5G or 3G) communication, other suitable communication, or a combination thereof. Communication between base station 300 and monitors 200, 250 may be bi-directional or uni-directional. Antenna 330 may be a high-gain antenna, and in some exemplary embodiments base station 300 includes multiple (e.g., 2) such antennas 330. In some exemplary embodiments, base station 300 includes an antenna configured to send and/or receive a positioning signal such as that of a satellite-based positioning system (e.g., GPS). Base station 300 can then determine metrics from the received data. FIG. 8 depicts a diagram of an exemplary embodiment of group monitoring system 100. As shown in FIG. 8, base station 300 includes a data reception module 302, a data processing module 304, a central synchronization (sync) module 310, a logic module 312, a web server module 314, and a base station database 316.

As described above, base station 300 receives data from monitors 200, 250. Data reception module 302 of base station 300 may be in communication with each active monitor 200, 250. In some exemplary embodiments data reception module 302 receives data from monitors 200, 250 via antenna 330 in communication with monitors 200, 250 through the RF link described above. Data reception module 302 writes the received data to a data file, which may be, for example, a comma-separated values file or a tab delimited file. The file may be, for example, a single file used to write the data to, or a rolling file (file roll) based on, for example, time, number of entries, or size. The data file may be updated using any suitable interval and parameters. For example, 30 monitors 200, 250 may be active and updating 5 data points at 2 Hz, in order to update the data file in near real time.

Data reception module 302 may perform a data integrity check on the received data. In some exemplary embodiments data reception module 302 decrypts the received data. In some exemplary embodiments data reception module 302 is agnostic to the received data, and does not decrypt the received data. In some exemplary embodiments data reception module 302 buffers content as needed.

Data reception module 302 may include a data read module 332 that reads the data from the data file and transmits it to data processing module 304. Data read module 332 may run at any suitable interval, such as, for example, 500 ms (milliseconds), to read the change in the data written to the data file.

Prior to monitors 200, 250 being used during a session of athletic activity, each monitor 200, 250 may be connected to base station 300 (e.g., by docking in docking port 318, or wirelessly) and may be assigned an encryption key by data processing module 304. Monitors 200, 250 can use this encryption key to securely transmit data to data reception module 302. Data processing module 304 receives data from data reception module 302, as described above, and decrypts the data, if encrypted, by using the unique encryption key assigned to a particular monitor 200, 250. Data processing module 304 transmits the decrypted data to base station database 316, for storage.

Base station database 316 is preferably configured for short term storage of data generated during sessions of athletic activity, while long term storage is accomplished by web server system 500, as will be discussed in greater detail below. Base station database 316 may include sufficient storage space for at least all data expected to be generated in 1 session of the athletic activity. In some exemplary embodiments, base station database 316 includes sufficient storage space for at least all data expected to be generated in 3 sessions of the athletic activity (e.g., greater than approximately 2 gigabytes). In some exemplary embodiments, base station database 316 is configured for long term storage, and includes sufficient storage space, for example, for at least all data expected to be generated in 10 years of use monitoring athletic activities (e.g., greater than approximately 600 gigabytes).

Logic module 312 polls base station database 316 and applies algorithms to the polled data to determine metrics and alerts. Logic module 312 can determine a wide variety of metrics, including custom-designed metrics, by application of appropriate algorithms. Logic module 312 can transmit such metrics to web server module 314. More detailed description of exemplary metrics and their use will be provided below.

In some embodiments, system components (e.g., sensors 202, individual monitors 200, object monitors 250, base stations 300, group monitoring devices 400, web server systems 500, analysis devices 600, camera monitoring systems 700) may include assessment hardware and/or software to monitor on-board operating conditions, and/or operating conditions of other system components. Such monitored operating conditions may include, for example, component serial number, strength (including presence) of GPS signal at component, strength (including presence) of communication signal at component, remaining battery power of battery of component, whether battery of component is charging or discharging, data sent from and/or received by component (e.g., active data transmission, time of last data transmission, volume of data transmitted, rate of data transmission), available memory of component, current software or firmware version installed on component, target software or firmware version for component, synchronization status of component, errors in operation of component, time since last communication received from component, number of other components docked at component, whether component is properly located and/or oriented with respect to an associated individual, object, or area).

In some embodiments, data relating to operating conditions of system components can be transmitted between system components (e.g., as described herein for any other data transfer, including metric-related data transfer). For example, operating conditions data relating to monitors 200, 250 can be transmitted from monitors 200, 250 to base station 300. Also for example operating conditions data relating to monitors 200, 250 and/or base station 300 can be transmitted from base station 300 (e.g., via logic module 312 and web server module 314) to a remote device (e.g., group monitoring device 400, analysis device 600). Further, in some embodiments operating conditions data can be stored (e.g., as described herein for any other data storage, including metric-related data storage). For example, operating conditions data can be stored in base station database 316.

In some exemplary embodiments, trainers 20 or other persons (e.g., system supervisors, doctors, medical staff, equipment manufacturers) can create performance alerts for individuals 10 in order to inform trainer 20 or such other persons of the occurrence of events. Such performance alerts can be used to, for example, measure workout effectiveness, manage training load, identify achievement of training targets, or identify dangerous situations. Performance alerts can be based on a number of metrics, such as, for example, distance (total and/or time within particular speed ranges), heart rate (present and/or cumulative time within particular heart rate zones, heart rate moving outside particular heart rate zones), power or training load, goals scored, contact with ball (or other sports object 40). Such performance alerts can be generally applied to all individuals 10 (individually or in groups), or can be tailored to be specific to a particular individual 10. Such performance alerts can be generally applied to all sessions of athletic activity, or can be tailored to be specific to a particular session of athletic activity. Similar performance alerts can be created for sports objects 40.

In some embodiments, training sessions can be planned with performance alerts that allow a trainer 20 to see in real time whether training targets are being reached. Once a training target has been reached the trainer can end the training session for the individual 10 that has reached the target, to prevent over training. In some embodiments, trainers 20 can also monitor drills (or other athletic activity) in real time to see if the athletes are reaching training targets (e.g., target intensities) and recovering as intended. If targets are not being reached as desired by trainer 20, trainer 20 may adjust training in real time to help reach the targets.

In some embodiments, such a performance alert may itself include specific coaching advice based on the alert. For example, an alert indicating that an individual 10 is running at a speed above a speed threshold may be accompanied by a recommendation for the individual 10 to slow down. Also for example, an alert indicating fatigue of a player 10 (e.g., a heart rate sustained above a threshold level for a threshold period of time, a heart rate above a threshold level in combination with a speed below a threshold level) may be accompanied by a recommendation for the individual 10 to be replaced. Also for example, an alert indicating a number of hits given or received by an individual 10 per unit time being below a threshold may be accompanied by a recommendation for the individual 10 to hit more.

Trainers 20 can create such performance alerts via an administrative device, which may be a device such as, for example, group monitoring device 400 or analysis device 600, described in greater detail below. In some exemplary embodiments, performance alerts can be created using a remote computer (e.g., by a team manager or medical support person) and can be transferred to the base station and to any of monitors 200, 250, group monitoring devices 400, or analysis devices 600 (e.g., via the Internet, and/or any of the communications channels described herein). Trainers 20 can create a performance alert by, for example, selecting a metric, selecting conditions (e.g., target metric value, time frame for maintaining target metric value, date range for achieving target, target metric range), specifying exceptions, assigning the performance alert to an individual 10 and/or sports object 40 (or a group of individuals 10 and/or sports objects 40), and associating the performance alert with a session of athletic activity.

Figure 16:
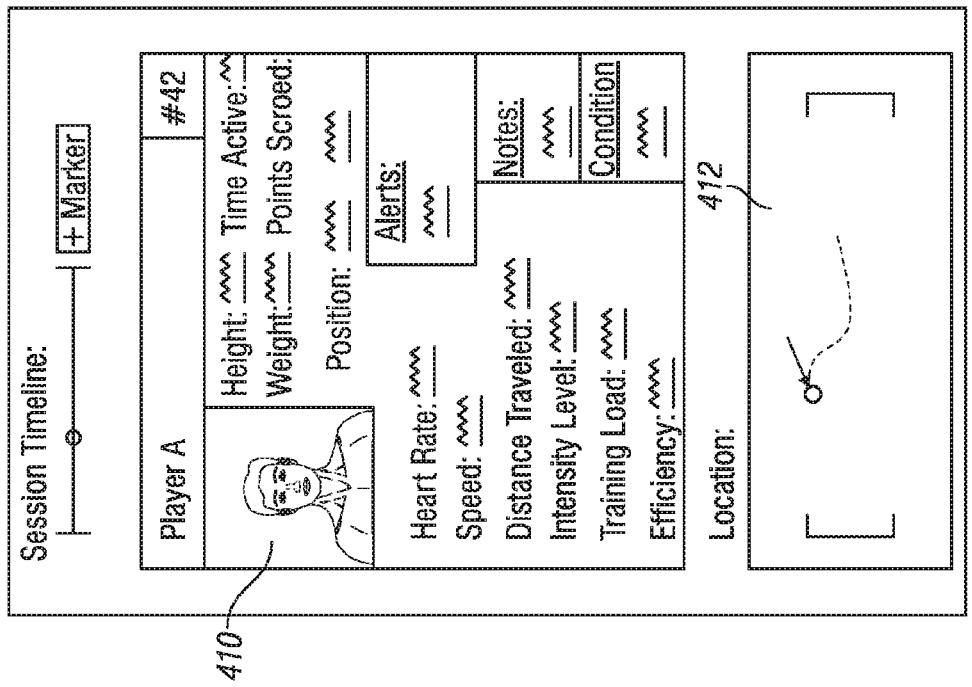
FIG. 16 depicts a display of a group monitoring device according to an exemplary embodiment of the present invention.
Figure 20:
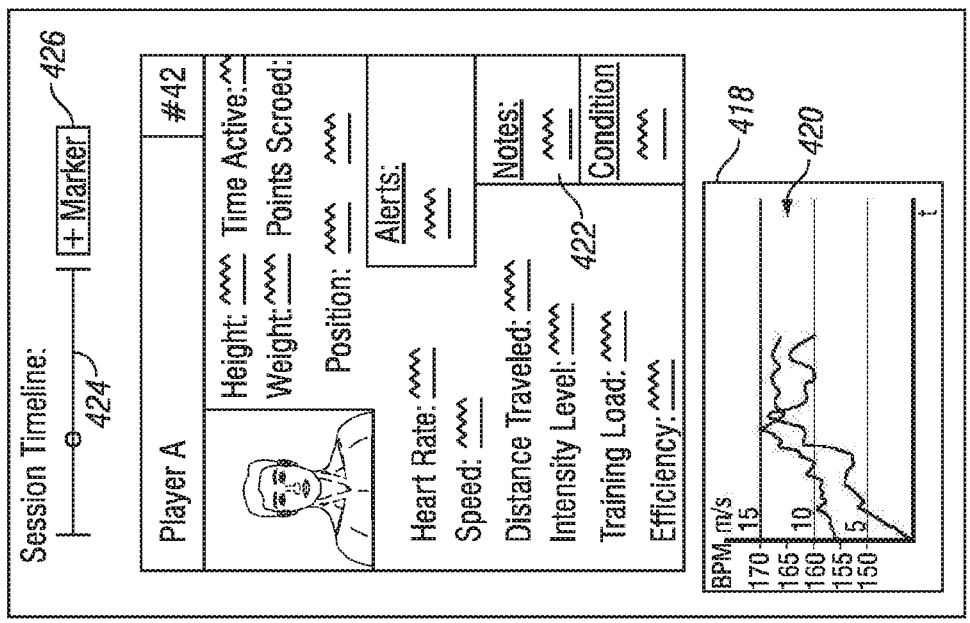
FIG. 20 depicts a display of a group monitoring device according to an exemplary embodiment of the present invention.

The created performance alert may be viewed in association with its associated individual 10 and/or sports object 40 when viewing a dashboard (such as, for example, a dashboard showing information relating to the associated individual 10 and/or sports object 40 displayed by group monitoring device 400 or analysis device 600, see, e.g., FIGS. 16 and 20). Progress of individual 10 and/or sports object 40 toward triggering a performance alert (triggering occurs when the conditions of the performance alert are met) can be monitored during a session of athletic activity via group monitoring device 400. Past performance alerts that have been triggered can be stored in association with individual 10 and/or sports object 40 or a group of individuals 10 and/or sports objects 40, and these performance alert histories may be viewed using, for example, group monitoring device 400 or analysis device 600. Examples of potential performance alerts include exhibiting an irregular heart rate, exhibiting a body temperature above 38 degrees C. (potentially a sign of hyperthermia), maintaining a heart rate of 85% of maximum or higher for 10 minutes or more, traveling a distance of 900 meters at a speed of 6.0 meters per second or more, achieving a training load of 700 Watt or more.

In some exemplary embodiments, trainers 20 or other persons can create system alerts for system components (e.g., individual monitors 200, object monitors 250, base stations 300, group monitoring devices 400, web server systems 500, analysis devices 600, camera monitoring systems 700). System alerts can be configured to, for example, communicate operating conditions (statuses) of system components. In some embodiments, an alert for a component can be triggered in response to a determination (e.g., by the associated component, or another system component in communication therewith) that an operating condition has crossed a system alert threshold. For example, a system alert may be triggered for a particular individual monitor 200 in response to a determination by the individual monitor 200 that the remaining battery power of a battery of the individual monitor 200 has dropped below 5% of capacity. Also for example, a system alert may be triggered for a particular individual monitor 200 in response to a determination by a base station 300 in communication with individual monitor 200 that a data transmission has not been received from the individual monitor 200 for a predetermined period of time.

Logic module 312 can transmit information about such alerts (including, e.g., information indicating progress toward triggering an alert and information indicating an alert is triggered) to group monitoring device 400 (via web server module 314 of base station 300) during athletic activity of individual 10 and/or use of sports object 40. The information about such alerts can be stored in base station database 316.

Web server module 314 can receive metric and alert information from logic module 312 for individual monitor 200, individual 10, object monitor 250, and/or sports object 40, or for multiple individual monitors 200, individuals 10, object monitors 250, and/or sports objects 40 (including groups of individual monitors 200, individuals 10, object monitors 250, and/or sports objects 40). Web server module 314 can render display code (such as, for example, html5 (hypertext markup language 5) compliant code) based on a request from a client device such as, for example, group monitoring device 400. In some embodiments, web server module 314 uses JavaScript® to open and maintain a web socket. Web server module 314 can also serve a security function, by ensuring that a requesting client device is properly authenticated and that all data is passed using https (hypertext transfer protocol secure). Web server module 314 may provide group monitoring device 400 with requested metrics and generated alerts during the athletic activity, via, for example, an API layer.

Figure 68:
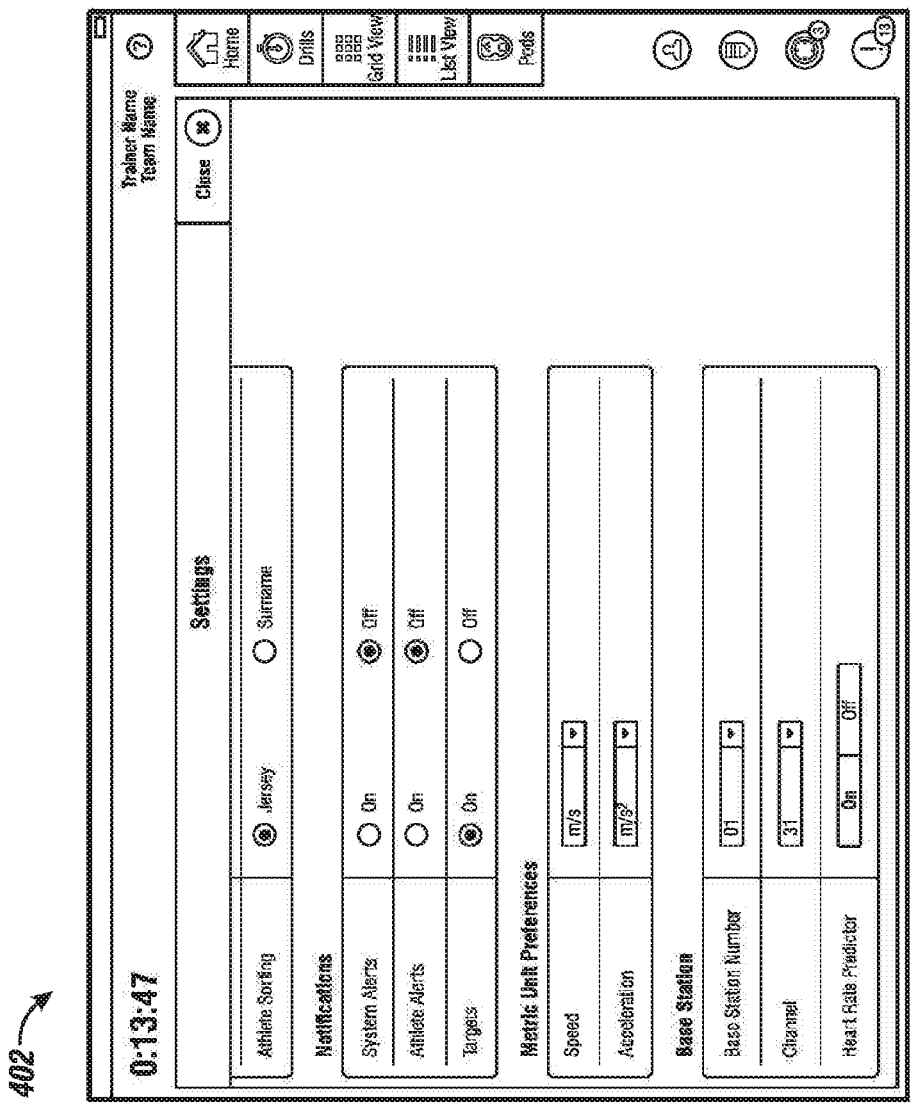
FIG. 68 depicts a display of a group monitoring device according to an exemplary embodiment of the present invention.
Figure 69:
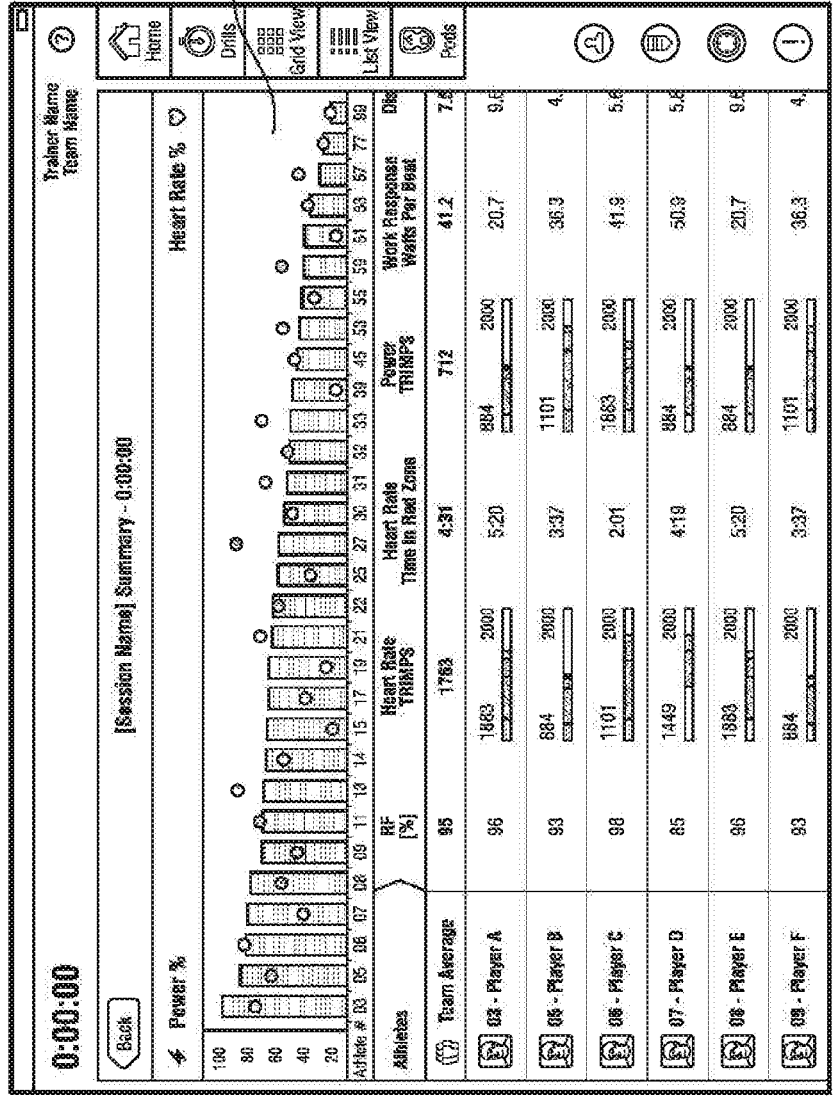
FIG. 69 depicts a display of a group monitoring device according to an exemplary embodiment of the present invention.
Figure 70:
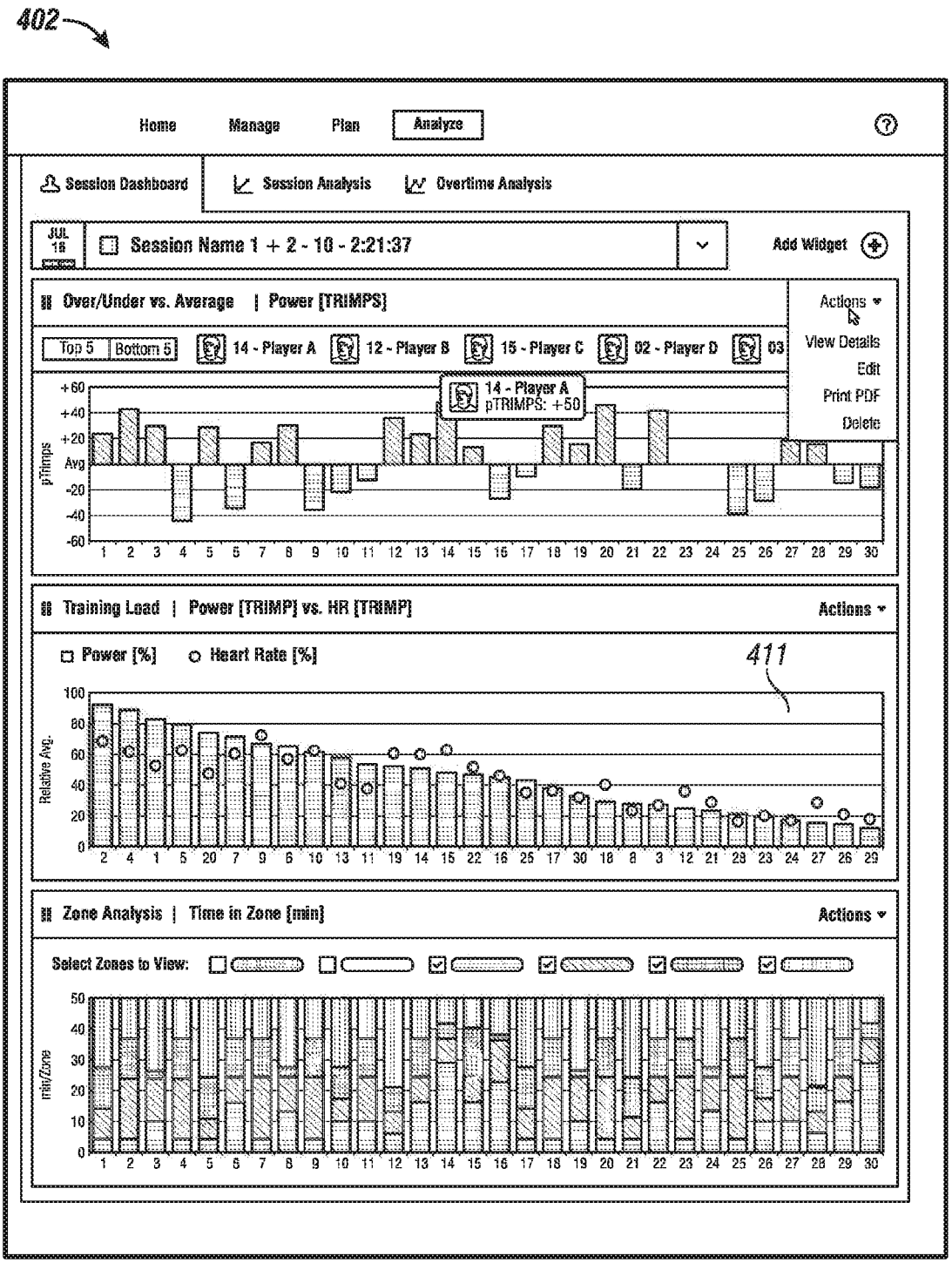
FIG. 70 depicts a display of a group monitoring device according to an exemplary embodiment of the present invention.
Figure 71:
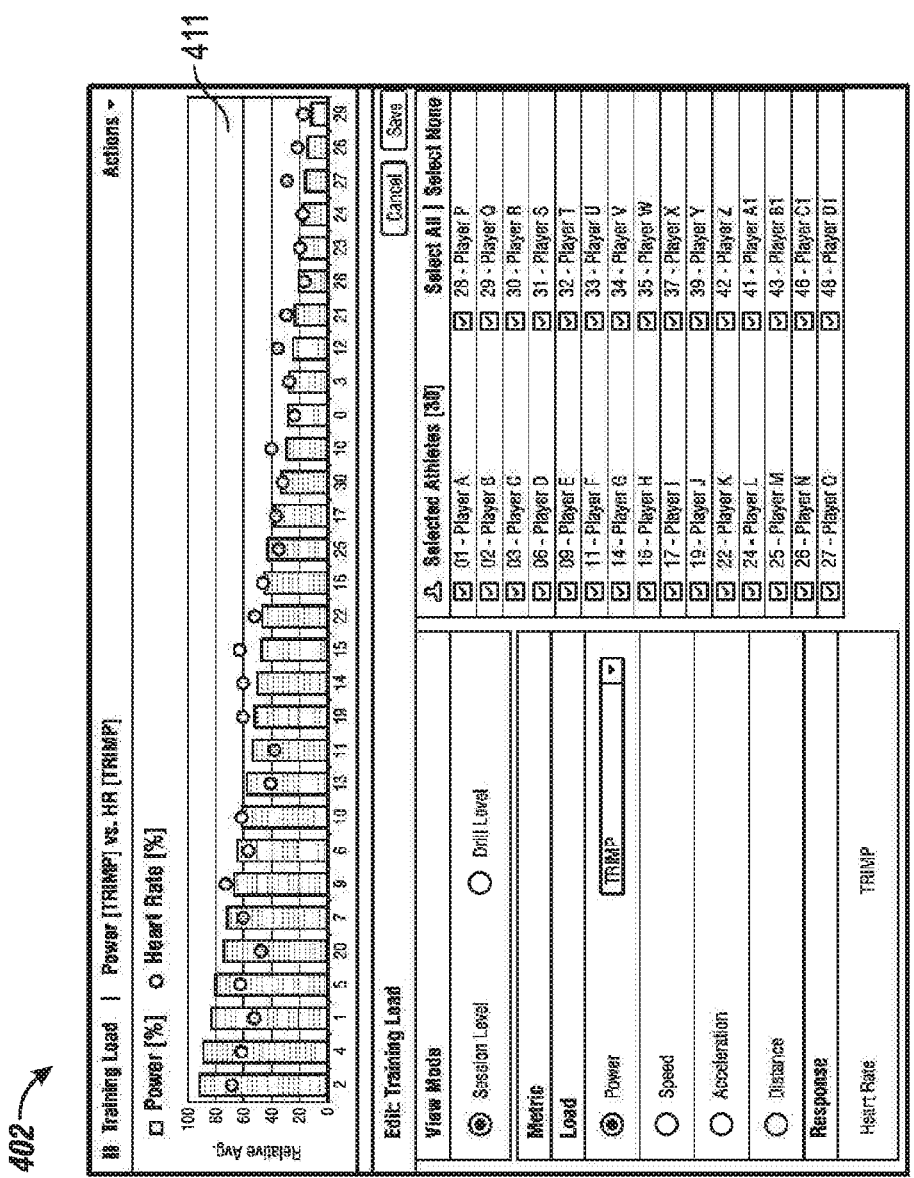
FIG. 71 depicts a display of a group monitoring device according to an exemplary embodiment of the present invention.
Figure 72:
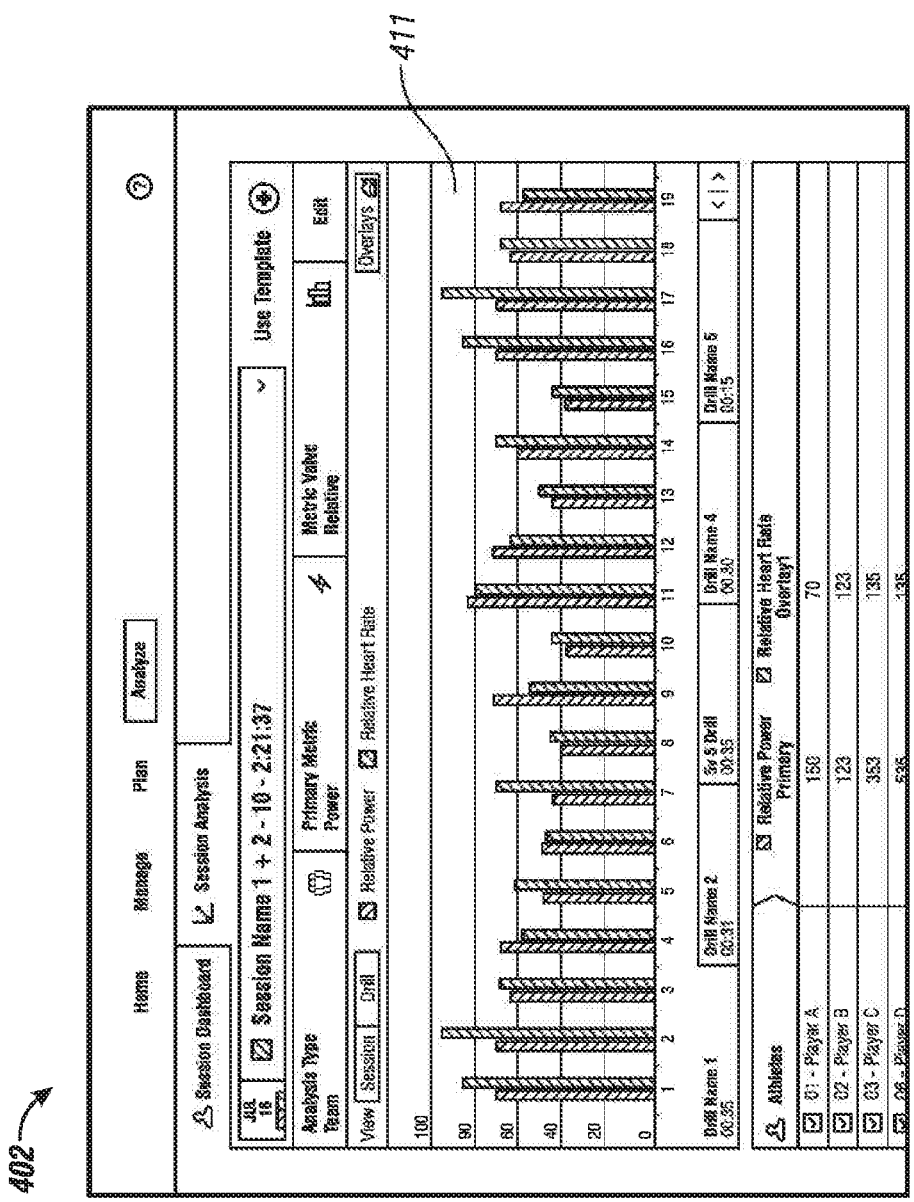
FIG. 72 depicts a display of a group monitoring device according to an exemplary embodiment of the present invention.
Figure 73:
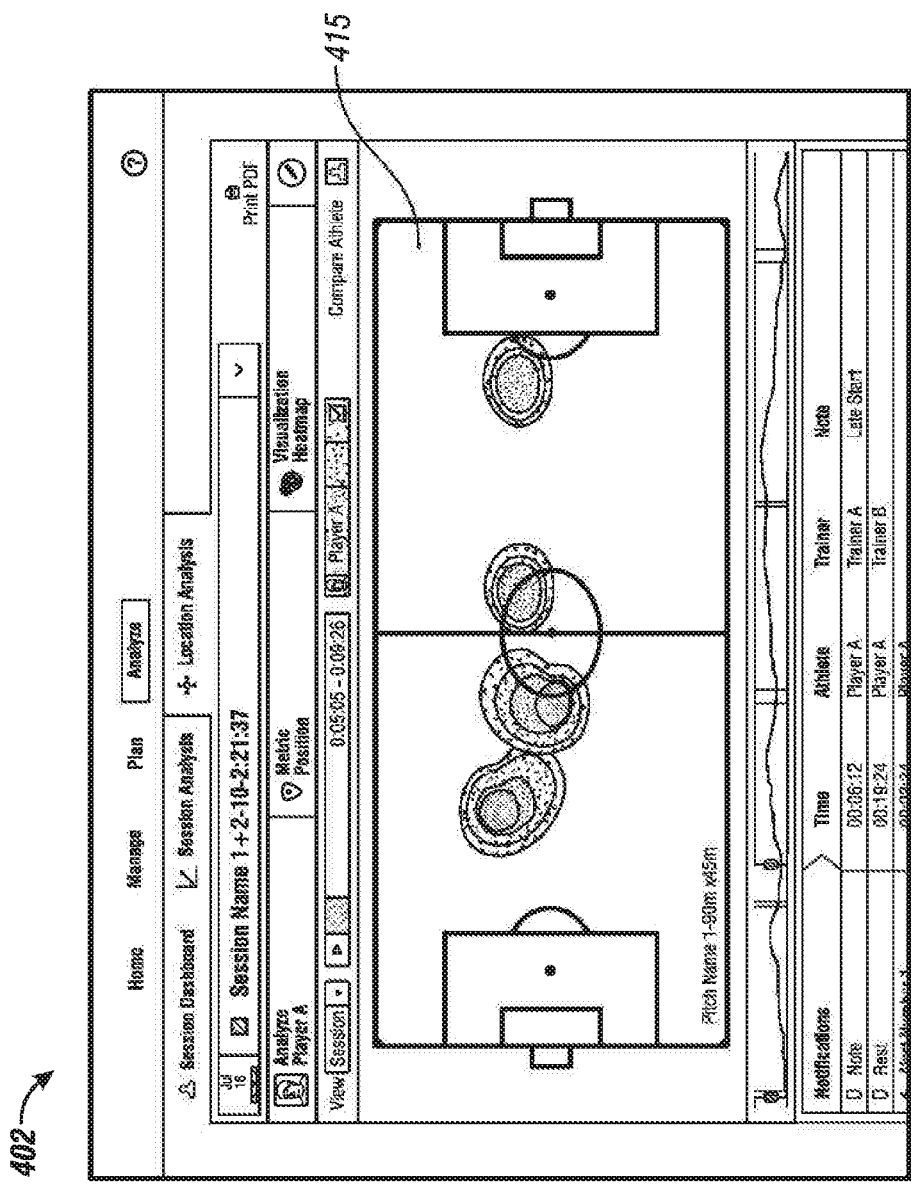
FIG. 73 depicts a display of a group monitoring device according to an exemplary embodiment of the present invention.
Figure 74:
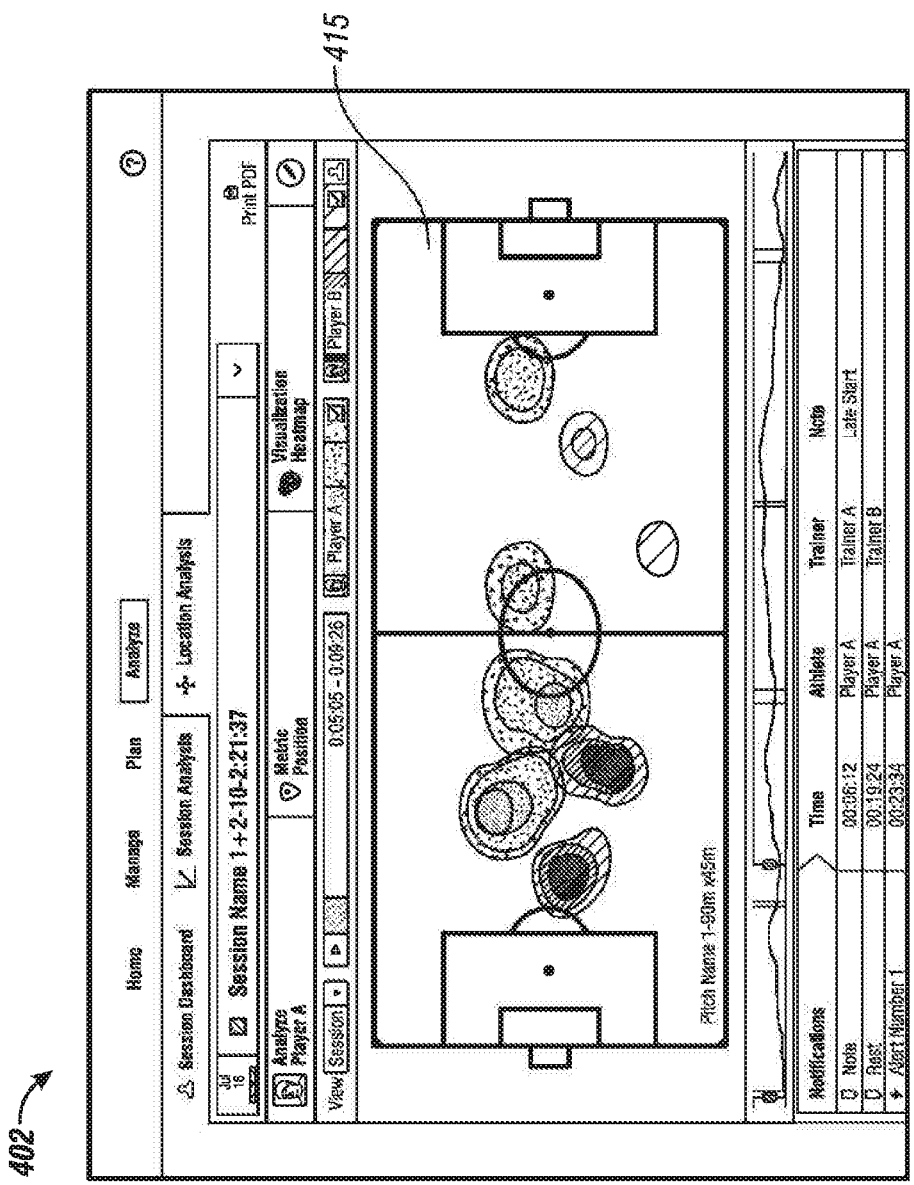
FIG. 74 depicts a display of a group monitoring device according to an exemplary embodiment of the present invention.
Figure 75:
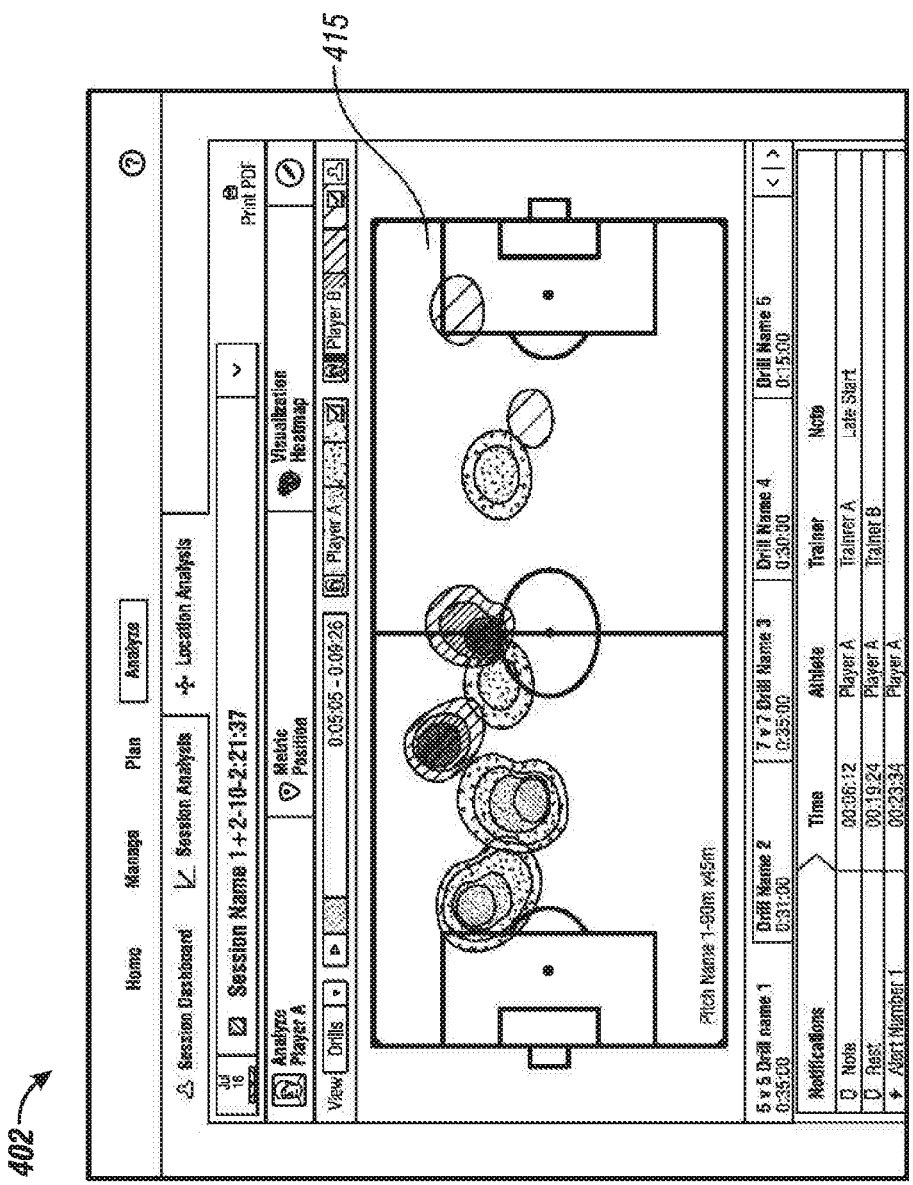
FIG. 75 depicts a display of a group monitoring device according to an exemplary embodiment of the present invention.
Figure 77:
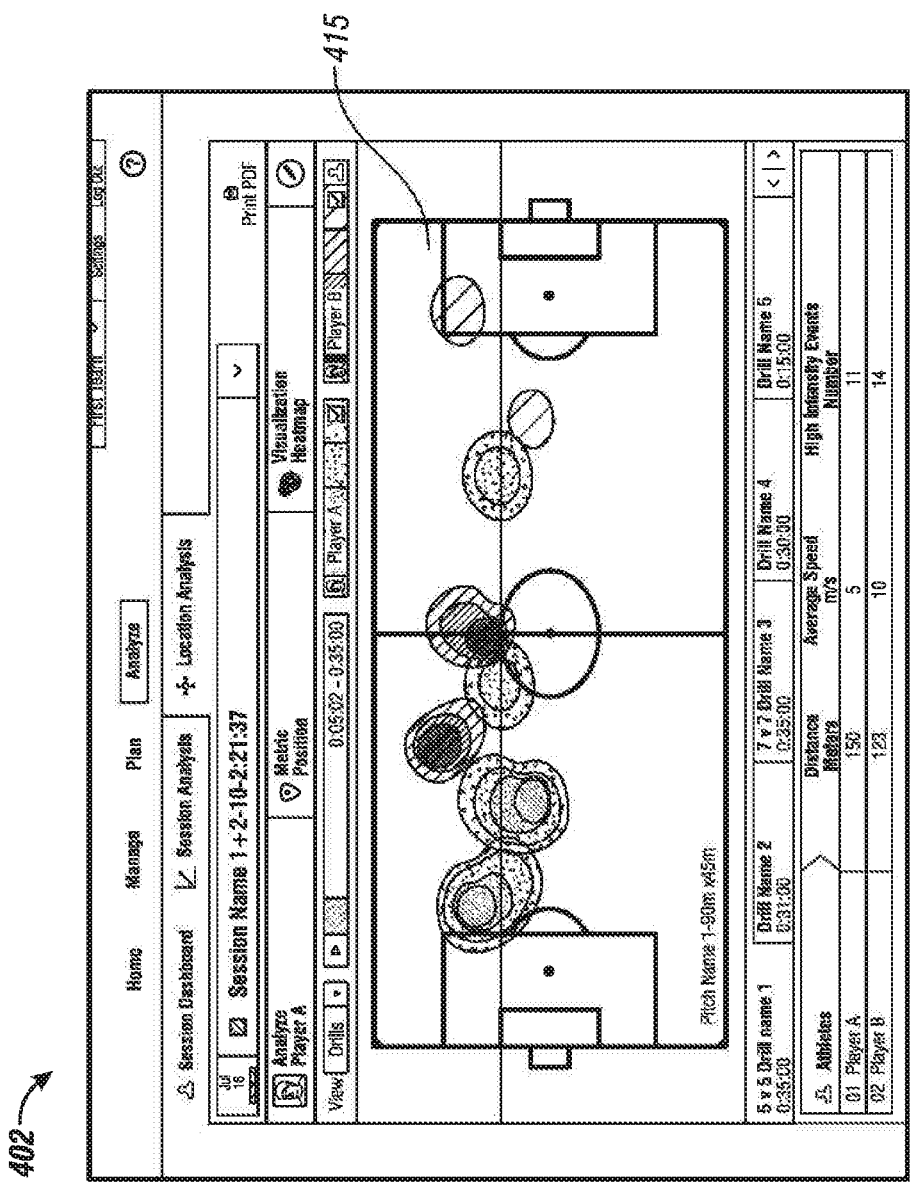
FIG. 77 depicts a display of a group monitoring device according to an exemplary embodiment of the present invention.

Group monitoring device 400 can wirelessly receive metrics, alerts, and other information (e.g., identification information and attributes of individual monitors 200, individuals 10, object monitors 250, and/or sports objects 40; statistics related to individual monitors 200, individuals 10, object monitors 250, and/or sports objects 40, or statistics related to the athletic activity generally) from base station 300. A single group monitoring device 400 may be in communication with base station 300, or multiple group monitoring devices 400 may be in communication with base station 300 simultaneously. Group monitoring devices 400 may be portable with respect to base station 300 and may communicate with base station 300 via, for example, WLAN (wireless local area network), 2.4 GHz ISM (industrial, scientific, and medical) band, Bluetooth® (or Bluetooth® Low Energy (BTLE)), or cellular protocols. In some embodiments, modes and/or channels of communication may be selected (e.g., via inputs of base station 300 or remote deices). See, for example, FIG. 68, which shows an embodiment of display 402 of group monitoring device 400, displaying a settings page that presents an option to select a communication channel for base station 300.

In some exemplary embodiments, group monitoring device 400 includes a module selection element 446 which allows selection of one or more operation modules to be displayed. The operation modules may be selectable using operation module icons. In some exemplary embodiments, selection of a plan module icon 464 may trigger display of a plan module including features designed to be used to plan a session of athletic activity. In some exemplary embodiments, selection of a monitor module icon 466 may trigger display of a monitor module including features designed to be used to monitor a session of athletic activity in real time during the session of athletic activity, as described further herein. In some exemplary embodiments, selection of an analyze module icon 468 may trigger display of an analyze module including features designed to be used to analyze a session of athletic activity in real time during the session of athletic activity, or after completion of the session of athletic activity, as described further herein. In some exemplary embodiments, selection of a report module icon 470 may trigger display of a report module including features designed to be used to develop reports (e.g., printable or displayable summaries of selected information) related to a session of athletic activity.

Figure 9:
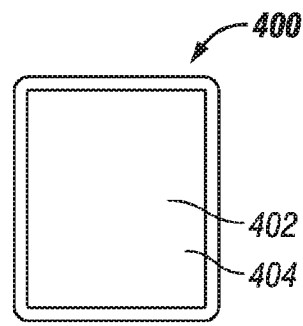
FIG. 9 depicts a group monitoring device according to an exemplary embodiment of the present invention.

In some exemplary embodiments, group monitoring device 400 includes a display 402 and an input 404, as shown, for example, in FIG. 9. In a preferred embodiment, group monitoring device 400 is a tablet computing-style device (such as a tablet personal computer or an iPad®, marketed by Apple Inc.®). Group monitoring device 400 may be, however, any other suitable device, such as, for example, a laptop computer, a smartphone, a personal computer, a mobile phone, an e-reader, a PDA (personal digital assistant), a smartphone, a wristwatch device, a display integrated into a garment (e.g., into a sleeve or arm band), or other similar device capable of receiving and displaying information and receiving input. In some embodiments, group monitoring system 100 includes a plurality of group monitoring devices 400, which may be carried by individuals 10 (e.g., during participation in a monitored athletic activity). For simplicity and clarity of explanation, group monitoring device 400 is herein described primarily as used by trainer 20. Group monitoring device may be used similarly, however, by any person, including individuals 10.

In some exemplary embodiments, during a session of athletic activity, trainer 20 may use group monitoring device 400 to receive real time information about individuals 10 and/or sports objects 40. This information may enable trainer 20 to more easily accomplish a variety of goals. In the case that the athletic activity is a fitness exercise, trainer 20 can leverage real time data received about the fatigue of particular individuals 10 or groups of individuals 10 in order to, for example, inform data-driven real time decisions that optimize the performance of individuals 10 and reduce the potential for injury. For example, trainer 20 may modify a current session of athletic activity (e.g., shorten, extend, pause, end, or change the schedule of activity for the session) based on the information received from group monitoring device 400. Trainer 20 may modify the session for particular individuals 10, or for groups of individuals 10. In the case that a present session of athletic activity has been scheduled using a plan module of monitoring device 400 (as described further herein), the planned schedule can be changed in real time to correspond to decisions of trainer 20. Similarly, in the case that the athletic activity is a competition (e.g., a soccer game), trainer 20 can leverage real time data received about the performance of particular individuals 10 and/or sports objects 40 or groups of individuals 10 and/or sports objects 40 in order to, for example, inform data-driven real time decisions that optimize the chance for success in the competition. In an exemplary embodiment, group monitoring device 400 can be used to monitor a single individual 10 and/or sports object 40 alone, as well as a group of individuals 10 and/or sports objects 40.

In some exemplary embodiments, group monitoring device 400 may be used by broadcasters of an athletic activity in order to, for example, determine and relay to their audience information about individuals 10 participating in the athletic activity and/or sports objects 40 being used for the athletic activity.

Figure 15:
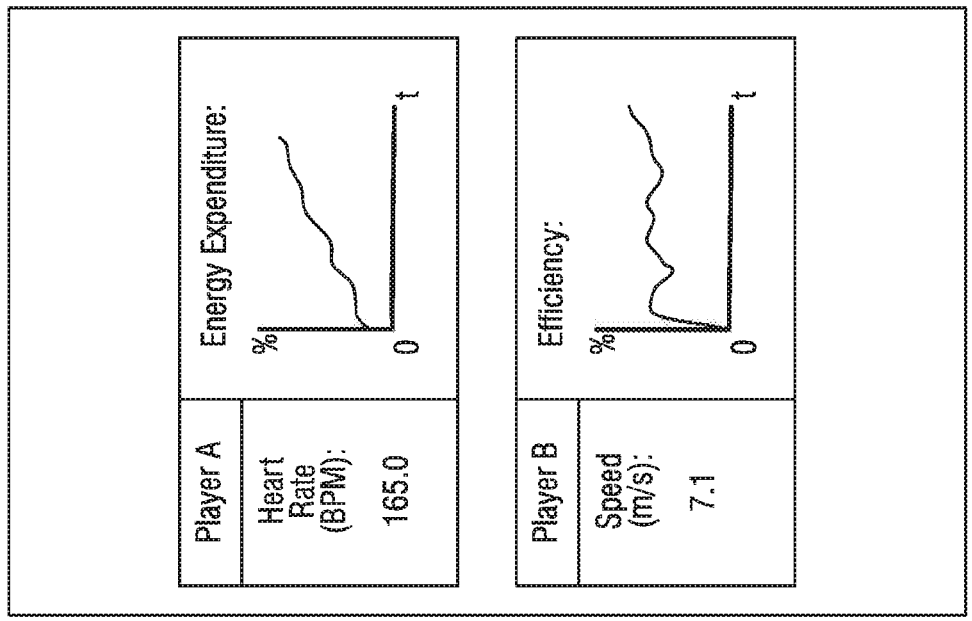
FIG. 15 depicts a display of a group monitoring device according to an exemplary embodiment of the present invention.

Display 402 functions to display representations of individual monitors 200, individuals 10, object monitors 250, and/or sports objects 40 (including, for example, identification information, attributes, metrics, and alerts) during participation in a session of athletic activity by individuals 10 and/or sports objects 40. The representations can take many forms, including, for example, charts (see FIGS. 13 and 14), dashboards (see FIG. 16), graphs (see FIG. 15), maps (see FIG. 16), colors, symbols, text, images, and icons.

Various representations capable of being displayed by display 402 are described in detail herein. For simplicity and clarity of explanation, many of the representations are described with reference to individuals 10, and may not refer to sports objects 40. Information relating to one or more sports objects 40 may be displayed in any of these representations, or in formats similar to any of these representations, similarly as described for individuals 10. Information (including metrics) relating to such sports objects 40 may be displayed separately from information relating to individuals 10, or may be displayed together with information relating to individuals 10. Displayed information relating to sports objects 40 may be of the same or a different type (e.g., a different metric) than that displayed for individuals 10, whether displayed separately or together.

Input 404 is an interface that allows a user, such as trainer 20, to manipulate the representations displayed by display 402. In a preferred embodiment input 404 is a touch-screen input. Input 404 may be, however, any other suitable input, such as, for example, a keyboard, a voice-recognition audio input, or push-button inputs. Input 404 may further include a combination of various types of inputs. Input 404 may be manipulated by trainer 20 to cause display 402 to show desired representations. The representations can update in real time during the athletic activity through the communication of group monitoring device 400 with base station 300, which is in turn in communication with individual monitors 200 worn by individuals 10 participating in the athletic activity and/or object monitors 250 carried by sports objects 40 used for the athletic activity, as described above.

In an exemplary embodiment, trainer 20 accesses group monitoring device 400 by inputting unique login credentials via input 404. Alternatively, trainer 20 accesses group monitoring device 400 without inputting login credentials. Upon accessing group monitoring device 400, trainer 20 may manipulate input 404 to use group monitoring device 400 to monitor individuals 10 and/or sports objects 40 in real time. Display 402 of group monitoring device 400 can be fully customizable, and different persons using different displays 402 may customize their displays differently. For example, different trainers may have different training philosophies and may desire to view training results in a ways unique to their training philosophy (e.g., with more emphasis on one metric or set thereof than another metric or set thereof). Group monitoring device 400 may be configured according to the specific needs or desires of the particular trainer using group monitoring display device 400. Further, a web dashboard (displayed by, for example, analysis device 600, a personal computer, or other analysis device, via, for example web server system 500 or base station 300) for a particular trainer 20 may be similarly configured to present the information or analysis in the way that the trainer 20 finds most useful. Multiple monitoring devices 400 can be used simultaneously by multiple trainers 20, and each can be customized independently from the others. Each of multiple monitoring devices 400 may monitor different individuals 10 and/or sports objects 40, or groups thereof. Each of multiple monitoring devices 400 may monitor and present different information and/or the same information in different formats. For example, representations of metrics (e.g., numerically or graphically) may be presented as absolute values (e.g., power output) or relative values (e.g., relative power output). Also for example, colors used to present metrics or other information may be selected by a user.

Each of multiple monitoring devices 400 may be customized to include different alerts and/or markers (as discussed further herein). Such customizability may allow each of a group of trainers 20 to focus on and monitor different aspects of individuals 10 and/or sports objects 40, or groups thereof. Each display feature described herein can be modified and/or included in a particular view of display 402 at the option of a user of display 402 (e.g., trainer 20). For ease of description, however, display 402 will be presented herein as representing a variety of different "dashboards", a dashboard being a visual representation of one or more elements. In some exemplary embodiments, dashboards can be defined as default views, which can then be used or modified at the option of the user. For example, a team view dashboard may represent information relating to each individual 10 on a team, as well as information relating to the team as a whole, while an individual view dashboard may represent information relating to a particular individual 10.

In an exemplary embodiment, display 402 of group monitoring device 400 shows a team view dashboard (see, for example, the exemplary display 402 of FIGS. 13, 17, 18, and 27-32, 33A, 33B, 34, 35A-35D, and 69-72). The team view dashboard may simultaneously display identification information and summary metrics for all individuals 10 presently participating in the monitored athletic activity, and/or all sports objects 40 presently being used for the monitored activity, or one or more groups thereof. The identification information may include individual name 406 and individual jersey number 408, or sports object type 417, for example. In some embodiments, a photograph 410 or other graphic of each individual 10 and/or sports objects 40 is also included as identification information (see, e.g., FIGS. 27, 28, 31, 32, and 33A). The summary metrics shown in the team view dashboard can be configured to be the metrics most applicable or most beneficial to trainer 20. In the exemplary display 402 of FIG. 13, present heart rate, speed, training load, and power are shown for each of Player A through Player H (Player A through Player H being individuals 10 presently participating in the monitored athletic activity), and speed is shown for a ball (the ball being the sports object 40 presently used for the monitored athletic activity). The metrics shown in FIG. 13 are shown as numerical values. Display of metrics is not limited to display of numerical values, however. Metrics may be represented in other suitable ways as would be appreciated by one of skill in the art, such as, for example, graphically (see, e.g., FIG. 15), or in map form (see, e.g., FIGS. 16 and 17).

In some embodiments, metrics may be displayed as relative values. For example, a present value for a metric may be displayed as a percentage of a value for that metric. For example, a value for a metric may be displayed as a percentage of a reference value for that metric. The reference value can vary for each individual 10 and/or sports object 40, and can be based on the personal ability of an associated individual 10. The reference value can be determined by experiment (e.g., via a calibration assessment activity), can be estimated, can be calculated, or can be otherwise determined.

For example, a relative power metric of an individual 10 may be expressed as a percentage value, which may represent the present power output of individual 10 as a percentage of a reference (e.g., maximum) power output of the individual 10. In some embodiments power output of individual 10 can be approximated based on movement of an upper torso of individual 10 (e.g., where an individual monitor 200 is positioned to the upper torso, and thus closely coupled to the individual 10's center of mass). Such approximation may not account for power output due to movement of limbs of individual 10 (i.e., it may only account for power output due to movement of the torso of individual 10), or other unknown factors, such as, for example, wind resistance and gait differences.

A relative power metric can compensate for such unknown and unaccounted-for factors, by determining a reference power output value based on a calibration assessment activity. During the calibration assessment activity, individual 10 participates in an athletic activity at a high level of intensity (or as otherwise directed), performing movements typical to the type of athletic activity to be subsequently monitored (or as otherwise directed). During this calibration assessment activity individual monitor 200 approximates the power output of movement of individual 10 (e.g., based on sensed movement of individual 10). A reference power output can be determined (e.g., after completion of the calibration assessment activity) based on the power output approximated during the activity (in some embodiments, in conjunction with other monitored metrics, such as, for example, heart rate).

The reference power output can be calculated by an algorithm with input of data from the calibration assessment activity, or can be selected by a person visually analyzing a representation of such approximated power output as a function of time (e.g., via group monitoring device 400). The reference power output may be selected as representative of the approximated power output of individual 10 during the calibration assessment activity, and can be based on approximated power output during a period of relatively stable power output (e.g., the mean approximated power output during such a period).

Relative power output of individual 10 can be determined as a measure of measured power output (approximated by individual monitor 200), relative to the reference power output determined during the calibration assessment activity. For example, relative power output of individual 10 can be calculated as power output measured (or approximated) by individual monitor 200, divided by the reference power output (and, in some embodiments, multiplied by 100 to express relative power output as a percentage value). Thus, relative power output of individual 10 can be expressed as the percentage power of the individual 10's reference power output that the individual 10 is currently delivering (or was delivering at the time of measurement). Because such unknown and unaccounted for factors as described above occur both during the calibration assessment activity and the monitored athletic activity, errors introduced into power output measurements thereby will substantially cancel out in a relative power calculation.

In some embodiments, a trainer 20 may run calibration assessment activities for multiple individuals 10, to establish a personalized reference power output for each individual 10. In this way, power output can be directly compared across multiple individuals 10 (e.g., relative power can be displayed for multiple individuals 10 simultaneously on, for example, display 402 of group monitoring device 400). Relative power for multiple individuals 10 can be displayed to trainer 20 (e.g., via group monitoring device 400) to facilitate such comparison.

Relative metrics may assist trainer 20 in understanding the intensity of an individual 10's performance. For example, two individuals 10 of very different fitness levels may have very different power outputs in absolute terms, even where both individuals 10 are working at similar intensities. Thus, a representation of absolute power outputs would not necessarily convey the intensity at which individuals 10 are working. But a representation of relative power outputs would, being that relative power output is normalized for each individual. Representations of relative power outputs for each individual 10 can act as a normalization on absolute power output for each individual, to convey to a trainer 20 how hard monitored individuals 10 are working comparatively.

In some embodiments, a trainer may monitor multiple individuals 10 using a common training plan, where the common training plan is based on relative metrics. By being based on relative metrics, training targets (e.g., of the common training plan) may be effectively normalized over multiple individuals 10, allowing meaningful evaluation of multiple individuals 10 of differing personal abilities under the common training plan.

In some embodiments, a personal training plan may be developed for a first individual 10 based on relative metrics. Because the personal training plan is based on relative metrics, it can be applied to a second individual 10 without need for adjustment. For example, a personalized training plan may be developed for a famous athlete, based on relative metrics. A fan of that athlete can perform the same training plan, even if he is not as physically capable as the famous athlete, because the plan will be normalized to his abilities by use of his own relative metrics. Such a plan can be scheduled into group monitoring system 100 as described herein.

In some embodiments, training recommendations or automatic training plan adjustments may be provided via an administrative device, which may be a device such as, for example, group monitoring device 400 or analysis device 600. During or after an athletic performance, data relating to the performance may be analyzed by one or more system components of group monitoring system 100 (such data may be analyzed for a single individual 10 or for multiple individuals 10 as a group). In analyzing the performance data, group monitoring system 100 may identify an area for improvement (e.g., a weakness) in performance. Such a weakness may be, for example, a metric for an individual 10 that is more than a threshold amount lower than an average for that metric among individual 10's teammates, or a metric for a team of individuals 10 that is improving at a lower rate than other metrics for the team. Group monitoring system 100 may determine training recommendations to address the identified area for improvement based on such analysis. In some embodiments, training recommendations are based on data from individual monitors 200 only, from object monitors 250 only, or from both individual monitors 200 and object monitors 250.

In some embodiments, group monitoring device 400 may display a representation of such training recommendation. In some embodiments, where a training plan is established in association with group monitoring system 100, group monitoring system 100 may compare the training plan (for the relevant individual 10 or group) with the training recommendation. If the training plan does not include training of the training recommendation, group monitoring system may recommend or automatically adjust the training plan based on such analysis, to include training of the training recommendation. In some embodiments, where a training plan is not established in association with group monitoring system 100, group monitoring system 100 may recommend or automatically establish a training plan (for the relevant individual 10 or group) with the training recommendation.

For example, where analyzed metrics or alerts indicate sub-optimal running-related performance by an individual 10 or group of individuals 10 (e.g., a number of alerts above a threshold number), a training recommendation to provide more or different running training may be provided, or a training plan may be automatically established or adjusted to include more or different running-related drills. Also for example, where analyzed metrics or alerts indicate sub-optimal energy output by an individual 10 or group of individuals 10, a training recommendation to eat particular energy-providing foods may be provided, or a diet plan may be automatically established or adjusted to include particular energy-providing foods. Also for example, where analyzed metrics or alerts indicate sub-optimal fatigue tolerance by an individual 10 or group of individuals 10, a training recommendation to sleep at a particular time or for a particular amount of time may be provided, or a sleep plan may be automatically established or adjusted to include a particular time or for a particular amount of time for sleep. Also for example, a training recommendation to adjust a technique for performing an athletic act (e.g., a kick of a ball, a swing of a bat) may be provided based on analyzed metrics or alerts relating to a previous act by individual 10 (e.g., to achieve greater distance, height, or speed of the kicked ball; or to achieve more consistent contact with a ball with a swing of the bat).

In some embodiments, training plans can be exported, sold, or shared (e.g., using secondary servers as described herein). In this way, an individual 10 may acquire, for example, a training plan used by a famous athlete or sports team, a training plan tailored to improve a weakness of the individual 10, a training plan tailored to the position played by the individual 10, or a training plan tailored to a particular training philosophy (e.g., training in the mornings, training in warm weather, or training in sunshine).

Further, sharing of plans among coaches, trainers, physicians, and other interested parties of a given team can facilitate collaboration and development of comprehensive training strategies. For example, the group monitoring system 100 may enable coaches and trainers to analyze and prepare reports based on the data they collect from one or more training sessions. (Such data may include, for example, customized metrics and performance alerts created by the coach or trainer.) This may allow the coach or trainer to quickly and easily share the reports of each session with other coaches or trainers, to receive reports from other coaches or trainers, and to plan for the next session based on the reports. The reports may be tailored to provide a custom analysis to support each coach or trainer's philosophy for training, and may be provided via, for example, a web system (e.g., web server system 500).

In some embodiments, group monitoring device 400 may provide real-time analysis and summary reports during training that help trainers 20 respond in real time to characteristics of individuals 10 and/or sports objects 40. Trainers 20 may compare individual metrics with those of the rest of the team. This feedback can help trainers 20 motivate individuals 10, or even other trainers.

In some embodiments, a relative metric may be incorporated into an efficiency metric. For example, an efficiency metric may be based on relative power of an individual 10 in comparison to heart rate of the individual 10 (e.g., a relative heart rate, determined similarly as described above for relative power output), to determine a measure of individual 10's relative power as a function of relative heart rate, which can be considered a measure of the efficiency of individual 10.

Figure 27:
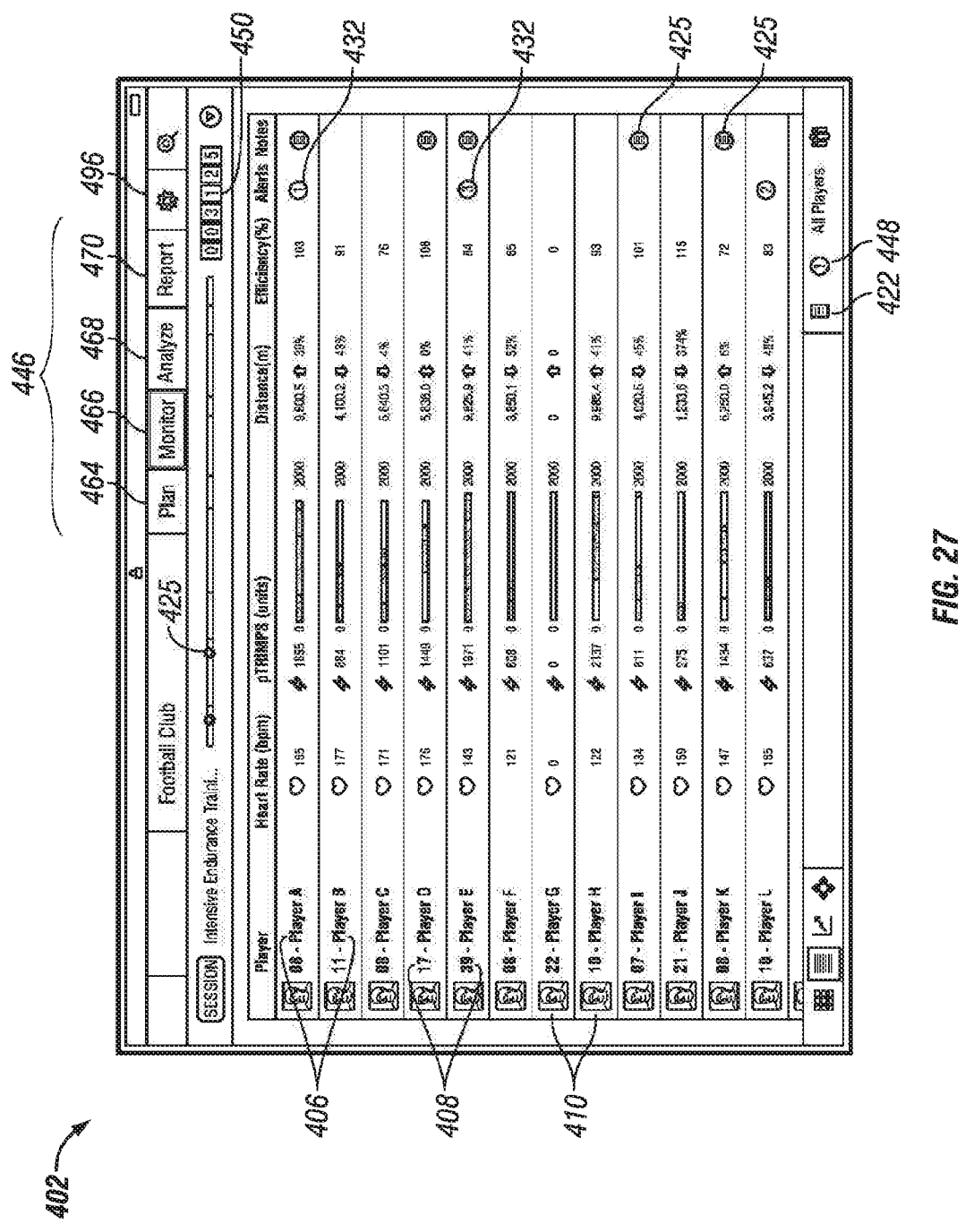

In some exemplary embodiments, for example, display 402 of FIG. 27, heart rate, power, distance, and efficiency are shown for each of Player A through Player L, with these values for additional players available to be viewed by scrolling down past Player L. Also shown for each of Player A through Player L are fields for alerts (e.g., performance alerts) and notes. In some exemplary embodiments, as depicted in, for example, FIGS. 27 and 31, note icons 425 and alert icons 432 may indicate the presence of notes or alerts. Selection of such note icons 425 and alert icons 432 may trigger display of additional information related to an associated note or icon. For example, the team view dashboard of FIG. 27 indicates that player A has 1 alert, Player E has 3 alerts, and Player L has 2 alerts, and that each of Players A, D, E, I, and K have notes associated with their entries. Such notes and alerts are described in greater detail herein. Such notes and alerts may be displayed similarly for sports object 40.

In some exemplary embodiments, display 402 displays a subset of all monitored individuals 10. In this way trainer 20 can focus on particular individuals 10. In some exemplary embodiments, the subset of individuals 10 displayed can be defined by trainer 20, and display 402 can include a selection feature, for example, selection feature 428 of FIGS. 28 and 29, that allows trainer 20 to select to include or not include particular individuals 10 in the viewable subset.

Additionally or alternatively, the team view dashboard may show group summary metrics for groups of individuals 10 participating in the monitored athletic activity. The group summary metrics may be averages of the corresponding metrics for each individual 10 belonging to the group, or the group summary metrics may be calculated using an independent algorithm designed to reflect a desired attribute of the group as a whole. In the exemplary display 402 of FIG. 13, present average heart rate, speed, training load, and power are shown for the team (i.e., Player A through Player H), and for a group including a sub-set of the team (i.e., Player A, Player C, and Player E). The values for heart rate, speed, training load, and power may update in real time during the athletic activity so as to reflect present values.

Team view dashboard is not limited to display of heart rate, speed, training load, and power, and is not limited to the display of 4 metrics. Team view dashboard can be customized to display those metrics most applicable or most beneficial to trainer 20, and may display, for example 3 to 5 distinct metrics for each individual 10 and/or sports objects 40. In some exemplary embodiments the metrics displayed can be set prior to the athletic activity during a setup procedure. In some exemplary embodiments the metrics displayed can be changed during the athletic activity by manipulation of input 404.

In some exemplary embodiments, for example, display 402 of FIGS. 69-72, relative metrics of a plurality of individuals 10 may be displayed. For example, in the embodiments of FIGS. 69-72, relative power and relative heart rate are displayed in chart 411 for a plurality of individuals 10. Also in the embodiments of FIGS. 69-72, efficiency of individuals 10 is displayed. Efficiency is represented by the overlay comparison of relative heart rate and relative power output in the same chart 411, which conveys a measure of the difference between relative heart rate and relative power output for each individual 10.

A particular metric of the displayed metrics in team dashboard view may be designated as a featured metric 414, which may be displayed with emphasis relative to other metrics. A featured metric may be independently designated (e.g., by trainer 20) for an individual 10, or for a group of individuals 10. Featured metric 414 may be displayed more prominently or in greater detail than other metrics, in order to allow trainer 20 to easily get an at-a-glance view of the featured metric across all individuals 10 participating in the athletic activity. In some exemplary embodiments featured metric 414 may be changed during monitoring of the athletic activity to any available metric, by appropriate manipulation of input 404 (e.g., selecting the metric desired to be featured, such as by selecting one of featured metric options 430 shown in, for example, FIG. 30). In some exemplary embodiments trainer 20 can toggle back and forth between featured metric views.

Featured metric 414 may be featured in a variety of ways. For example, it may be displayed in a color (or with a background color) different from that of the other displayed metrics, it may be displayed larger than the other metrics, it may flash or blink, it may include a larger background area than that of other metrics, it may be positioned closest to the identification information of individuals 10, it may include a status bar, chart, or graph (e.g., status bar 462), or it may exhibit a combination of these or other characteristics. In the exemplary display 402 of FIG. 13, heart rate is featured by including a larger background area than that of the other metrics and by being positioned closest to the identification information of individuals 10. In the exemplary display 402 of FIG. 27, power is featured by including a status bar next to the power entry for each individual 10. In the exemplary display of FIGS. 30 and 32, power is further featured by additionally displaying a value representing power larger than other values. In the exemplary display 402 of FIG. 31, heart rate is featured by including a status bar and by presenting a value representing heart rate larger than other values.

Some exemplary embodiments may, if alerts have been established (e.g., performance alerts for a metric of an individual 10, or system alerts for a system component), include an indication of whether a value of the metric or status is within particular zones relative to the alert parameters. For example, a color of the background area of the metric or status may change, or an icon may appear, based on, for example, whether the value is within or outside the zone, or on the proximity of the value to a threshold. In an exemplary embodiment where an alert is established for maintaining a heart rate of 85% of maximum or higher for 10 minutes or more, when a value of the heart rate of individual 10 is at 85% of maximum or higher, the background of the area containing the heart rate value of individual 10 is green, and when the heart rate has been at 85% of maximum or higher for 10 minutes or more, a star icon appears in the area containing the heart rate value of individual 10, and an audio sound is played by a speaker of group monitoring device 400. In some exemplary embodiments, as shown in, for example, FIGS. 31-33A, an indication that an alert has been triggered can be provided by a change in color of the area around the name of an associated individual 10, and a circle or other alert icon 432 representing the alert can be presented indicating the presence and/or number of alerts that are associated with the individual 10. The change in color may be maintained as long as an alert is active, or may change at the triggering of the alert, and fade or change back to its original color after a period of time. In some exemplary embodiments, individual monitors 200 can provide indication of an alert to an associated individual 10 via, for example, emitting an audible noise (e.g., via a speaker), vibrating, or providing a visual indication (e.g., via an LED or LCD display).

Figure 33A:
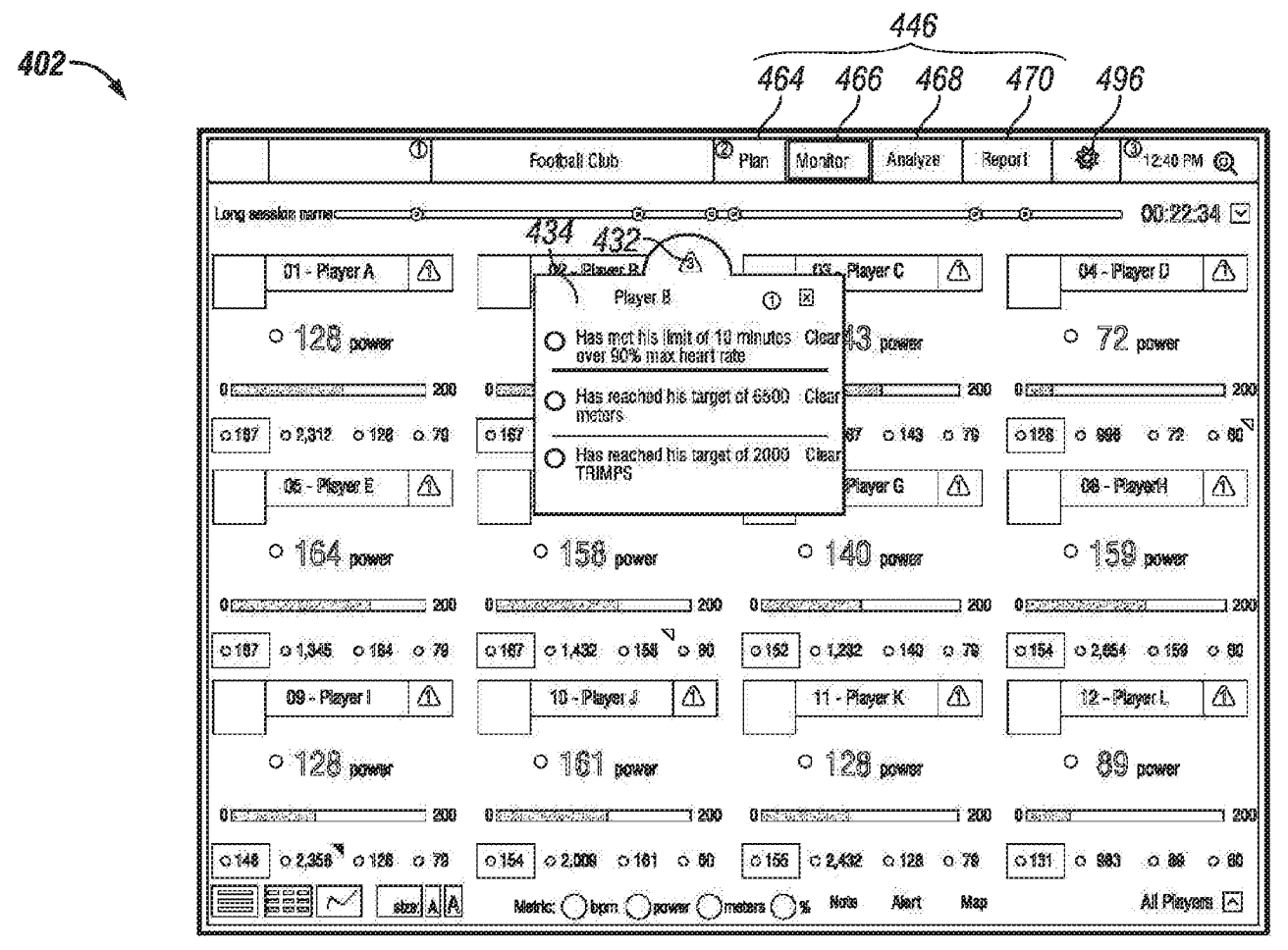
Figure 33B:
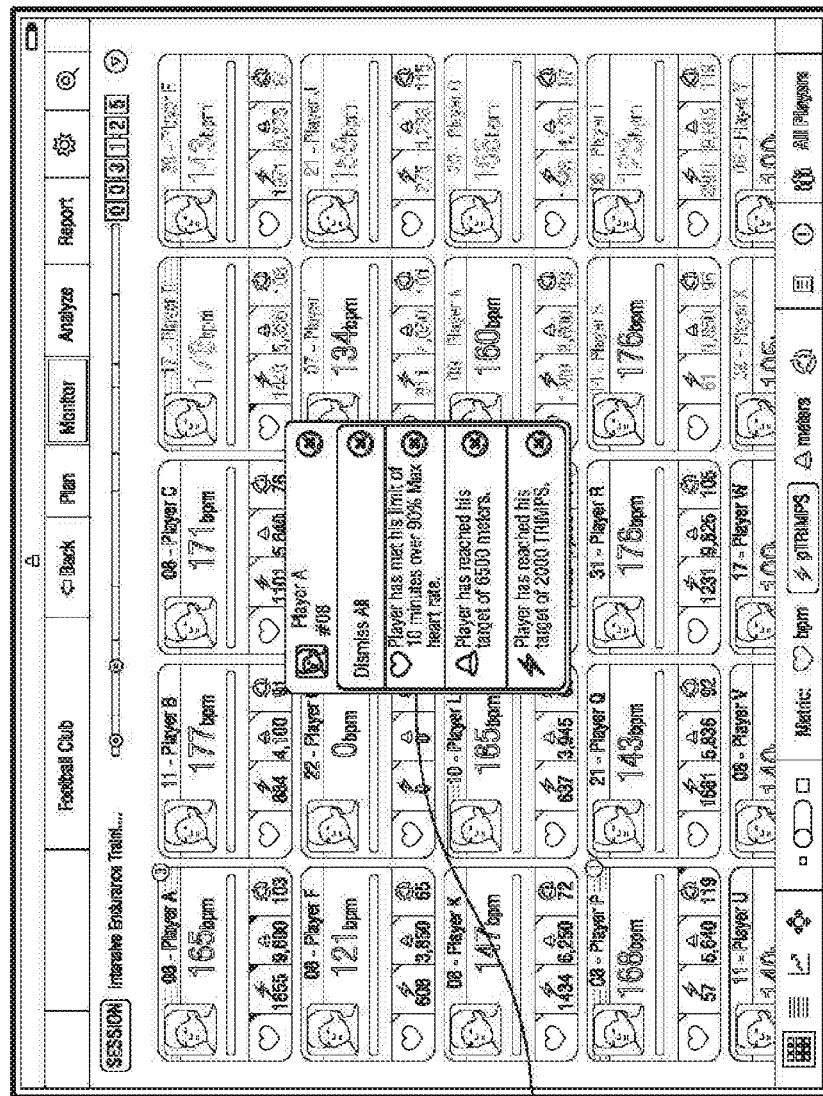
FIG. 33B depicts a display of a group monitoring device according to an exemplary embodiment of the present invention.
Figure 34:
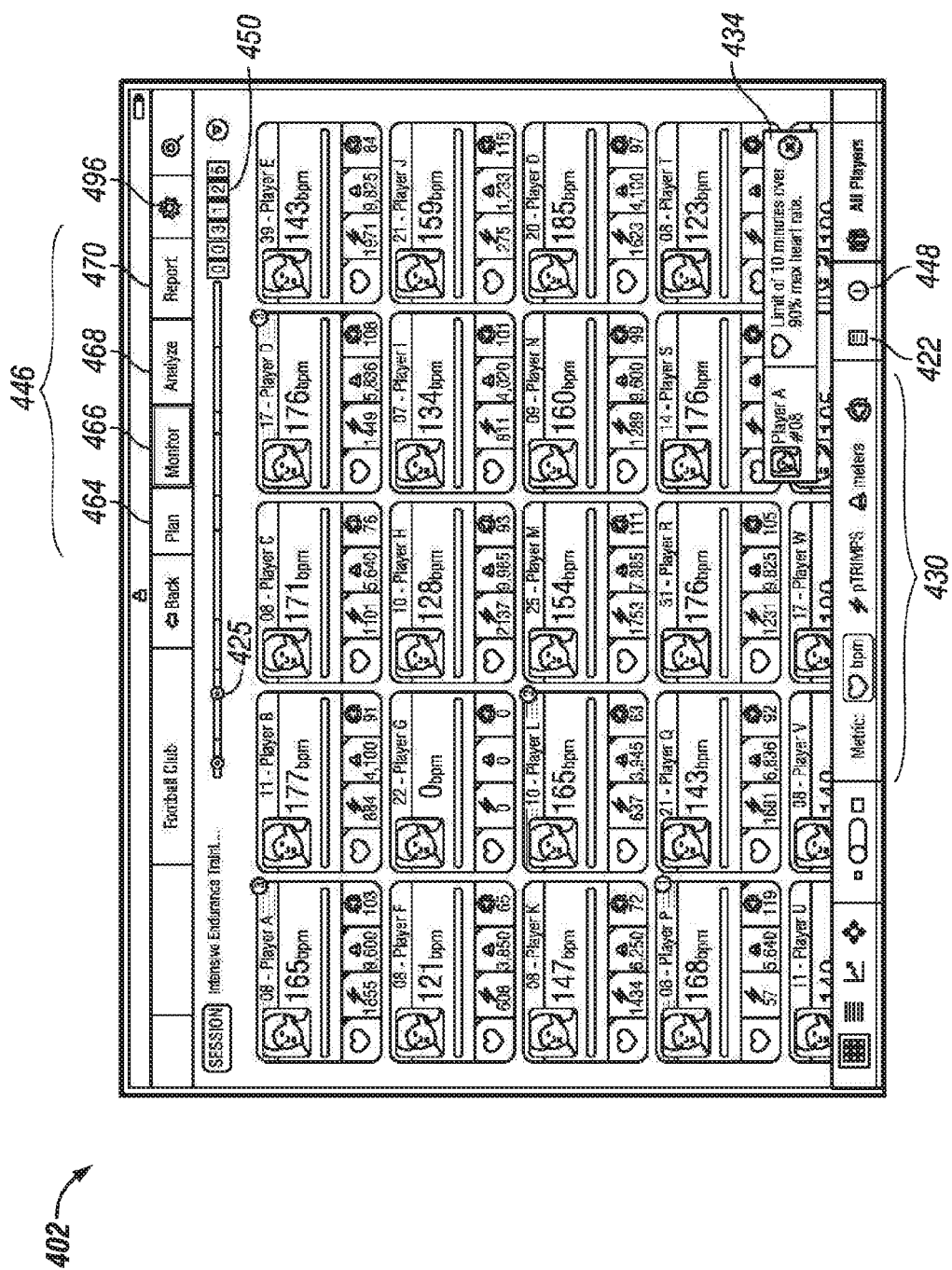
FIG. 34 depicts a display of a group monitoring device according to an exemplary embodiment of the present invention.

In some exemplary embodiments, if an alert is triggered, trainer 20 can select a representation of the alert to thereby access more information about the alert, as shown in, for example, FIGS. 33A and 34. In some exemplary embodiments, selecting the representation of the alert leads to a detailed chart view of the metric that triggered the alert. In some exemplary embodiments, display 402 may display all active alerts, at a point or period in time, for all monitored individuals 10 or subsets thereof. In some exemplary embodiments, new alerts can be indicated by, for example, a flashing icon or a temporary pop-up box 434 showing information relating to the new alert, as is shown in the exemplary embodiments of FIGS. 33A, 33B, 34, and 35A-35D, for example.

Figure 65:
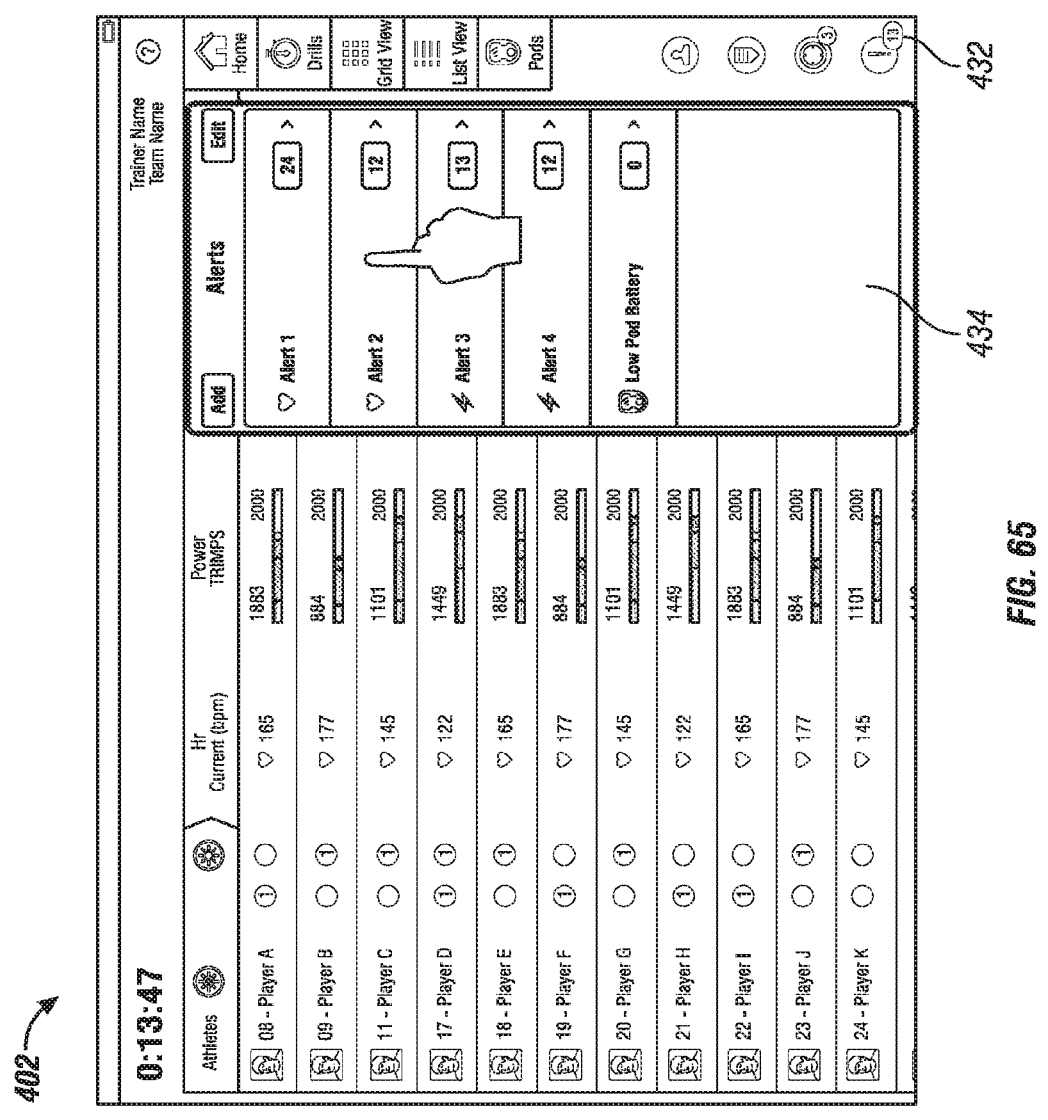
Figure 66:
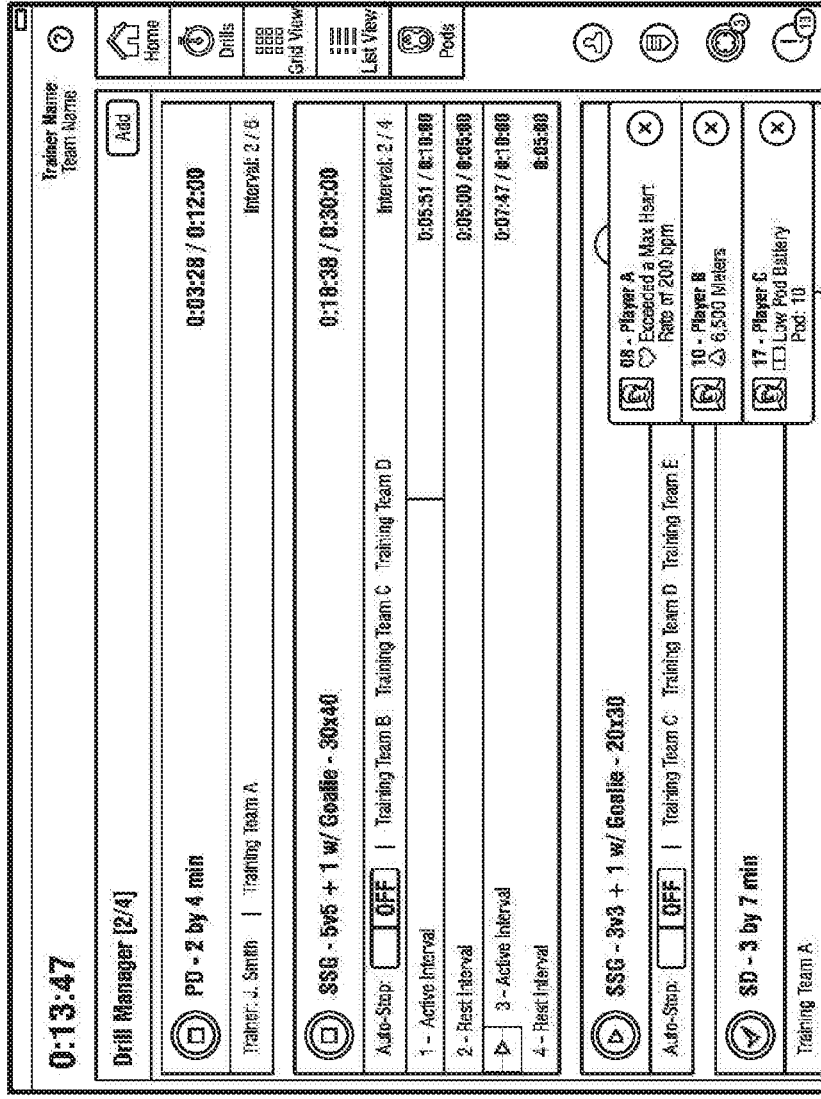
FIG. 66 depicts a display of a group monitoring device according to an exemplary embodiment of the present invention.

In some exemplary embodiments, pop-up box 434 includes information about a single alert (e.g., FIG. 33A). In some exemplary embodiments, pop-up box 434 includes information about multiple alerts (e.g., FIGS. 33B, 65, 66). The multiple alerts can be displayed according to any suitable criteria. For example, the multiple alerts may be active alerts related to a particular or group of individual monitors 200, individuals 10, object monitors 250, and/or sports objects 40, may be all active alerts, or may be alerts triggered within some time period prior to the present time. In some exemplary embodiments, pop-up box 434 indicates the presence and/or number of alerts triggered. This number may include, for example, all active alerts, all unviewed alerts, or the number of alerts triggered within some time period prior to the present time (e.g., FIGS. 35C, 65). In some exemplary embodiments, a pop-up box 434 indicating the number of alerts triggered appears in the place of a pop-up box 434 including additional alert information when the number of alerts to be displayed is above some threshold number.

Figure 35A:
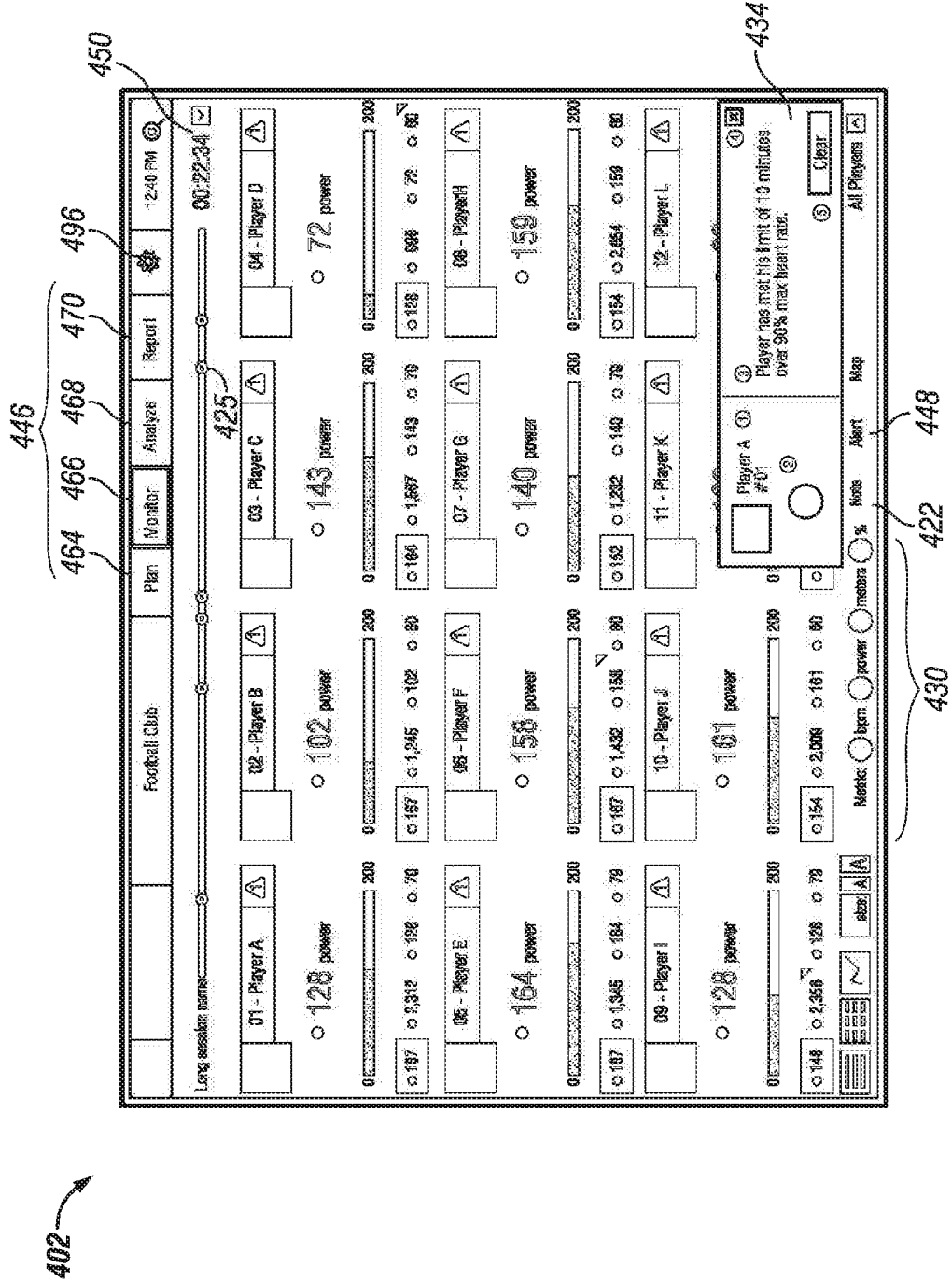
FIG. 35A depicts a display of a group monitoring device according to an exemplary embodiment of the present invention.
Figure 35B:
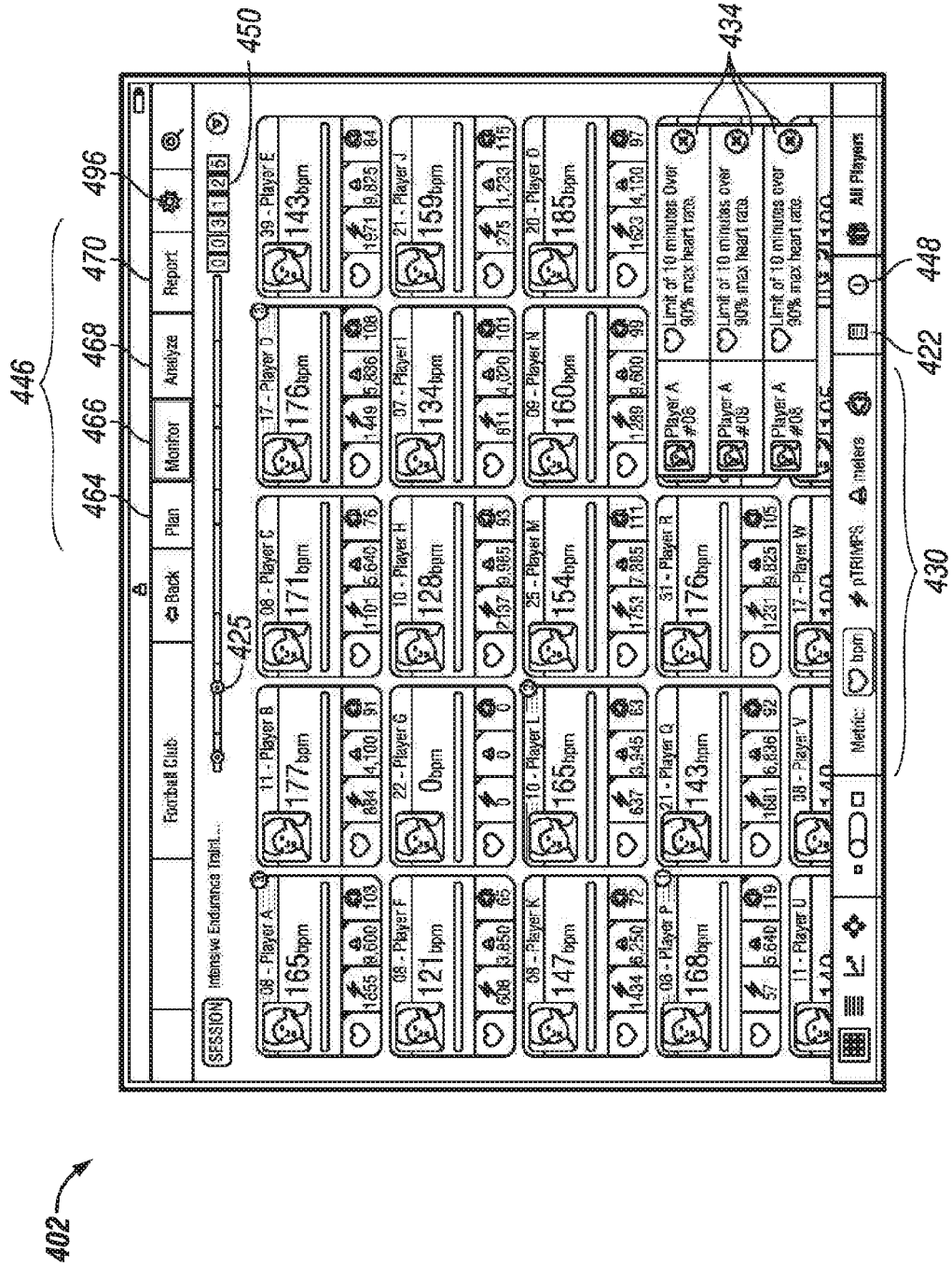
FIG. 35B depicts a display of a group monitoring device according to an exemplary embodiment of the present invention.
Figure 35C:
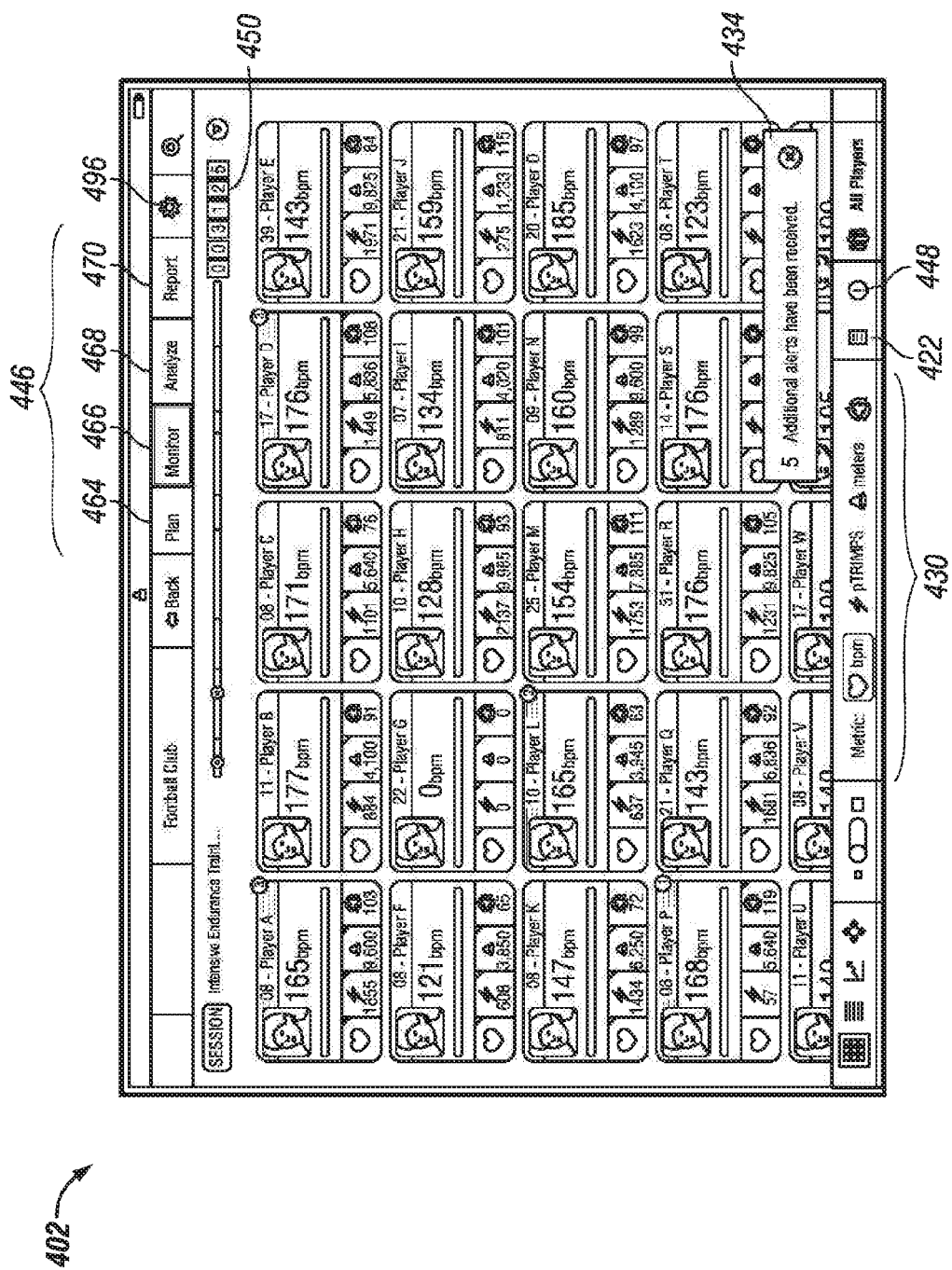
FIG. 35C depicts a display of a group monitoring device according to an exemplary embodiment of the present invention.
Figure 35D:
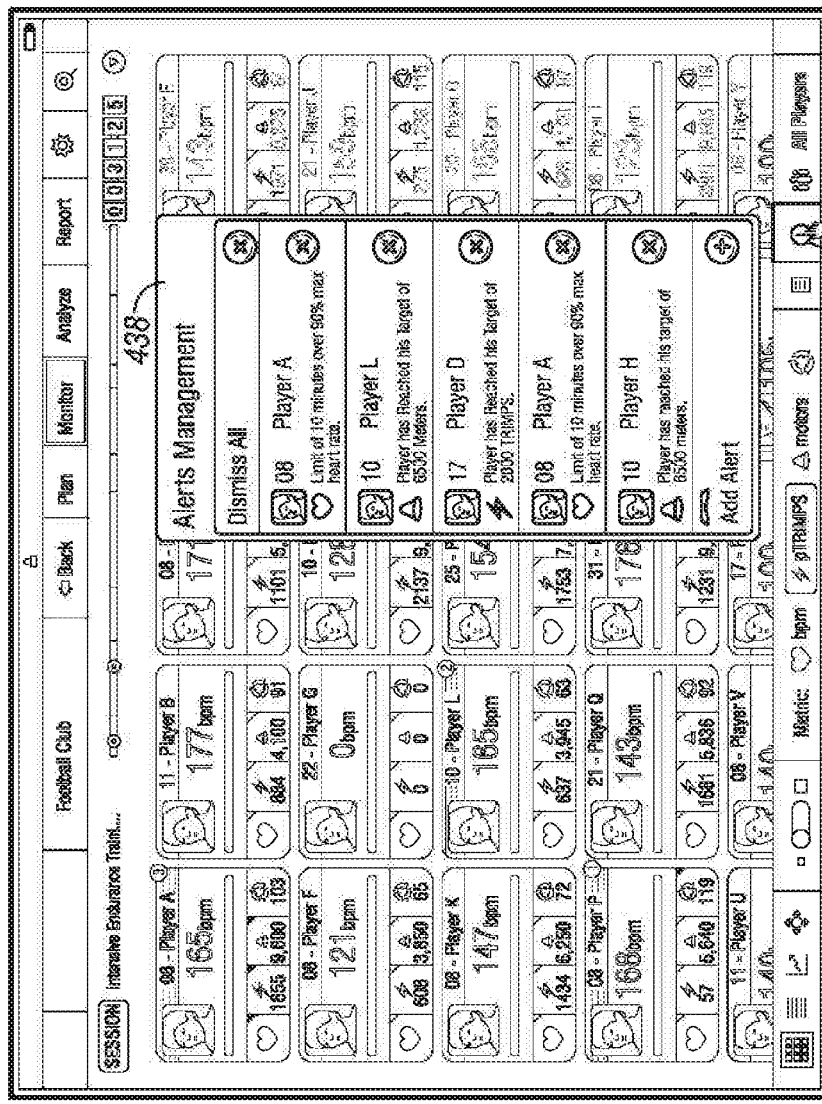
FIG. 35D depicts a display of a group monitoring device according to an exemplary embodiment of the present invention.
Figure 36A:
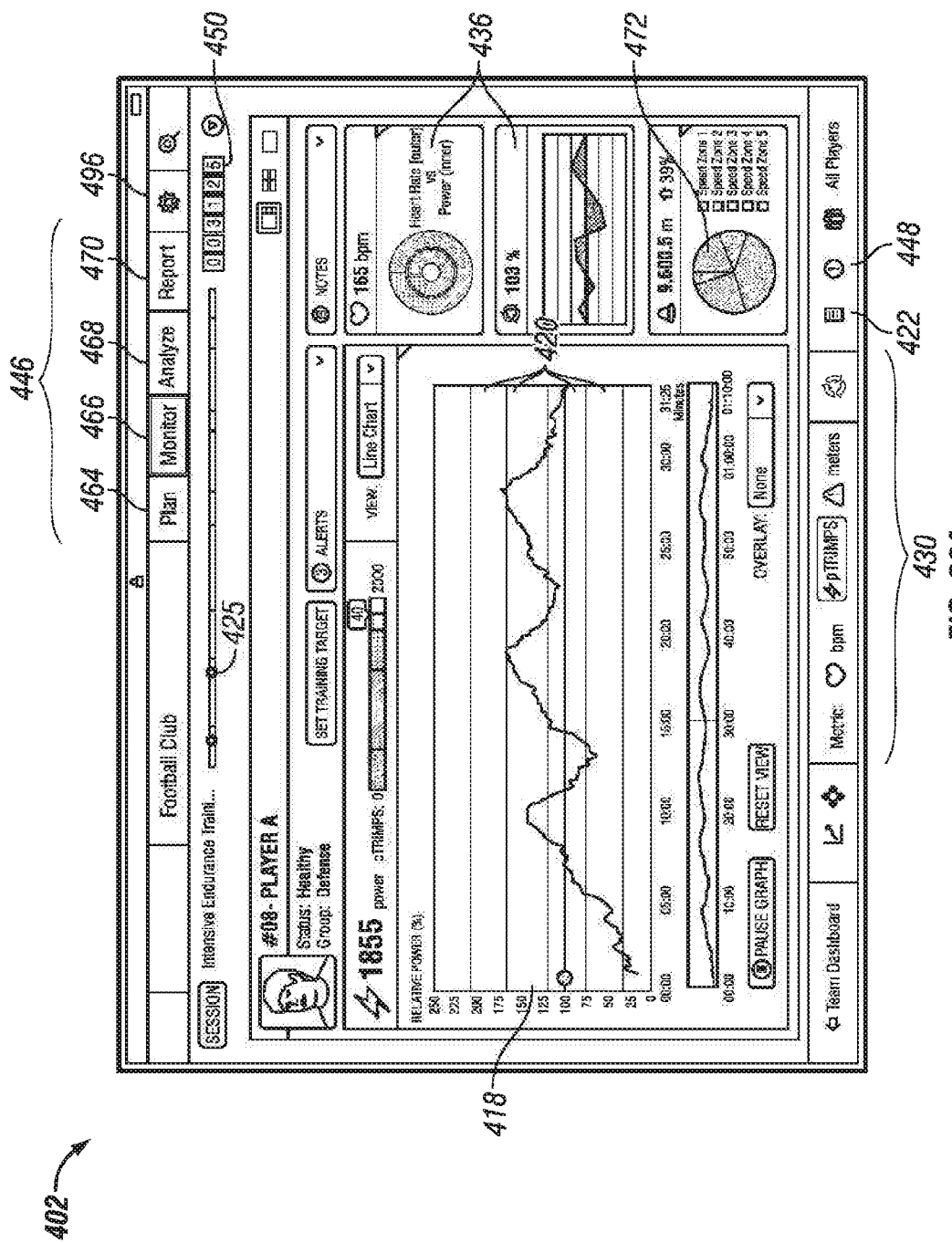
FIG. 36A depicts a display of a group monitoring device according to an exemplary embodiment of the present invention.
Figure 36B:
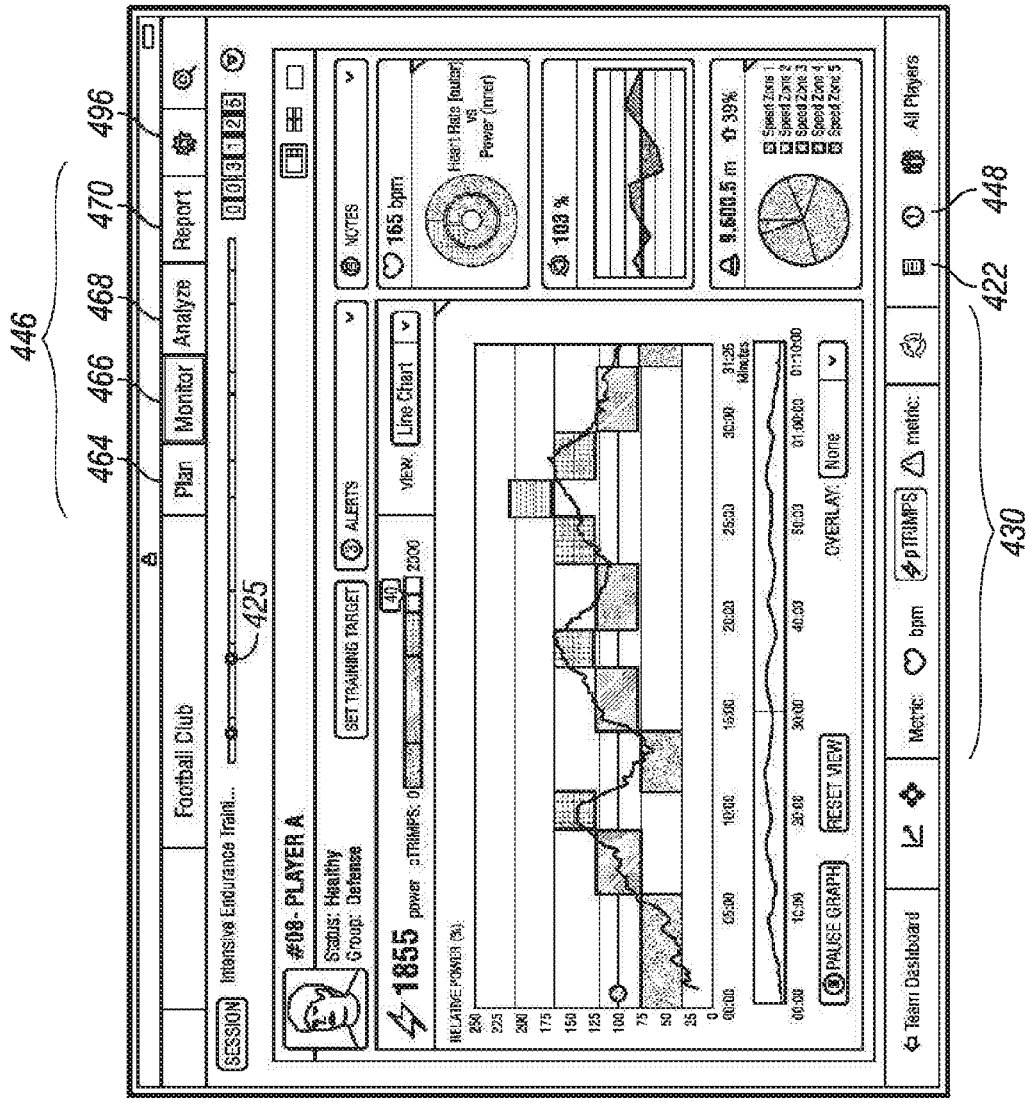
FIG. 36B depicts a display of a group monitoring device according to an exemplary embodiment of the present invention.
Figure 37A:
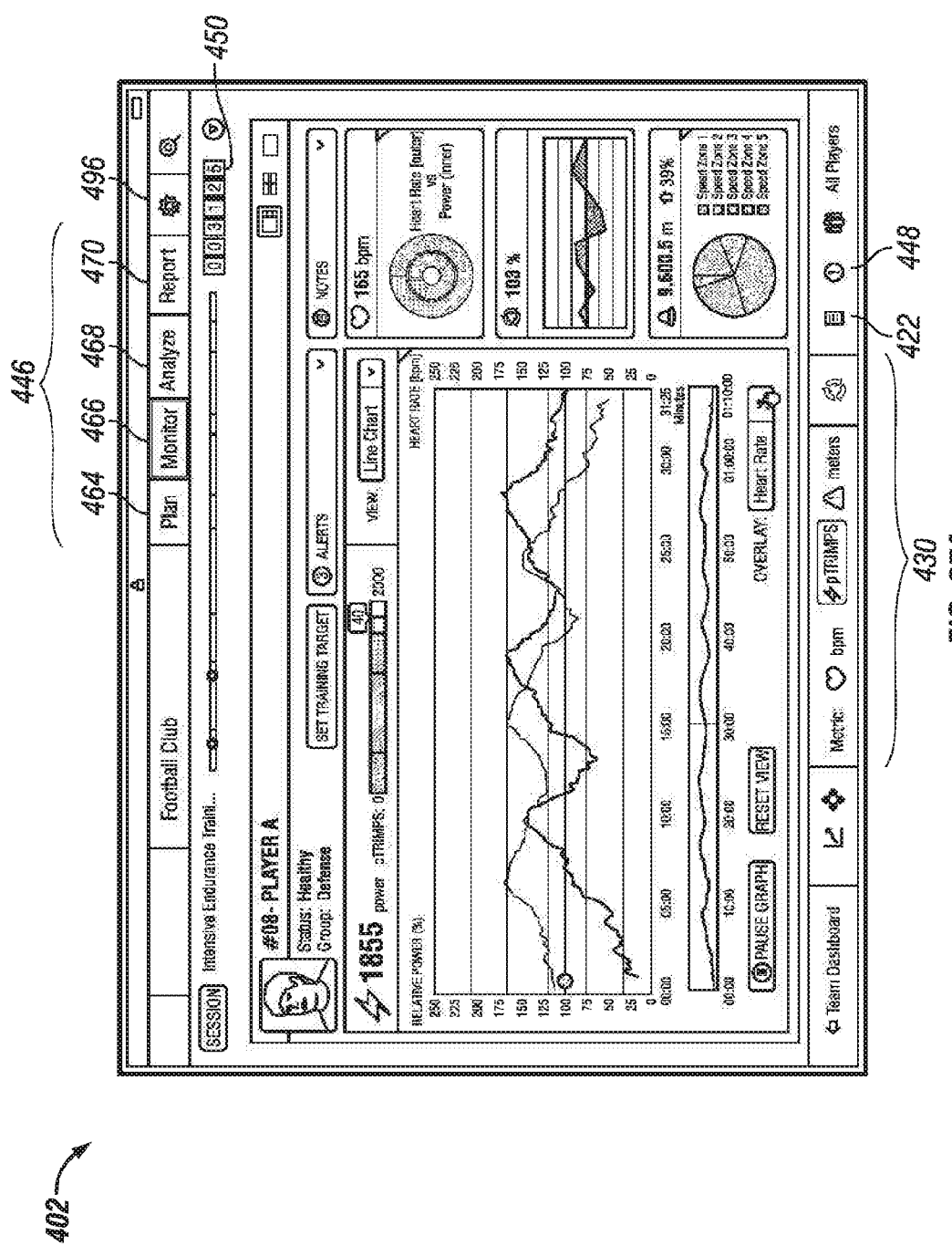
FIG. 37A depicts a display of a group monitoring device according to an exemplary embodiment of the present invention.
Figure 37B:
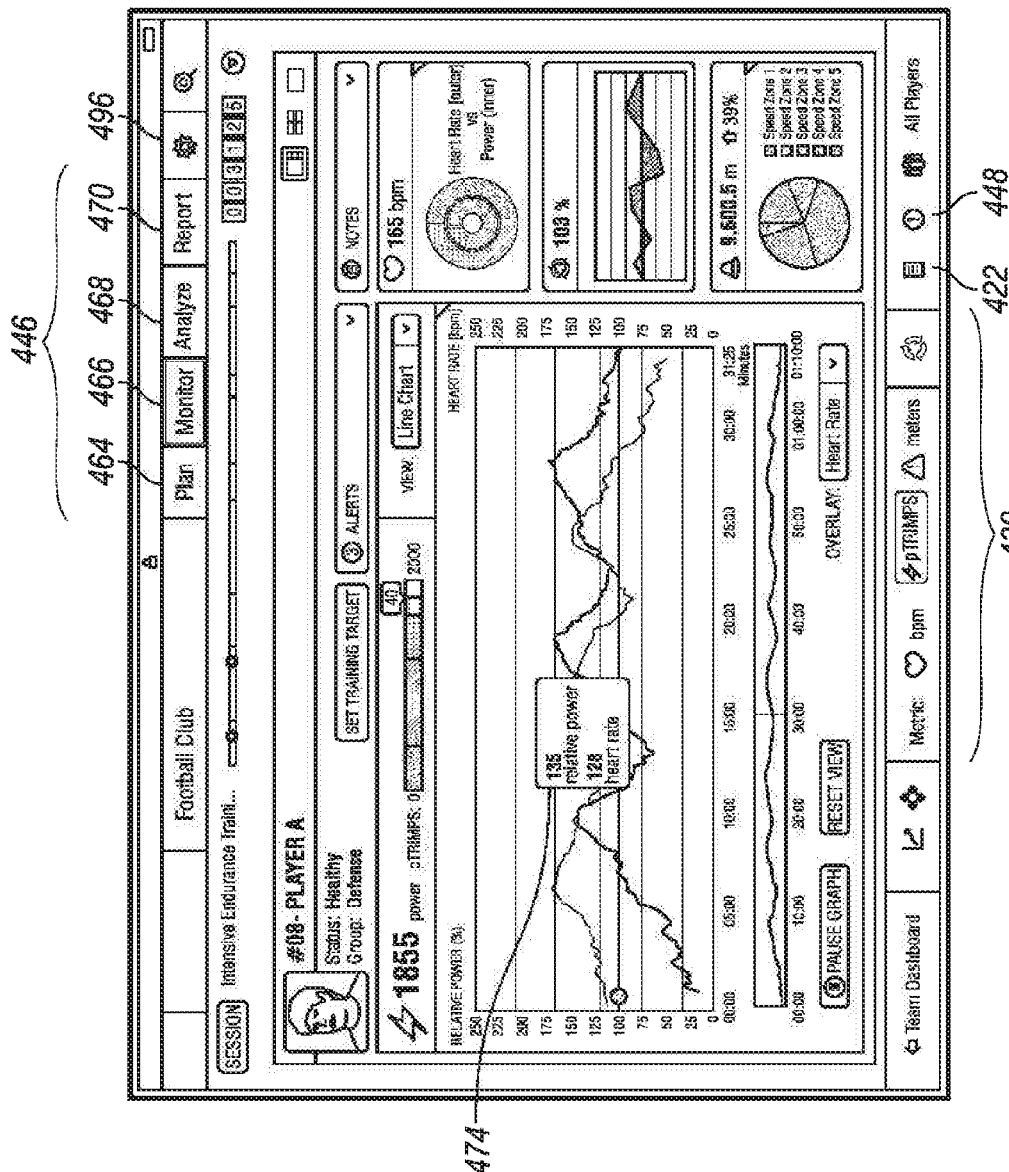
FIG. 37B depicts a display of a group monitoring device according to an exemplary embodiment of the present invention.
Figure 38:
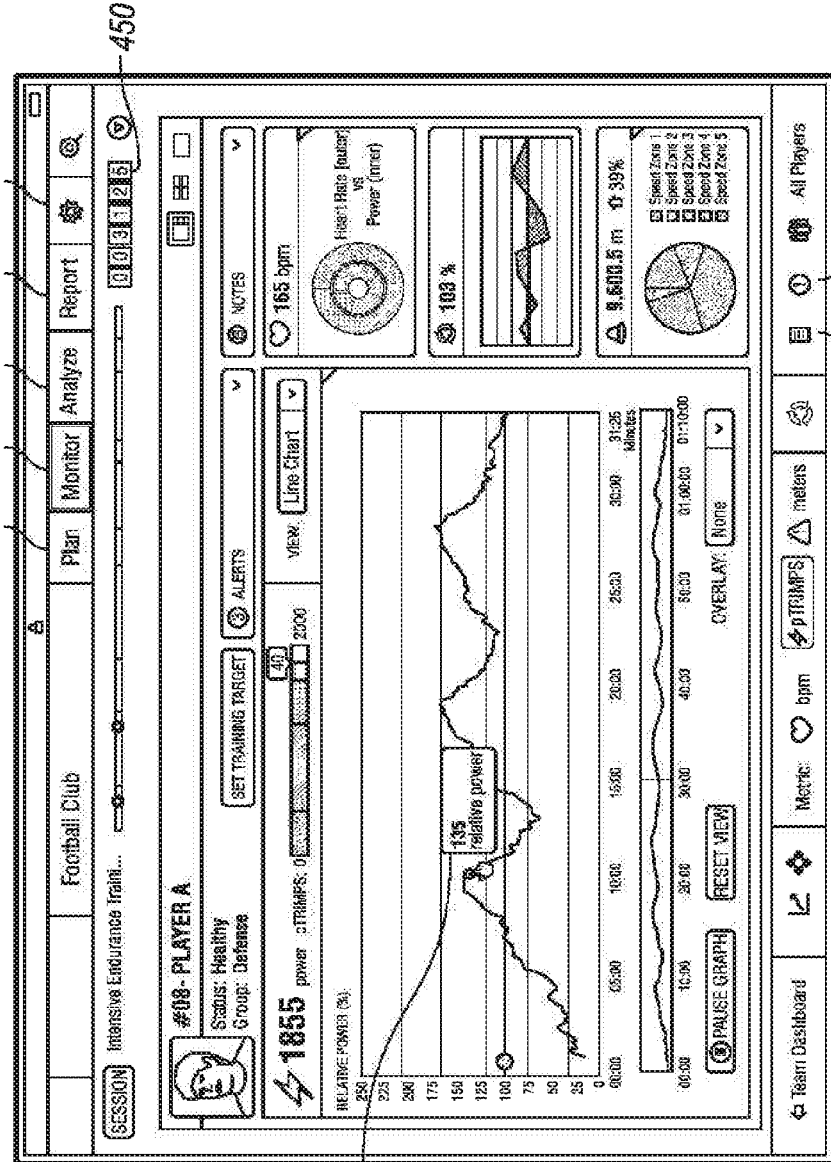
FIG. 38 depicts a display of a group monitoring device according to an exemplary embodiment of the present invention.
Figure 39:
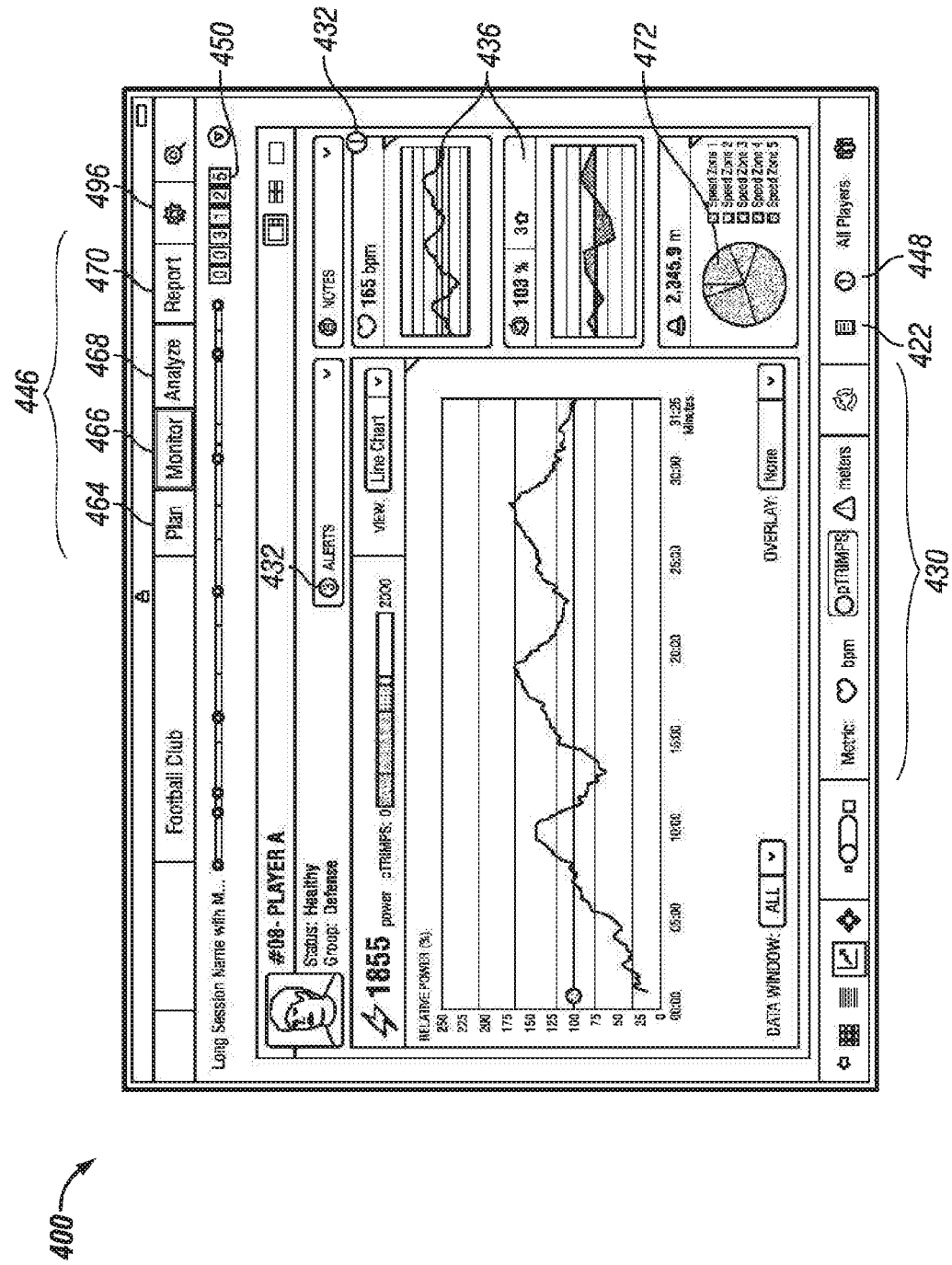
FIG. 39 depicts a display of a group monitoring device according to an exemplary embodiment of the present invention.

In some exemplary embodiments, an alert management window 438 can be displayed in response to selection of an alert management icon 448, as depicted in, for example, FIG. 35D. Alert management window 438 may include information about all active alerts or a subset thereof, and may allow dismissal or acknowledgement of such alerts.

Figure 19:
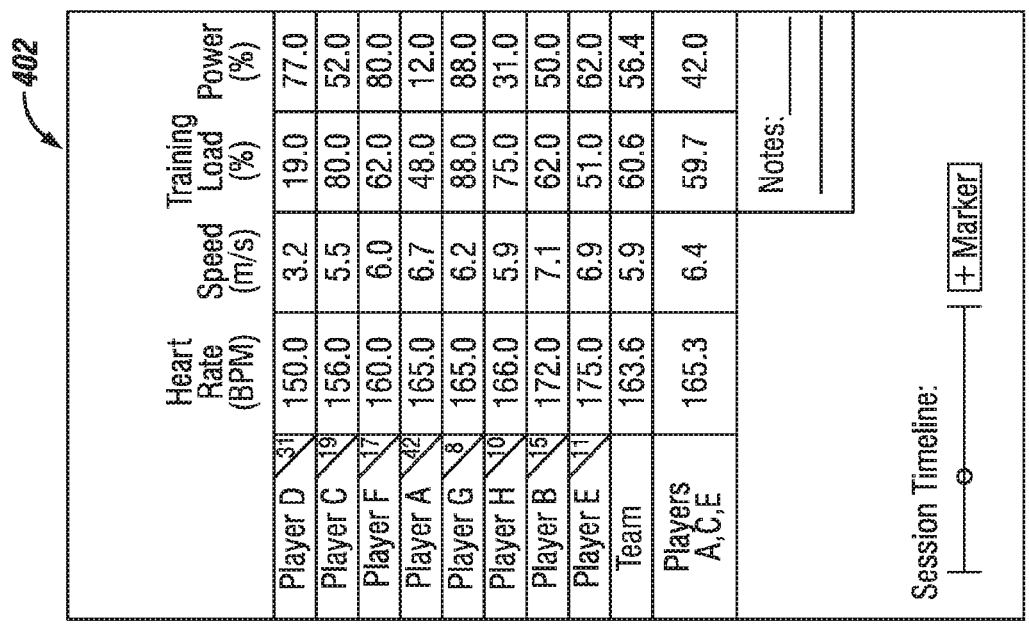
FIG. 19 depicts a display of a group monitoring device according to an exemplary embodiment of the present invention.
Figure 21:
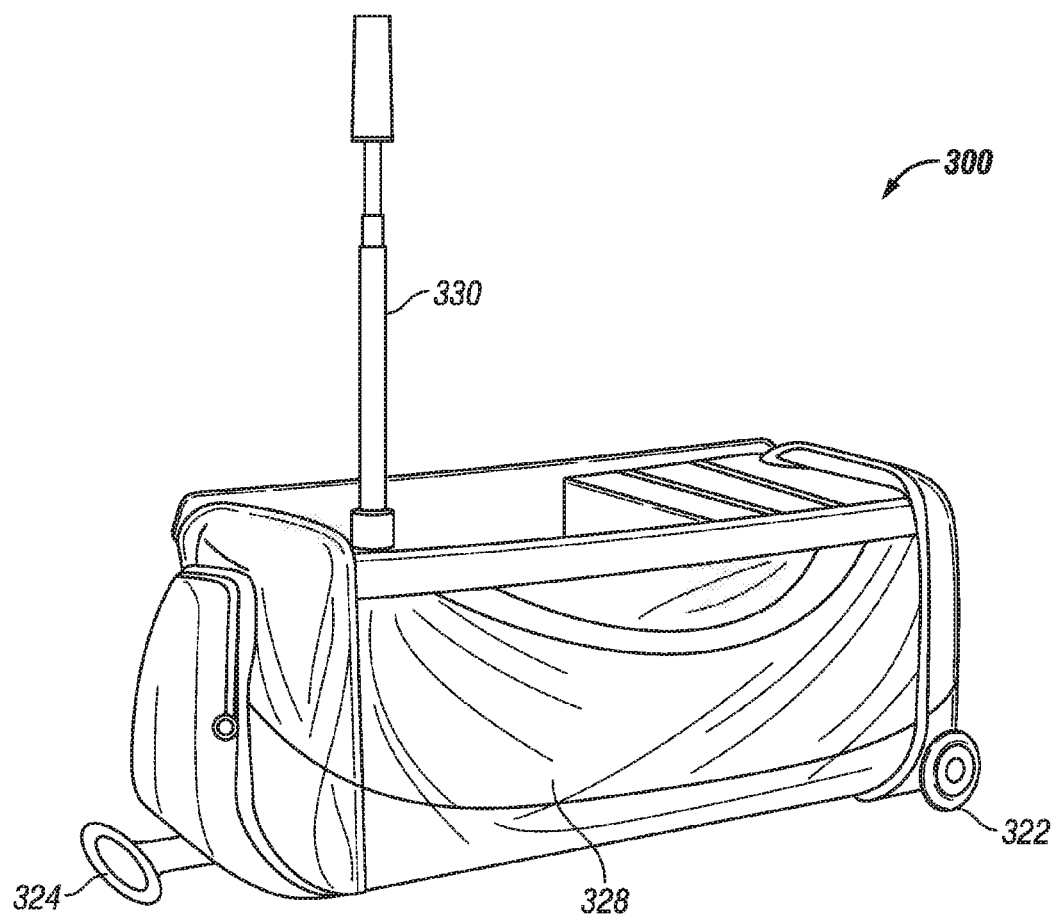
FIG. 21 depicts a base station according to an exemplary embodiment of the present invention.
Figure 22:
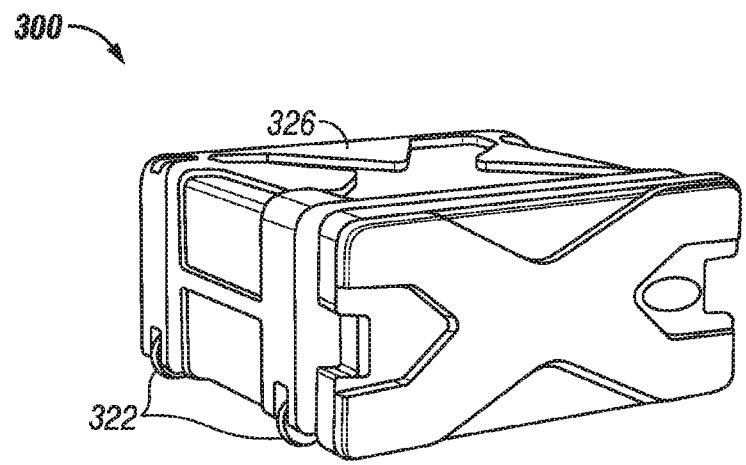
FIG. 22 depicts a base station according to an exemplary embodiment of the present invention.

In some exemplary embodiments, the team view dashboard is sortable in real time. Trainer 20 may manipulate input 404 so as to cause display 402 to show information for individuals 10 sorted by a desired metric. For example, trainer 20 may select a displayed heart rate metric (by, for example, selecting the metric label or a sort icon associated with the metric), and the information for individuals 10 may be rearranged so as to be represented in ascending or descending order. For example, FIG. 19 shows individuals 10 rearranged from the individual 10 with the lowest heart rate to the individual 10 with the highest heart rate. Further selections of the heart rate metric may cause the information for individuals 10 to change from ascending to descending representations, and vice versa. In some exemplary embodiments, trainer 20 may similarly sort by, for example, name 406, position in space (e.g., location on the field or court), position on team (e.g., goalkeeper, defender, point guard), jersey number 408, physiological status, connection status, or active alerts. Such features can allow trainer 20 to easily see which individuals 10 have high and low metrics relative to other individuals 10.

In some exemplary embodiments, the team view dashboard is filterable in real time. Trainer 20 may manipulate input 404 so as to cause display 402 to show information for a subset of individuals 10. For example, trainer 20 may select one or more groups representing a subset of individuals 10. Groups can be selected in a variety of ways. In some exemplary embodiments trainer 20 selects a group label or a filter icon associated with the group. In some exemplary embodiments trainer 20 selects individuals to create a group in real time. In some exemplary embodiments trainer 20 inputs information used to identify members of a group, such as, for example, all individuals 10 having higher than a particular a heart rate, all individuals 10 having higher than a particular training load percentage, all individuals assigned a particular position, or all individuals having a particular physiological status. When a group is selected the display may change such that information for only those individuals 10 that are included in the group is displayed. Such features can allow trainer 20 to easily focus on the metrics associated with a group of individuals 10.

In some exemplary embodiments, the team view dashboard can also be used to monitor the status of connection of individual monitors 200 to base station 300. If, for example, an individual 10 travels out of range of base station 300, base station 300 may not receive normal transmissions from the individual monitor 200 of that individual 10. The team view dashboard can indicate that no data is being received by base station 300 for that individual 10 by, for example, graying out the identification information of that individual 10 (see, e.g., Player G of FIGS. 27, 31, 32, and 34), by including a strikethrough through information relating to that individual 10, or by including an icon in association with the identification information of that individual 10.

Figure 60:
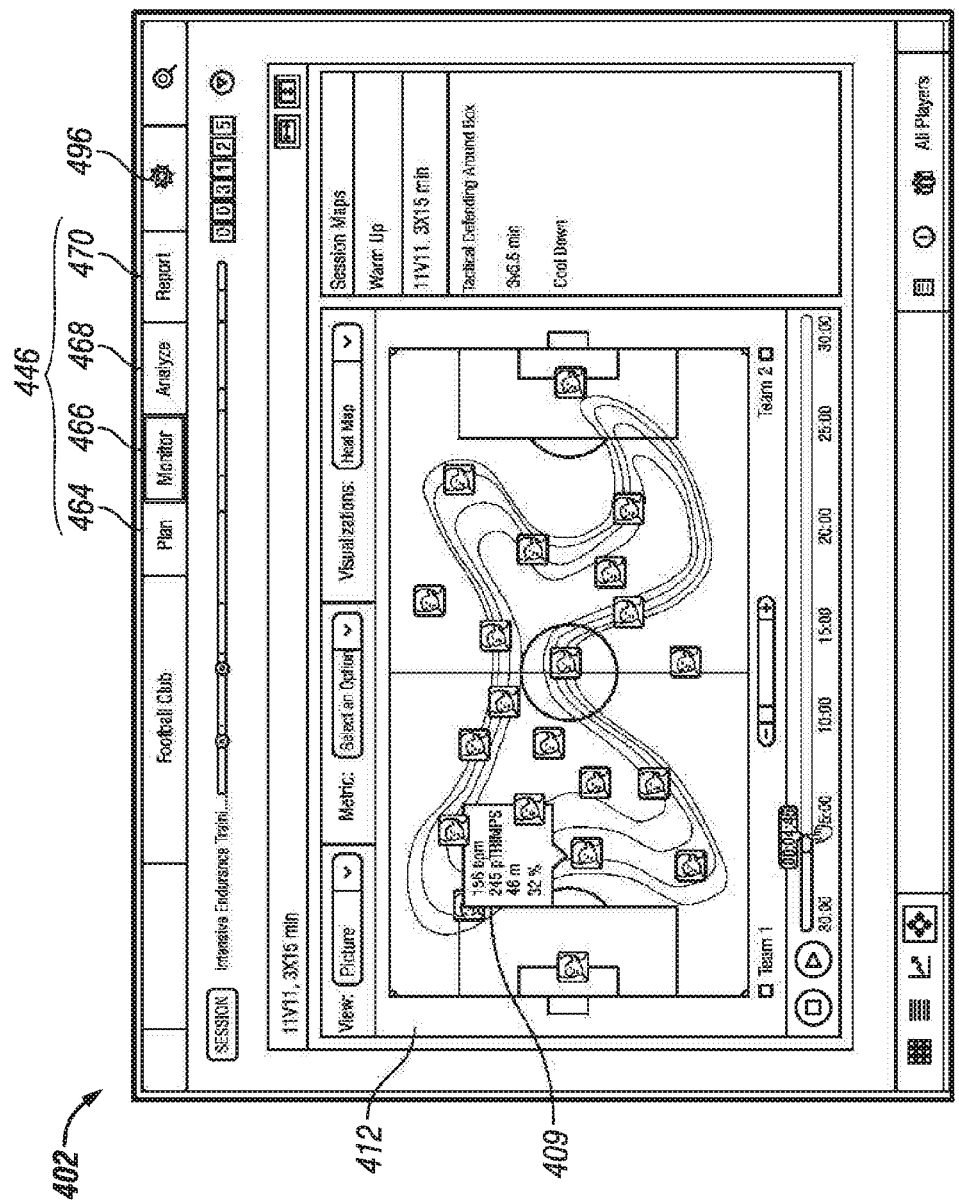
FIG. 60 depicts a display of a group monitoring device according to an exemplary embodiment of the present invention.

In some exemplary embodiments, alternative representations can replace the above-described representation of FIG. 13, or can be used as selectable alternative views, allowing trainer 20 to choose between the above-described representation and the alternative representations. The alternative representations of FIGS. 17 and 18 include multiple panels, each showing information for a particular individual 10. FIG. 17 includes a location component 412 showing the present location of individuals 10 on playing field 30, where individuals 10 are depicted represented by their identifying numbers. In some exemplary embodiments, as depicted in, for example, FIG. 60, individuals 10 are represented by their photographs. FIG. 18 includes a featured metric 414 (heart rate) displayed prominently in the center of each panel, as well as a key 416 showing what metric the values in each panel represent. Trainer 20 may select a metric on key 416 to have it displayed as the featured metric 414. FIG. 18 also includes a list of individuals 10 not actively monitored. Trainer 20 may select an individual 10 from this list to actively monitor that individual. Operation of the alternative representations of FIGS. 17 and 18 is similar to operation of the above-described representation of FIG. 13.

In some exemplary embodiments, location component 412 shows the present location of individuals 10 on the playing field, and selection of a representation of one of individuals 10 triggers display of a status box displaying information about the current status of the selected individual 10. In some exemplary embodiments, as depicted in, for example, FIG. 60, location component 412 may include a heat map 413, providing a visual indication of concentrations of individuals 10 in areas of the playing field, which information may help trainer 20 determine whether to redistribute individuals 10. Such visual indication may include coloring areas of higher concentration of individuals 10 differently from areas of lower concentrations of individuals 10. Location component 412 can be used to monitor individuals 10 in real time, or can be used to review the locations of individuals 10 from a past session of athletic activity or earlier in the present session of athletic activity.

In an exemplary embodiment, display 402 of group monitoring device 400 shows an individual view dashboard (see, for example, the exemplary displays 402 of FIGS. 16 and 36A, 36B, 37A, 37B, and 38-41). Trainer 20 may access an individual view dashboard by, for example, selecting an individual 10 on the team view dashboard. The individual view dashboard may show information about the selected individual 10, such as, for example, biographical information (e.g., photograph 410, name 406, jersey number 408, position), attributes (e.g., height, weight), metrics (e.g., time active, heart rate, speed, distance traveled, intensity level, training load, efficiency, location), statistics (e.g., points scored), alerts, notes, and condition (e.g., active, healthy, rehabilitation). In some exemplary embodiments the individual view dashboard shows different information about the selected individual 10 than that shown in the embodiment of FIG. 16.

In some exemplary embodiments, when trainer 20 selects an information entry, a detailed view of that information may be displayed. For example, if trainer 20 selects 'heart rate' on the individual view dashboard for Player A shown in FIG. 16, display 402 may display a detailed chart and/or graph 418 showing a history of Player A's heart rate throughout the present athletic activity (see, e.g., FIG. 20). In some exemplary embodiments, trainer 20 may select a 'power' indicator on the individual view dashboard, and display 402 may display a detailed chart and/or graph 418 showing a history of the selected player's power (see, e.g., FIG. 36A).

In some exemplary embodiments, any applicable alert information (e.g., training zones, thresholds) specific to the selected metric for selected individual 10 is displayed in the detailed view. For example, as shown in the detailed views of FIGS. 20 and 36A, training zones 420 for Player A's heart rate are overlaid on graph 418 of Player A's heart rate. In some exemplary embodiments, areas of zones 420 may be highlighted where coincident with data of graph 418, as depicted in, for example, FIG. 36B. Also, for example, as shown in the detailed view of FIG. 36A, training zones 420 (e.g., for a player's speed) may be displayed in a pie chart 472. In some exemplary embodiments, alerts relevant to a particular metric may be indicated by an icon displayed in association with the chart and/or graph indicative of that metric. For example, in the detailed view of FIG. 39, an alert icon 432 indicates an alert associated with the player's heart rate, and an alert icon 432 indicates 3 alerts associated generally with the player.

Figure 40:
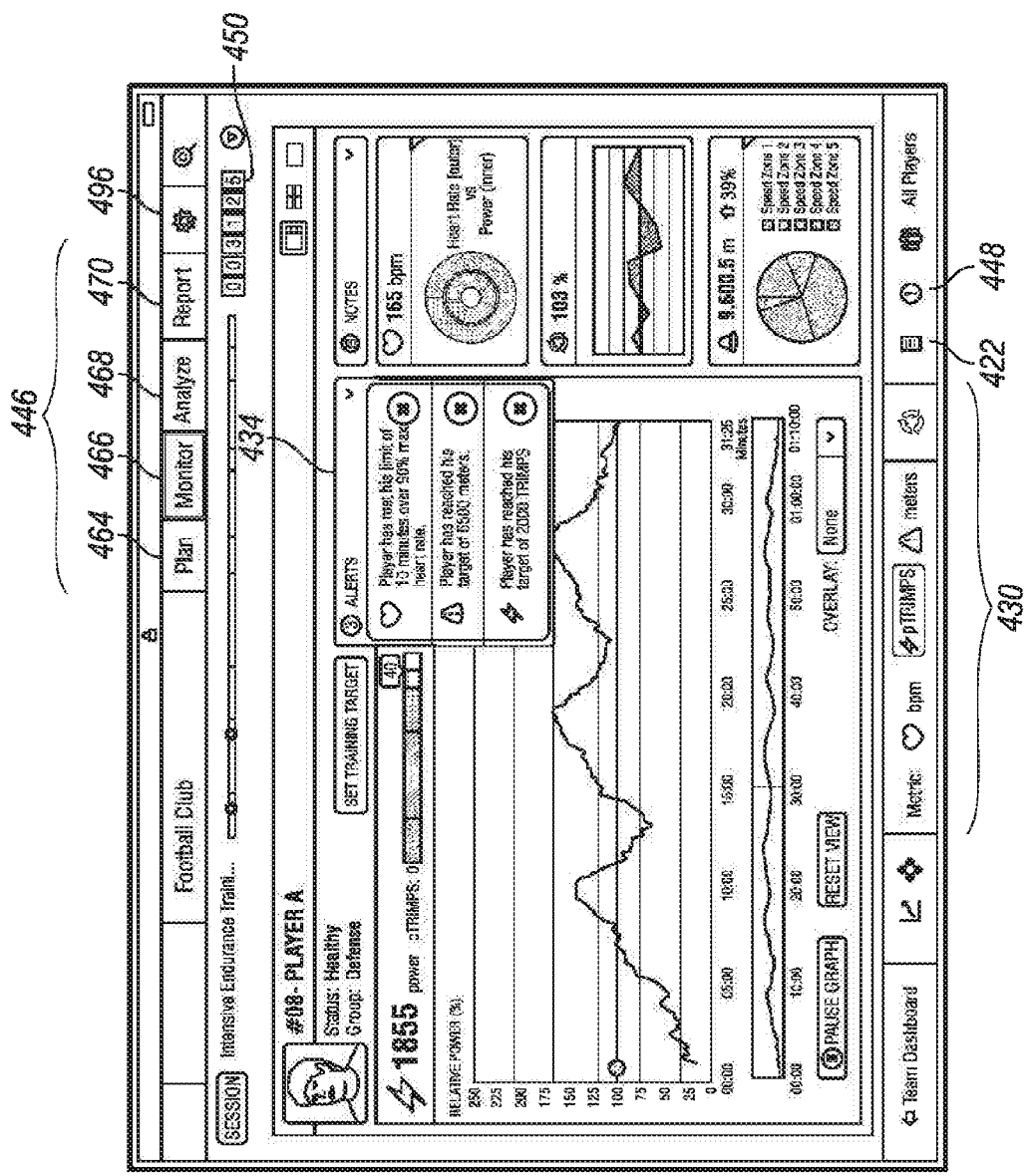
FIG. 40 depicts a display of a group monitoring device according to an exemplary embodiment of the present invention.

Selection of these alerts may trigger presentation of more detailed information about the alert, for example, in the form of a pop-up graphic 434, as shown in FIG. 40. In some exemplary embodiments, trainer 20 can select multiple information entries and display 402 can incorporate information regarding the selected multiple information entries in the detailed view. For example, FIG. 20 shows Player A's speed shown in graph 418 of display 402. In some exemplary embodiments, display 402 may display additional detailed charts and/or graphs 436 while displaying the primary chart and/or graph 418. In some exemplary embodiments, the additional detailed charts and/or graphs 436 are displayed less prominently (e.g., smaller) than the primary chart and/or graph 418, as depicted in, for example, FIGS. 36A and 39. In some exemplary embodiments, if an area on chart and/or graph 418 is selected (e.g., by trainer 20), more detailed information about the displayed metric may be displayed. For example, selecting near a particular point on a line graph may trigger display of a graphic 474 indicating the value of one or more metrics at that point (see, e.g., FIGS. 37B and 38). In some exemplary embodiments, chart and/or graph 418 may include information indicative of more than one metric. For example, chart and/or graph 418 may include power and heart rate on the same chart and/or graph (see, e.g., FIGS. 37A and 37B).

In some exemplary embodiments, chart and/or graph 418 may include metric information for past sessions of athletic activity, which may be stored within group monitoring device 400 or transmitted thereto by, for example, base station 300. In some exemplary embodiments, chart and/or graph 418 may include information indicative of more than one time period for one or more metrics. For example, chart and/or graph 418 may include heart rate information for the present or most recent session of athletic activity separate from or overlaid with heart rate information for one or more prior sessions of athletic activity on the same chart and/or graph.

Figure 41:
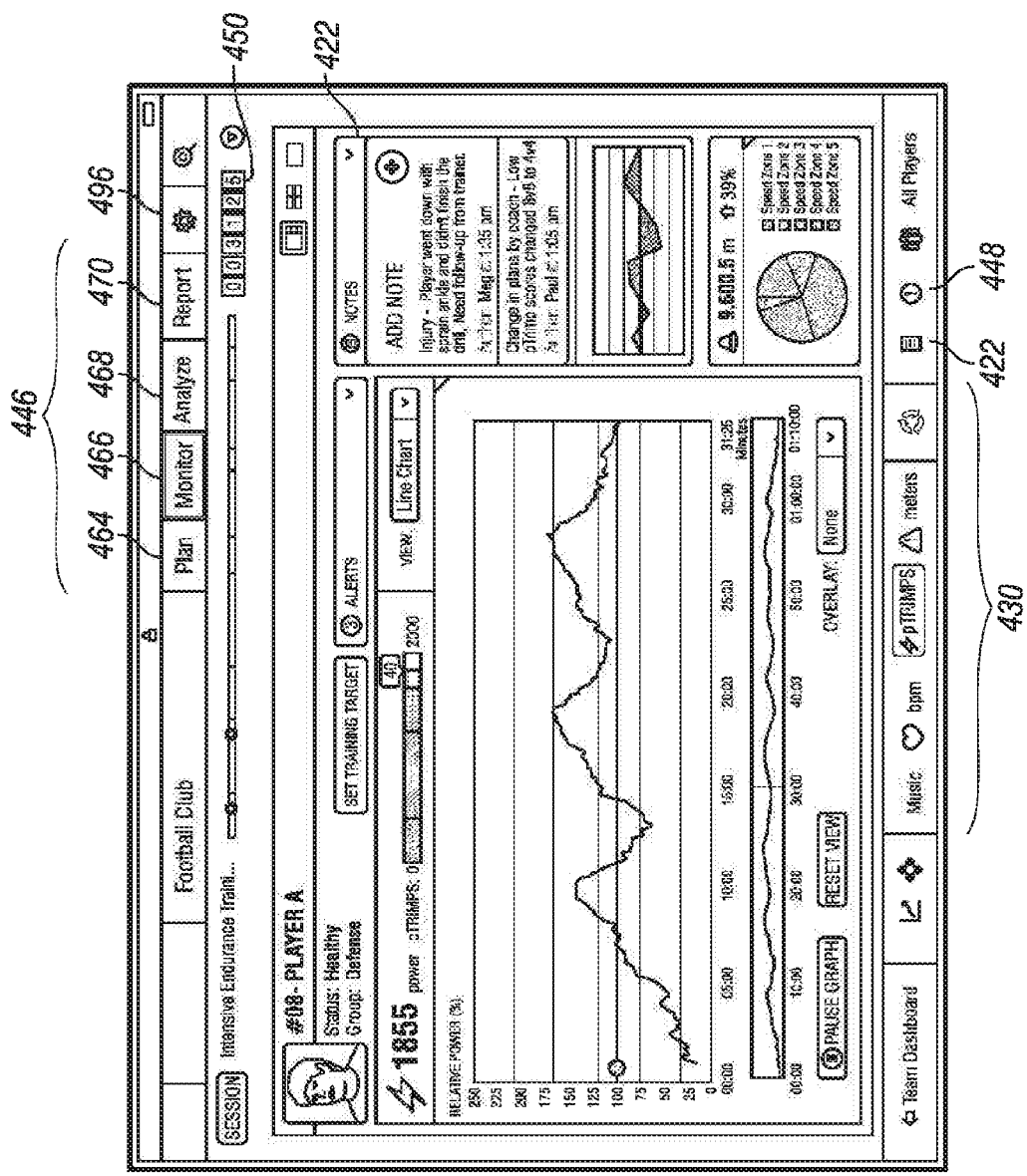
FIG. 41 depicts a display of a group monitoring device according to an exemplary embodiment of the present invention.
Figure 44:
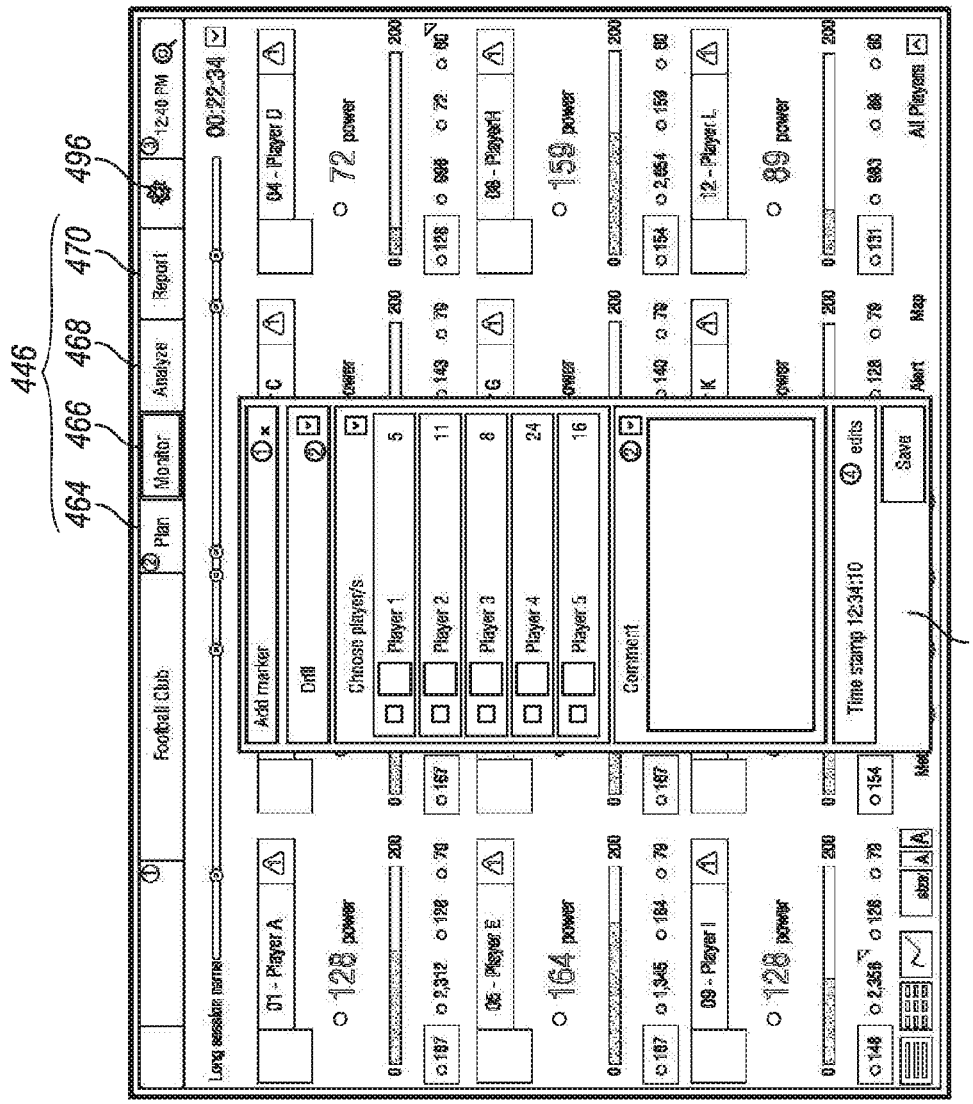
FIG. 44 depicts a display of a group monitoring device according to an exemplary embodiment of the present invention.
Figure 45:
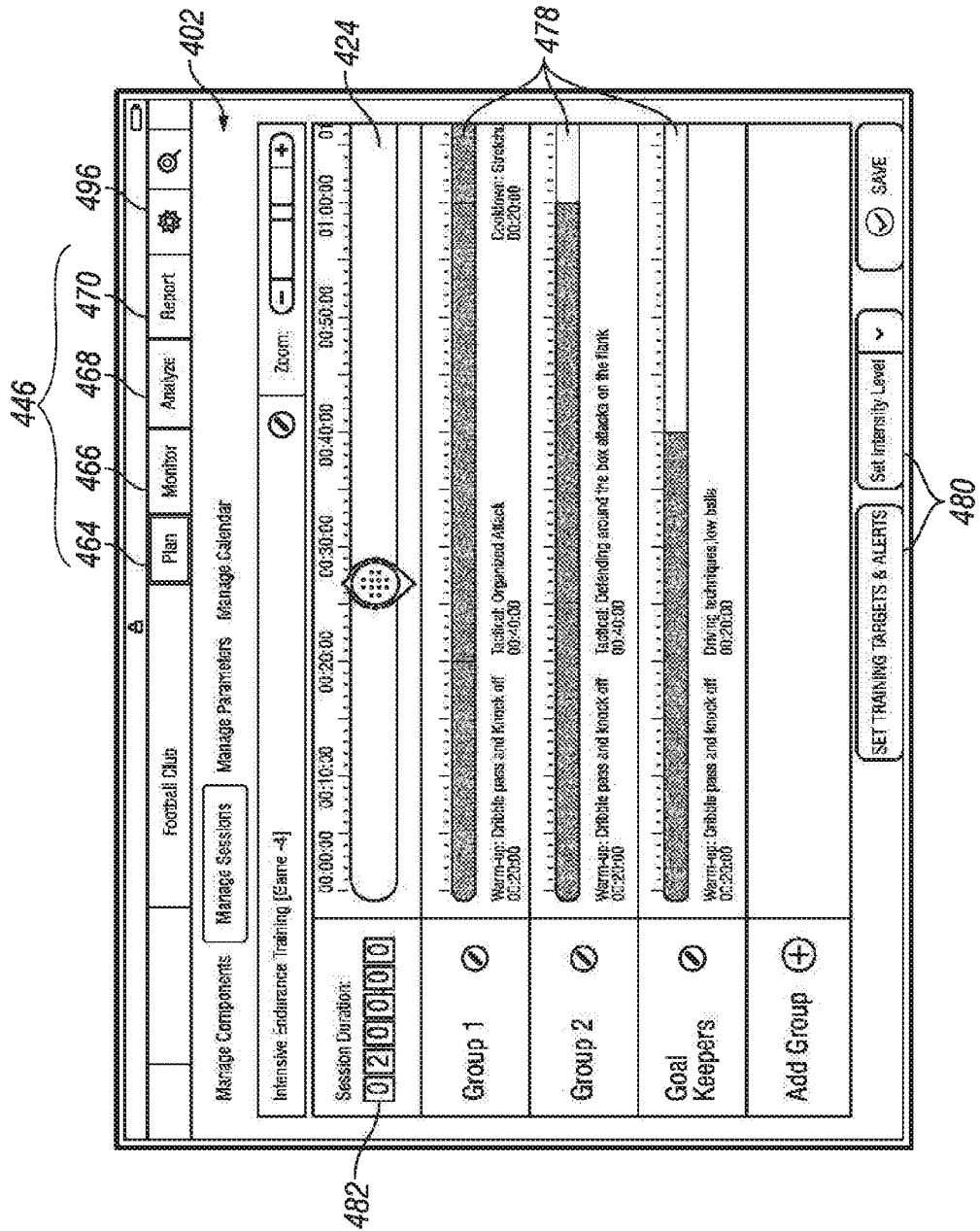
FIG. 45 depicts a display of a group monitoring device according to an exemplary embodiment of the present invention.
Figure 46:
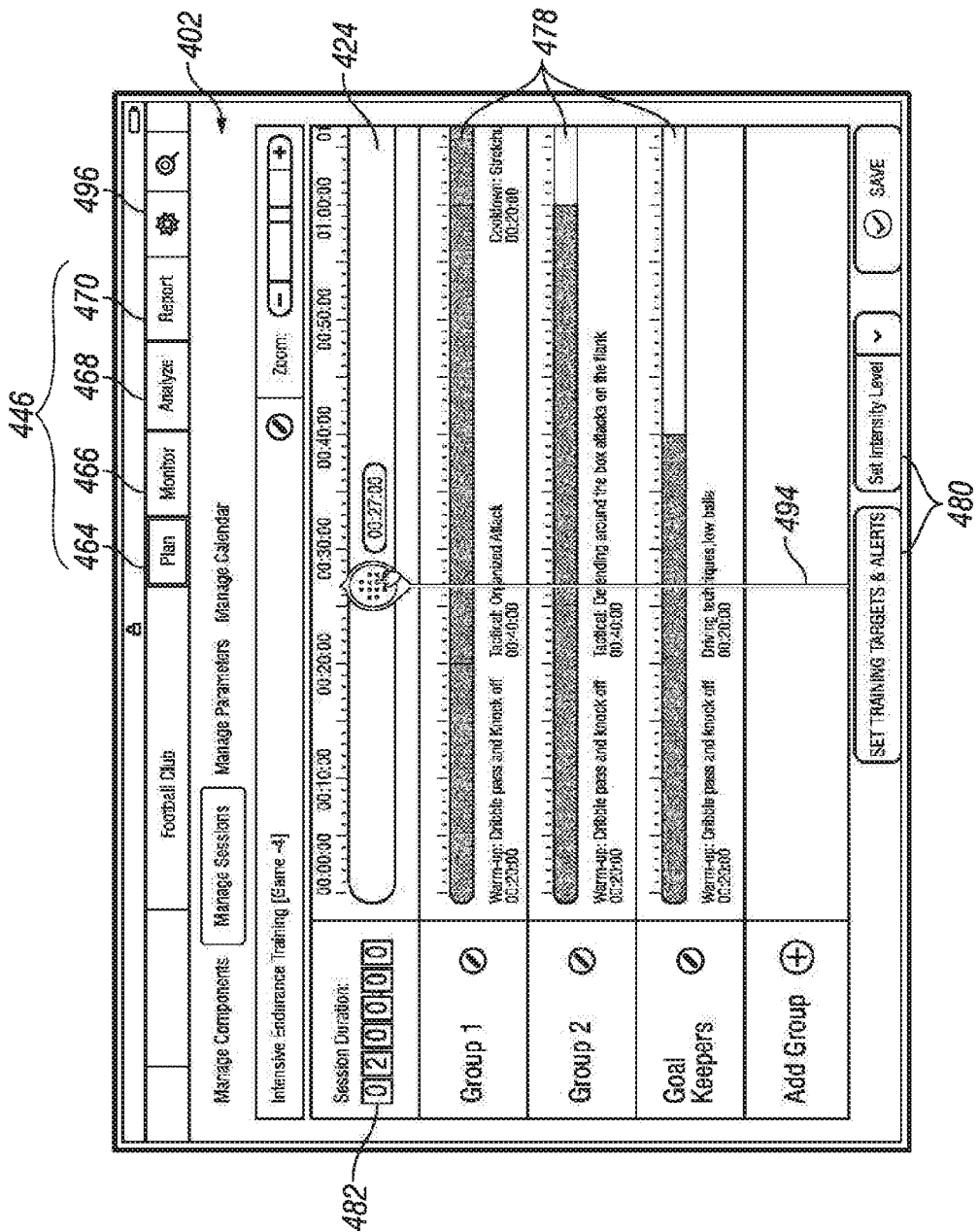
FIG. 46 depicts a display of a group monitoring device according to an exemplary embodiment of the present invention.

In some exemplary embodiments, trainer 20 may input notes about a particular individual 10, group of individuals 10, or team, by, for example, selecting a note field 422 of the individual view dashboard, as shown in, for example, FIGS. 16 and 41. In some exemplary embodiments, note field 422 may indicate the presence of notes, display notes, and/or provide an option or input to create new notes. In some exemplary embodiments, selection of note field 422, or otherwise accessing note adding capability, may cause display 402 to display a create note window 439 where trainer 20 can input a note, as shown in, for example, FIG. 44.

Selecting note field 422 may cause a free-text note entry field to appear, into which trainer 20 can enter text. In some embodiments, selecting note field 422 causes a microphone in group monitoring device 400 to activate and record voice input of trainer 20, allowing trainer 20 to record a voice note. Trainer 20 may input desired information in note field 422, such as, for example, a reminder to closely monitor the heart rate of individual 10, a reminder that individual 10 appears dehydrated, a determination that individual 10 should be congratulated for a good play, or a determination that the team should practice a particular play. In some exemplary embodiments, notes include time information, indicating, for example, the time to which a note pertains, or the time a note was created or modified, which can be useful for a later correlation between recorded data and the notes. Such time information may be entered manually or determined automatically.

In some exemplary embodiments, trainer 20 may select markers 440 to include in a session timeline 424. Such markers 440 may be selected before (e.g., using a plan module, as described further herein), during, or after the athletic activity. Session timeline 424 may keep track of the time elapsed or remaining in a session of athletic activity, or in a subset or interval of the session of athletic activity, and may be represented by, for example, numerical values (e.g., numerical value 450) or a moving point on a line representing total session time, as shown in, for example, FIGS. 13, 16, 19, 20, and 27-44. A marker 440 may be used to identify events within a training session. A trainer 20 may select a marker 440 by, for example, selecting an add marker button 426 (see, e.g., FIGS. 13, 16, 20, and 42A), or by selecting a point on session timeline 424, for example.

Figure 42A:
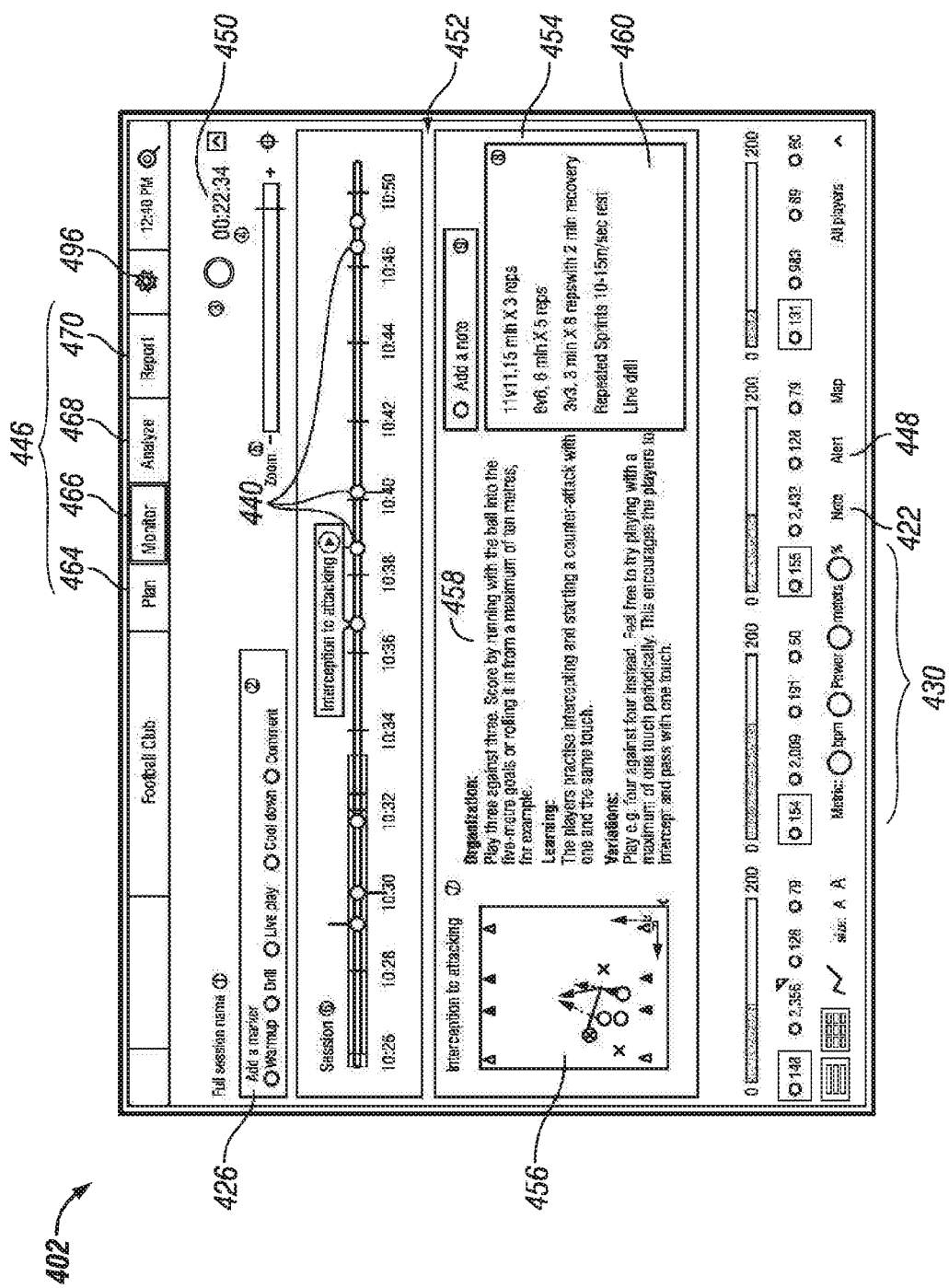
FIG. 42A depicts a display of a group monitoring device according to an exemplary embodiment of the present invention.
Figure 42B:
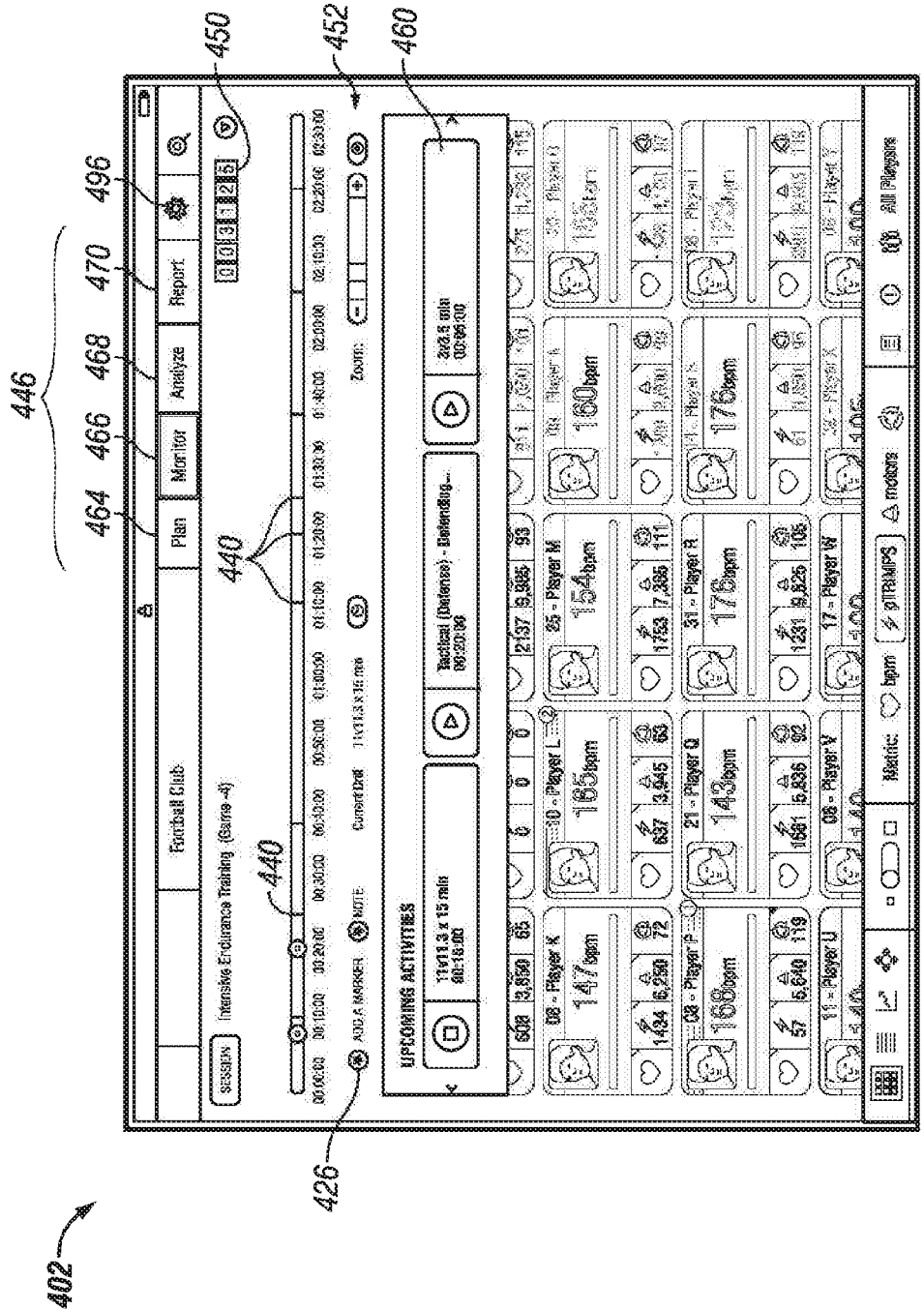
FIG. 42B depicts a display of a group monitoring device according to an exemplary embodiment of the present invention.
Figure 42C:
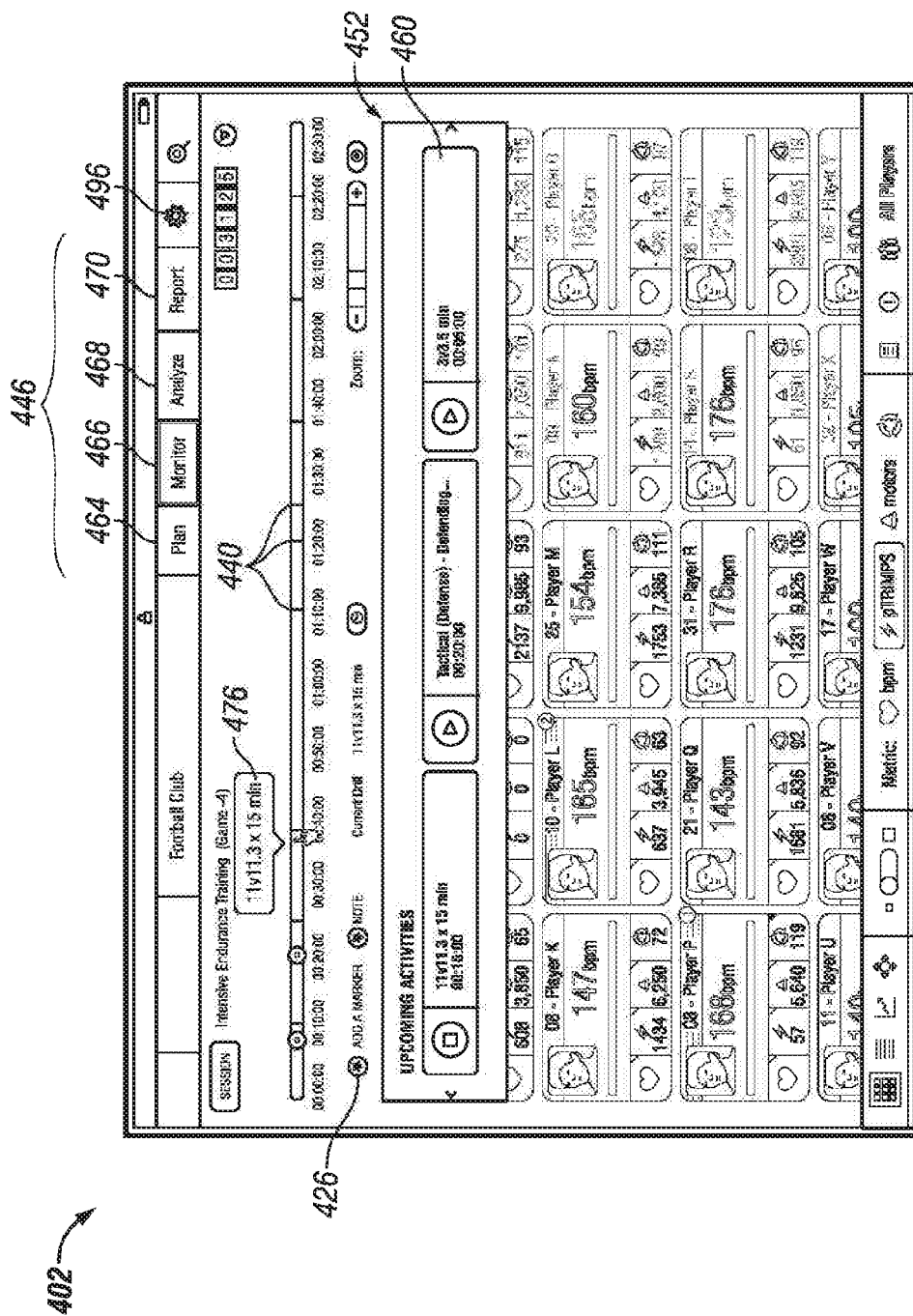
FIG. 42C depicts a display of a group monitoring device according to an exemplary embodiment of the present invention.
Figure 42D:
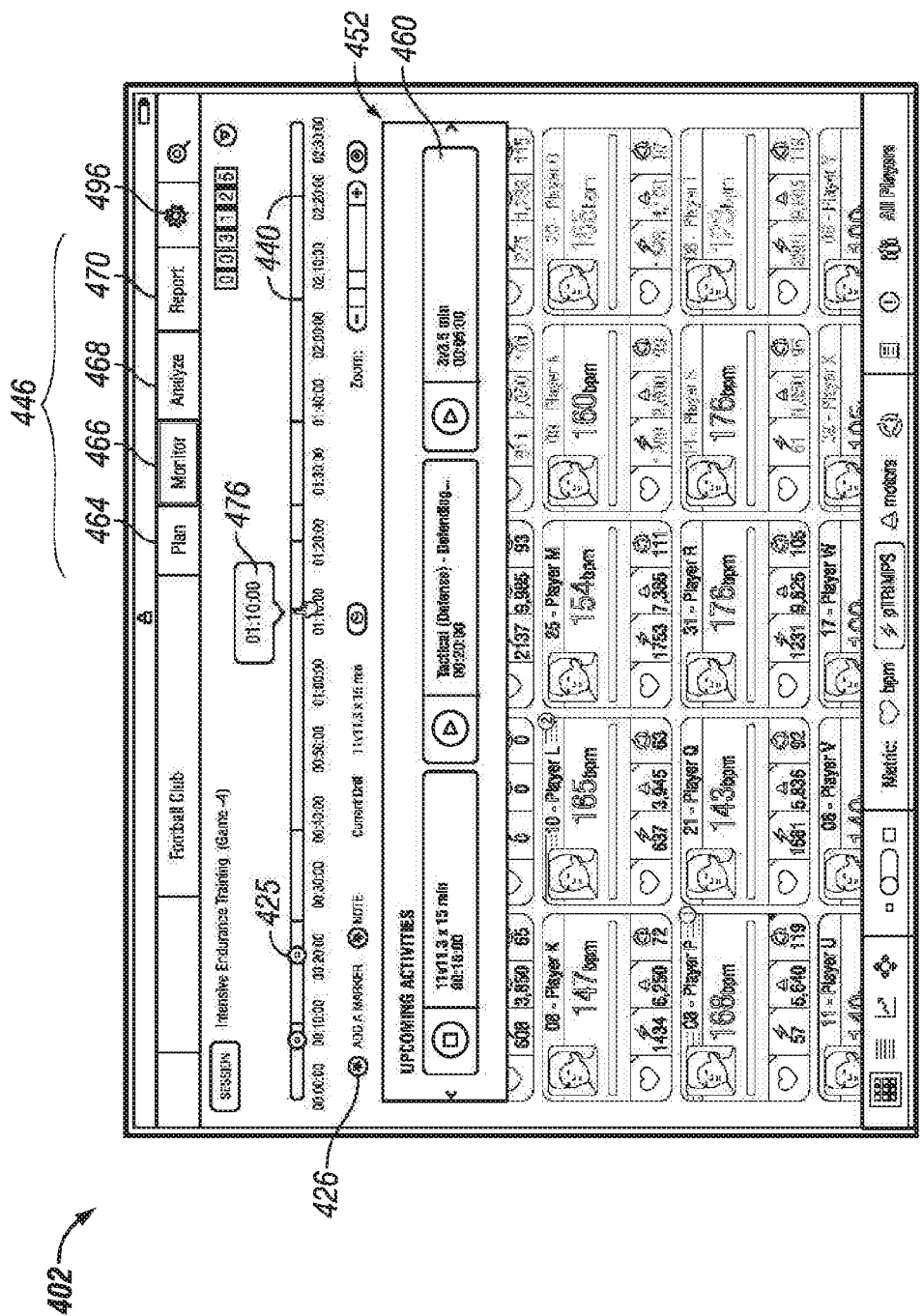
FIG. 42D depicts a display of a group monitoring device according to an exemplary embodiment of the present invention.
Figure 42E:
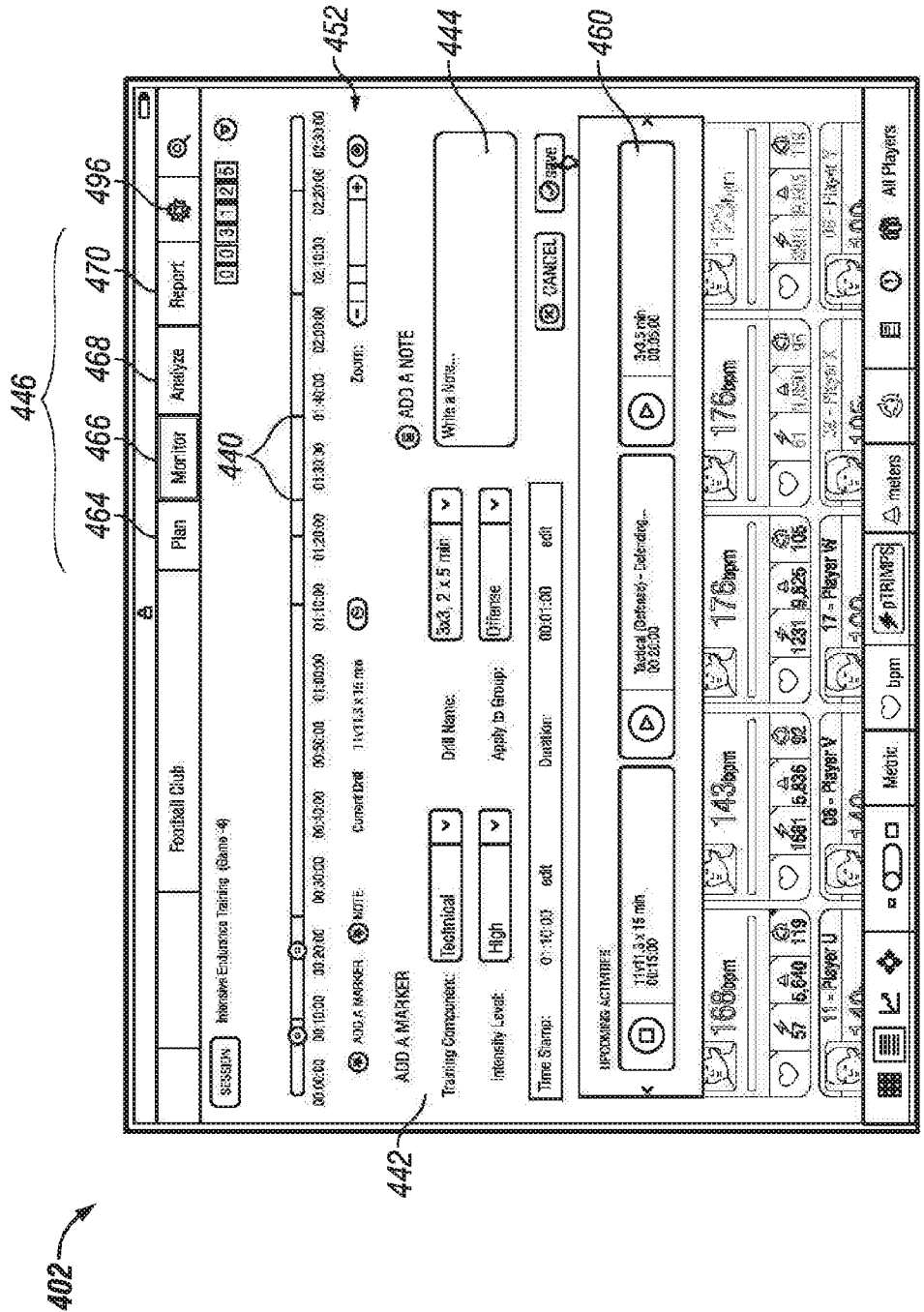
FIG. 42E depicts a display of a group monitoring device according to an exemplary embodiment of the present invention.
Figure 43:
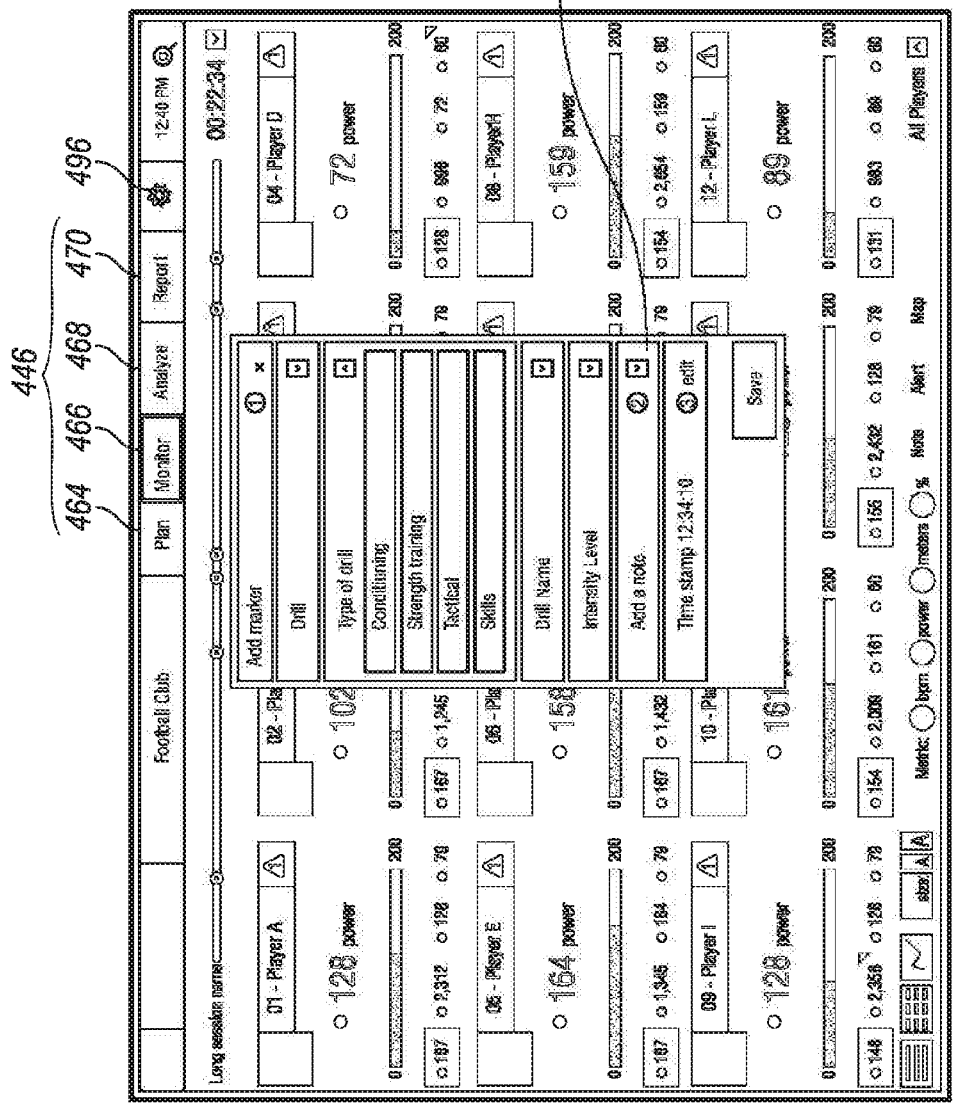
FIG. 43 depicts a display of a group monitoring device according to an exemplary embodiment of the present invention.

In some exemplary embodiments, selection of add marker button 426 causes display 402 to display an add marker window 442, allowing input of parameters to define the marker, as shown in, for example, FIGS. 42E and 43. Add marker window 442 may include a note input area 444 where trainer 20 can input a note associated with a marker 440. A marker 440 may be associated with a team as a whole, with sub-groups of individuals 10, or with a particular individual 10. When selecting a marker 440, trainer 20 may designate the marker type, which can be, for example, an "activity start" marker to designate the point at which an activity starts, an "activity stop" marker to designate the point at which an activity stops, or a "flag marker" to designate the point at which a particular event occurs. For activity-based markers, marker attributes may include the type of activity (e.g., cardio, drill, strength, recovery, other) and the activity name, for example. For flag-based markers, marker attributes may include the type of flag (e.g., injury, rest, off field, out of range).

In some exemplary embodiments, markers 440 include time information, indicating, for example, the time to which a marker 440 pertains, or the time a marker 440 was created and/or modified, which can be useful for a later correlation between recorded data and the markers. Such time information may be entered manually or determined automatically. In some exemplary embodiments, trainer 20 can input notes to be associated with the marker, or with a particular point on session timeline 424. In some exemplary embodiments, as depicted in, for example, FIGS. 27 and 31, note icons 425 positioned at points on session timeline 424 can represent such notes. Attributes of markers 440 may be designated by trainer in real time, or can be pre-defined. Markers 440 can be associated with session timeline 424 at the time they are created, or can be associated with any other time on session timeline 424. Markers can be useful to trainer 20 in analyzing the performance of individuals 10 during the athletic activity as well as after the athletic activity, by associating contextual information with particular times and individuals. In some exemplary embodiments, if a part of a session is marked with activity markers, past data from the same types of activities of an individual 10 can be retrieved and overlaid with more recent (including presently generated) data of the individual 10, thereby facilitating comparison of data for an individual 10. Markers 440 and their use, as described herein, can apply to a particular individual 10, or to groups of individuals 10 (e.g., one or more teams or leagues of individuals 10, or one or more sub-groups of one or more teams or leagues of individuals 10).

In some exemplary embodiments, analysis markers 440 can be defined and manipulated by a user (e.g., trainer 20). Analysis markers 440 can be used as boundaries to define a subset of metric information as a function of an interval parameter. Group monitoring device 400 may then display metric information (e.g., performance metric information, such as, for example, heart rate) corresponding only to the subset of metric information defined by analysis markers 440. Analysis markers 440 can be defined for a particular individual 10, or for a group of individuals 10. An interval parameter may be any parameter that can have a designated first point and second point, which can be designated by, for example, a first analysis marker 440 and a second analysis marker 440, thereby defining an interval therebetween suitable to measure performance. For example, the interval parameter may be time or distance.

In some exemplary embodiments, analysis markers 440 define a portion of the athletic activity engaged in by individuals 10. The portion of athletic activity may be, for example, warmup, a drill, live play, cool down, a line drill, sprints, repeated sprints, a conditioning drill, a strength training drill, a tactical drill, or a skills drill for a particular sport. For example, if a conditioning drill begins 10 minutes into an athletic activity, and ends 15 minutes into the athletic activity, a first analysis marker 440 may designate a time 10 minutes into the athletic activity, and a second analysis marker 440 may designate a time 15 minutes into the athletic activity, thereby defining a 5 minute interval therebetween, corresponding to the conditioning drill.

In some exemplary embodiments, analysis markers 440 may be defined based on past metric information, by manipulating input 404 after the session of athletic activity (e.g., defining an interval in the past). In some exemplary embodiments, analysis markers 440 may be defined based on present metric information, by manipulating input 404 during the session of athletic activity (e.g., defining a beginning point in real time during the athletic activity, and then an ending point in real time). In some exemplary embodiments, analysis markers 440 may be defined based on expected future metric information or expected activity, by manipulating input 404 before the session of athletic activity (e.g., defining expected beginning and ending points in time during a planned session of athletic activity).

When defined based on expected future metric information, group monitoring device 400 can be used to coordinate the planned session of athletic activity, by scheduling intervals of particular athletic activity. For example, analysis markers 440 may define a conditioning drill to take place in the first 5 minutes of athletic activity, a strength training drill in the following 5 minutes, and a skills drill in the following 5 minutes. Group monitoring device 400 may indicate to trainer 20 when an interval is scheduled to begin and end, and when a transition between intervals is scheduled to take place, and trainer 20 may communicate this information to individuals 10. In some exemplary embodiments, base station 300 may send a signal to individual monitors 200 indicating the transition between intervals, or the beginning or end of a particular interval, and individual monitors 200 may communicate this information to individuals 10 via, for example, emitting an audible noise (e.g., via a speaker), vibrating, or providing a visual indication (e.g., via an LED or LCD display). In this way, individuals 10 can be alerted as to the start or end of a portion of athletic activity corresponding to a defined interval.

In some exemplary embodiments, to facilitate planning a session of athletic activity, display 402 may display a plan module, which may include utilities useable to plan the session of athletic activity, as depicted in, for example, FIGS. 45-51. Display 402 may include session duration 482, which may be manipulated by a user to define the duration of a session of athletic activity. Display 402 may display a session timeline 424, which may indicate a timeline for a planned session of athletic activity. Trainer 20 may select points and portions of session timeline 424 in order to define intervals of athletic activity scheduled at the selected times. Such intervals of athletic activity may be scheduled for an entire team of individuals 10, for other groups of individuals 10, or for single individuals 10. In an exemplary embodiment, depicted, for example, in FIG. 45, intervals of athletic activity are scheduled for groups of individuals 10, and these groups are displayed with their own timelines 478. In some exemplary embodiments, timelines 478 are aligned with session timeline 424 such that, upon selection of a point on session timeline 424, or upon occurrence of a time corresponding to the point, a line or other indicator 494 extends to corresponding points on timelines 478, as depicted in, for example, FIG. 46. In some exemplary embodiments, plan module may include utilities useable to schedule multiple sessions of athletic activity, as depicted in, for example, FIGS. 50 and 51.

Various parameters can be defined in association with a planned session of athletic activity and/or the intervals thereof, including, for example, markers, training targets and alerts, as well as intensity levels. In some exemplary embodiments, such parameters can be defined by selection using options and/or menus 480, as depicted in, for example, FIGS. 45-47, selection of which may trigger display of a training target and alert window 486, as depicted in, for example, FIG. 49. Training target and alert window 486 may allow selection of a metric (e.g., heart rate, power, speed), and definition of training or alert zones relative to a percentage of a maximum value for the metric. Training target and alert window 486 may also allow for definition of training or alert zones bounded by definite values of the metric. In some exemplary embodiments, markers 440 defined in association with a planned session of athletic activity may be displayed on session timeline 424 during the session of athletic activity, as depicted in, for example, FIG. 42E. Display 402 may be configured to allow modification, addition, or deletion of such markers 440 by trainer 20 during the session of athletic activity.

Figure 47:
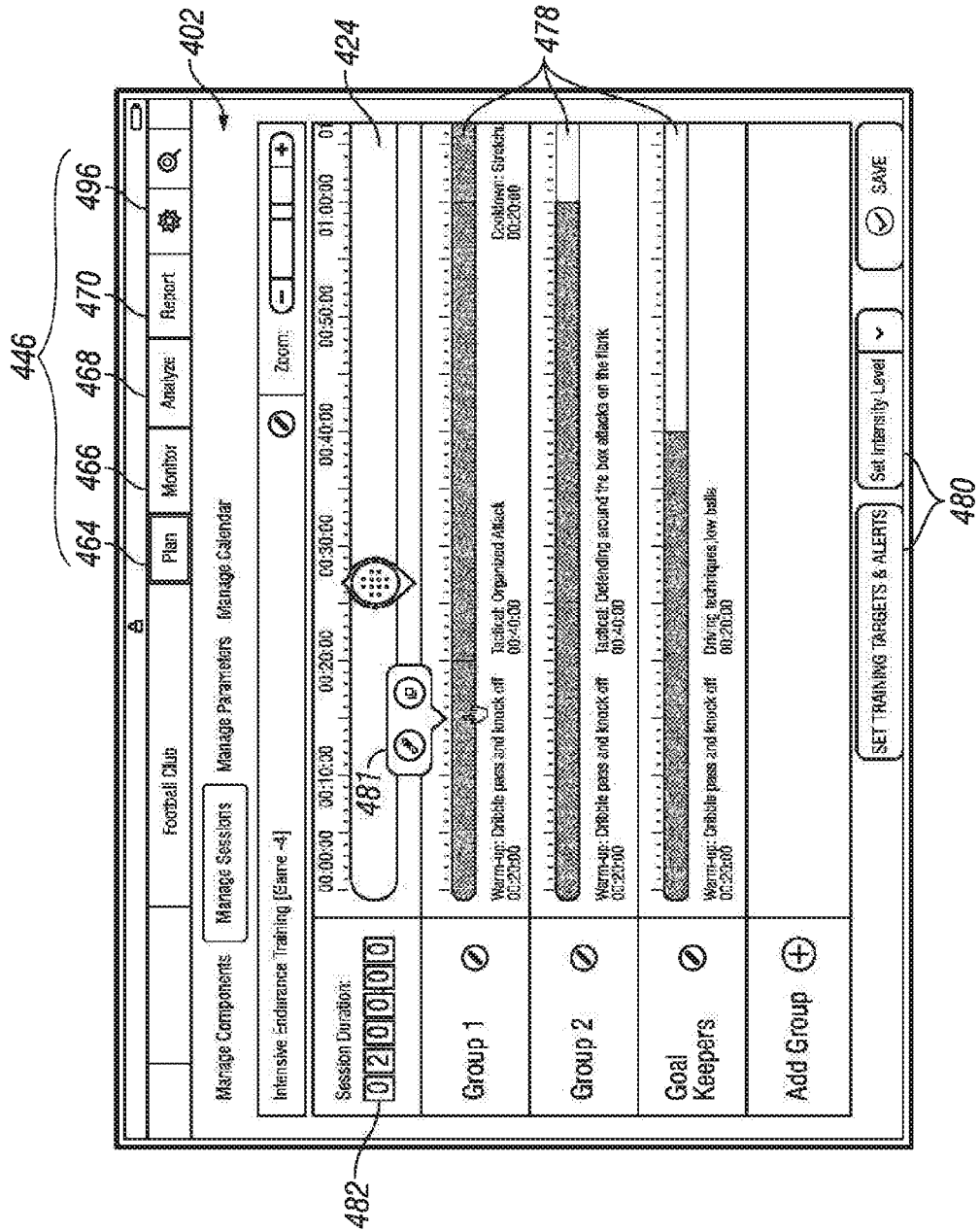
FIG. 47 depicts a display of a group monitoring device according to an exemplary embodiment of the present invention.

In some exemplary embodiments, such parameters (e.g., markers, training targets, alerts, intensity levels) can be defined by selection of a point on timeline 478, as depicted in, for example, FIG. 47. In some exemplary embodiments, such selection of a point on timeline 478 may trigger display of options and/or menus 481 for input of markers, training targets, alerts, and/or intensity levels associated with a point in time or interval corresponding to the selected point. In some exemplary embodiments, such selection of a point on timeline 478 may trigger a window for input of an alert or marker associated with the point in time or interval corresponding to the selected point.

Figure 48:
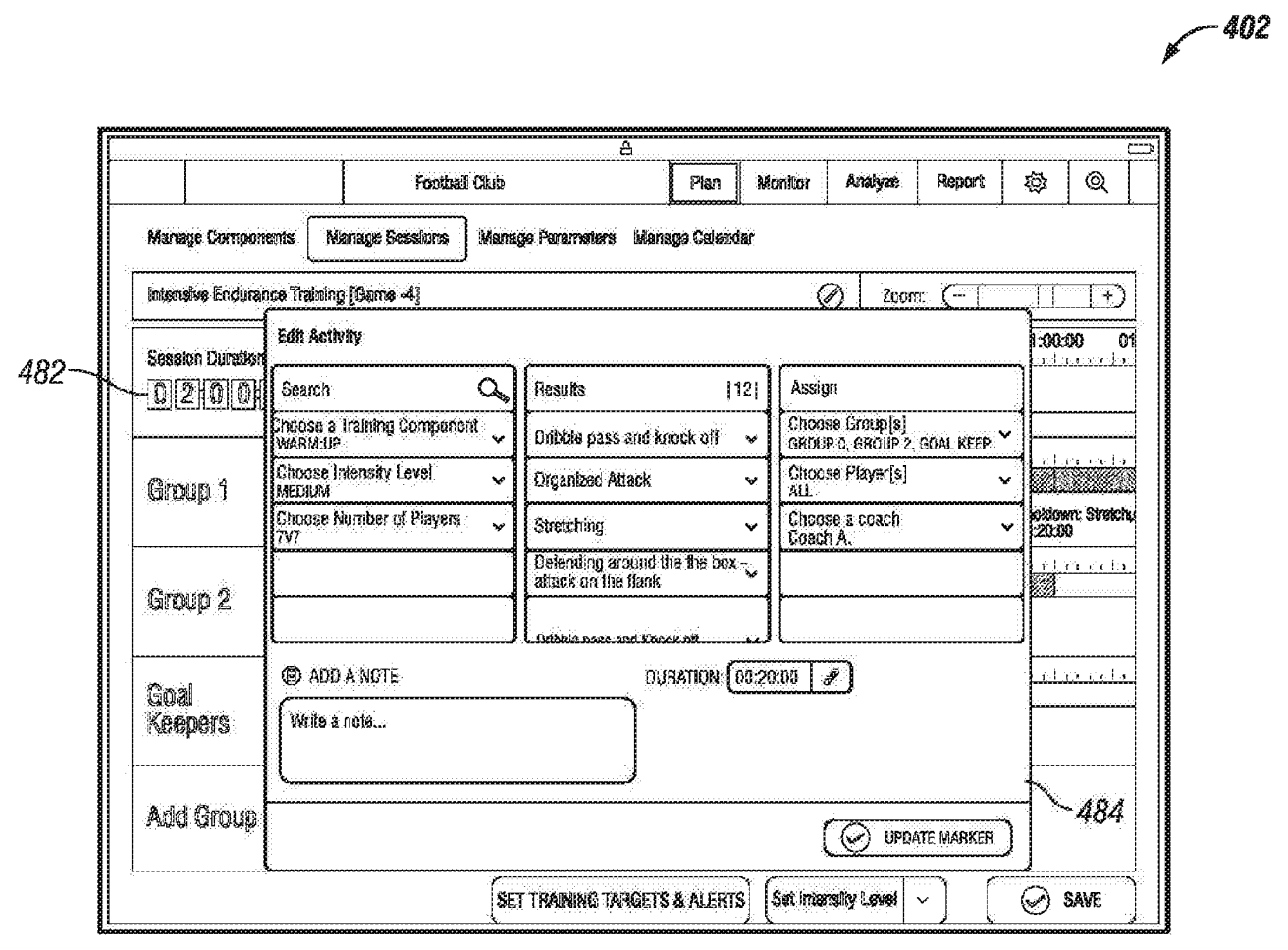

In some exemplary embodiments, as depicted in, for example, FIG. 48, display 402 displays an edit activity window 484, which includes options and inputs facilitating defining of various aspects of an activity associated with an interval of a session of athletic activity. Various activities (e.g., drills, games, tests, training components) may be stored in a database (e.g., base station database 316, or a memory included in group monitoring device 400). Edit activity window 484 may allow a user to search for an activity by choosing a training component (e.g., warm up, drills, competition), choosing an intensity level (e.g., low, medium, high), and choosing the number of players involved. Edit activity window 484 may provide results showing activities matching the input search criteria. Edit activity window 484 may provide an option to assign the resultant activities to individuals 10 or groups thereof, and to choose coaches or trainers 20 to manage the assigned activities. Edit activity window may also allow association of such an activity with a time and duration, thereby scheduling an interval of the session of athletic activity. Such activities may be designated by markers 440, which may be displayed on session timeline 424 during the session of athletic activity, as depicted in, for example, FIG. 42E. Such activities may be designated prior to a session of athletic activity (e.g., using a plan module of group monitoring device 400), during a session of athletic activity, or after a session of athletic activity.

Figure 50:
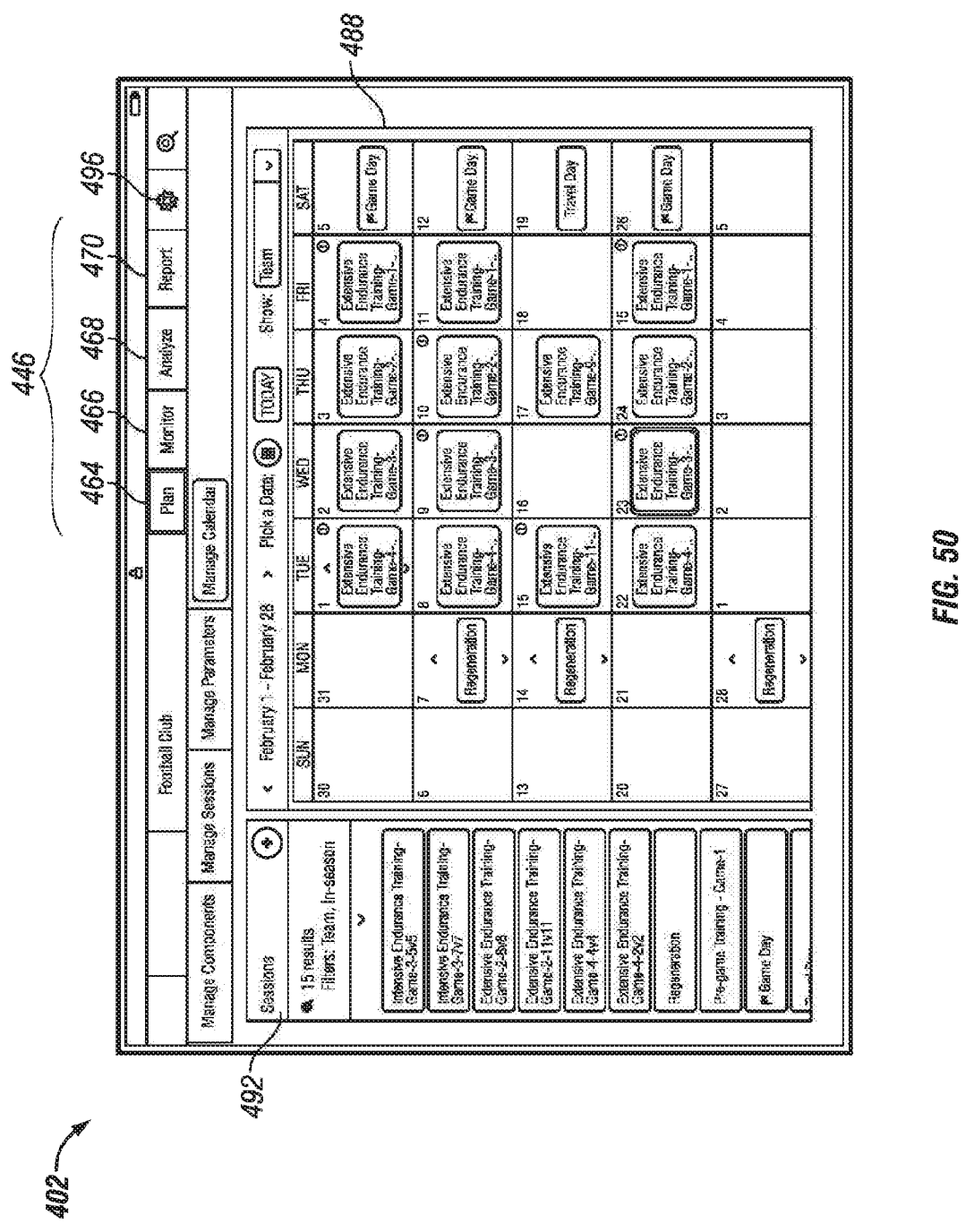

In some exemplary embodiments, as depicted in, for example, FIG. 50, display 402 may display a calendar 488 representing sessions of athletic activity and intervals thereof that are scheduled for a set time period (e.g., one week, one month, five days, one day). The displayed time period may be defined by a user. Display 402 may display sessions of athletic activity and intervals thereof scheduled for the past, present, and/or future. In some exemplary embodiments, the types of sessions of athletic activity and intervals thereof displayed may be filtered according to criteria input or selected by a user. In some embodiments, sessions of athletic activity can be scheduled via a device (e.g., group monitoring device 400, analysis device 600, a remote computer) in communication with base station 300. In some embodiments, sessions of athletic activity can be scheduled in a training calendar, such as, for example, calendar 488. In some embodiments, athletic events (e.g., games, performances, competitions) can be scheduled in the training calendar. In some embodiments, a training program (e.g., multiple training sessions) can be scheduled in the training calendar. In some embodiments, group monitoring system 100 may suggest (e.g., via group monitoring device 400) scheduling for a training program, based around events already scheduled (e.g., group monitoring system may suggest an easy training activity the day before a competition scheduled in the training calendar, or a day of no training following a race scheduled in the training calendar).

Figure 51:
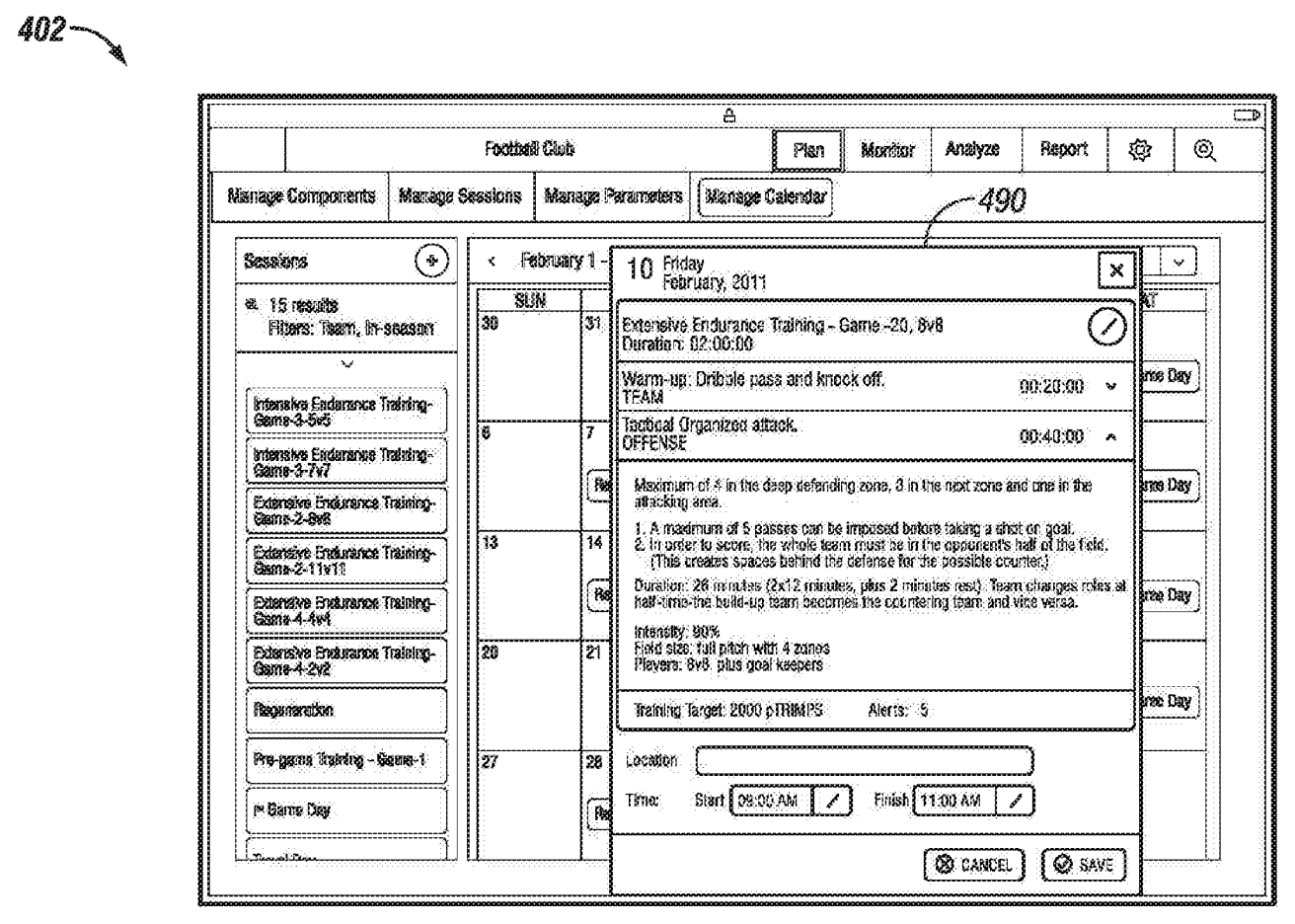

In some exemplary embodiments, as depicted in, for example, FIG. 51, selection of a particular time period displayed in calendar 488 (e.g., a particular day), may trigger display of a detailed view of scheduled events for the selected time period. For example, a detailed schedule window 490 may display an overall session of athletic activity scheduled for the selected time period, as well as intervals of the session of athletic activity and their characteristics (e.g., type of interval, applicability of interval to particular groups or individuals 10, beginning and end times of interval, description of activities to be performed during interval, location of interval).

In some exemplary embodiments, as depicted in, for example, FIG. 52, display 402 displays a session list 492, which may depict a list of scheduled sessions of athletic activity, as well as intervals of athletic activity associated therewith. Session list 492 may display sessions of athletic activity scheduled for times that have passed, scheduled for the present (e.g., the present time or day), and scheduled for the future.

In some exemplary embodiments, display 402 may display a session control monitor 452, which may provide information relating to a past, ongoing, or future session of athletic activity, as depicted in, for example, FIGS. 42A and 42B. When used during a session of athletic activity, session control monitor 452 may help trainer 20 facilitate the session, by, in addition to providing information about individuals 10, by providing a session information feature 454, as depicted in, for example, FIGS. 42A and 42F. Session information feature 454 may provide information about, for example, a present interval of athletic activity. In some exemplary embodiments, session information feature 454 may include a diagram 456 depicting intended movement of individuals 10 during, for example, a particular play or other strategic action. In some exemplary embodiments, session information feature 454 may include description 458 of, for example, a particular play or other strategic action. In some exemplary embodiments, session information feature 454 may include a schedule 460 of, for example, past and/or upcoming intervals of athletic activity.

Figure 42F:
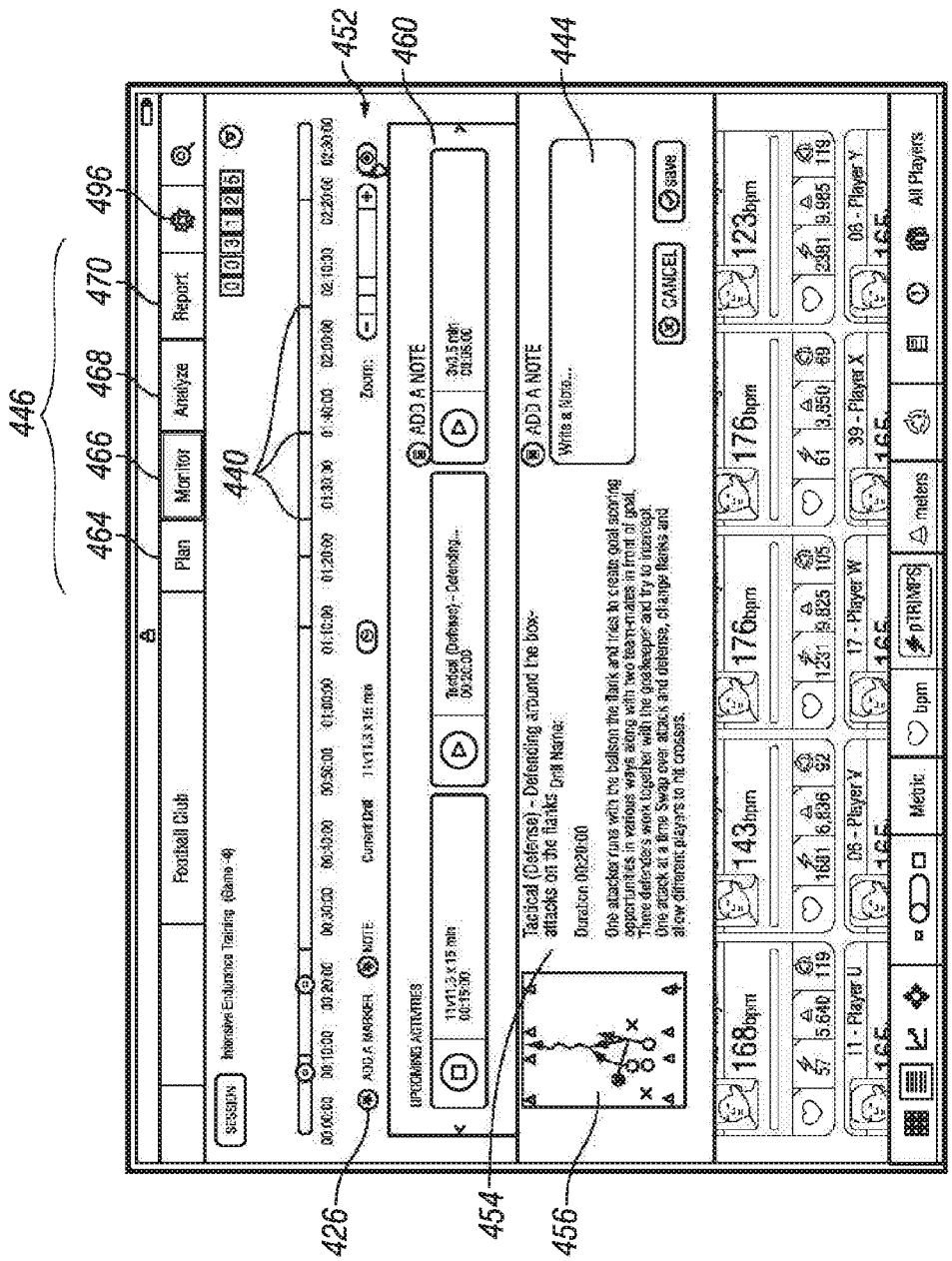
FIG. 42F depicts a display of a group monitoring device according to an exemplary embodiment of the present invention.

In some exemplary embodiments, selection of an entry in schedule 460 may trigger display of a session information feature 454 related to that entry, as depicted in, for example, FIG. 42F. Session timeline 424 may include information displayed in schedule 460, such that selection of a point on session timeline may trigger display of information relevant to that point in the session (e.g., time selected, interval of athletic activity scheduled for time selected). Such information may be displayed in, for example, a timeline information window 476, as depicted in, for example, FIGS. 42C and 42D. This information can be useful to trainer 20 to facilitate an ongoing session of athletic activity, and can be defined in advance of the session of athletic activity. In some exemplary embodiments, information in session information feature 454 can be defined after, and applied to, a past session of athletic activity, and can be used, for example, to help trainer 20 analyze the past session.

Figure 54:
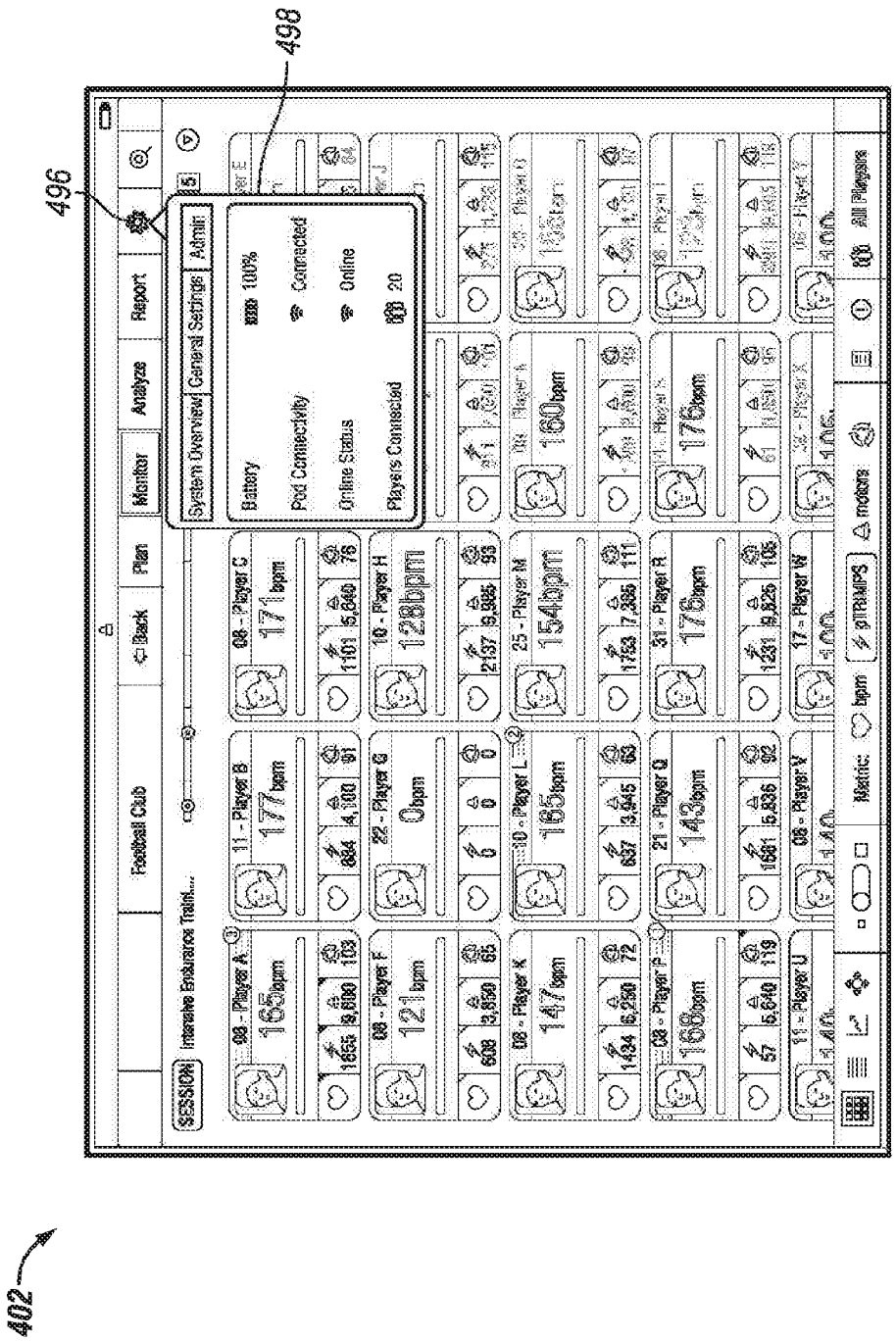
FIG. 54 depicts a display of a group monitoring device according to an exemplary embodiment of the present invention.

In some exemplary embodiments, as depicted in, for example, FIG. 54, display 402 includes a status icon 496 that, when selected, triggers display of a status menu 498. Status menu 498 may display information about the statuses of various components of group monitoring system 100. Status menu 498 may include information about, for example, the battery life remaining in group monitoring device 400 or base station 300, the connectivity and/or signal strength between group monitoring device 400 and base station 300, the connectivity and/or signal strength between group monitoring device 400 and the Internet or other network, and the number of individuals connected to base station 300.

In some embodiments, individual monitor 200 and/or object monitor 250 each includes a position module 216 for determining data indicative of the location of individual monitor 200 and/or object monitor 250 (and thus the location of individual 10 carrying individual monitor 200 and/or sports object 40 carrying object monitor 250). In some embodiments, display 402 of group monitoring device 400 depicts the location of individuals 10 and/or sports objects 40, based on the data indicative of the location of individual monitor 200 and/or object monitor 250.

In some embodiments, such depiction of the location of individuals 10 and/or sports objects 40 may be in the form of a graphical representation such as, for example, a map (e.g., a map of the playing field on which individuals 10 and/or objects 40 are located, showing the locations of individuals 10 and/or objects 40 in relation to features of the playing field such as, for example, boundary lines and goals). For example, FIG. 17 includes location component 412 showing the location of individuals 10 and a sports object 40 on playing field 30, where individuals 10 are represented by their identifying numbers. Depiction of individuals 10 and/or sports object 40 with respect to features of the playing field can be helpful to a viewer of display 402 (e.g., a referee or official charged with overseeing the athletic activity) to monitor the activity (e.g., to determine whether an individual 10 traveled outside a boundary line, or whether a ball entered a goal zone).

In some embodiments, display 402 of group monitoring device 400 depicts the present locations of individuals 10 and/or sports objects 40. In some embodiments, display 402 of group monitoring device 400 depicts past locations of individuals 10 and/or sports objects 40 (e.g., replays display of the locations). In some embodiments display 402 of group monitoring device 400 depicts the past locations during the athletic activity. In some embodiments display 402 of group monitoring device 400 depicts the past locations after the athletic activity.

In some exemplary embodiments, display 402 of group monitoring device 400 depicts locations of individuals 10 and/or sports objects 40 simultaneously with orientations of individuals 10 and/or sports objects 40.

In some exemplary embodiments, display 402 of group monitoring device 400 displays recommendations based on metrics. For example, display 402 may display a recommendation based on location information of one or more individuals 10 (e.g., based on location information showing a concentration of individuals 10 in one area, display 402 may display a recommendation that individuals 10 spread out over the playing field). Such recommendations can be tailored as desired (e.g., to a particular situation, type of game, to play against a particular opposing team or player, to a particular situation).

In some exemplary embodiments, display 402 of group monitoring device 400 can display one or more alerts based on location information of one or more individuals 10 and/or sports objects 40. An alert may be triggered based on a determination that location(s) of one or more individuals 10 and/or sports object 40 meet an alert condition. For example, an alert may be triggered in response to a location of an individual being greater than a threshold distance from a target position, where the target position may be defined relative to, for example, a playing field or feature thereof, another individual 10, or a sports object 40. Also for example, an alert may be triggered based on a determination that there are no individuals 10 within a threshold distance of a goal (e.g., the goal area is unguarded). Also for example, an alert may be triggered based on a determination an individual 10 has crossed a boundary line (e.g., stepped out-of-bounds). Also for example, an alert may be triggered based on a determination that sports object 40 is within a goal area (e.g., a goal has been scored). Also for example, an alert may be triggered based on the character of movement of an individual 10's location (e.g., rapid alternating between faster and slower movement of an individual 10 may trigger an alert indicating that individual 10 is limping, and may be injured; minimal movement combined with orientation data showing individual 10 is prone or supine may trigger an alert indicating that individual 10 has fallen, and may be injured). Display 402 may display representations of such alerts as described herein. In some embodiments, a representation of an individual 10 to whom an active alert applies may be displayed in a different color when the alert applies than when the alert doesn't apply. In some embodiments, such an alert may itself include specific coaching advice based on the alert. For example, an alert indicating that an individual 10 is greater than a threshold distance from a target position may be accompanied by a recommendation for the individual 10 to move closer to the target position. Also for example, an alert indicating that there are no individuals 10 within a threshold distance of a particular area (i.e., there is a "gap" in field coverage) may be accompanied by a recommendation for one or more individuals 10 to move closer to the particular area (e.g., to eliminate or reduce the size of the gap).

Also for example, an alert may be triggered based on locations of multiple individuals 10 and/or sports objects 40. For example, an alert may be triggered where a first individual 10 is within a threshold distance from a sports object 40 (e.g., the first individual may be handling the ball), and wherein a second individual 10 is greater than a threshold distance from any opposing individual 10. The alert may provide notification (e.g., to trainer 20, first individual 10) that the second individual 10 is unguarded, which may be useful (e.g., to trainer 20, first individual 10) to prompt consideration of whether first individual 10 should pass the ball to second individual 10. In some embodiments, such an alert may itself include a recommendation for a strategic play, or for a modification to a current strategy (e.g., a calculated "best play," or a new target location for one or more individuals 10, given the known metrics, including location information). For example, the alert may provide a recommendation that the ball be passed from the first individual 10 to the second individual 10. Such alerts can be defined and tailored to any desired game situation, in order to facilitate analysis and speed decision-making during an athletic activity.

In some embodiments, display 402 of group monitoring device 400 depicts the path of one or more individuals 10 or sports objects 40. The path may be a curve tracing past locations of the one or more individuals 10 or sports objects 40 on a map of the playing field. The displayed path may be static (i.e., displaying the curve for a period of time with a defined beginning and end) or dynamic (e.g., displaying the curve for a period of time where either or both of the beginning and end is dependent on, for example, the current time). In depicting the path of one or more individuals 10 or sports objects 40, display 402 may show the position of the one or more individuals 10 or sports objects 40 as a function of time.

In some exemplary embodiments, as depicted in, for example, FIGS. 73-77, display 402 includes a heat map 415, which may provide a visual indication of time spent by one or more individual 10 in areas of the playing field. Such visual indication may include colored areas of a representation of the playing field that correspond to areas where individual 10 has spent more time, colored differently than colored areas of the representation of the playing field that correspond to areas where individual 10 has spent less time. In some embodiments (see, e.g., FIG. 73), heat map 415 may represent a single individual 10. In some embodiments (see, e.g., FIGS. 74-77), heat map 415 may represent multiple individuals 10, where visual indications of time spent by different individuals 10 are represented by different colors, or where individuals 10 on one team are represented by the same color while individuals 10 from an opposing team are represented by a different color. In some embodiments, heat map 415 may represent one or more sports objects 40 similarly as described with respect to individuals 10. In some embodiments, where individual 10 is wearing a garment having an illuminable area, the illuminable area may illuminate in a color corresponding to the color used to represent individual 10 on display 402 (e.g., on heat map 415).

Alternatively or additionally, heat map 415 may provide a visual indication of, for example, areas of the playing field where player 10 performed a certain type of activity (e.g., running, jumping), areas of the playing field where player 10 had a metric value above or below a threshold value, or areas of the playing field where player 10 had possession of or contact with a sports object (e.g., a ball). In some embodiments, heat map 415 may provide a visual indication of, for example, optimum positioning of one or more players 10 the playing field.

In some embodiments, display 402 of group monitoring device 400 depicts the location of an individual 10 or sports object 40 with respect to some other feature (which may be, for example, another individual 10 or sports object 40, or a point on the playing field). Such depiction can take the form of a distance measurement between (i.e., magnitude of separation of) the individual 10 or sports object 40 and the other feature, which may be represented, for example, as a history of the separation (e.g., a graph showing time v. separation) or as an integral map (e.g., a histogram) of the separation over a set period.

The various depictions of locations of individuals 10 and/or sports objects 40 can help a viewer (e.g., trainer 20, individual 10) to analyze plays made during a session of athletic activity. For example, the depictions may be useful in facilitating tactical training or strategy development, by facilitating design and monitoring of pre-planned plays, or the analysis of successful or failed plays to seek areas for improvement. Also for example, the depictions may be useful to determine the extent of separation between two individuals 10 with the same role on a team (e.g., two fullbacks), to optimize their coverage of the playing field (e.g., to ensure that the two fullbacks maintained at least a threshold separation during a game in order to ensure that areas of the field were not left undefended). Also for example, the depictions may be useful to analyze the effect of positioning of individuals 10 on game events, including the outcome of the game (e.g., the distance and frequency with which a fullback strayed from the corner of the penalty box, or the distances between the two fullbacks and the goalkeeper can be analyzed at key points, like when a goal against has been scored, to help identify and improve sub-optimal positioning and to help prevent future goals against from being scored). Also for example, the depictions may be useful to determine possession or change thereof (e.g., a successful pass) of a sports object 40 (e.g., ball) by an individual 10 (e.g., by identifying separation between the individual 10 and sports object 40 below a threshold distance for a threshold period of time).

Figure 12:
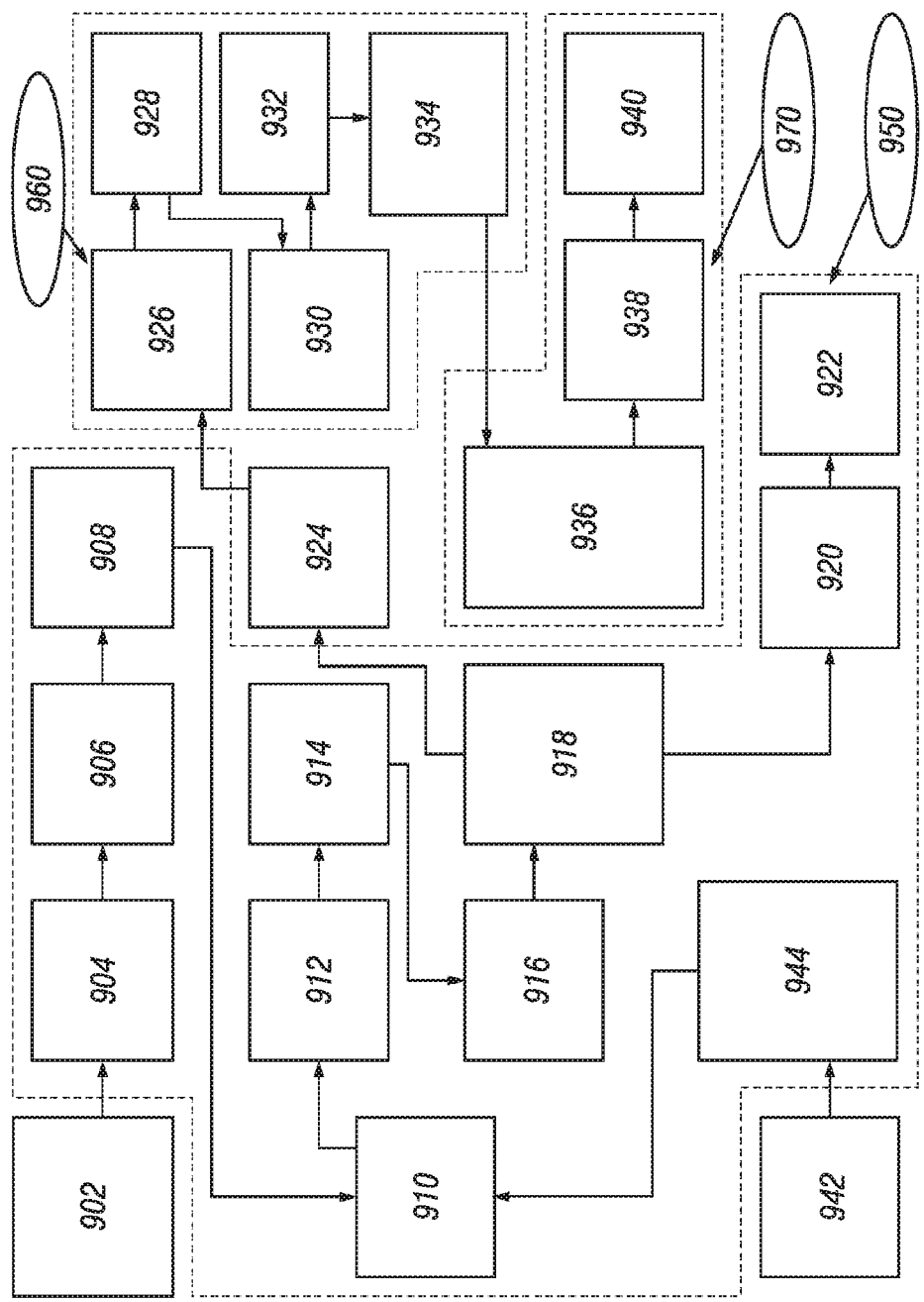
FIG. 12 depicts a monitoring flow diagram according to an exemplary embodiment of the present invention.

Exemplary embodiments of the present invention may include data flows such as that shown in FIG. 12, which depicts a data flow including a real-time monitoring flow 950, a post-session data integrity flow 960, and a post-session analysis flow 970. At box 902 of FIG. 12, data processing module 304 of base station 300 assigns encryption keys to each individual monitor 200 (also referred to as a "player pod"), and each individual monitor 200 is connected to sensors 202. At box 904, sensors 202 determine raw data indicative of characteristics of a monitored individual 10 (data indicative of, e.g., physiological characteristics, performance characteristics, position characteristics, and/or orientation characteristics). At box 906, sensors 202 send the raw data to individual monitor 200 via a wired or wireless connection. At box 908, individual monitor 200 transmits the data to data reception module 302 of base station 300 via a wireless connection, in real time. At box 942, cameras (e.g., camera monitoring system 700, video feed camera 804) determine image data. At box 944, the cameras send the image data to data reception module 302 of base station 300.

At box 910, data reception module 302 of base station 300 writes the data to a file. At box 912, data reception module 302 of base station 300 sends the file to data processing module 304 of base station 300. At box 914, data processing module 304 of base station 300 validates and decrypts the data. At box 916, data processing module 304 of base station 300 stores the decrypted data in base station database 316. At box 918, logic module 312 of base station 300 accesses the decrypted data and, using algorithms, determines metrics and alerts. At box 920, logic module 312 of base station 300 sends the metrics to web server module 314 of base station 300. At box 922, web server module 314 of base station 300 sends the metrics to live monitoring devices 400.

At box 924, logic module 312 of base station 300 stores the metrics and alerts in base station database 316. At box 926 individual monitors 200 are connected to base station 300 via a wired connection and upload data to data reception module 302 of base station 300. At box 928, data reception module 302 of base station 300 writes the data to a file. At box 930, data reception module 302 of base station 300 sends the file to data processing module 304 of base station 300. At box 932, data processing module 304 of base station 300 validates and decrypts the data. At box 934, data processing module 304 of base station 300 performs data filtering (e.g., data de-duplication) if necessary, and stores the decrypted data in base station database 316. At box 936, central sync module 310 of base station 300 accesses and sends decrypted data, metrics, and alerts ("session data") to web server system 500. At box 930, web server system 500 stores the session data in web server database 502 of web server system 500. At box 940, web server system 500 sends the session data to analysis devices 600.

In an exemplary embodiment, display 402 of group monitoring device 400 shows a system view dashboard (see, for example, the exemplary display 402 of FIGS. 61-64 and 67). In some embodiments the system view dashboard may simultaneously display identification information and statuses of one or more system components (e.g., sensors 202, individual monitors 200, object monitors 250, base stations 300, group monitoring devices 400, web server systems 500, analysis devices 600, camera monitoring systems 700). In some embodiments the system view dashboard may simultaneously display identification information and statuses of one or more system components and of one or more objects 40 and/or individuals 10 participating in an athletic activity and associated with a monitor 200, 250. Further, the system view dashboard may simultaneously display statuses of system components, individuals 10, and/or sports objects 40 along with metrics of individuals 10 and/or sports objects 40.

Operating conditions displayed by display 402 may include indications of statuses of system components and/or alerts (e.g., performance alerts of individuals 10 and system alerts of system components). Display 402 may display related identification information (e.g. name 406 and/or jersey number 408 of individuals 10, and unique identifier 409 of monitors 200, 250). The operating conditions shown in the system view dashboard can be configured as desired (e.g., to be the statuses most applicable or most beneficial to trainer 20). Presentation of the operating conditions can be configured as desired. For example, operating conditions can be displayed as alerts (e.g., indications of whether or not an alert has been triggered), graphic representations of a status (e.g., bar graphs, pie charts), or numeric representations of a status (e.g., absolute values, percentage values).

Operating conditions displayed by display 402 may include statuses and/or alerts for any system component. In some embodiments, a system view dashboard may display indications of, for example, remaining battery power of a battery of base station 300 and/or monitors 200, 250; the number of monitors 200, 250 docked with and/or charging at base station 300; GPS signal status at monitors 200, 250 and/or base station 300; proper operation of monitors 200, 250 and/or base station 300; proper placement of monitors 200, 250 and/or base station 300; proper placement of sensors 202 (e.g., proper fit of sensor garment 204).

Figure 61:
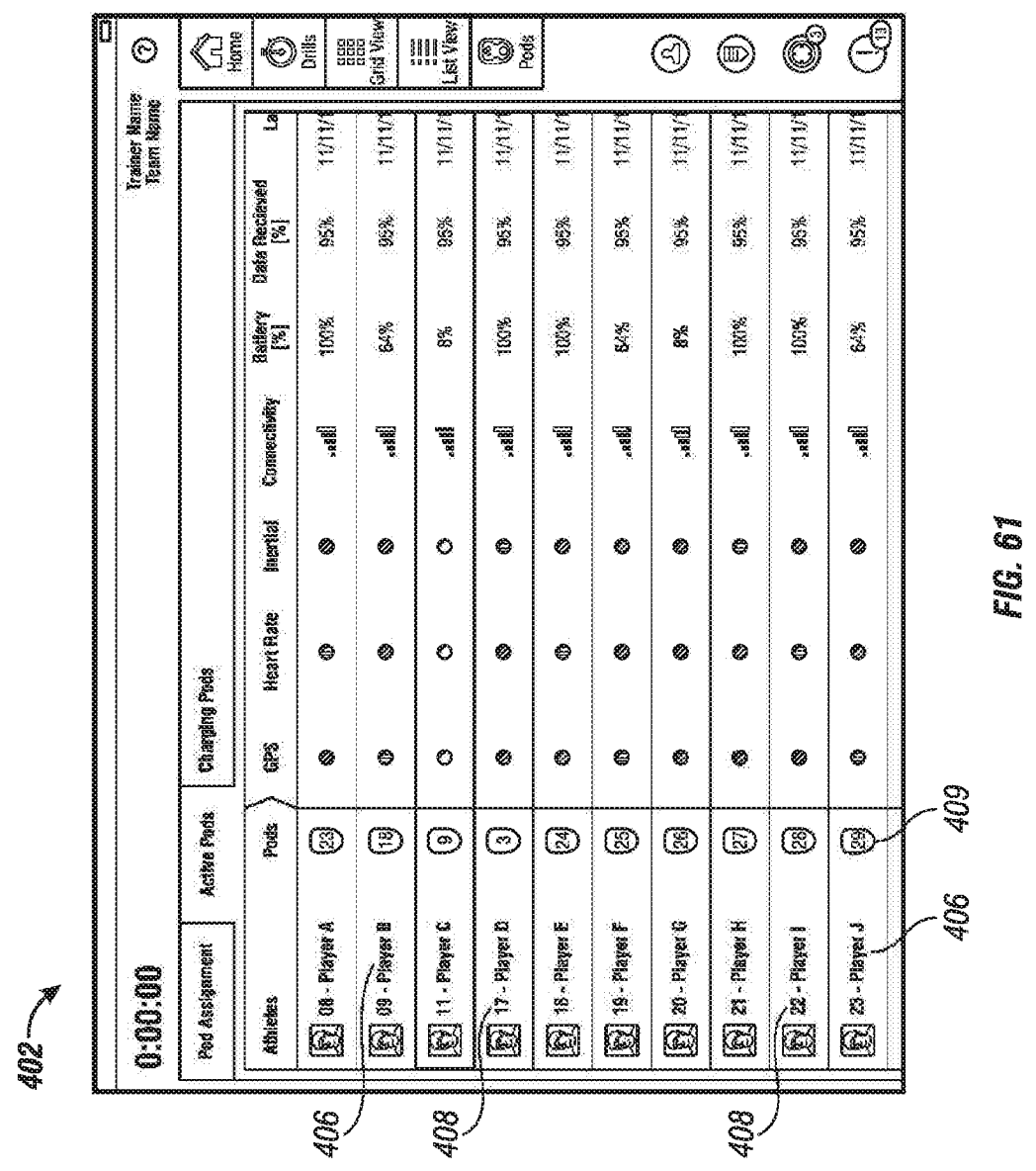

In the exemplary display 402 of FIG. 61, a system view dashboard provides an indication of GPS signal status at individual monitors 200. The GPS signal status is displayed as a system alert that indicates whether the GPS signal strength at each individual monitor 200 is above or below a predetermined system alert threshold. Also in FIG. 61, an indication of heart rate status of individuals 10 is provided. The heart rate status is displayed as a performance alert that indicates whether the heart rate of each individual 10 is above or below a predetermined threshold. Also in FIG. 61, an indication of inertia status of individuals 10 is provided. The inertia status is displayed as a performance alert that indicates whether the inertia of each individual 10 is above or below a predetermined threshold. Also in FIG. 61, an indication of connectivity status (e.g., strength of communication signal) of individual monitors 200 is provided. The connectivity status is displayed as a graphic that indicates provides a visual representation of the communication signal strength at each individual monitor 200. Also in FIG. 61, an indication of remaining battery power of a battery (e.g., battery 212) of individual monitors 200 is provided. The remaining battery power is displayed numerically as a percentage of battery power capacity. Also in FIG. 61, an indication of remaining amount of data received by base station 300 from each individual monitor 200 is provided. The amount of data received is displayed numerically as a percentage of total data sent (or expected to have been sent) by each individual monitor 200.

In some embodiments, statuses can be simultaneously displayed as a numerical value and a system alert. For example, remaining battery power can be displayed as a numerical value, as described above, and can be simultaneously displayed as a system alert that indicates whether the remaining battery power of individual monitors 200 is above or below a predetermined threshold. For example, the numerical value for battery power of an individual monitor 200 below the predetermined threshold may be displayed in a different color than numerical values for battery power of individual monitors 200 having battery power above the predetermined threshold. Display 402 of FIG. 61 depicts statuses of individual monitors 200, however, the depiction of the statuses described with reference to FIG. 61 can be applied to any system component (e.g., sensors 202, individual monitors 200, object monitors 250, base stations 300, group monitoring devices 400, web server systems 500, analysis devices 600).

Figure 62:
FIG. 62 depicts a display of a group monitoring device according to an exemplary embodiment of the present invention.

In the exemplary display 402 of FIG. 62, a system view dashboard provides an indication of whether a battery (e.g., battery 212) of each individual monitor 200 is charging. Also in FIG. 62, an indication of available space of a memory (e.g., memory 228) of individual monitors 200 is provided. The available space is displayed numerically as a percentage of memory capacity. Also in FIG. 62, an indication of the current firmware version of individual monitors 200 is provided. Also in FIG. 62, an indication of the target firmware version for individual monitors 200 is provided. Display 402 of FIG. 62 depicts statuses of individual monitors 200, however, the depiction of the statuses described with reference to FIG. 62 can be applied to any system component (e.g., sensors 202, individual monitors 200, object monitors 250, base stations 300, group monitoring devices 400, web server systems 500, analysis devices 600, camera monitoring systems 700).

Figure 63:
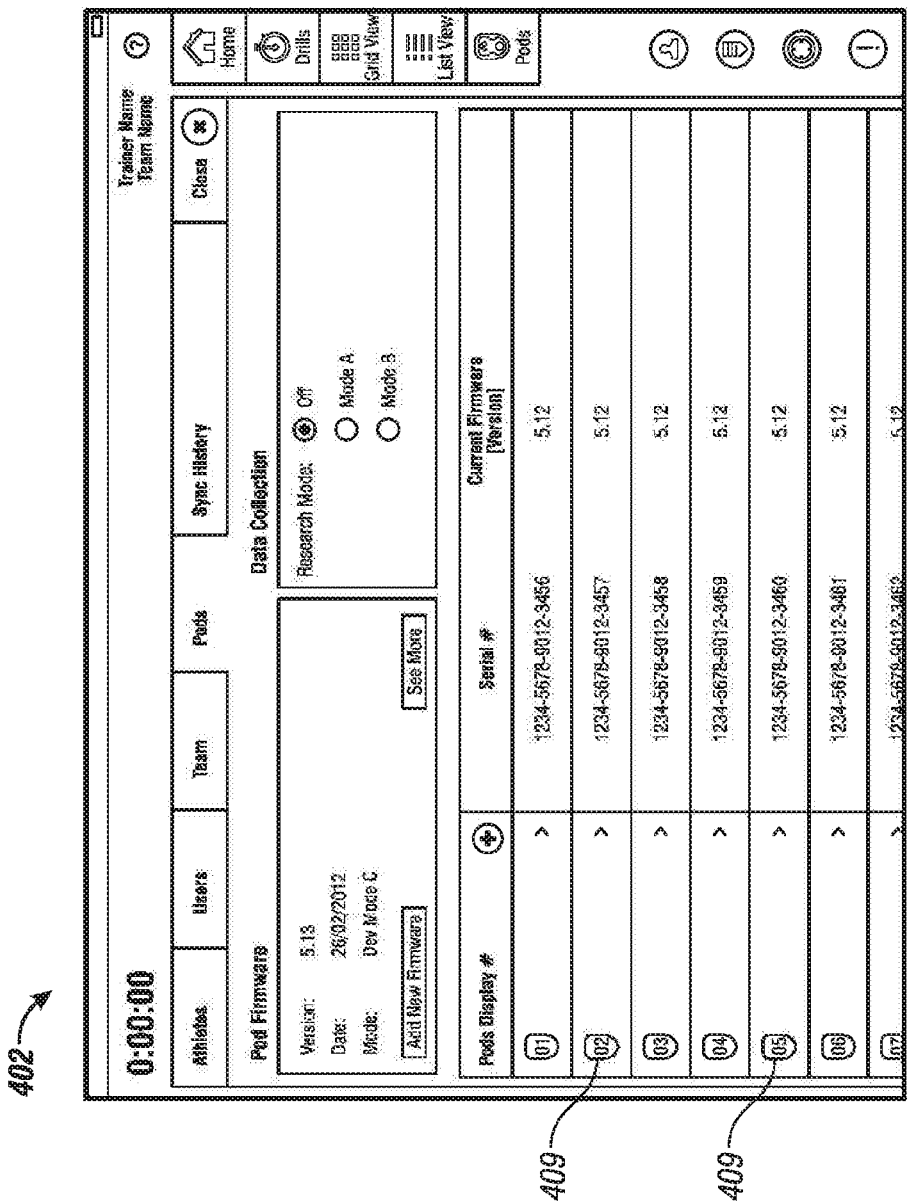
FIG. 63 depicts a display of a group monitoring device according to an exemplary embodiment of the present invention.

In the exemplary display 402 of FIG. 63, a system view dashboard provides an indication of a serial number of each individual monitor 200. Display 402 of FIG. 63 depicts statuses of individual monitors 200, however, the depiction of the statuses described with reference to FIG. 63 can be applied to any system component (e.g., sensors 202, individual monitors 200, object monitors 250, base stations 300, group monitoring devices 400, web server systems 500, analysis devices 600, camera monitoring systems 700).

Figure 64:
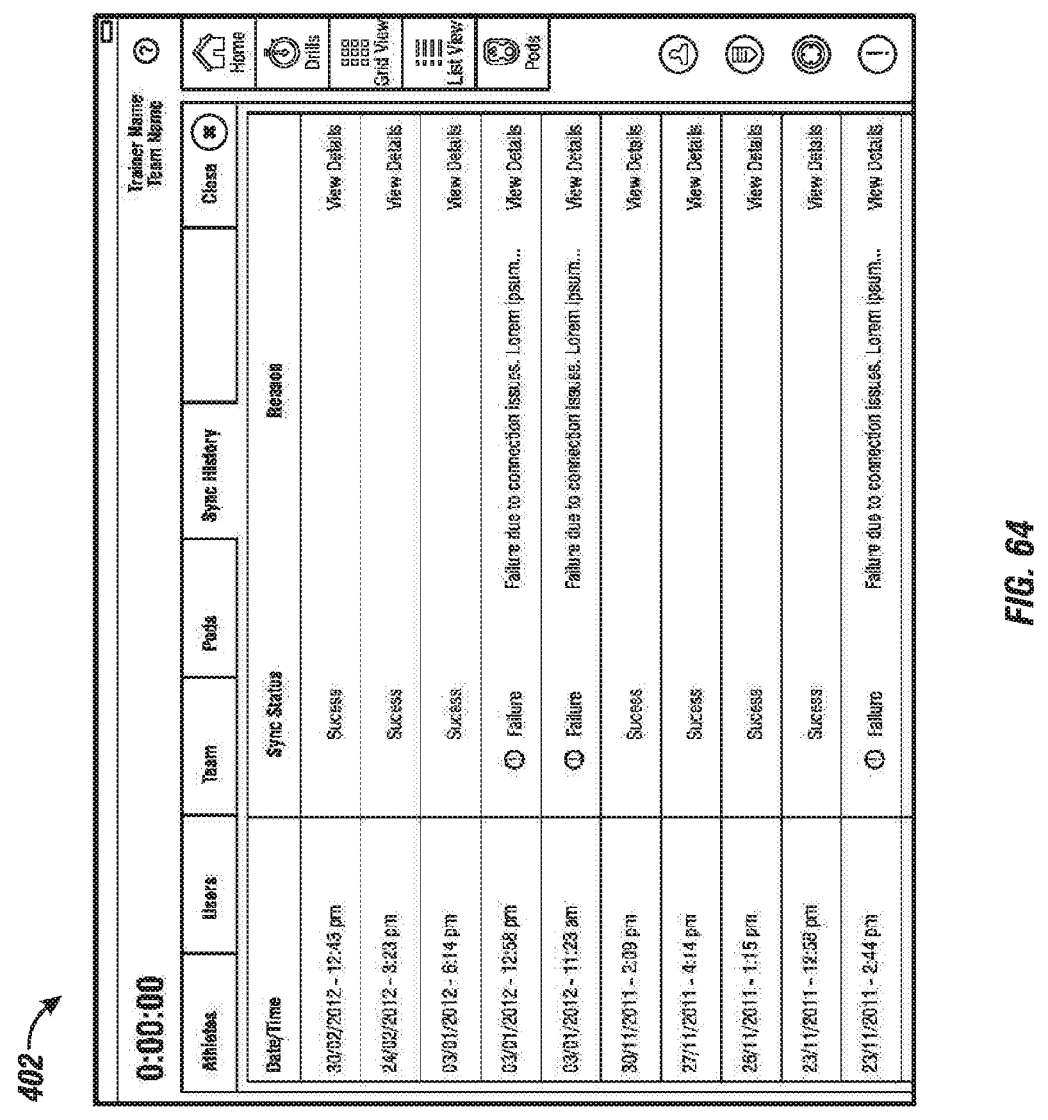

In the exemplary display 402 of FIG. 64, a system view dashboard provides an indication of a synchronization status of each individual monitor 200. Display 402 of FIG. 64 depicts statuses of individual monitors 200, however, the depiction of the statuses described with reference to FIG. 64 can be applied to any system component (e.g., sensors 202, individual monitors 200, object monitors 250, base stations 300, group monitoring devices 400, web server systems 500, analysis devices 600, camera monitoring systems 700).

Figure 67:
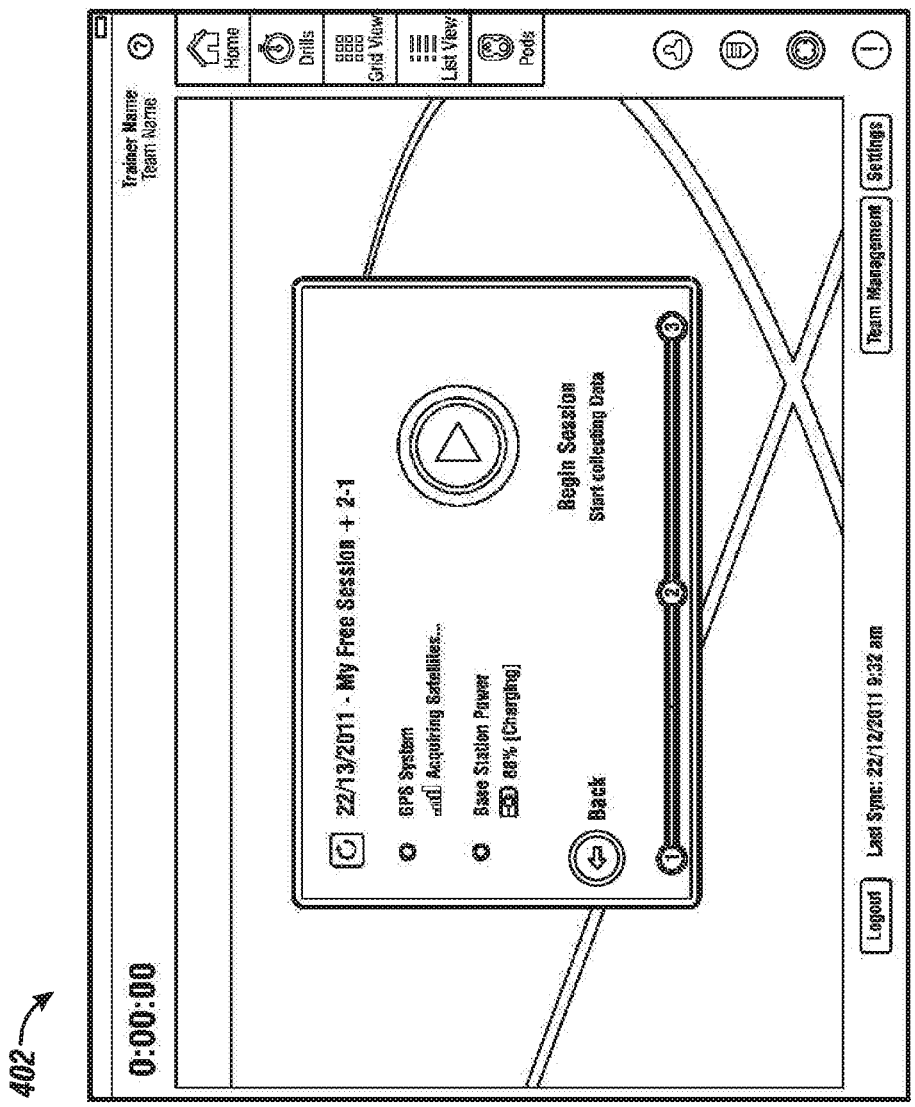
FIG. 67 depicts a display of a group monitoring device according to an exemplary embodiment of the present invention.

In the exemplary display 402 of FIG. 67, a system view dashboard provides an indication of a GPS signal status of base station 300, an indication of remaining battery power of a battery of base station 300, and an indication of the charging status of the battery of base station 300. In the exemplary display 402 of FIG. 65, such statuses of base station 300 are shown before commencement of a session of athletic activity, simultaneously with a selectable option to begin the session. Alternatively, these and other statuses of base station 300 and other system components may be displayed at any other time.

In some embodiments, a system view dashboard may provide an indication of how many individual monitors 200 (and/or object monitors 250) are docked at base station 300.

In some embodiments, a system view dashboard may provide an indication of whether a system component (e.g., individual monitor 200) is operating properly. For example, a system component (e.g., individual monitor 200, base station 300) may receive data from another system component that is outside accepted ranges for normal operation (e.g., individual monitor 200 may transmit metric data to base station 300 that indicates physical activity of a monitored individual 10 that is beyond the physical capabilities of a human). In some embodiments, a system view dashboard may provide an alert to indicate that a system component is not operating properly.

In some embodiments, where individual monitor 200 includes a sensor garment (e.g., sensor garment 204), a system view dashboard may provide an indication of whether sensor garment 204 properly fits an individual 10 wearing sensor garment 204. For example, where sensor garment includes sensors (e.g., heart rate monitor electrodes, respiration sensor) intended to be positioned at areas of the wearer's body well-suited to gather data (e.g., about a chest area), poor data collection by those sensors (e.g., a weak heart or respiration signal) may indicate that sensor garment 204 does not fit individual 10 wearing sensor garment 204 (e.g., the sensors may not be positioned at the optimum areas, because sensor garment 204 was sized for a smaller or larger person than individual 10). In some embodiments, a system view dashboard may provide an alert to indicate that sensor garment 204 does not properly fit individual 10 wearing sensor garment 204.

In some embodiments, a system view dashboard provides an indication of whether a system component (e.g., individual monitor 200) is properly placed (e.g., in and/or maintaining a proper orientation). For example, a system component (e.g., individual monitor 200, base station 300) may receive data sensed by sensors 202 of individual monitor 200 that may have characteristics that do not correspond to characteristics expected were the individual monitor 200 in a proper orientation (e.g., acceleration due to gravity may be sensed by individual monitor 200 in a relative "up" direction, which may indicate that the individual monitor 200 is oriented upside-down; or acceleration signals may change orientation erratically, which may indicate that the individual monitor 200 is not being maintained in a constant orientation with respect individual 10, which may indicate undesirable movement of the individual monitor 200 within a restraining component, such as a pocket). In some embodiments, a system view dashboard may provide an alert to indicate that an individual monitor 200 is not properly placed.

In some embodiments, a status and/or system alert is displayed (e.g., via group monitoring device 400) in response to a system alert being triggered (e.g., when the status has passed a system alert threshold, such as, for example, remaining battery power below a threshold percentage of capacity, or GPS signal strength below a threshold level). In some exemplary embodiments, new system alerts, and/or statuses related thereto, can be indicated by, for example, a flashing icon or a temporary pop-up box.

In some exemplary embodiments, system components having an active alert (e.g., performance alert or system alert) associated therewith (e.g., associated with the component itself or with its associated individual 10 or sports object 40) can provide an alert indication by for example, emitting an audible noise (e.g., via a speaker), vibrating, or providing a visual indication (e.g., via an illuminated LED or LCD display). In some exemplary embodiments, a system component may send a signal to a device connected thereto (such as, for example, a garment, watch, or band) to cause the connected device to provide such an alert indication. The device may include, and provide the alert indication via, for example, a display, illuminable area, speaker, or vibration module (e.g., integrated into the sleeve of a garment, or face of a watch).

For example, group monitoring system 100 may include a garment (e.g., sensor garment 204, which may be, for example, a shirt) including an illuminable area. The illuminable area may illuminate in response to the active alert (e.g., in the form of a color or graphic corresponding to or simply indicating the presence of the active alert). For example, an alert may be triggered, and an individual 10's shirt may illuminate, in response to a determination that the individual 10 achieved the most recent goal or greatest number of goals during an athletic activity, compared to other individuals 10 participating in the activity, or in response to a determination that the individual 10 is the most recent individual 10 to have had contact with a ball (e.g., sports object 40). Alternatively or additionally, an illuminable area in a garment worn by individual 10 may provide a visual indication (e.g., may illuminate) of, for example, performance by individual 10 of a certain type of activity (e.g., running, jumping), a metric value of individual 10 being above or below a threshold value, possession of or contact with a sports object (e.g., a ball) by individual 10, or optimum or acceptable placement of individual 10 the playing field.

Group monitoring system 100 can include any suitable number of components such as individual monitors 200, object monitors 250, base stations 300, group monitoring devices 400, or analysis devices 600. In an exemplary embodiment, group monitoring system includes 30 individual monitors 200, 1 object monitor 250, 1 base station 300, and 2 group monitoring devices 400.

In some embodiments, multiple teams (including competing teams) can use the same base station 300, each team having one or more individuals 10 monitored by an individual monitor 200. In some embodiments where multiple teams use the same base station, base station 300 may be configured to restrict access to data relating to a first team to only those accessing devices (e.g., group monitoring devices 400, analysis devices 600) that are associated with the first team (thereby blocking access to a second team, which may be in competition with the first team). In some embodiments, base station 300 may be configured to provide access to data from more than one team to other parties (i.e., non-team parties). For example, base station 300 may be configured to provide access to data relating to one or more teams to television broadcasters or web services (e.g., to enable them to compare or otherwise analyze statistics or to present statistics to viewers or fans), or to referees or other sporting event staff (e.g., to facilitate conducting a sporting event, including making game-related rulings).

After completion of a session of athletic activity, individuals 10 may dock their individual monitors 200 in one of docking ports 318 of base station 300. When docked with docking port 318, batteries 212 of individual monitors 200 can be charged, and data can be transferred from individual monitors 200 to base station 300. As noted above, individual monitors 200 store sensed data and also transfer sensed data wirelessly to base station 300 during an athletic activity. In order to most efficiently use bandwidth, data may be transferred wirelessly during the athletic activity at a lower resolution than it is sensed and stored in individual monitors 200. Due to communication errors, some data may not be transmitted successfully from individual monitors 200 to base station 300 (e.g., if an individual moves out of range of base station 300). Thus, the data stored in individual monitors 200 at the conclusion of a session of athletic activity may be more complete or accurate than the data stored in base station database 316.

In some exemplary embodiments, data can be transferred from individual monitor 200 to base station 300 at full resolution (i.e., raw data) and stored in base station database 316 (and/or web server database 502, once transferred thereto) at full resolution as well. Storing such raw data for each individual 10 for each session may be useful for subsequent data analysis, for example to perform recalculations of metrics or calculations of new and different metrics using new and different algorithms.

In some exemplary embodiments, data and metrics can be stored in a general database (e.g., a database shared by several of the systems described herein, or a general sports database for individuals).

While docked in docking ports 318 of base station 300, individual monitors 200 can directly transmit their stored data to data processing module 304 (via data reception module 302). Data processing module 304 can then filter the data received from individual monitors (e.g., data processing module 304 can perform a de-duplication process on the data to avoid storing duplicate data in base station database 316) and store the data in base station database 316.

In some exemplary embodiments, base station 300 includes a central sync module 310. Central sync module 310 of base station 300 can communicate through an Internet connection with a web server system 500, web server system 500 being external to base station 300. If base station 300 is connected to the Internet via an Ethernet (or other wired) connection, such communication can take place over the Ethernet (or other wired) connection. If base station 300 is not connected to the Internet via an Ethernet (or other wired) connection, communication can take place wirelessly, for example over a cellular network (e.g., GSM broad band 2.5G or 3G). Central sync module 310 includes data upload and download capabilities for uploading session data about a monitored athletic activity, or diagnostic information about base station 300 and other components, and to download user data such as, for example, updated firmware to be installed in individual monitors 200 via docking port 240, or updated software for use in base station 300. Central sync module 310 can upload data stored in base station database 316 to web server system 500. Such data may include data, metrics, and alerts generated during the athletic activity. When receiving such data, web server system may store it in a web server database 502.

Web server system 500 can render display code (such as, for example, html5 compliant code) based on a request from a client device such as, for example, analysis device 600. Web server system 500 can also serve a security function, by ensuring that a requesting client device is properly authenticated and that all data is passed using https. Web server system 500 may provide analysis device 600 with requested metrics and generated alerts stored in web server database 502, via, for example, an API layer. Web server system 500 may include one or more servers, which may receive, store, and/or provide data to one or more remote devices (e.g., analysis device 600).

One or more servers of web server system 500 may receive, store, and/or provide all or a subset of metrics from base station 300. Some servers may be configured to receive, store, and provide metrics different from those metrics received, stored, and provided by other servers. In some embodiments, servers of web server system 500 may be configured to allow different levels of access for different types of accessing devices and/or for different permissions associated with an accessing device. Servers of web server system 500 may provide data (including metrics and operating conditions of system components as described herein) to a variety of accessing devices for a variety of uses.

For example, web server system 500 may provide data to general personal computing devices (e.g., to provide an Internet-connected database for public use). Also for example, web server system 500 may provide data to on-site display systems (e.g., to communicate data to spectators at the monitored event using displays at the event). Also for example, web server system 500 may provide data to media coverage devices (e.g., to communicate data to television or Internet viewers of media coverage of the monitored event). Also for example, web server system 500 may provide data to smartphones or other personal portable devices (e.g., to communicate data to users of such devices through application interfaces, or "apps").

Also for example, web server system 500 may provide data to secondary servers. For example, such secondary servers may communicate data to viewers of a website in association with the website—or advertisements presented thereon—provided by secondary server. Also for example, such secondary servers may communicate data to players of a videogame in association with the videogame provided by the secondary server.

Also for example, web server system 500 may provide data to a social networking service (including a social networking website). Monitored individual 10 may have an account with such social networking service. Such data may be provided, for example, via secondary servers as described herein. Such social networking service may access such data relating to monitored individual 10 to associate it with the account of the monitored individual 10. In some embodiments, representations of such data (including metrics related to performance of individual 10) may be displayed in association with social networking account information of individual 10 (e.g., on a profile page for individual 10, in comparison with similar data associated with the accounts of others on the social networking site). Such a social networking service may accept individual data or team data, and may provide an interface for individuals or teams to communicate with each other and share their data. For example, individuals or teams can share coaching recommendations, experiences, or training plans based on their data. Also for example, individuals or teams can schedule meeting or games with other individuals or teams, and may rely on shared data to help identify appropriate individuals or teams with which to compete (e.g., teams or individuals with comparable abilities). In some embodiments, such data can be relied upon to determine a handicap of one team or individual compared to another team or individual, thereby facilitating competition between teams or individuals with non-comparable abilities.

Also for example, such secondary servers may provide data to a retail service. For example, products or services (including, e.g., training plans, apparel, awards, equipment, personal training) may be available or not available to a monitored individual 10 based on data relating to the monitored individual 10. Also for example, products or services may be promoted or not promoted to a monitored individual 10 based on data relating to the monitored individual 10. In other words, availability and promotion of products and services may be based on personal attributes or performance of individual 10. For example, availability and promotion of products and services may be based on the individual 10's membership in or association with a particular team, the individual 10's overall past monitored performance, the individual 10's performance in the individual 10's most recent athletic activity, alerts triggered by the individual 10, or the type of sport(s) played by the individual 10. Such a retail service may be provided in any suitable medium, for example, as a standalone website, in association with a website (e.g., a social networking website as described above), within an app, or within any of the dashboards described herein.

Also for example, such secondary servers may communicate data to an advertising service. For example, products or services may be advertised to a monitored individual 10 based on data relating to the monitored individual 10. In other words, advertisement of products and services may be based on personal attributes or performance of individual 10. For example, advertisement of products and services may be based on the individual 10's membership in or association with a particular team, the individual 10's overall past monitored performance, the individual 10's performance in the individual 10's most recent athletic activity, alerts triggered by the individual 10, or the type of sport(s) played by the individual 10. Such an advertising service may be provided in any suitable medium, for example, as a standalone website, in association with a website (e.g., a social networking website as described above), within an app, or within any of the dashboards described herein.

Also for example, web server system 500 may provide data to a voting or wagering website or service (e.g., via secondary servers as described herein). In some embodiments, such voting or wagering website or service may access such data relating to monitored individuals 10, and may provide an interface for users of the website or service to vote for individuals 10 to receive accolades or other recognition (e.g., a most valuable player award), based on the user's review of provided data. In some embodiments, such voting or wagering website or service may provide an interface for users of the website or service to make predictions or place wagers on game events (e.g., which team will win, how many points the winning team will win by) and/or future metrics of individuals 10 (e.g., that Player A will achieve a heart rate of 170 beats per minute by halftime), based on the user's review of provided data.

Also for example, web server system 500 may provide data to a gaming device. Such a gaming device may be, for example, a videogame console or a device otherwise having gaming capabilities (e.g., a (smart)phone with game software/apps). In some embodiments, the data provided by web server system 500 may be used to unlock gameplay features. For example, where a player of the videogame is a monitored individual 10, metrics based on past real-world performance of the player of the videogame can be compared by the game console to targets for those metrics, and if the targets are met, a previously locked feature of the game (e.g., a virtual player to virtually play the game as, or a virtual stadium to virtually play the game at) may be unlocked and made available to the player of the videogame. In some embodiments, the data provided by web server system 500 may be used to affect the performance of a virtual player corresponding to a monitored individual 10, to correspond the virtual performance of the virtual player with the actual performance of the monitored individual 10. Such monitored individual 10 may be the player of the videogame, and/or may be one or more other individuals (e.g., individuals corresponding to videogame console-controlled virtual representations of such individuals, which may be the virtual player controlled by the player of the videogame, or virtual teammates or opponents thereof). In this way, the player of the videogame can control a virtual player having virtual capabilities corresponding to the real-world capabilities of the player of the videogame or another player (e.g., a famous player represented in the videogame), and virtual teammates or opponents thereof can similarly have virtual capabilities corresponding to those of real-world counterparts. In some embodiments, the data provided by web server system 500 may be used to produce a virtual reproduction of actual play of monitored individuals 10 during a session of athletic activity.

Also for example, web server 500 may provide data to a training device (e.g., a display device configured to facilitate training of a trainee). Such training device may be, for example, a personal computer running a software program to schedule and track training progress of the trainee, or a portable device carried by the trainee while training, such as, for example, a sports watch. The training device may be in communication with sensors (such as, for example, sensors described herein) to monitor the trainee during training. The training device may access data via web server 500 (or in some embodiments, from base station 300 directly) to compare metrics of the trainee's performance with metrics downloaded from web server 500 (or base station 300). A representation of such comparison can be provided to the trainee in real-time during training, or after completion of a training session. Such comparison can be based on downloaded metrics of the trainee himself (in the case where trainee was a monitored individual 10) or of a different monitored individual 10.

Access to data from web server 500 may be licensed and provided to third parties (e.g., via secondary servers). For example, media outlets (television stations, newspapers, Internet blogs) and medical researchers may be provided licensed access to data from web server 500, and such access may be limited based on the scope of licensed access. For example, only access to a particular individual 10 or group of individual 10, or to particular type(s) of data (e.g., heart rate data, speed data) may be granted).

Data provided by web server system 500 may be presented in any manner as described herein, subject to limitations of the device used for such presentation (e.g., a user accessing such data via a smartphone or computer may interact with the device to change the data represented, or the mode of presentation, while a viewer of a media broadcast may not have the ability to interact with the data, and may simply view the data presented). Presentation of data about monitored individuals 10 engaged in an athletic activity to non-participants (e.g., spectators, fans) may help promote engagement in the athletic activity by the non-participants. In some embodiments, non-participants can be prompted to vote or wager on results of an athletic activity (e.g., via an interface of a remote device in communication with web server system 500), on the basis of information provided via web server system 500.

As described herein, base station 300 can receive data from monitors (e.g., monitors 200, 250), store such data, and make such data available to remote devices (e.g., group monitoring device 400, analysis device 600). In some embodiments, multiple base stations 300 may be provided (e.g., a first base station 300 and a second base station 300), and one base station 300 (e.g., a first base station 300) may be configured to receive, store, and provide metrics (e.g., a first set of metrics indicative of the performance of individuals 10) different from those metrics (e.g., a second set of metrics indicative of the performance of individuals 10) received, stored, and provided by another base stations 300 (e.g., a second base station 300).

In some embodiments, base station(s) 300 may be configured to allow different levels of access for different types of accessing devices and/or for different permissions associated with an accessing device (e.g., a first base station 300 may be configured to send a first set of metrics to a first remote device, while a second base station 300 may be configured to send a second, different, set of metrics to a second remote device). Base station(s) 300 may provide stored data (including metrics and operating conditions of system components as described herein) to a variety of accessing devices for a variety of uses, including those described herein with respect to web server system 500.

In embodiments where group monitoring system 100 includes multiple base stations 300, remote devices may be configurable to select which base station(s) to send and/or receive data from. For example, a settings page may be displayed (e.g., via display 402 of group monitoring device 400) which may allow selection of different base stations (see, e.g., FIG. 68).

Figure 10:
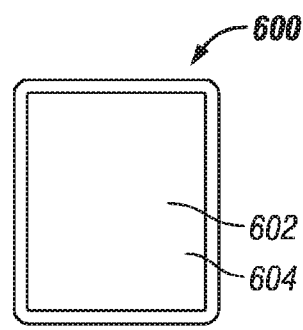
FIG. 10 depicts an analysis device according to an exemplary embodiment of the present invention.

A remote device (analysis device 600) is depicted in FIG. 10 and includes a display 602 and an input 604. In an exemplary embodiment, analysis device 600 is a tablet computing-style device (such as a tablet personal computer or an iPad®, marketed by Apple Inc.®). Analysis device 600 may be, however, any other suitable device, such as, for example, a laptop computer, a smartphone, or a personal computer. Analysis device 600 can access data in web server database 502 and display the information to a user of analysis device 600 (e.g., trainer 20). In some embodiments, the information may be displayed using dedicated or general-purpose software (e.g., a dedicated software interface, a web browser). Although analysis device 600 and group monitoring device 400 are described separately herein, in some exemplary embodiments, group monitoring device 400 and analysis device 600 are the same device.

In some exemplary embodiments, analysis device 600 can be located at a remote location with respect to base station 300 or the relevant athletic activity, and can be used to access and display data and metrics in real time. In such an embodiment, base station 300 can transfer the data and metrics to web server 500 in real time, so that the data and metrics can be accessed for display by analysis device 600, as described above. Such an embodiment may be useful for a user to monitor an ongoing session of athletic activity from a remote location (e.g., a trainer 20 that could not be present at a match, or a team owner that desires to monitor a training session without physically attending the session).

After completion of a session of athletic activity, a trainer 20 may use analysis device 600 to review and analyze information about individuals 10, including information about past performances of individuals 10 during past sessions of athletic activity. Depending on the number of past sessions of athletic activity for which data is available, and other available data in web server database 502, post-session analysis of an individual 10 using analysis device 600 may provide trainer 20 with information spanning a longer period than the information provided during an athletic activity by group monitoring device 400, which may facilitate long-term evaluation of individual(s) 10. Trainer 20 may access and view the data using analysis device 600, however, in much the same way as has been described above with respect to group monitoring device 400. For example, analysis device 600 may be configured to display a team view dashboard, and an individual view dashboard, as described above with reference to group monitoring device 400. Some differences applicable to some exemplary embodiments of team view dashboard and individual view dashboard of analysis device 600 include that the displayed information may not be updated in real time when using analysis device 600, that the information displayed may span multiple sessions of athletic activity, and that alerts can be created that apply to data across multiple sessions.

Moreover, the team view dashboard and individual view dashboard of analysis device 600 may be customizable. Display components (e.g., photograph 410 of individual 10, list of all individuals 10, location component 412 showing a map of positions of individuals 10 on playing field, detailed charts and/or graphs 418) can be added or removed by trainer 20 so as to create a customized view dashboard, which can be saved and referred to in the future. In some embodiments, customized view dashboards can be sent to or otherwise used by group monitoring devices 400, thereby allowing trainer 20 to view real-time data in a custom format.

In some exemplary embodiments, analysis device 600 includes an analysis chart view that displays a detailed view of a metric, in for example, a chart format or a graph format. Trainer 20 may input desired parameters for the analysis chart view via input 604. For example, trainer 20 may input parameters indicating that the analysis chart view should be generated to show data for all drills performed by Player A during August 2010. Alternatively, analysis device 600 may show trainer 20 a list of all data entries corresponding to the parameters input by trainer 20, allowing trainer 20 to select the entries desired to be included in an analysis chart view. Trainer 20 may also be given the option to select a type of analysis chart view. For example, trainer 20 may be able to choose from a stacked view, where several charts or graphs, each pertaining to a different metric, are stacked one above the other; or an overlay view, where multiple metrics are displayed on a single chart or graph. In some exemplary embodiments, the overlay view allows trainer 20 to view data from one time period (e.g., current data or most recent data) overlaid with data from another time period (e.g., older data) to allow easy comparison of performance at different times.

Figure 55:
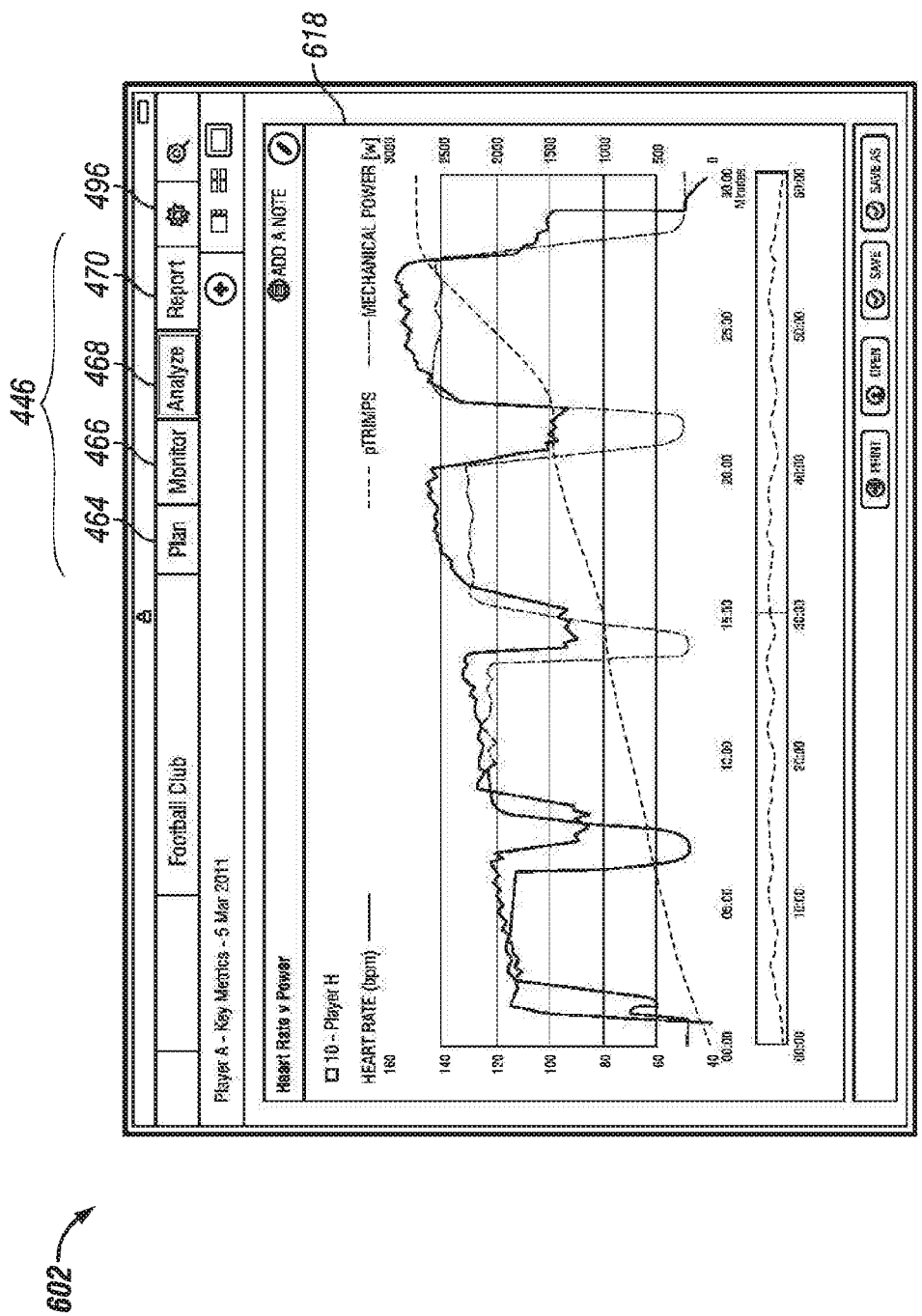
FIG. 55 depicts a display of an analysis device according to an exemplary embodiment of the present invention.

In some exemplary embodiments, to facilitate analysis of one or more sessions of athletic activity, display 402 of group monitoring device 400 or display 602 of analysis device 600 may display an analysis module, which may include utilities useable to analyze the session of athletic activity, as depicted in, for example, FIG. 55. Display 602 of analysis device 600 may display charts or graphs 618 that display metrics comparatively. For example, graph 618 may display heart rate for an individual 10 plotted over a session of athletic activity, or any other time period. Also displayed plotted on the same graph 610 may be other metrics, for example, training impact and mechanical power of individual 10. By plotting multiple metrics on the same graph 618, analysis device 600 may facilitate comparison of these metrics, and may evidence a correlation that can be useful to trainer 20 in monitoring the performance of individual 10.

Figure 56:
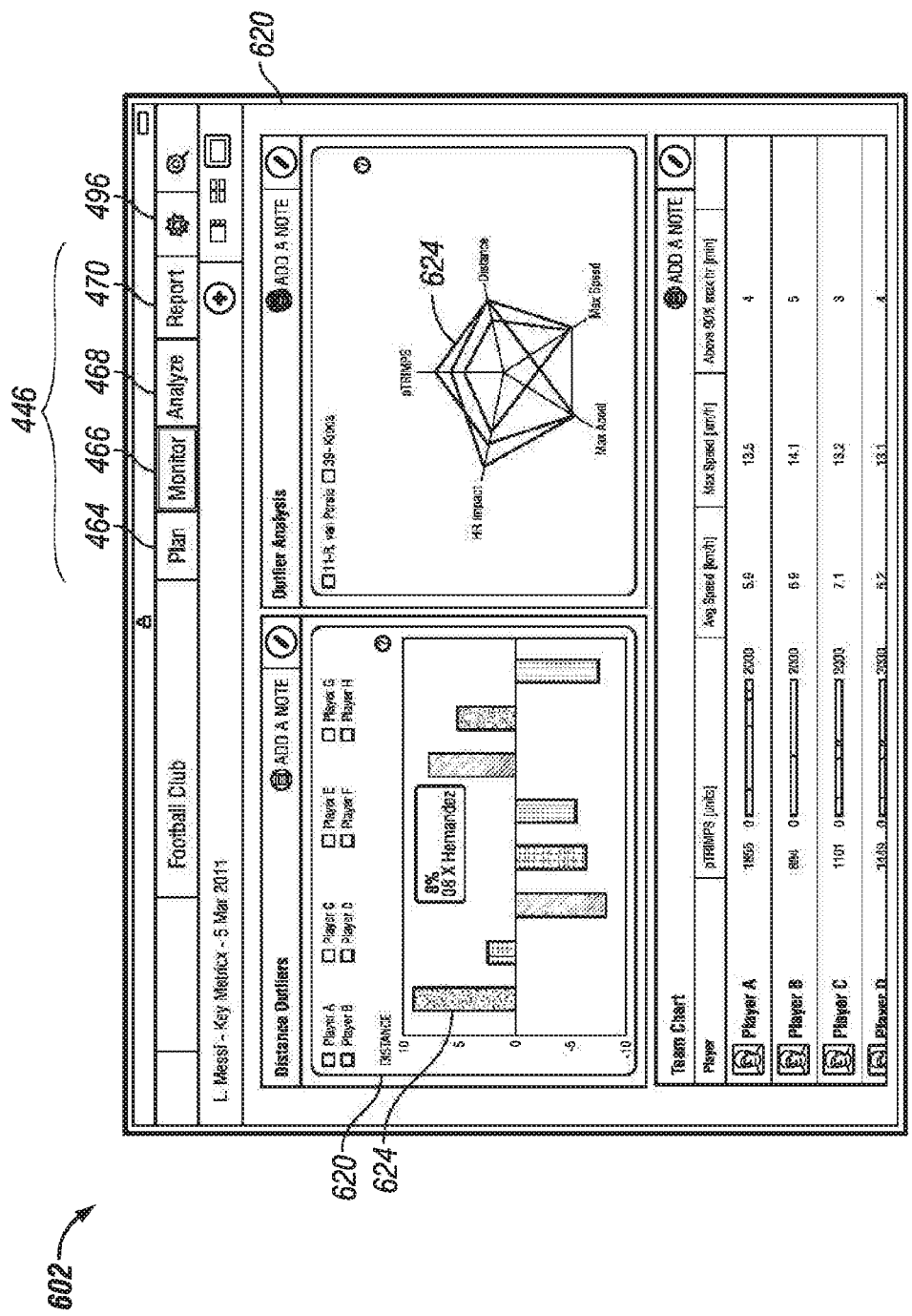
FIG. 56 depicts a display of an analysis device according to an exemplary embodiment of the present invention.

In some exemplary embodiments, as depicted in, for example, FIG. 56, display 602 of analysis device 600 may display outlier analyses 620 for comparing metric information of one or more individuals with one or more other individuals, and determining when one or more individuals have achieved a particular metric value that falls outside a baseline value. Outlier analyses 620 can be presented in a variety of ways, and can be useful in presenting data for multiple individuals 10 in a context that facilitates comparison of individuals 10. In some exemplary embodiments, a bar graph 622 showing percentage or value above or below an average (or other baseline) for a metric may be displayed. In some exemplary embodiments, a star graph 624 showing percentage or value of a variety of metrics for one or more individuals 10 may be displayed.

In some exemplary embodiments, analysis device 600 can recalculate past data based on new algorithms, thereby refining metric calculations or defining new metrics. In some exemplary embodiments, analysis device 600 can apply new alerts to past data. Such features can be useful to trainer 20 by facilitating historical investigation and analysis of data of individuals 10.

In some exemplary embodiments, analysis device 600 can be used by trainer 20 to predict future performance of individuals 10. Appropriate algorithms can be applied to past data that generate predictions of data of a future session for a particular player or group. For example, if a performance trend is recognized (e.g., increasing efficiency or relative power), it can be predicted that that trend may continue in a future session of athletic activity. Trainer 20 can use this information to inform decisions regarding future sessions of athletic activity.

Figure 57:
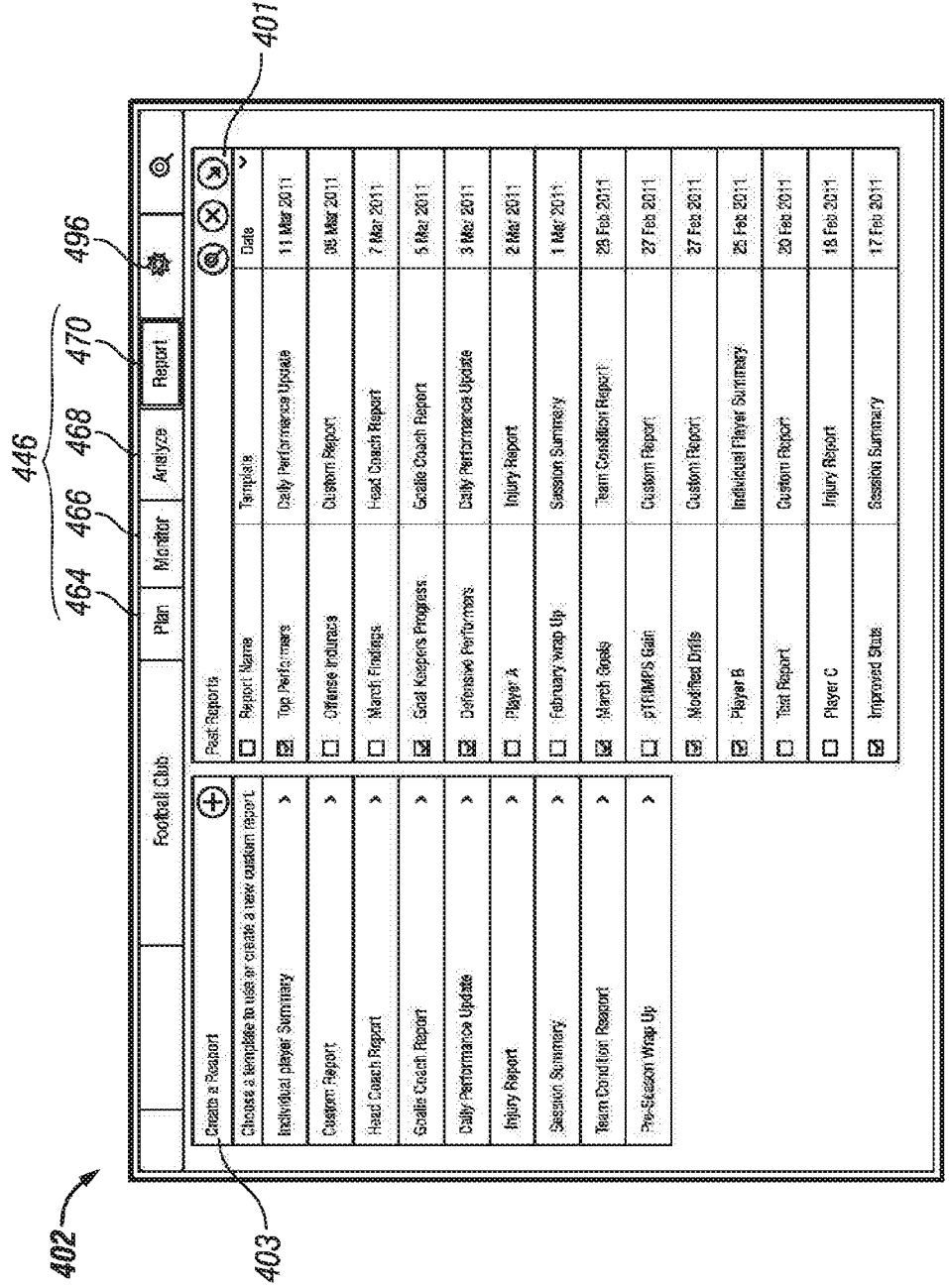
FIG. 57 depicts a display of a group monitoring device according to an exemplary embodiment of the present invention.

In some exemplary embodiments, as depicted in, for example, FIG. 57, group monitoring device 400 may include a report module, which may include a report generator 403 that allows a user to generate reports based on data and metrics of individuals 10. Reports can be predefined, or can be customized to generate desired information. A variety of types of reports can be generated, for example, individual player summaries, reports designed for a head coach, reports designed for a coach of a sub-group of a team (e.g., a goalie coach), daily performance update reports, injury reports, session summary reports, and team condition reports. Such reports can be presented (e.g., via display 402 of group monitoring device 400) in real time for individuals 10 and/or sports objects 40, or groups thereof, to compare individuals 10 and/or sports objects 40 with other individuals 10 and/or sports objects 40.

Figure 58:
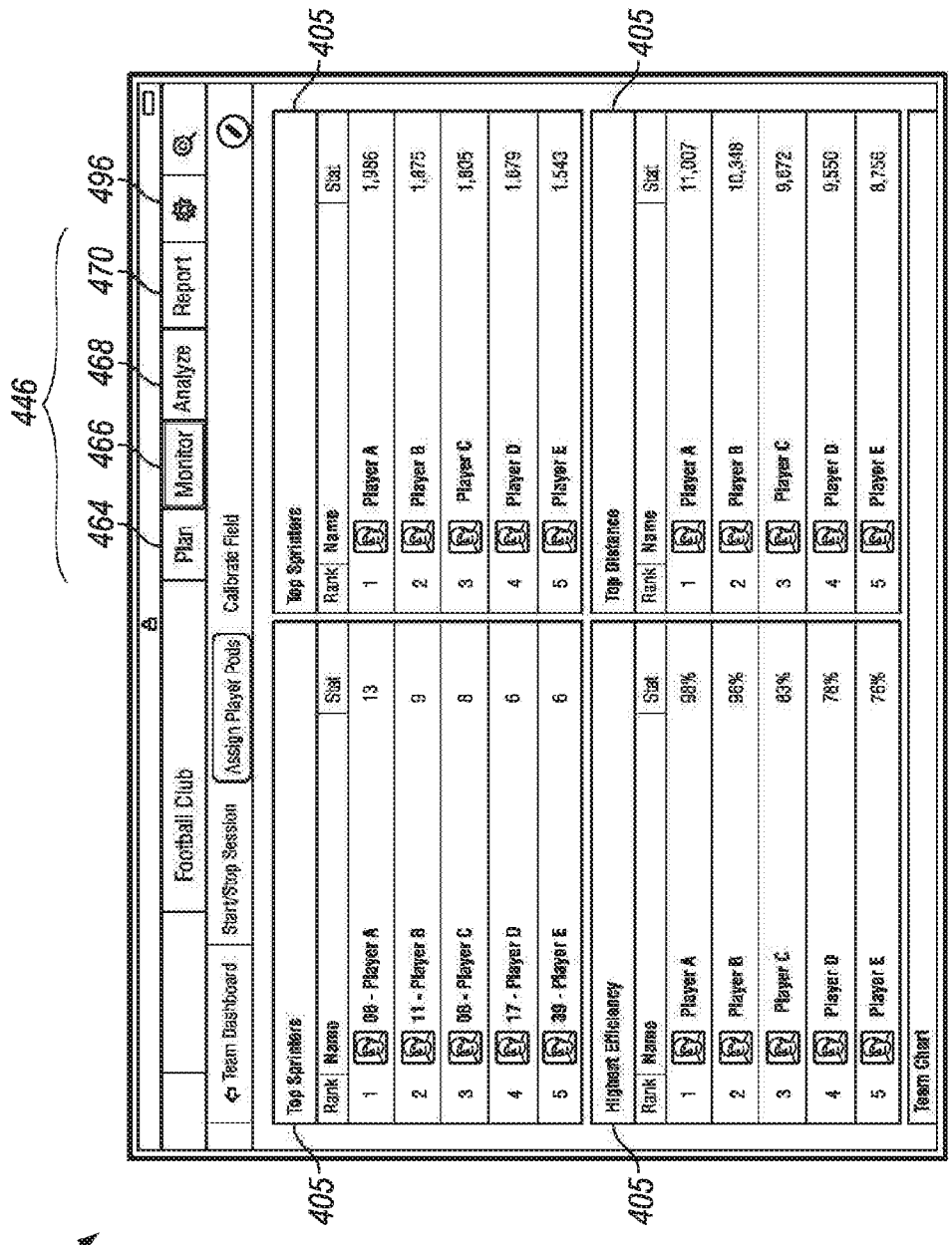
FIG. 58 depicts a display of a group monitoring device according to an exemplary embodiment of the present invention.
Figure 59:
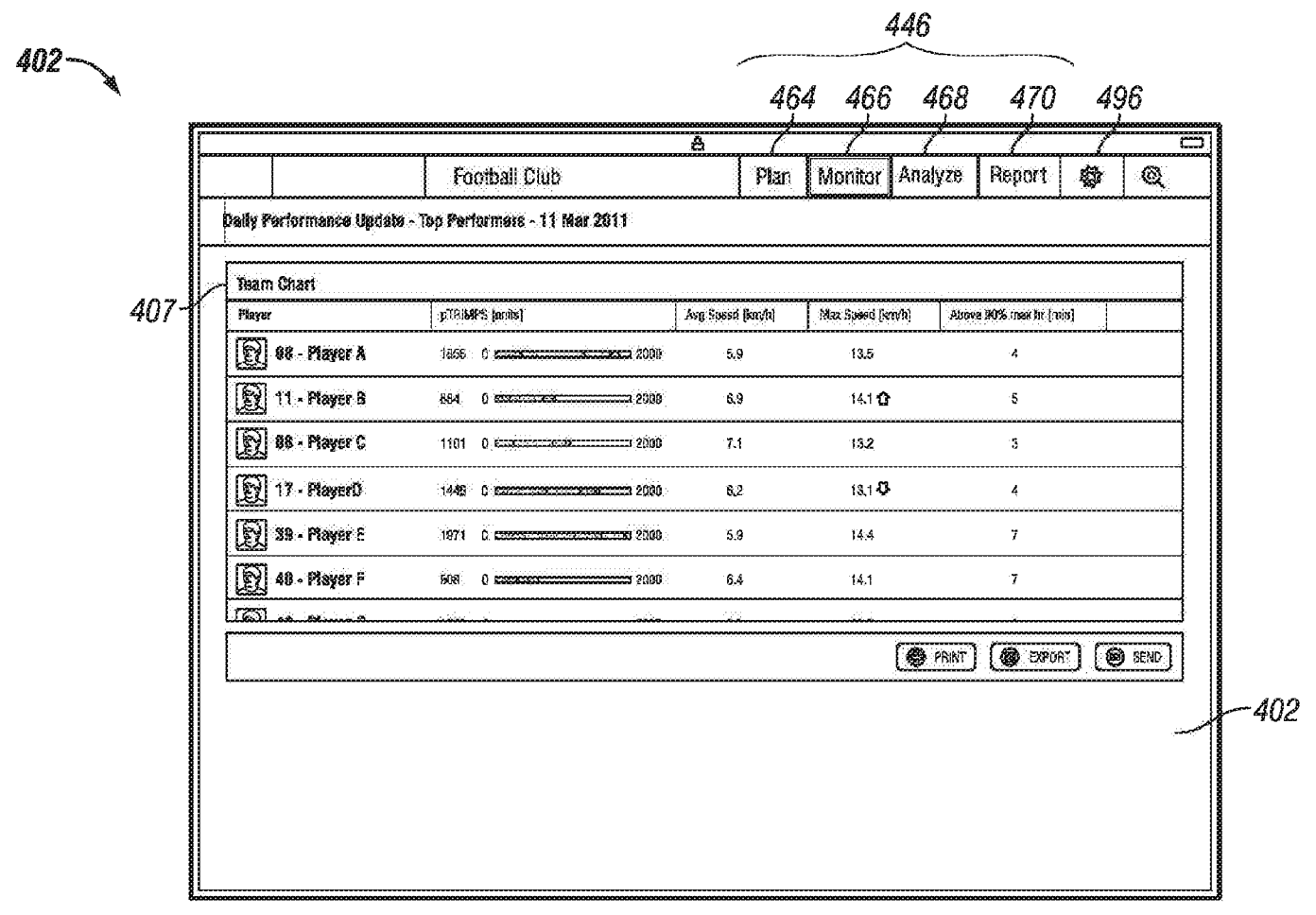

For example, as depicted in FIGS. 58 and 59, a daily performance update may include information regarding top performing individuals 10. Such a daily performance update may include listings 405 showing individuals 10 that are top sprinters, are top power producers, have highest efficiency, and have top distance. In some exemplary embodiments, past reports can be saved and accessed from a past reports menu 401. Such a daily performance update may also include a team chart 407 showing present information for a group of individuals 10 making up a team. Team chart 407 may further indicate differences in the displayed information that may exist between the displayed information and information displayed in previous reports, thereby indicating changes in the performance of individuals 10.

In this document, terms such as "computer-usable medium" may be used to generally refer to media such as a removable storage unit or a hard disk installed in hard disk drive. Computer-usable medium may also refer to memories, such as a main memory or a secondary memory, which can be memory semiconductors (e.g., DRAMs, etc.). These computer program products provide software to computer systems and other components of the present invention.

Computer programs (also called computer control logic) may be stored on main memory and/or secondary memory. Computer programs may also be received via a communications interface. Such computer programs, when executed, may enable computer systems of the present invention to implement embodiments described herein. Where embodiments are implemented using software, the software can be stored on a computer program product and loaded into a computer system using, for example, a removable storage drive, an interface, a hard drive, and/or communications interface.

Based on the description herein, a person skilled in the relevant art will recognize that the computer programs, when executed, can enable one or more processors to implement processes described above, such as, for example, determining, recording, and transmitting information related to individuals 10 engaged in an athletic activity, or presenting to a user of any of the herein-described displayable or audible elements (e.g., information related to individuals 10 engaged in an athletic activity). Information and/or instructions (e.g., a computer program product) for maintaining and/or rendering any module, function, or feature described herein (e.g., plan module, monitor module, analyze module, report module) may be stored in a computer-useable medium (e.g., memory or database) of any component described herein (e.g., base station 300, individual monitors 200, group monitoring device 400, web server system 500, analysis device 600, camera monitoring system 700, and/or video feed system 800).

In some exemplary embodiments, the one or more processors can be part of a computing device incorporated in a clustered computing environment or server farm. In some exemplary embodiments, the computing process performed by the clustered computing environment may be carried out across multiple processors located at the same or different locations. In some exemplary embodiments, the one or more processors can be part of any of the components described herein (e.g., base station 300, individual monitors 200, group monitoring device 400, web server system 500, analysis device 600). In some exemplary embodiments, one or more of the plan module, monitor module, analyze module, and report module may comprise, for example, an application for a device such as a smartphone, and may be configured to be downloaded in whole or in part.

Software of the present invention may be stored on any computer-usable medium. Such software, when executed in one or more data processing devices, such as, for example, any suitable component described herein (e.g., base station 300, individual monitors 200, group monitoring device 400, web server system 500, analysis device 600) causes the data processing device to operate as described herein. Embodiments of the invention employ any computer-usable or -readable medium, known now or in the future. Examples of computer-usable mediums include, but are not limited to, primary storage devices (e.g., any type of random access or read only memory), secondary storage devices (e.g., hard drives, floppy disks, CD ROMS, ZIP disks, tapes, magnetic storage devices, optical storage devices, MEMS, nanotechnological storage devices, memory cards or other removable storage devices, etc.), and communication mediums (e.g., wired and wireless communications networks, local area networks, wide area networks, intranets, etc.).

In some exemplary embodiments, group monitoring system 100 includes or is in communication with a camera monitoring system 700, which may include, for example, one or more video cameras trained on playing field 30 in order to record image data (e.g., still images, video, data related thereto and/or derived therefrom) indicative of motions of individuals 10. This image data can be transmitted to base station 300 (e.g., to data processing module 304 of base station 300), and can be used in the determination of metrics in much the same way as described above with reference to data transmitted from individual monitors 200 and/or object monitors 250.

In some embodiments, metrics can be determined based on image data alone, or based on image data and data derived from other sensors (e.g., sensors 202 of individual monitors 200 and/or object monitors 250). This image data can be stored in base station database 316, and can be transferred to web server system 500 (e.g., via central sync module 310), where it can be accessed by a video feed system 800 and displayed by a video display 802 of video feed system 800. In some embodiments, the image data can be accessed from base station 300 and displayed by a remote device such as, for example, group monitoring device 400 and/or analysis device 600. Such image data may be displayed in any format, such as, for example, as images, or as metrics derived therefrom.

In some exemplary embodiments, video feed system 800 includes a video feed camera 804. Video feed camera 804 can also be trained on playing field 30 to record image data. This image data can be transmitted to web server system 500 to be retrieved for later viewing by video display 802 of video feed system 800.

Image data recorded by camera monitoring system 700 and/or video feed system can be accessed from web server system 500 by analysis device 600 and displayed on display 602 of analysis device 600.

In some exemplary embodiments, camera monitoring system 700 can be used to determine positions of individuals 10 and/or sports objects 40. Image data generated by camera monitoring system 700 can be received by base station 300 and analyzed to determine positions of individuals 10 and/or other objects/areas of interest (e.g., sports objects 40). Camera monitoring system 700 can be used in this way to replace or supplement position sensor 208, and may be particularly useful for determining position in an indoor area or an area that otherwise receives no (or a weak) GPS or other positioning signal.

In some exemplary embodiments, image data generated by camera monitoring system 700 can be overlaid or identified with data and metrics described herein. In such an embodiment the image data may be displayed synchronously with the data and metrics by or in conjunction with a display device (e.g., group monitoring device 400 or analysis device 600). This can help correlate data and metrics with actual images of individuals 10 and/or sports objects 40.

In some embodiments, as described above, one or more metrics may be based on a determination of position of individual 10 and/or sports object 40 with respect to a playing field or feature thereof. For example, in some embodiments location signals (e.g., signals generated by position modules 216) are correlated with positions on playing field 30 using GPS data, where the GPS coordinates of the playing field are known by group monitoring system 100. Also for example, in some embodiments location signals are correlated with positions on playing field using relative location data (e.g., data representing a relative location with respect to a reference, which may be, for example, base station 300 or some other stationary beacon connected thereto), where the relative position of the playing field is known by group monitoring system 100. In some embodiments, the position of the playing field becomes known to group monitoring system by being defined by a user.

Figure 78:
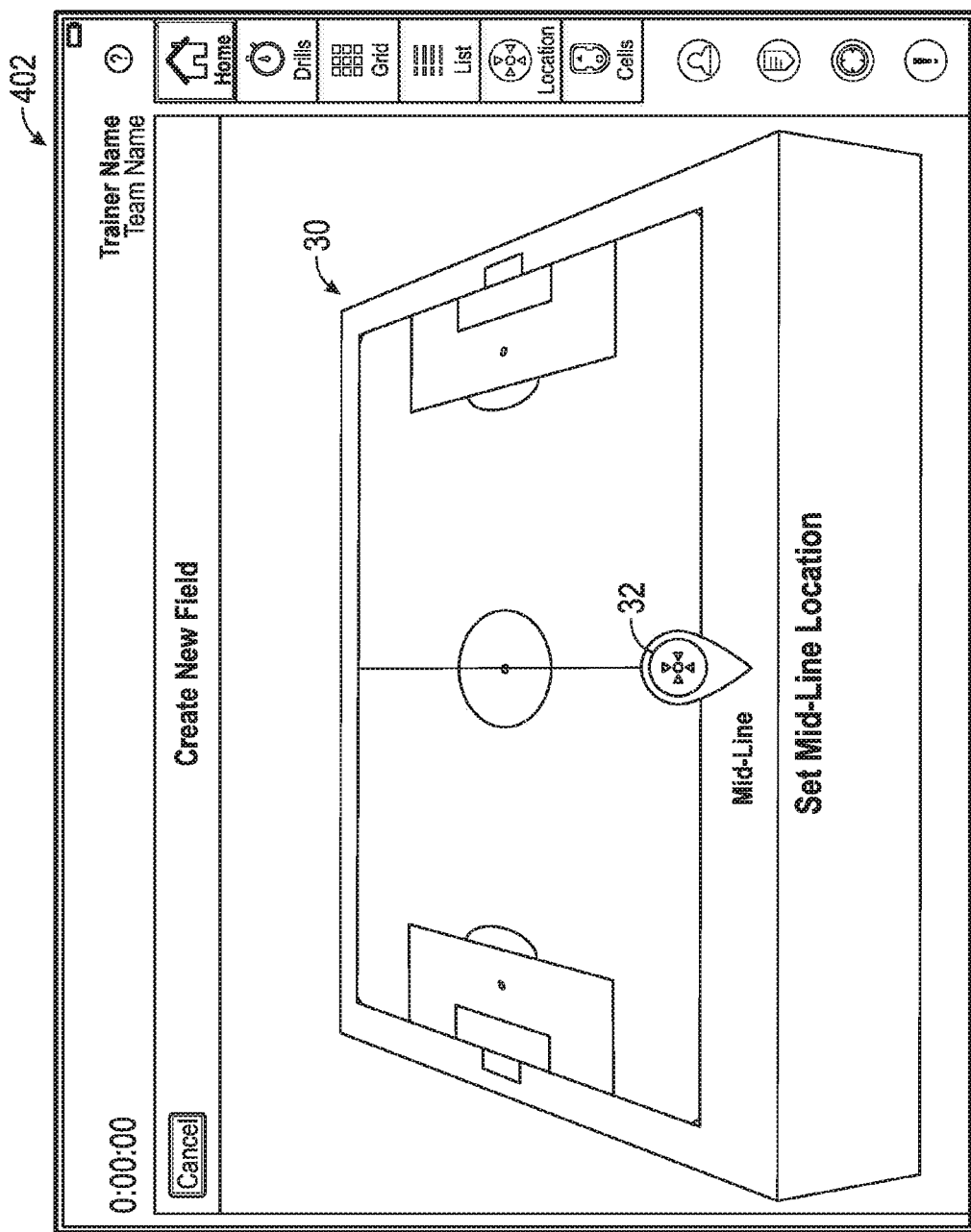
FIG. 78 depicts a display of a group monitoring device according to an exemplary embodiment of the present invention.
Figure 79:
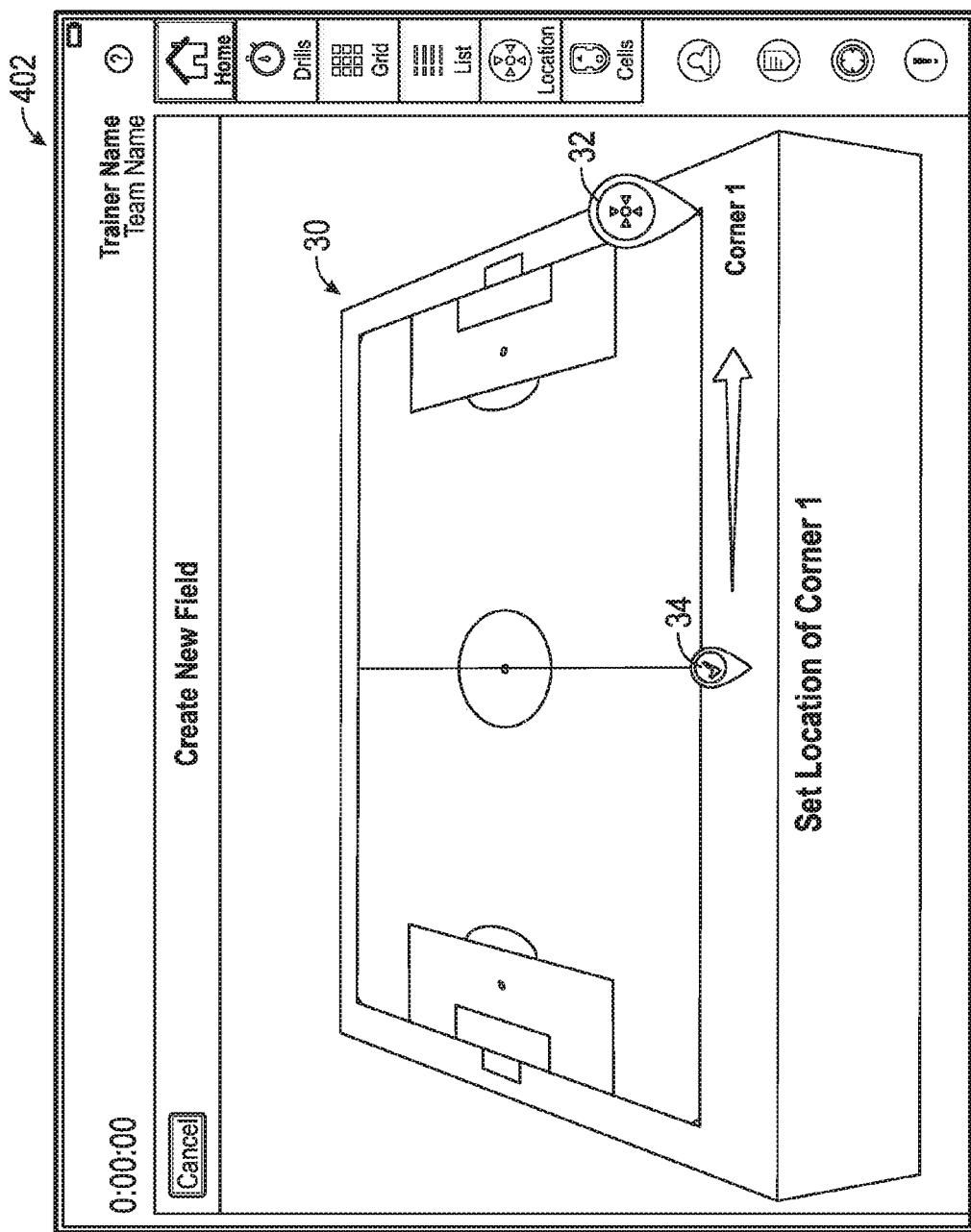
FIG. 79 depicts a display of a group monitoring device according to an exemplary embodiment of the present invention.

In some embodiments, a portable system component (e.g., an individual monitor 200, an object monitor 250, or group monitoring device 400) can be used to define the playing field (which may be, for example, a soccer field, a racing track, or other area). For example, in a field definition mode, display 402 of group monitoring device 400 or other administrative device may display an instruction to locate a position sensor at a first location on a playing field. For example, as shown in FIG. 78, display 402 may instruct a user to locate a position sensor at a mid-line location of a soccer field. Display 402 may display a graphical representation of the playing field 30, with an instruction marker 32 showing the user the location at which to position the sensor. The user may position the group monitoring device 400 at the location on the playing field corresponding to the displayed location, and may optionally provide input through input 404 of group monitoring device 400 to indicate that the group monitoring device 400 is positioned at the instructed location. Alternatively or additionally, in some embodiments, the user of group monitoring device 400 may direct an associated other portable device (e.g., an individual monitor 200 or object monitor 250 carried by another person) communicatively connected to the group monitoring device to the location on the playing field corresponding to the displayed location, and may optionally provide input through input 404 of group monitoring device 400 to indicate that the associated other portable device is positioned at the instructed location. Group monitoring device 400 may then receive position data identifying the location of the position sensor, and may define this position data as corresponding to the instructed location. As noted, such position data may be determined based on GPS data or data representing relative location with respect to a reference).

Figure 80:
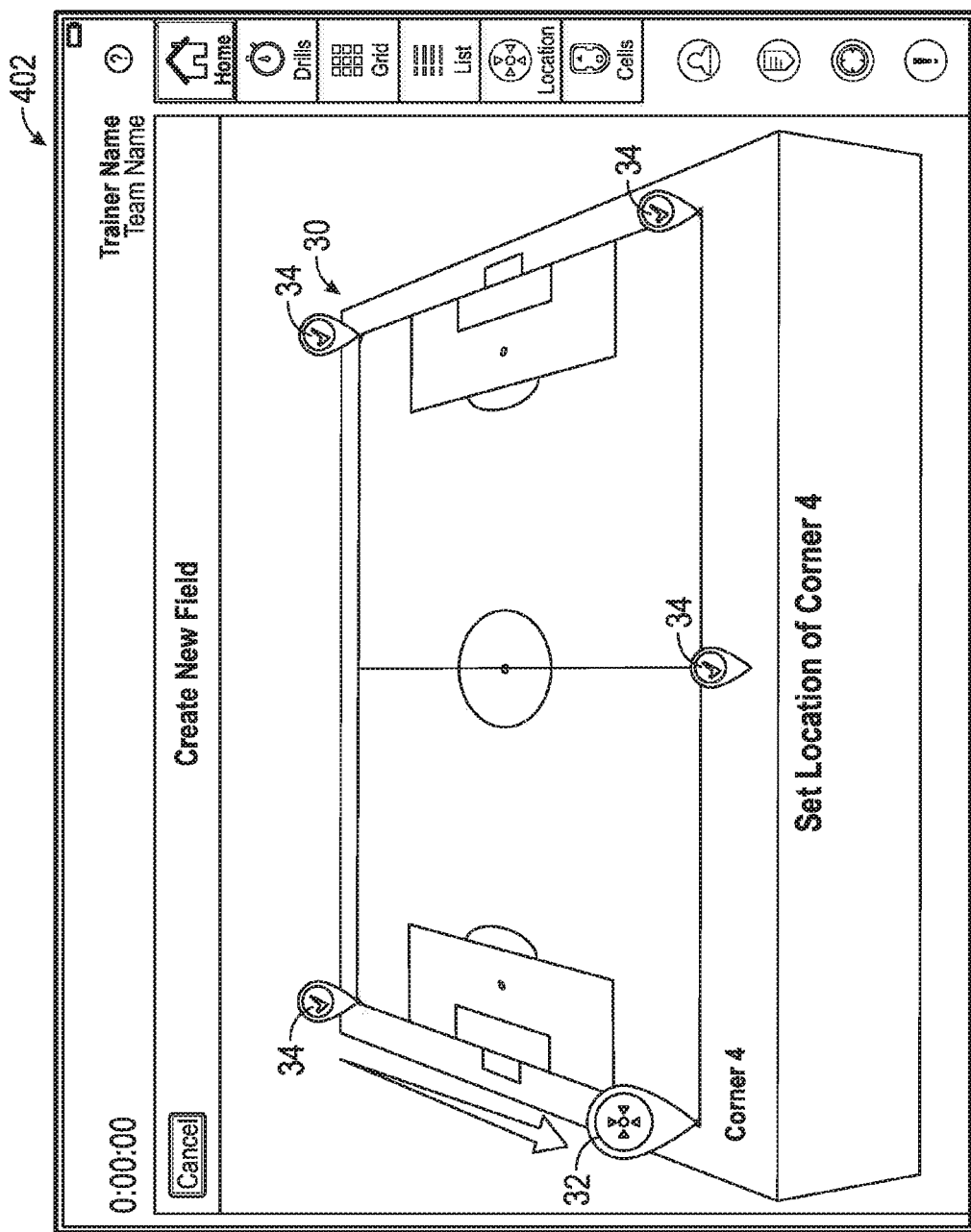
FIG. 80 depicts a display of a group monitoring device according to an exemplary embodiment of the present invention.

Display 402 of group monitoring device 400 may then display an instruction to locate the position sensor at additional locations on the playing field 30, which can be defined similarly as described for the first. For example, as shown in FIG. 78, display 402 may depict a confirmation marker 34 showing that the first point has been defined, and may show an instruction marker 32 showing the user a second location to be defined (e.g., a first corner of a soccer field). Display 402 of group monitoring device 400 may continue to show additional instructions to define additional locations on the playing field 30 (see, e.g., FIG. 80, showing four confirmation markers 34 indicating four defined positions, and one instruction marker 32 indicating a final position to be defined). The positions of the various defined locations may together define the playing field.

Group monitoring system 100 may be applied as described to define any playing field or other area, whether regular or irregular in shape. For example, group monitoring system 100 can be used to define a soccer field, tennis court, running track, football field, basketball court, baseball field, golf course, ski slope, or mountain bike track. The number of positions needed to fully define a playing field 30 may vary and may depend on the geometry of the playing field to be defined. For example, a typical soccer field (or other symmetrical rectangular-shaped field) can be considered fully defined with a minimum of three positions defined (e.g., three corners where the fourth corner can be determined based on the location of the defined three corners). The minimum positions needed to fully define a playing field 30 may increase with increasing geometric complexity of the field shape as well as the extent and geometric complexity of field features to be defined. In some cases, defining some field features may be optional, or may be determined by group monitoring system based on known relationships with defined positions.

For example, defining a baseball field or golf course may involve defining a greater number of positions than does defining a soccer field or tennis court. For example, when defining a baseball field, it may be desired to define its field of play (which is often irregular and can vary from field to field), its foul lines, its base positions, its warning track, and its boundary between infield and outfield. When defining a soccer field or tennis court, simply defining three corners of the field or court may be sufficient for group monitoring system to determine remaining field features. Group monitoring system 100 may instruct definition of the minimum positions needed, or of more than the minimum positions needed (including optional positions). Defining more than the minimum number of positions needed may increase the accuracy of the field definition. Further, group monitoring system 100 may instruct definition of the same position once, or more than once. Defining the same position more than once may increase the accuracy of the definition of that position, thereby increasing the accuracy of the field definition.

Figure 81:
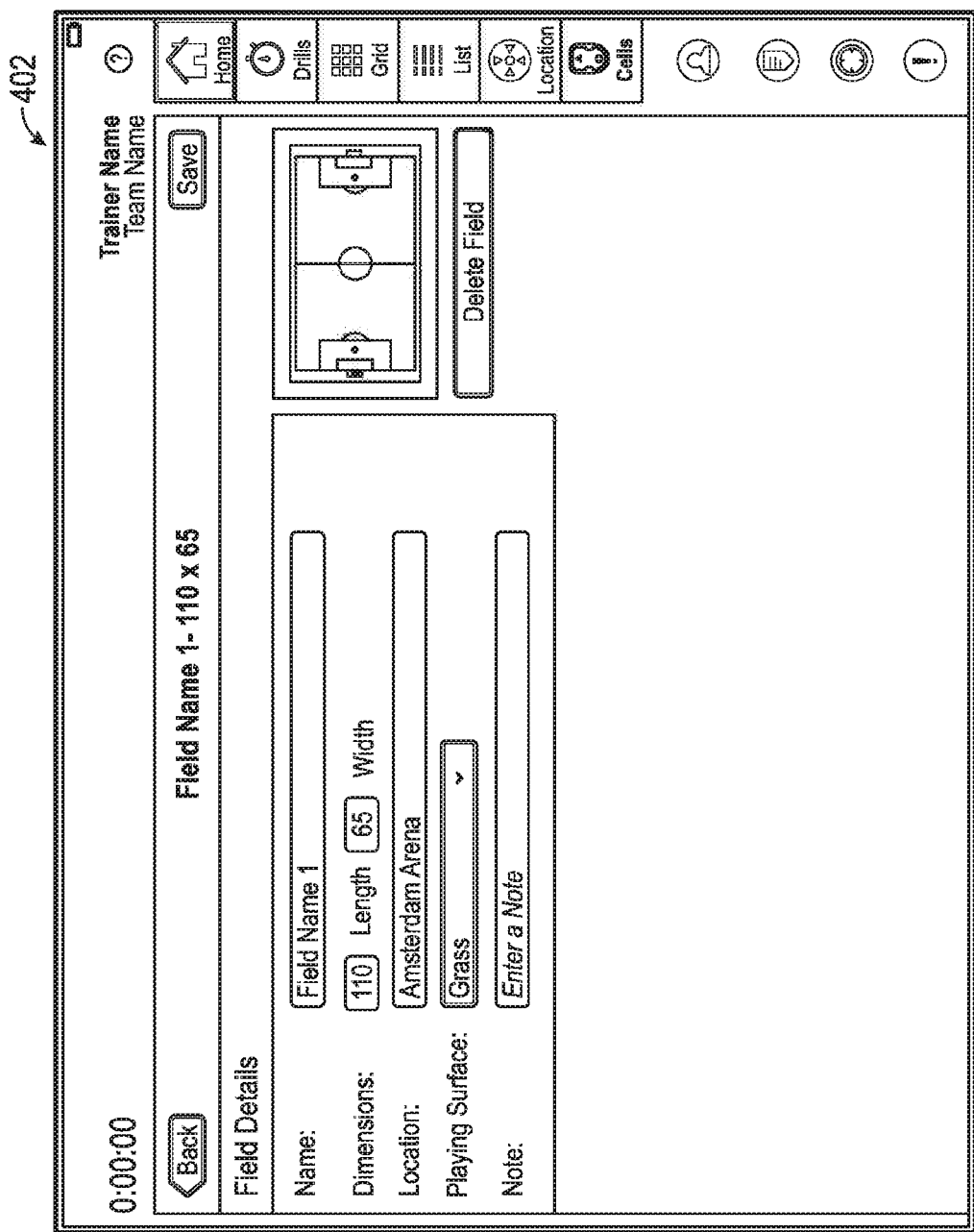
FIG. 81 depicts a display of a group monitoring device according to an exemplary embodiment of the present invention.

Once defined or otherwise obtained, a playing field may be saved in a storage medium of any system component (e.g., group monitoring device 400, base station 300, web server system 500). Attributes of the defined field may be saved in association therewith. For example, a field save screen is depicted on display 402 of group monitoring device 400 in FIG. 81. The field save screen includes fields for a user to input a field name, the field dimensions, the field location, the field playing surface, and any desired notes about the field. In some embodiments, certain field attributes may be determined by group monitoring system 100 (e.g., via a system component such as, for example, group monitoring device 400). For example, once a field is defined, group monitoring system 100 may calculate its dimensions or location (e.g., using GPS data).

As described above, group monitoring system 100 is portable, so it can be transported between and used at different areas during different sessions of athletic activity. The ability of group monitoring system 100 to define a new playing field and monitor activity thereon facilitates this portability. For example, the same group monitoring system 100 can be used to monitor training sessions at a team's training facility, at the team's home playing field, and at the playing fields of opposing teams visited by the team on the road. Each different field can be defined as described above. This facilitates use of group monitoring system 100 across different playing fields, and gives trainers 20 the ability to keep a consistent, repeatable set of measurements even when sessions of athletic activity occur at different locations (e.g., over the course of a season). Many conventional monitoring technologies require fixed installations, which prevents trainers from collecting data or requires them to use different technologies during a session of athletic activity away from their installation (e.g., when they are traveling).

In some embodiments, once group monitoring system 100 receives signals from individual monitors 200 or object monitors 250 monitoring individuals 100 or sports objects 40 in motion on the defined playing field, group monitoring system 100 may determine the type of playing surface of the defined field, based on the character of motion signals received from the individual monitors 200 or object monitors 250. For example, an object monitor 250 monitoring a sports object 40 traveling toward the ground at a given speed may sense different impact characteristics for the sports object 40 upon its striking the ground depending on the type of field, and may determine the type of field based on these characteristics. For example, a duration of impact may be shorter and bounce height may be higher for a hard-surfaced playing field (e.g., clay, hardwood, or asphalt) than for a soft-surfaced playing field (e.g., grass, sand). Also for example, an individual monitor 200 monitoring an individual 10 running on the ground may sense different impact characteristics for the footfalls of the individual 10 depending on the type of field, and may determine the type of field based on these characteristics.

In some embodiments, instead of or in addition to defining a field based on a plurality of positions, a playing field can be defined by lines that correspond to a path moved by a portable system component along boundaries of the playing field. The definition of such lines can be effected similarly as described above with respect to the definition of positions relative to the playing field. A line-based definition technique may be beneficial, for example, in defining fields having complex or non-standard shapes.

Saved fields may be stored and re-used, and may be shared or sold (e.g., via a website or social networking service, as described elsewhere herein). In some embodiments, group monitoring system 100 can download data representing a pre-defined field (e.g., via a system component, such as, for example, group monitoring device 400). Data defining such pre-defined fields may be available for download from, for example, a database, or directly from another user or website. Such pre-defined fields may have been defined previously by, for example, a user of the same or a different group monitoring system 100, or of any other suitable system (e.g., a position-recording or surveying system). In some embodiments, group monitoring system 100 can provide an interface to search for data representing a particular pre-defined field (e.g., via group monitoring device 400), or may suggest download of data representing particular pre-defined fields based on the position of one or more system components. For example, if base station 300 is determined to have GPS coordinates proximate to those of Playing Field A, where data representing Playing Field A is pre-defined and available for download by group monitoring system 100, group monitoring system 100 may suggest such download (e.g., via an interface of, for example, group monitoring device 400), thereby eliminating the need to re-define Playing Field A before holding a session of athletic activity thereon.

A metric may be a representation of data indicative of a characteristic of individual 10 or sports object 40 sensed as described above, or may be a representation of a characteristic derived from such data. In general, group monitoring system 100 can operate as a multi-level analysis tool. In an exemplary embodiment, group monitoring system 100 can use signals from an accelerometer, GPS sensor, electrocardiograph (ECG), gyroscope, clock, and magnetometer to directly determine data indicating position, orientation, activity, and time related to each monitored individual 10 or sports object 40, as well as data indicating heart rate of an individual 10 monitored by an individual monitor 200 or interacting with a sports object 40 monitored by an object monitor 250. This data can be processed to calculate metrics including mechanical power, mechanical power zones, speed, speed zones, metabolic power, metabolic power zones, motion state, and distance. These metrics can be processed in conjunction with values indicating time, mass of each individual 10 and/or sports object 40, and motion state of each individual 10 and/or sports object 40, to calculate metrics including fatigue, training impact (TRIMPS), acceleration zones, acceleration work, efficiency, total distance, and acceleration.

In some embodiments, group monitoring system 100 may determine two or more metrics measuring the same characteristic in a different way. For example, group monitoring system 100 may provide a training load metric based on a number of different metrics. Conventionally, distance is used as a measure of training load, and distance can be used in this way by group monitoring system 100. However, sports like soccer and basketball that involve frequent starts and stops demand quick accelerations, decelerations, and changes in direction such that a training load metric based solely on distance may not be accurate. Thus, in addition to, or as an alternative to determining a training load metric based on distance, group monitoring system 100 can determine training load using heart rate, speed, acceleration, and power. These movements contribute significantly to the load an athlete experiences in training, and may better represent actual training load. By analyzing training load by using a variety of metrics trainers are able to determine and understand total training load much more accurately.

As described herein, group monitoring system 100 can determine data about sensed characteristics from multiple sources (sensors), can process this data to determine metrics, and can output representations of such metrics to an observer (e.g., trainer 20). The data can represent characteristics of an individual that are unobservable, and the volume of such data can be so great (e.g., millions of data points) as to be effectively uninterpretable by a person (e.g., trainer 20). As described, group monitoring system 100 can process and present this data to a user in an observable and interpretable manner, even combining data streams from different sources, thus providing the user with greater insight and knowledge about the monitored activity and monitored individuals 10 than would be possible otherwise. This can help the trainer understand how their training is impacting an individual 10's ability to perform.

For example, group monitoring system 100 may monitor data streams representing heart rate, power, speed, distance, acceleration, and position on a playing field. By combining these data streams and basing calculations on more than just a single data stream, group monitoring system can determine and output representations of new insights such as, for example, intensity and efficiency of an individual 10 or group thereof. Display 402 of group monitoring device 400 can display such representations in real time, thus enabling trainers to act on these insights during a training session to ensure that they are meeting their training goals.

For example, heart rate is a measure of the body's response to training. During a training session, a trainer can use a live dashboard (e.g., displayed on display 402) to monitor heart rate recovery, making sure not to begin the next training interval until the majority of athletes are ready (i.e., their heart rates have sufficiently recovered).

Also for example, power is a measure of how hard a person is working. Power training is widely used in cycling where it has been possible to measure by putting a meter on the bike. Sensors and algorithms in group monitoring system 100 will facilitate the determination of power in other sports (e.g., soccer).

Also for example, by combining power and heart rate, trainers are provided a complete picture of how hard a monitored individual is working and how their body is responding to the work. This combination of metrics allows coaches to look at the overall efficiency of the individual. Individuals that are putting out more work per heart beat are in better condition (i.e., more efficient).

Also for example, speed is typically used as a measure of intensity. Speed is an important part of many athletic activities. By monitoring an individual's speed a trainer can see if the individual is training at a target level (e.g., a level considered to correspond to success in a game). When a trainer plans a speed training session he or she can customize a live dashboard (e.g., displayed on display 402) to view speed-related data including peak speed, average speed, and number of high intensity sprints. The ability to manage speed training carefully can help prevent overtraining and can reduce the risk of injury.

Also for example, distance covered has long been a reference for training volume. The distance an individual covers (e.g., runs) during a session of athletic activity (e.g., a game or scrimmage) can vary. A real time measure of distance covered can allow a trainer to set individual or team targets for distance and ensure that all individuals have reached the target. At the end of a session of athletic activity the trainer can refer to the live dashboard to check distance covered. Individuals that fell short of the target may be instructed to continue to run.

Also for example, acceleration (including deceleration) can be a significant measure of performance. Acceleration can be important in sports where rapid change of direction is required. Understanding the rate and frequency of acceleration can influence a determination of overall training load.

Also for example, knowledge of position on the field may allow a trainer to see where the monitored individuals are or have been on the field. This can promote insights into tactical movements of the players. As described above, such positioning can be shown on a map, for instance a heat map, where positions are determined using GPS.

Though particular metrics have been described above in the context of the described exemplary embodiments, these particular metrics are exemplary only, and other metrics besides those particularly disclosed may be used in the described exemplary embodiments. Examples of metrics are presented below in Table 1. Such metrics may apply to individual 10, sports object 40, or both.

TABLE 1

| Metric Examples |
| --- |
| Acceleration |
| Epoch acceleration (mean accelerometer output over defined epoch) |
| Peak acceleration (maximum positive acceleration for a defined period) |
| Peak acceleration trend (plot of peak positive acceleration as a function of successive defined periods) |
| Average acceleration (mean positive acceleration for a defined period) |
| Average acceleration trend (plot of average acceleration as a function of successive defined periods) |
| Deceleration |
| Peak deceleration (maximum negative acceleration for a defined period) |
| Peak deceleration trend (plot of peak negative acceleration as a function of successive defined periods) |
| Acceleration zones (accumulated time spent in defined acceleration zones) |
| Collision impact (e.g., energy absorbed) |
| Training impact/TRIMPS (heart rate- or power-based) |
| Activity type |
| Step rate |
| Stride length |
| Time of ground contact (e.g., per step, or for a defined period) |
| Heart rate |
| Individual heart rate zones |
| Heart rate recovery |
| Heart rate recovery assessment (rate of recovery) |
| Location and Orientation (coordinate location, may be relative to base station) (e.g., x, y, z) |
| Location and Orientation (heat map) (e.g., 2 dimensional histogram of position) |
| Location and Orientation (movement path) (e.g., 2 dimensional time series plot) |
| Location and Orientation (relative to playing field) (e.g., standing, falling, laying down) |
| Location and Orientation (relative to playing field) (e.g., facing opposing goal) |
| Location and Orientation (relative to athletic activity equipment) (e.g., facing ball) |
| Location and Orientation (heading, absolute, relative to Earth) (e.g., facing east) |
| Location and Orientation (on-field spacing) |
| Location and Orientation (distance between individuals and/or objects) |
| Speed |
| Peak speed (maximum speed for a defined period) |
| Peak speed trend (plot of peak speed as a function of successive defined periods) |
| Average speed (mean speed for a defined period, may discount speeds below a defined threshold to account for non-mobile time) |
| Average speed trend (plot of average speed as a function of successive defined periods) |
| Speed zones (accumulated time spent in defined speed zones) |
| Distance traveled |
| Vertical displacement (time off of ground) |
| Vertical displacement (height) |
| Work (training load) (e.g., intensity over time; may take into account a combination of, for example, distance, number of sprints, number of accelerations/decelerations, time in speed zones, time in acceleration zones, body weight) |
| Work (mechanical work) (e.g., energy required to move individual through a distance) |
| Work (power/intensity) (e.g., rate of doing work, power delivered, energy converted from chemical to mechanical) |
| Work (energy expenditure) (e.g., energy used to deliver mechanical work) |
| Work (efficiency) (e.g., ratio between energy expended and work; may account for state of body resulting from, for example, mental state, sleep, diet) |
| Power (constant power) (e.g., lactate threshold assessment, ventilatory threshold assessment) |
| Power (power output) (e.g., related to distance or acceleration) |
| Power (relative power output) (e.g., normalized to an individual's constant power at a point in time) |
| Power (acceleration) |

TABLE 1-continued

Metric Examples

Power (relative training impact) (e.g., cumulative power delivered over time, weighted by zones or activities)
Power (calories) (e.g., metabolic consumption, energy expenditure) (e.g., based on heart rate and accelerometry)
Power (activity)
Efficiency/performance effectiveness (relative efficiency) (mechanical power generated divided by metabolic energy consumption, e.g., normalized based on a known maximum state)
Efficiency/performance effectiveness (linear running efficiency) (e.g., efficiency of forward power vs. total power)
Efficiency/performance effectiveness (absolute efficiency) (e.g., ratio of absolute mechanical work to calories)
Fatigue (physiologic response to training load, measure of total work done) (e.g., change in EMG (electrogyogrphy) wavelet frequency, summed calorie rate consumption vs. expected standard, change in accelerometer spectral content, decay in sprint speeds, lengthening recovery times, change in heart rate recovery after exertion)
Core body temperature
Respiration rate
Running based Anaerobic Sprint Test (RAST)
Multi-stage fitness test performance (also known as the Yoyo test or beep test)
Maximal oxygen consumption (also known as $VO_2$ max)
Perceived exertion
X meter sprint performance (where X is a defined distance)
Blood lactate level
Rotation rate
Rotation plane
Trajectory
Launch angle
Flight time
Reaction time
Impact force The metrics described herein can relate to an individual (such as individual 10), a base station (such as base station 300), any relevant athletic equipment (such as, for example, sports object 40), or other persons or objects to the extent possible, necessary, or desired. The metrics described herein are exemplary, and other metrics besides those disclosed herein are useable with the present invention, as would be appreciated by one of skill in the art.

The present invention has been described above by way of exemplary embodiments. Accordingly, the present invention should not be limited by any of the above-described exemplary embodiments, but should be defined only in accordance with the following claims and their equivalences.

What is claimed is:

1. A system for monitoring a plurality of individuals engaged in an athletic activity, the system comprising:
    an individual monitor coupled to an individual engaged in the athletic activity, the individual monitor configured to transmit individual data indicative of a characteristic of the individual;
    an object monitor coupled to a sports object used in the athletic activity, the object monitor configured to transmit object data indicative of a characteristic of the object; and
    a garment having an illuminable area,
    wherein the system is configured to compare the individual data with the object data and make a determination based on the comparison, and
    wherein the garment is configured to illuminate based on the determination.

2. The system of claim 1, further comprising a base station configured to receive the individual data from the individual monitor and the object data from the object monitor.

3. The system of claim 2, wherein the determination is made at the base station.

4. The system of claim 1, wherein the determination is made at the object monitor.

5. The system of claim 1, further comprising a plurality of individual monitors, each individual monitor coupled to an individual engaged in the athletic activity.

6. The system of claim 1, wherein the garment is a shirt.

7. The system of claim 1, wherein the garment is a shoe.

8. The system of claim 1, wherein the determination comprises determining which of the plurality of individuals last contacted the sports object.

9. The system of claim 1, wherein the determination comprises determining that the sports object has been passed from the individual.

10. The system of claim 1, wherein the determination comprises determining that the individual scored a goal.

11. The system of claim 1, wherein the determination comprises determining that the individual has possession of the sports object.

12. The system of claim 1, wherein the sports object is a ball.

13. The system of claim 1, further comprising a sensor in communication with the object monitor, wherein the sensor is configured to sense the characteristic of the object.

14. The system of claim 1, wherein the object monitor comprises a sensor.

15. A method for monitoring a plurality of individuals engaged in an athletic activity, the method comprising:
    receiving, at an individual monitor, individual data indicative of a characteristic of an individual engaged in the athletic activity;
    receiving, from an object monitor, object data indicative of a characteristic of a sports object;
    comparing the individual data with the object data;
    determining a characteristic of a kick based on the individual data and the object data; and
    illuminating a garment based on determining the characteristic of the kick.

16. The method of claim 15, wherein the characteristic of the sports object comprises at least one of a speed of the sports object, a direction of motion of the sports object, and a predicted landing location of the sports object.

17. The method of claim 15, wherein determining a characteristic of the kick comprises determining which of the plurality of individuals kicked the sports object.

18. The method of claim 15, wherein the kick comprises a kick of the individual.

19. The method of claim 18, further comprising providing a recommendation on how to improve the individual's kick.

20. An object monitor comprising:
    a plurality of sensors configured to sense a characteristic of a sports object and provide data indicative of the characteristic of the sports object;
    a processor configured to determine metrics based on the data provided by the plurality of sensors; and
    a transceiver configured to transmit the metrics, wherein the transceiver is configured to receive individual performance data from an individual monitor, the individual performance data indicative of a performance characteristic of an individual engaged in an athletic activity involving the sports object,
    wherein the object monitor is configured to make a determination based on the metrics.

21. The object monitor of claim 20, wherein the determination comprises determining that a goal has been scored.

22. The object monitor of claim 20, wherein the metrics comprise at least one of speed, trajectory, flight time, reaction time, acceleration, flight distance, launch angle, orientation, and rotation rate.

23. The object monitor of claim 20, wherein the plurality of sensors comprises a position sensor, an acceleration sensor, a gyroscope, and a magnetometer.

24. The object monitor of claim 20, wherein the object monitor is configured to make a determination based on the metrics and the individual performance data.

25. The object monitor of claim 20, wherein the object monitor is integrated within the sports object.

\* \* \* \* \*